(12) United States Patent
Broughton et al.

(10) Patent No.: US 6,255,305 B1
(45) Date of Patent: Jul. 3, 2001

(54) SUBSTITUTED TRIAZOLO-PYRIDAZINE DERIVATIVES AS LIGANDS FOR GABA RECEPTORS

(75) Inventors: Howard Barff Broughton, Harlow; William Robert Carling; Jose Luis Castro Pineiro, both of Bishops Stortford; Alexander Richard Guiblin, Welwyn Garden City; Andrew Madin, Sawbridgeworth; Kevin William Moore, Buntingford; Michael Geoffrey Russell, Welwyn Garden City; Leslie Joseph Street, Harlow, all of (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 0 days.

(21) Appl. No.: 09/155,587

(22) PCT Filed: Jul. 17, 1997

(86) PCT No.: PCT/GB97/01946

§ 371 Date: Nov. 10, 1998

§ 102(e) Date: Nov. 10, 1998

(87) PCT Pub. No.: WO98/04559

PCT Pub. Date: Feb. 5, 1998

(30) Foreign Application Priority Data

Jul. 25, 1996 (GB) ................................. 9615645
Dec. 6, 1996 (GB) ................................. 9625397
Jul. 9, 1997 (GB) ................................. 9714420

(51) Int. Cl.[7] ................... A61K 37/5025; C07D 487/04; C07D 487/14
(52) U.S. Cl. .................. 514/248; 514/228.5; 514/233.2; 544/58.4; 544/61; 544/115; 544/118; 544/229; 544/233; 544/234; 544/236
(58) Field of Search ............. 544/236, 61, 58.4, 544/118; 514/248, 228.5, 233.2

(56) References Cited

U.S. PATENT DOCUMENTS

| 4,487,930 | 12/1984 | Peet et al. | 544/236 |
|---|---|---|---|
| 4,578,464 | 3/1986 | Cregge et al. | 544/236 |
| 4,783,461 | 11/1988 | Occelli et al. | 514/248 |
| 4,810,705 | * 3/1989 | Bourguignon et al. | 514/248 |
| 5,905,079 | * 5/1999 | Sargent et al. | 514/248 |
| 6,107,296 | * 8/2000 | Pineiro | 514/248 |

FOREIGN PATENT DOCUMENTS

| 2741763 | 3/1978 | (DE) . |
|---|---|---|
| 085840A1 | 8/1983 | (EP) . |
| 134946A1 | 3/1985 | (EP) . |
| WO95/10521 | 4/1995 | (WO) . |

OTHER PUBLICATIONS

G. Tarzia, et al., Benzodiazepine receptor ligands, Il Farmaco, vol. 43, pp. 189–201, 1998.

* cited by examiner

*Primary Examiner*—Emily Bernhardt
(74) *Attorney, Agent, or Firm*—Shu Muk Lee; Philippe L. Durette

(57) ABSTRACT

Substituted triazolo-pyridazine derivative compounds represented by

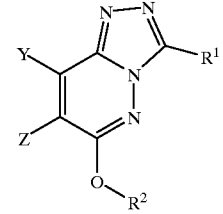

wherein the variables are disclosed herein are selective ligands for GABA-A receptors, particularly for the $\alpha 2$ and/or $\alpha 3$ subunits.

15 Claims, No Drawings

SUBSTITUTED TRIAZOLO-PYRIDAZINE DERIVATIVES AS LIGANDS FOR GABA RECEPTORS

The present invention relates to a class of substituted triazolo-pyridazine derivatives and to their use in therapy. More particularly, this invention is concerned with substituted 1,2,4-triazolo[4,3-b]pyridazine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to thirteen (six $\alpha$ subunits, three $\beta$ subunits, three $\gamma$ subunits and one $\delta$ subunit). It may be that further subunits remain to be discovered; however, none has been reported since 1993.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, a $\delta$ subunit also exists, but is present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha 1\beta 2\gamma 2$, $\alpha 2\beta 2/3\gamma 2$, $\alpha 3\beta \gamma 2/3$, $\alpha 2\beta \gamma 1$, $\alpha 5\beta 3\gamma 2/3$, $\alpha 6\beta \gamma 2$, $\alpha 6\beta \delta$ and $\alpha 4\beta \delta$. Subtype assemblies containing an $\alpha 1$ subunit are present in most areas of the brain and are thought to account for over 40% of $GABA_A$ receptors in the rat. Subtype assemblies containing $\alpha 2$ and $\alpha 3$ subunits respectively are thought to account for about 25% and 17% of $GABA_A$ receptors in the rat. Subtype assemblies containing an $\alpha 5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha 1$ subunit in combination with a $\beta$ subunit and $\gamma 2$. This is the most abundant $GABA_A$ receptor subtype, and is believed to represent almost half of all $GABA_A$ receptors in the brain.

Two other major populations are the $\alpha 2\beta\gamma 2$ and $\alpha 3\beta\gamma 2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha 5$-containing subtype assemblies. The physiological role of these subtypes has hitherto been unclear because no sufficiently selective agonists or antagonists were known.

It is now believed that agents acting as BZ agonists at $\alpha 1\beta\gamma 2$, $\alpha 2\beta\gamma 2$ or $\alpha 3\beta\gamma 2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha 1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha 1$ subunit. Accordingly, it is considered that $GABA_A$ receptor agonists which bind more effectively to the $\alpha 2$ and/or $\alpha 3$ subunit than to $\alpha 1$ will be effective in the treatment of anxiety with a reduced propensity to cause sedation. Also, agents which are antagonists or inverse agonists at $\alpha 1$ might be employed to reverse sedation or hypnosis caused by $\alpha 1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; and depressive or bipolar disorders, for example single-episode or recurrent major depressive disorder, dysthymic disorder, bipolar I and bipolar II manic disorders, and cyclothymic disorder.

In DE-A-2741763, and in U.S. Pat. Nos. 4,260,755, 4,260,756 and 4,654,343, are described various classes of 1,2,4-triazolo[4,3-b]pyridazine derivatives which are alleged to be useful as anxiolytic agents. The compounds described in DE-A-2741763 and in U.S. Pat. Nos. 4,260,755 and 4,654,343 possess a phenyl substituent at the 6-position of the triazolo-pyridazine ring system. The compounds described in U.S. Pat. No. 4,260,756, meanwhile, possess a heteroaryl moiety at the 6- or 8-position. In none of these publications, however, is there any disclosure or suggestion of 1,2,4-triazolo[4,3-b]pyridazine derivatives wherein the substituent at the 6-position is attached through a directly linked oxygen atom.

EP-A-0085840 and EP-A-0134946 describe related series of 1,2,4-triazolo[3,4-a]phthalazine derivatives which are stated to possess antianxiety activity. However, there is no disclosure nor any suggestion in either of these publications of replacing the benzo moiety of the triazolo-phthalazine ring system with any other functionality.

The present invention provides a class of triazolo-pyridazine derivatives which possess desirable binding properties at various $GABA_A$ receptor subtypes. The compounds in accordance with the present invention have good affinity as ligands for the $\alpha 2$ and/or $\alpha 3$ subunit of the human $GABA_A$ receptor. The compounds of this invention may display more effective binding to the $\alpha 2$ and/or $\alpha 3$ subunit than to the $\alpha 1$ subunit. Desirably, the compounds of the invention will exhibit functional selectivity in terms of a selective efficacy for the α2 and/or α3 subunit relative to the α1 subunit.

The compounds of the present invention are $GABA_A$ receptor subtype ligands having a binding affinity ($K_i$) for the α2 and/or α3 subunit, as measured in the assay described hereinbelow, of 100 μM or less, typically of 50 nM or less, and ideally of 10 nM or less. The compounds in accordance with this invention may possess at least a 2-fold, suitably at least a 5-fold, and advantageously at least a 10-fold, selectivity affinity for the α2 and/or α3 subunit relative to the α1 subunit. However, compounds which are unselective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

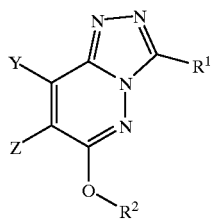

(I)

wherein
Y represents hydrogen or $C_{1-6}$ alkyl; and
Z represents $C_{1-6}$ alkyl, $C_{3-7}$ cycloalkyl, $C_{4-7}$ cycloalkenyl, aryl, $C_{3-7}$ heterocycloalkyl, heteroaryl or di($C_{1-6}$)alkylamino, any of which groups may be optionally substituted; or
Y and Z are taken together with the two intervening carbon atoms to form a ring selected from $C_{5-9}$ cycloalkenyl, $C_{6-10}$ bicycloalkenyl, tetrahydropyridinyl, pyridinyl and phenyl, any of which rings may be optionally benzo-fused and/or substituted;
$R^1$ represents $C_{3-7}$ cycloalkyl, phenyl, furyl, thienyl or pyridinyl, any of which groups may be optionally substituted; and
$R^2$ represents cyano($C_{1-6}$)alkyl, hydroxy($C_{1-6}$)alkyl, $C_{3-7}$ cycloalkyl($C_{1-6}$)alkyl propargyl, $C_{3-7}$ heterocycloalkylcarbonyl($C_{1-6}$)alkyl, aryl($C_{1-6}$)alkyl or heteroaryl($C_{1-6}$)alkyl, any of which groups may be optionally substituted;
provided that, when Y and Z are taken together with the two intervening carbon atoms to form an optionally substituted phenyl ring, then $R^2$ is other than hydroxy ($C_{1-6}$)alkyl.

In addition, the present invention provides a compound of formula I as defined above, or a salt or prodrug thereof, wherein
Y represents hydrogen or $C_{1-6}$ alkyl; and
Z represents $C_{1-6}$ alkyl, $C_{3-7}$ cycloalkyl, aryl, $C_{3-7}$ heterocycloalkyl or heteroaryl, any of which groups may be optionally substituted; or
Y and Z are taken together with the two intervening carbon atoms to form a ring selected from $C_{5-9}$ cycloalkenyl, $C_{6-10}$ bicycloalkenyl, tetrahydropyridinyl pyridinyl and phenyl, any of which rings may be optionally benzo-fused and/or substituted; and
$R^1$ and $R^2$ are as defined above;
provided that, when Y and Z are taken together with the two intervening carbon atoms to form an optionally substituted phenyl ring, then $R^2$ is other than hydroxy ($C_{1-6}$)alkyl.

The present invention also provides a compound of formula I as defined above, or a salt or prodrug thereof, wherein
Y represents hydrogen or $C_{1-6}$ alkyl; and
Z represents $C_{1-6}$ alkyl, $C_{3-7}$ cycloalkyl, aryl, $C_{3-7}$ heterocycloalkyl or heteroaryl, any of which groups may be optionally substituted; or
Y and Z are taken together with the two intervening carbon atoms to form a ring selected from $C_{5-9}$ cycloalkenyl, $C_{6-10}$ bicycloalkenyl, tetrahydropyridinyl, pyridinyl and phenyl any of which rings may be optionally benzo-fused and/or substituted;
$R^1$ is as defined above; and
$R^2$ represents hydroxy($C_{1-6}$)alkyl, $C_{3-7}$ cycloalkyl($C_{1-6}$) alkyl, $C_{3-7}$ heterocycloalkylcarbonyl($C_{1-6}$)alkyl, aryl ($C_{1-6}$)alkyl or heteroaryl($C_{1-6}$)alkyl, any of which groups may be optionally substituted;
provided that, when Y and Z are taken together with the two intervening carbon atoms to form an optionally substituted phenyl ring, then $R^2$ is other than hydroxy ($C_{1-6}$)alkyl.

The present invention further provides a compound of formula I as defined above, or a salt or prodrug thereof, wherein
Y represents hydrogen or $C_{1-6}$ alkyl; and
Z represents $C_{1-6}$ alkyl $C_{3-7}$ cycloalkyl aryl, $C_{3-7}$ heterocycloalkyl or heteroaryl any of which groups may be optionally substituted; or
Y and Z are taken together with the two intervening carbon atoms to form a ring selected from $C_{5-9}$ cycloalkenyl, $C_{6-10}$ bicycloalkenyl tetrahydropyridinyl and pyridinyl, any of which rings may be optionally benzo-fused and/or substituted;
$R^1$ is as defined above; and
$R^2$ represents hydroxy($C_{1-6}$)alkyl, $C_{3-7}$ cycloalkyl($C_{1-6}$) alkyl $C_{3-7}$ heterocycloalkylcarbonyl($C_{1-6}$)alkyl, aryl ($C_{1-6}$)alkyl or heteroaryl($C_{1-6}$)alkyl, any of which groups may be optionally substituted.

Where Y and Z are taken together with the two intervening carbon atoms to form a ring, the resulting compounds of formula I above incorporate the relevant cycloalkenyl, bicycloalkenyl tetrahydropyridinyl, pyridinyl or phenyl ring fused to the central triazolo-pyridazine ring system as depicted in formula I.

Where Y and Z are taken together with the two intervening carbon atoms to form a $C_{5-9}$ cycloalkenyl ring, this ring may be a cyclopentenyl, cyclohexenyl, cycloheptenyl, cyclooctenyl or cyclononenyl ring, suitably cyclohexenyl or cycloheptenyl.

Where Y and Z are taken together with the two intervening carbon atoms to form a $C_{6-10}$ bicycloalkenyl ring, this ring may be a bicyclo[2.1.1]hex-2-enyl, bicyclo[2.2.1]hept-2-enyl, bicyclo[2.2.2]oct-2-enyl, bicyclo[3.2.2]non-6enyl or bicyclo[3.3.2]dec-9-nyl ring, suitably bicyclo[2.2.1]hept-2-enyl, bicyclo[2.2.2]oct-2-enyl or bicyclo[3.2.2]non-6-enyl and especially bicyclo[2.2.2]oct-2-enyl.

Where Y and Z are taken together with the two intervening carbon atoms to form a ring, this ring may be optionally benzo-fused. By way of illustration, Y and Z taken together with the two intervening carbon atoms may represent a benzo-fused cyclohexenyl ring, whereby the resulting ring is dihydronaphthyl.

The groups Y, Z, $R^1$ and $R^2$ may be unsubstituted, or substituted by one or more, suitably by one or two, substituents. In general, the groups Y, Z, $R^1$ and $R^2$ will be unsubstituted or monosubstituted. Examples of optional substituents on the groups Y, Z, $R^1$ and $R^2$ include $C_{1-6}$ alkyl, aryl($C_{1-6}$)alkyl, pyridyl($C_{1-6}$)alkyl, halogen, halo($C_{1-6}$) alkyl, cyano, cyano($C_{1-6}$)alkyl, hydroxy, hydroxymethyl, $C_{1-6}$ alkoxy, $C_{3-7}$ cycloalkyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl piperazinyl($C_{1-6}$)alkyl, morpholinyl ($C_{1-6}$)alkyl, di($C_{1-6}$)alkylmorpholinyl($C_{1-6}$)alkyl and imidazolyl($C_{1-6}$)alkyl. Illustrative substituents include $C_{1-6}$ alkyl, aryl($C_{1-6}$)alkyl, pyridyl($C_{1-6}$)alkyl, halogen, halo($C_{1-6}$) alkyl, cyano, cyano($C_{1-6}$)alkyl, hydroxy, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, di($C_{1-6}$)alkylaminocarbonyl ($C_{1-6}$)alkyl morpholinyl($C_{1-6}$)alkyl and imidazolyl($C_{1-6}$) alkyl. Representative substituents include $C_{1-6}$ alkyl, aryl ($C_{1-6}$)alkyl, halogen, cyano, hydroxy, hydroxymethyl, $C_{1-6}$ alkoxy and $C_{3-7}$ cycloalkyl($C_{1-6}$)alkoxy.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl and 1,1-dimethylpropyl. Derived expressions such as "$C_{1-6}$ alkoxy" are to be construed accordingly.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs,* ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, Y represents hydrogen or methyl, especially hydrogen.

Examples of suitable values for the substituent Z include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, phenyl, pyrrolidinyl, methyl-pyrrolidinyl, piperidinyl, morpholinyl, thiomorpholinyl, pyridinyl, furyl, thienyl, chloro-thienyl and diethylamino. Illustrative values of Z include methyl, ethyl, isopropyl, tert-butyl, methyl-cyclopropyl, cyclobutyl, methyl-cyclobutyl, cyclopentyl, methyl-cyclopentyl, cyclohexyl, phenyl, pyrrolidinyl, methyl-pyrrolidinyl, piperidinyl, morpholinyl, thiomorpholinyl, pyridinyl, furyl, thienyl and chloro-thienyl. Typical values include methyl, ethyl, phenyl, piperidinyl, pyridinyl and thienyl.

In a particular embodiment, the substituent Z represents $C_{3-7}$ cycloalkyl, either unsubstituted or substituted by $C_{1-6}$ alkyl, especially methyl. Favourably, Z represents cyclobutyl.

When Y and Z are taken together with the two intervening carbon atoms to form a ring, representative compounds according to the invention include those of structure IA to IL, especially IA to IK:

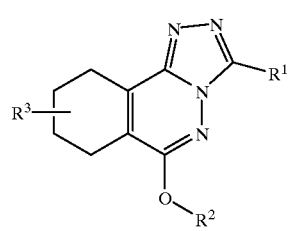

(IA)

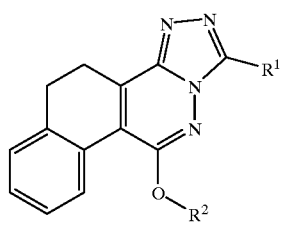
(IB)

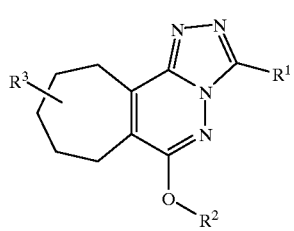
(IC)

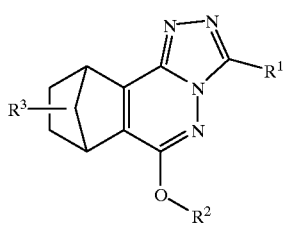
(ID)

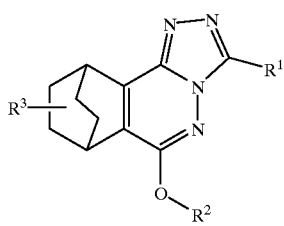
(IE)

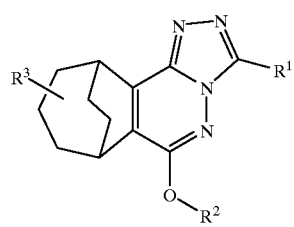
(IF)

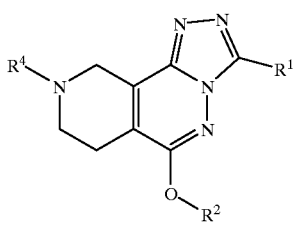
(IG)

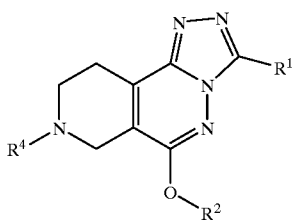
(IH)

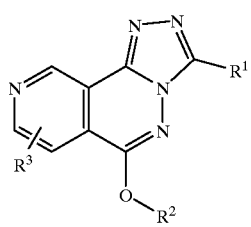
(IJ)

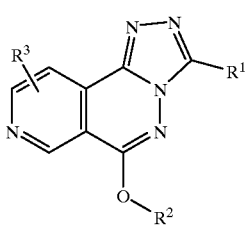
(IK)

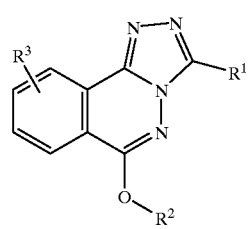
(IL)

wherein $R^1$ and $R^2$ are as defined above;
$R^3$ represents hydrogen, $C_{1-6}$ alkyl, aryl($C_{1-6}$)alkyl, halogen, cyano, hydroxy, hydroxymethyl or $C_{1-6}$ alkoxy; and
$R^4$ represents hydrogen or $C_{1-6}$ alkyl.

Suitably, $R^3$ represents hydrogen or $C_{1-6}$ alkyl, especially hydrogen or methyl.

Suitably, $R^4$ represents hydrogen or methyl.

Favoured triazolo-pyridazine derivatives according to the present invention include the compounds represented by formula IE as depicted above.

Examples of typical optional substituents on the group $R^1$ include methyl, fluoro and methoxy.

Representative values of $R^1$ include cyclopropyl, phenyl, methylphenyl, fluorophenyl, difluorophenyl, methoxyphenyl, furyl, thienyl, methyl-thienyl and pyridinyl. Particular values include cyclopropyl, phenyl, methylphenyl, fluorophenyl, methoxyphenyl and pyridinyl. More particularly, $R^1$ may represent unsubstituted or mono-substituted phenyl. Most particularly, $R^1$ represents phenyl.

Suitable values for the substituent $R^2$ in the compounds according to the invention include cyanomethyl, hydroxybutyl, cyclohexylmethyl, propargyl, pyrrolidinylcarbonylmethyl, benzyl, pyrazolylmethyl, isoxazolylmethyl, thiazolylmethyl, thiazolylethyl, imidazolylmethyl, benzimidazolylmethyl, oxadiazolylmethyl, triazolylmethyl, tetrazolylmethyl pyridinylmethyl, pyridazinylmethyl, pyrimidinylmethyl, pyrazinylmethyl, quinolinylmethyl, isoquinolinylmethyl and quinoxalinylmethyl, any of which groups may be optionally substituted by one or more substituents. Typical values of $R^2$ include hydroxybutyl, cyclohexylmethyl, pyrrolidinylcarbonylmethyl, benzyl, pyrazolylmethyl, thiazolylmethyl, imidazolylmethyl, triazolylmethyl, pyridinylmethyl, pyridazinylmethyl, pyrimidinylmethyl, pyrazinylmethyl, quinolinylmethyl, isoquinolinylmethyl, and quinoxalinylmethyl, any of which groups may be optionally substituted by one or more substituents.

Examples of suitable optional substituents on the group $R^2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxymethyl, $C_{1-6}$ alkoxy, $C_{3-7}$ cycloalkyl($C_{1-6}$)alkoxy, amino($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl ($C_{1-6}$)alkyl and di($C_{1-6}$)alkylmorpholinyl($C_{1-6}$)alkyl. Illustrative substituents include $C_{1-6}$ alkyl, aryl($C_{1-6}$)alkyl, pyridyl($C_{1-6}$)alkyl, halogen, halo($C_{1-6}$)alkyl, cyano, cyano ($C_{1-6}$)alkyl, hydroxymethyl, $C_{1-6}$ alkoxy, $C_{3-7}$ cycloalkyl ($C_{1-6}$)alkoxy di($C_{1-6}$)alkylamino($C_{1-6}$)alkyl, di($C_{1-6}$) alkylaminocarbonyl($C_{1-6}$)alkyl and morpholinyl($C_{1-6}$)alkyl. Typical substituents include $C_{1-6}$ alkyl, aryl($C_{1-6}$)alkyl, halogen, cyano, hydroxymethyl, $C_{1-6}$ alkoxy and $C_{3-7}$ cycloalkyl($C_{1-6}$)alkoxy.

Specific illustrations of particular substituents on the group $R^2$ include methyl ethyl n-propyl benzyl, pyridinylmethyl, chloro, chloromethyl, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl.

More specific illustrations of particular substituents on the group $R^2$ include methyl, ethyl, n-propyl, benzyl, pyridinylmethyl, chloro, chloromethyl, cyano, cyanomethyl, hydroxymethyl, ethoxy, cyclopropylmethoxy, dimethylaminomethyl, dimethylaminoethyl, dimethylaminocarbonylmethyl and morpholinylmethyl.

Representative values of $R^2$ include cyanomethyl, hydroxybutyl, hydroxymethyl-cyclohexylmethyl, propargyl, dimethylaminomethyl-propargyl, dimethylmorpholinylmethyl-propargyl, pyrrolidinylcarbonylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl, ethyl-imidazolylmethyl benzyl-imidazolylmethyl, benzimidazolylmethyl, methyl-oxadiazolylmethyl, triazolylmethyl, methyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylaminocarbonylmethyl-triazolylmethyl, N-methylpiperidinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyridinylmethyl, dimethyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl.

Illustrative values of $R^2$ include cyanomethyl, hydroxybutyl, hydroxymethylcyclohexylmethyl, propargyl, dimethylaminomethyl-propargyl, pyrrolidinylcarbonylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl ethyl-imidazolylmethyl, benzyl-imidazolylmethyl, benzimidazolylmethyl, methyl-oxadiazolylmethyl, triazolylmethyl, methyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, dimethylaminoethyl-triazolylmethyl, dimethylaminocarbonylmethyl-triazolylmethyl, morpholinylethyl-triazolylmethyl, methyl-tetrazolylmethyl, pyridinylmethyl, methyl-pyridinylmethyl, dimethyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl.

Particular values of $R^2$ include hydroxybutyl, hydroxymethyl-cyclohexylmethyl pyrrolidinylcarbonylmethyl, cyanobenzyl, hydroxymethyl-benzyl, pyrazolylmethyl, dimethyl-pyrazolylmethyl, thiazolylmethyl, methyl-thiazolylmethyl, ethyl-thiazolylmethyl, imidazolylmethyl, methyl-imidazolylmethyl, ethyl-imidazolylmethyl, benzyl-imidazolylmethyl, methyl-triazolylmethyl pyridinylmethyl, methyl-pyridinylmethyl, dimethyl-pyridinylmethyl, ethoxy-pyridinylmethyl cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl.

A favoured value of $R^2$ is methyl-triazolylmethyl.

A particular sub-class of compounds according to the invention is represented by the compounds of formula IIA, and salts and prodrugs thereof:

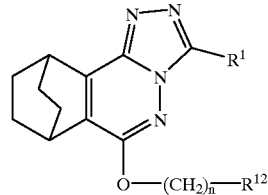

(IIA)

wherein $R^1$ is as defined above;

n is 1, 2, 3 or 4, typically 1; and $R^{12}$ represents hydroxy; or $C_{3-7}$ cycloalkyl, $C_{3-7}$ heterocycloalkylcarbonyl, aryl or heteroaryl, any of which groups may be optionally substituted.

Examples of optional substituents on the group $R^{12}$ suitably include $C_{1-6}$ alkyl, aryl($C_{1-6}$)alkyl, halogen, cyano, hydroxymethyl, $C_{1-6}$ alkoxy and $C_{3-7}$ cycloalkyl($C_{1-6}$) alkoxy. Typical substituents include methyl, ethyl, benzyl, chloro, cyano, hydroxymethyl, ethoxy and cyclopropylmethoxy.

Particular values of $R^{12}$ include hydroxy, hydroxymethylcyclohexyl, pyrrolidinylcarbonyl, cyanophenyl, hydroxymethyl-phenyl, pyrazolyl, dimethylpyrazolyl, thiazolyl, methylthiazolyl, ethylthiazolyl, imidazolyl, methylimidazolyl, ethylimidazolyl, benzylimidazolyl, methyltriazolyl, pyridinyl, methylpyridinyl, dimethylpyridinyl, ethoxypyridinyl, cyclopropylmethoxy-pyridinyl, pyridazinyl, chloropyridazinyl, pyrimidinyl, pyrazinyl, quinolinyl, isoquinolinyl and quinoxalinyl.

Another sub-class of compounds according to the invention is represented by the compounds of formula IIB, and salts and prodrugs thereof:

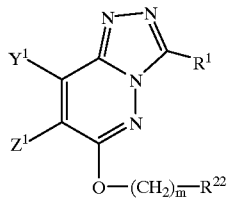

(IIB)

wherein $Y^1$ represents hydrogen or methyl;

$Z^1$ represents $C_{1-6}$ alkyl, $C_{3-7}$ cycloalkyl $C_{4-7}$ cycloalkenyl, aryl, $C_{3-7}$ heterocycloalkyl, heteroaryl or di($C_{1-6}$alkylamino), any of which groups may be optionally substituted;

$R^1$ is as defined with reference to formula I above;

m is 1 or 2, preferably 1; and $R^{22}$ represents aryl or heteroaryl either of which groups may be optionally substituted.

The present invention also provides a compound of formula IIB as defined above, or a salt or prodrug thereof, wherein $Z^1$ represents $C_{1-6}$ alkyl, $C_{3-7}$ cycloalkyl, aryl, $C_{3-7}$ heterocycloalkyl or heteroaryl, any of which groups may be optionally substituted; and $Y^1$, $R^1$, m and $R^{22}$ are as defined above.

Suitably, $Y^1$ represents hydrogen.

Examples of typical substituents on the group $Z^1$ include $C_{1-6}$ alkyl and halogen, especially methyl or chloro.

Representative values for the group $Z^1$ include methyl, ethyl, isopropyl tert-butyl 1,1-dimethylpropyl, methylcyclopropyl, cyclobutyl, methyl-cyclobutyl, cyclopentyl, methyl-cyclopentyl, cyclohexyl, cyclobutenyl, phenyl, pyrrolidinyl, methyl-pyrrolidinyl, piperidinyl, morpholinyl, thiomorpholinyl, pyridinyl, furyl, thienyl, chloro-thienyl and diethylamino.

Particular values for the group $Z^1$ include methyl, ethyl, isopropyl, tert-butyl, methyl-cyclopropyl cyclobutyl, methyl-cyclobutyl, cyclopentyl, methyl-cyclopentyl, cyclohexyl, phenyl, pyrrolidinyl, methyl-pyrrolidinyl, piperidinyl, morpholinyl, thiomorpholinyl, pyridinyl, furyl, thienyl and chloro-thienyl.

A favoured value of $Z^1$ is cyclobutyl.

Examples of typical substituents on the group $R^{22}$ include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, amino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl and morpholinyl($C_{1-6}$)alkyl. Representative substituents include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, di($C_{1-6}$)alkylaminocarbonyl($C_{1-6}$)alkyl and morpholinyl($C_{1-6}$)alkyl.

Illustrative values of specific substituents on the group $R^{22}$ include methyl, ethyl, n-propyl, benzyl, pyridinylmethyl, chloro, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl and morpholinylmethyl.

Representative values of specific substituents on the group $R^{22}$ include methyl, ethyl, n-propyl, benzyl, pyridinylmethyl, chloro, cyano, cyanomethyl, hydroxymethyl, ethoxy, cyclopropylmethoxy, dimethylaminomethyl, dimethylaminoethyl, dimethylaminocarbonylmethyl and morpholinylmethyl.

Particular values of $R^{22}$ include cyanophenyl hydroxymethyl-phenyl pyrazolyl, dimethyl-pyrazolyl, methyl-isoxazolyl, thiazolyl, methyl-thiazolyl, ethylthiazolyl, imidazolyl, methyl-imidazolyl, ethyl-imidazolyl, benzyl-imidazolyl, benzimidazolyl, methyl-oxadiazolyl, triazolyl, methyl-triazolyl, propyl-triazolyl, benzyl-triazolyl, pyridinylmethyl-triazolyl, cyanomethyl-triazolyl, dimethylaminomethyl-triazolyl, aminoethyl-triazolyl, dimethylaminoethyl-triazolyl, dimethylaminocarbonylmethyl-triazolyl, N-methylpiperidinyl-triazolyl, pyrrolidinylethyl-triazolyl, piperazinylethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

Specific values of $R^{22}$ include cyanophenyl, hydroxymethyl-phenyl, pyrazolyl, dimethyl-pyrazolyl, methyl-isoxazolyl, thiazolyl, methyl-thiazolyl, ethylthiazolyl, imidazolyl, methyl-imidazolyl, ethyl-imidazolyl, benzyl-imidazolyl, benzimidazolyl, methyl-oxadiazolyl, triazolyl, methyl-triazolyl, propyl-triazolyl, benzyl-triazolyl, pyridinylmethyl-triazolyl, cyanomethyl-triazolyl, dimethylaminomethyl-triazolyl, dimethylaminoethyl-triazolyl, dimethylaminocarbonylmethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

A favoured value of $R^{22}$ is methyl-triazolyl.

A particular subset of the compounds of formula IIB above is represented by the compounds of formula IIC, and pharmaceutically acceptable salts thereof:

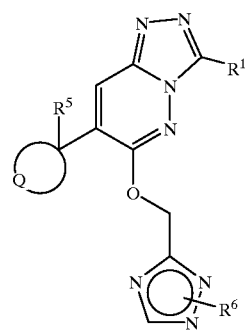

(IIC)

wherein $R^1$ is as defined with reference to formula I above;

Q represents the residue of a cyclopropyl, cyclobutyl, cyclopentyl or cyclohexyl ring;

$R^5$ represents hydrogen or methyl; and $R^6$ represents hydrogen or methyl.

In relation to formula IIC above, $R^1$ suitably represents phenyl.

In a favoured embodiment, Q suitably represents the residue of a cyclobutyl ring.

Suitably, $R^5$ represents hydrogen.

Suitably, $R^6$ represents methyl.

Specific compounds within the scope of the present invention include:

3-phenyl-6-(2-pyridyl)methyloxy-7,8,9,10-tetrahydro-(7,10-ethano)-1,2,4-triazolo[3,4-a]phthalazine;

3,7-diphenyl-6-(2-pyridyl)methyloxy-1,2,4-triazolo[4,3-b]pyridazine;

3-phenyl-6-(2-pyridyl)methyloxy-7,8,9,10-tetrahydro-1,2,4-triazolo[3,4-a]phthalazine;

7,8-dimethyl-3-phenyl-6-(2-pyridyl)methyloxy-1,2,4-triazolo[4,3-b]pyridazine;

7-methyl-3-phenyl-6-(2-pyridyl)methyloxy-1,2,4-triazolo[4,3-b]pyridazine;

7-ethyl-3-phenyl-6-(2-pyridyl)methyloxy-1,2,4-triazolo[4,3-b]pyridazine;

7,8-benzo-3-phenyl-6-(2-pyridyl)methyloxy-7,8,9,10-tetrahydro-1,2,4-triazolo[3,4-a]phthalazine;

8-methyl-3,7-diphenyl-6-(2-pyridyl)methyloxy-1,2,4-triazolo[4,3-b]pyridazine;

3-phenyl-6-(2-pyridyl)methyloxy-7,8,9,10-tetrahydro-(7,10-methano)-1,2,4-triazolo[3,4-a]phthalazine;

3-phenyl-5-(pyridin-2-ylmethoxy)-1,2,3a,4,7-pentaazacyclopenta-[α]naphthalene;

3-phenyl-5-(pyridin-2-ylmethoxy)-1,2,3a,4,8-pentaazacyclopenta-[α]naphthalene;

8-methyl-3-phenyl-6-(2-pyridyl)methyloxy-7,8,9,10-tetrahydro-1,2,4-triazolo[3,4-a]phthalazine;

3-phenyl-6-(2-pyridyl)methyloxy-(7,8-pentano)-1,2,4-triazolo[4,3-b]pyridazine;

8,8-dimethyl-3-phenyl-6-(2-pyridyl)methyloxy-7,8,9,10-tetrahydro-1,2,4-triazolo[3,4-a]phthalazine;

3-phenyl-7-(piperidin-1-yl)-6-(pyridin-2-ylmethoxy)-1,2,4-triazolo[4,3-b]pyridazine;

3-phenyl-7-pyridin-4yl)-6-(pyridin-2-ylmethoxy)-1,2,4-triazolo[4,3-b]pyridazine;

3-phenyl-5-(pyridin-2-ylmethoxy)-6,7,8,9-tetrahydro-1,2,3a,4,8-pentaazacyclopenta[α]naphthalene;

3-phenyl-5-(pyridin-2-ylmethoxy)-6,7,8,9-tetrahydro-1,2,3a,4,7-pentaazacyclopenta[α]naphthalene;

7-methyl-3-phenyl-5-(pyridin-2-ylmethoxy)-6,7,8,9-tetrahydro-1,2,3a,4,7-pentaazacyclopenta[α]naphthalene;

3-phenyl-6-(pyridin-2-ylmethoxy)-7-(thiophen-2-yl)-1,2,4-triazolo[4,3-b]pyridazine;

3-phenyl-6-(pyridin-2-ylmethoxy)-7-(thiophen-3-yl)-1,2,4-triazolo[4,3-b]pyridazine;

3-phenyl-6-(2-pyridyl)methyloxy-7,8,9,10-tetrahydro-(7,10-propano)-1,2,4-triazolo[3,4-a]phthalazine;

3-(4-methyl)phenyl-6-(2-pyridyl)methyloxy-7,8,9,10-tetrahydro-(7,10-ethano)-1,2,4-triazolo[3,4-a]phthalazine;

3-(3-methoxy)phenyl-6-(2-pyridyl)methyloxy-7,8,9,10-tetrahydro-(7,10-ethano)-1,2,4-triazolo[3,4-a]phthalazine;

3-(2-fluoro)phenyl-6-(2-pyridyl)methyloxy-7,8,9,10-tetrahydro-(7,10-ethano)-1,2,4-triazolo[3,4-a]phthalazine;

3-(3-pyridyl)-6-(2-pyridyl)methyloxy-7,8,9,10-tetrahydro-(7,10-ethano)-1,2,4-triazolo[3,4-a]phthalazine;

3-cyclopropyl-6-(2-pyridyl)methyloxy-7,8,9,10-tetrahydro-(7,10-ethano)-1,2,4-triazolo[3,4-a]phthalazine;

6-[(6-methyl)-2-pyridyl]methyloxy-3-phenyl-7,8,9,10-tetrahydro-(7,10-ethano)-1,2,4-triazolo[3,4-a]phthalazine;

6-[(3-methyl)-2-pyridyl]methyloxy-3-phenyl-7,8,9,10-tetrahydro-(7,10-ethano)-1,2,4-triazolo[3,4-a]phthalazine;

6-[(4-methyl)-2-pyridyl]methyloxy-3-phenyl-7,8,9,10-tetrahydro-(7,10-ethano)-1,2,4-triazolo[3,4-a]phthalazine;

6-[(5-methyl)-2-pyridyl]methyloxy-3-phenyl-7,8,9,10-tetrahydro-(7,10-ethano)-1,2,4-triazolo[3,4-a]phthalazine;

3-phenyl-6-(3-pyridyl)methyloxy-7,8,9,10-tetrahydro-(7,10-ethano)-1,2,4-triazolo[3,4-a]phthalazine;

3-phenyl-6-(4-pyridyl)methyloxy-7,8,9,10-tetrahydro-(7,10-ethano)-1,2,4-triazolo[3,4-a]phthalazine;

3-phenyl-6-[2-(1-methyl)imidazolyl]methyloxy-7,8,9,10-tetrahydro-(7,10-ethano)-1,2,4-triazolo[3,4-a]phthalazine;

6-(3-cyanophenyl)methyloxy-3-phenyl-7,8,9,10-tetrahydro-(7,10ethano)-1,2,4-triazolo[3,4a]phthalazine;

6-[1-(3,5-dimethyl)pyrazolyl]methyloxy-3-phenyl-7,8,9,10-tetrahydro-(7,10-ethanol-1,2,4-triazolo[3,4-a]phthalazine;

6-[4-(2-methyl)thiazolyl]methyloxy-3-phenyl-7,8,9,10-tetrahydro-(7,10-ethano)-1,2,4-triazolo[3,4a]phthalazine;

3-phenyl-6-(2-quinoxalinyl)methyloxy-7,8,9,10-tetrahydro-(7,10-ethano)-1,2,4-triazolo[3,4a]phthalazine;

3-phenyl-6-(3-pyridazinyl)methyloxy-7,8,9,10-tetrahydro-(7,10-ethano)-1,2,4-triazolo[3,4-a]phthalazine;

6-(1-benzylimidazol-2-yl)methyloxy-3-phenyl-7,8,9,10-tetrahydro-(7,10-ethano)-1,2,4-triazolo[3,4-a]phthalazine;

3-phenyl-6-(isoquinolin-1-yl)methyloxy-7,8,9,10-tetrahydro-(7,10-ethano)-1,2,4-triazolo[3,4a]phthalazine;

6-(1-ethylimidazol-2-yl)methyloxy-3-phenyl-7,8,9,10-tetrahydro-(7,10-ethano)-1,2,4-triazolo[3,4-a]phthalazine;

3-phenyl-6-(1-pyrazolyl)methyloxy-7,8,9,10-tetrahydro-(7,10-ethano)-1,2,4-triazolo[3,4-a]phthalazine;

3-phenyl-6-(N-pyrrolidinylcarbonyl)methyloxy-7,8,9,10-tetrahydro-(7,10-ethano)-1,2,4-triazolo[3,4a]phthalazine;

6-[4-(3-methyl)pyridyl]methyloxy-3-phenyl-7,8,9,10-tetrahydro-(7,10-ethano)-1,2,4-triazolo[3,4a]phthalazine;

3-phenyl-6-(2-quinolinyl)methyloxy-7,8,9,10-tetrahydro-(7,10-ethano)-1,2,4-triazolo[3,4-a]phthalazine;

6-(2-imidazolyl)methyloxy-3-phenyl-7,8,9,10-tetrahydro-(7,10-ethano)-1,2,4-triazolo[3,4-a]phthalazine;

3-phenyl-6-(2-thiazolyl)methyloxy-7,8,9,10-tetrahydro-(7,10-ethano)-1,2,4-triazolo[3,4-a]phthalazine;

6-[2-(5-methyl)thiazolyl]methyloxy-3-phenyl-7,8,9,10-tetrahydro-(7,10-ethano)-1,2,4-triazolo[3,4-a]phthalazine;

6-[2-(4-methyl)thiazolyl]methyloxy-3-phenyl-7,8,9,10-tetrahydro-(7,10-ethano)-1,2,4-triazolo[3,4-a]phthalazine;

6-[2-(3,5-dimethyl)pyridyl]methyloxy-3-phenyl-7,8,9,10-tetrahydro-(7,10-ethano)-1,2,4-triazolo[3,4-a]phthalazine;

3-phenyl-6-(2-pyrazinyl)methyloxy-7,8,9,10-tetrahydro-(7,10-ethano)-1,2,4-triazolo[3,4-a]phthalazine;

6-[2-(4,6-dimethyl)pyridyl]methyloxy-3-phenyl-7,8,9,10-tetrahydro-(7,10-ethano)-1,2,4-triazolo[3,4-a]phthalazine;

3-phenyl-6-(4-thiazolyl)methyloxy-7,8,9,10-tetrahydro-(7,10-ethano)-1,2,4-triazolo[3,4-a]phthalazine;

6-[2-(5,6-dimethyl)pyridyl]methyloxy-3-phenyl-7,8,9,10-tetrahydro-(7,10-ethano)-1,2,4-triazolo[3,4-a]phthalazine;
6-(4-methylimidazol-2-yl)methyloxy-3-phenyl-7,8,9,10-tetrahydro-(7,10-ethano)-1,2,4-triazolo[3,4-a]phthalazine;
3-phenyl-6-(4-pyrimidinyl)methyloxy-7,8,9,10-tetrahydro-(7,10-ethano)-1,2,4-triazolo[3,4a]phthalazine;
6-[4-(2-ethyl)thiazolyl]methyloxy-3-phenyl-7,8,9,10-tetrahydro-(7,10-ethano)-1,2,4-triazolo[3,4-a]phthalazine;
6-(6-chloropyridazin-3-yl)methyloxy-3-phenyl-7,8,9,10-tetrahydro-(7,10-ethano)-1,2,4-triazolo[3,4-a]phthalazine;
6-(2-imidazolyl)methyloxy-3-(4-methylphenyl)-7,8,9,10-tetrahydro-(7,10-ethano)-1,2,4-triazolo[3,4-a]phthalazine;
6-(4-hydroxymethylphenyl)methyloxy-3-phenyl-7,8,9,10-tetrahydro-(7,10-ethano)-1,2,4-triazolo[3,4-a]phthalazine;
6-(4-hydroxybutyl)oxy-3-phenyl-7,8,9,10-tetrahydro-(7,10-ethano)-1,2,4-triazolo[3,4-a]phthalazine;
6-(4-hydroxymethylcyclohexyl)methyloxy-3-phenyl-7,8,9,10-tetrahydro-(7,10-ethano)-1,2,4-triazolo[3,4-a]phthalazine;
6-(3-hydroxymethylphenyl)methyloxy-3-phenyl-7,8,9,10-tetrahydro-(7,10-ethano)-1,2,4-triazolo[3,4-a]phthalazine;
6-(1-methyl-1,2,4-triazol-3-yl)methyloxy-3-phenyl-7,8,9,10-tetrahydro-(7,10-ethano)-1,2,4-triazolo[3,4-a]phthalazine;
6-(2-methyl-1,2,4-triazol-3-yl)methyloxy-3-phenyl-7,8,9,10-tetrahydro-(7,10-ethano)-1,2,4-triazolo[3,4-a]phthalazine;
3-phenyl-6-(3-cyclopropylmethyloxy-2-pyridyl)methyloxy-7,8,9,10-tetrahydro-(7,10-ethano)-1,2,4-triazolo[3,4-a]phthalazine;
3-phenyl-6-(3-ethoxy-2-pyridyl)methyloxy-7,8,9,10-tetrahydro-(7,10-ethano)-1,2,4-triazolo[3,4-a]phthalazine;
6-(6-methylpyridin-2-yl)methyloxy-3-phenyl-1,2,4-triazolo[3,4-a]phthalazine;
6-(1-methyl-1H-1,2,4-triazol-3-ylmethoxy)-3,7-diphenyl-1,2,4-triazolo[4,3-b]pyridazine;
6-(2-methyl-2H-1,2,4-triazol-3-ylmethoxy)-3,7-diphenyl-1,2,4-triazolo[4,3-b]pyridazine;
3,7-diphenyl-6-(2H-1,2,4-triazol-3-ylmethoxy)-1,2,4-triazolo[4,3-b]pyridazine;
6-(2-methyl-2H-tetrazol-5-ylmethoxy)-3,7-diphenyl-1,2,4-triazolo[4,3-b]-pyridazine;
3,7-diphenyl-6-(2-propyl-2H-1,2,4-triazol-3-ylmethoxy)-1,2,4-triazolo[4,3-b]pyridazine;
3,7-diphenyl-6-(1-propyl-1H-1,2,4-triazol-3-ylmethoxy)-1,2,4-triazolo[4,3-b]pyridazine;
6-(1-methyl-1H-imidazol-4-ylmethoxy)-3,7-diphenyl-1,2,4-triazolo[4,3-b]pyridazine;
6-(3-methyl-3H-imidazol-4-ylmethoxy)-3,7-diphenyl-1,2,4-triazolo[4,3-b]pyridazine;
6-(4-methyl-4H-1,2,4-triazol-3-ylmethoxy)-3,7-diphenyl-1,2,4-triazolo[4,3-b]pyridazine;
6-(5-methyl-2H-1,2,4-triazol-3-ylmethoxy)-3,7-diphenyl-1,2,4-triazolo[4,3-b]pyridazine;
6-(3-methyl-3H-1,2,3-triazol-4ylmethoxy)-3,7-diphenyl-1,2,4-triazolo[4,3-b]pyridazine;
3-(4-methoxyphenyl)-6-(1-methyl-1H-1,2,4-triazol-3-ylmethoxy)-7-phenyl-1,2,4-triazolo[4,3-b]pyridazine;
6-(3-methylpyridin-2-ylmethoxy)-3-phenyl-7-(piperidin-1-yl)-1,2,4-triazolo[4,3-b]pyridazine;
7-(morpholin-4-yl)-3-phenyl-6-(pyridin-2-ylmethoxy)-1,2,4-triazolo[4,3-b]pyridazine;
3-phenyl-7-(pyridin-3-yl)-6-(pyridin-2-ylmethoxy)-1,2,4-triazolo[4,3-b]pyridazine;
8-methyl-6-(2-methyl-2H-1,2,4-triazol-3-ylmethoxy)-3,7-diphenyl-1,2,4-triazolo[4,3-b]pyridazine;
6-(1-methyl-1H-1,2,4-triazol-3-ylmethoxy)-7-(morpholin-4-yl)-3-phenyl-1,2,4-triazolo[4,3-b]pyridazine;
6-(2-methyl-2H-1,2,4-triazol-3-ylmethoxy)-7-(morpholin-4-yl)-3-phenyl-1,2,4-triazolo-[4,3-b]pyridazine;
7-cyclohexyl-6-(2-methyl-2H-1,2,4-triazol-3-ylmethoxy)-3-phenyl-1,2,4-triazolo[4,3-b]pyridazine;
7-cyclohexyl-6-(1-methyl-1H-1,2,4-triazol-3-ylmethoxy)-3-phenyl-1,2,4-triazolo[4,3-b]pyridazine;
7-cyclopentyl-6-(2-methyl-2H-1,2,4-triazol-3-ylmethoxy)-3-phenyl-1,2,4-triazolo[4,3-b]pyridazine;
8-methyl-6-(1-methyl-1H-1,2,4-triazol-3-ylmethoxy)-3,7-diphenyl-1,2,4-triazolo[4,3-b]pyridazine;
7-cyclobutyl-6-(1-methyl-1H-1,2,4-triazol-3-ylmethoxy)-3-phenyl-1,2,4-triazolo[4,3-b]pyridazine;
7-tert-butyl-6-(2-methyl-2H-1,2,4-triazol-3-ylmethoxy)-3-phenyl-1,2,4-triazolo[4,3-b]pyridazine;
7-cyclobutyl-6-(2-methyl-2H-1,2,4-triazol-3-ylmethoxy)-3-phenyl-1,2,4-triazolo[4,3-b]pyridazine;
7-ethyl-6-(2-methyl-2H-1,2,4-triazol-3-ylmethoxy)-3-phenyl-1,2,4-triazolo[4,3-b]pyridazine;
7-tert-butyl-6-(1-methyl-1H-1,2,4-triazol-3-ylmethoxy)-3-phenyl-1,2,4-triazolo[4,3-b]pyridazine;
7-ethyl-6-(1-methyl-1H-1,2,4-triazol-3-ylmethoxy)-3-phenyl-1,2,4-triazolo[4,3-b]pyridazine;
7-methyl-6-(2-methyl-2H-1,2,4-triazol-3-ylmethoxy)-3-phenyl-1,2,4-triazolo[4,3-b]pyridazine;
7-(1-methylcyclobutyl)-6-(2-methyl-2H-1,2,4-triazol-3-ylmethoxy)-3-phenyl-1,2,4-triazolo[4,3-b]pyridazine;
7-methyl-6-(1-methyl-1H-1,2,4-triazol-3-ylmethoxy)-3-phenyl-1,2,4-triazolo[4,3-b]pyridazine;
7-cyclobutyl-3-phenyl-6-(2H-1,2,4-triazol-3-ylmethoxy)-1,2,4-triazolo[4,3-b]pyridazine;
7-cyclopentyl-6-(pyridin-2-ylmethoxy)-3-(thiophen-2-yl)-1,2,4-triazolo[4,3-b]pyridazine;
7-cyclopentyl-3-(2,4-difluorophenyl)-6-(1-methyl-1H-1,2,4-triazol-3-ylmethoxy)-1,2,4-triazolo[4,3-b]pyridazine;
7-cyclopentyl-6-(1-methyl-1H-1,2,4-triazol-3-ylmethoxy)-3-(thiophen-2-yl)-1,2,4-triazolo[4,3-b]pyridazine;
7-cyclopentyl-6-(2-methyl-2H-1,2,4-triazol-3-ylmethoxy)-3-(thiophen-2-yl)-1,2,4-triazolo[4,3-b]pyridazine;
7-cyclopentyl-6-(2-methyl-2H-1,2,4-triazol-3-ylmethoxy)-3-(pyridin-4-yl)-1,2,4-triazolo[4,3-b]pyridazine;
7-cyclopentyl-3-(2-fluorophenyl)-6-(1-methyl-1H-1,2,4-triazol-3-ylmethoxy)-1,2,4-triazolo[4,3-b]pyridazine;
7-cyclopentyl-3-(2-fluorophenyl)-6-(2-methyl-2H-1,2,4-triazol-3-ylmethoxy)-1,2,4-triazolo[4,3-b]pyridazine;
7-cyclopentyl-3-(2-fluorophenyl)-6-(pyridin-2-ylmethoxy)-1,2,4-triazolo[4,3-b]pyridazine;
7-cyclopentyl-3-(2,4-difluorophenyl)-6-(2-methyl-2H-1,2,4-triazol-3-ylmethoxy)-1,2,4-triazolo[4,3-b]pyridazine;
7-cyclopentyl-3-phenyl-6-(pyridin-2-ylmethoxy)-1,2,4-triazolo[4,3-b]pyridazine;
7-cyclopentyl-8-methyl-6-(2-methyl-2H-1,2,4-triazol-3-ylmethoxy)-3-phenyl-1,2,4-triazolo[4,3-b]pyridazine;
7-cyclopentyl-3-phenyl-6-(2H-1,2,4-triazol-3-ylmethoxy)-1,2,4-triazolo[4,3-b]pyridazine;
3-(4-methylphenyl)-7-phenyl-6-(pyridin-2-ylmethoxy)-1,2,4-triazolo[4,3-b]pyridazine;
3-(4-methylphenyl)-6-(3-methylpyridin-2-ylmethoxy)-7-phenyl-1,2,4-triazolo[4,3-b]pyridazine;
6-(1-ethyl-1H-imidazol-2-ylmethoxy)-3-(4-methylphenyl)-7-phenyl-1,2,4-triazolo[4,3-b]pyridazine;

3-phenyl-6-(pyridin-2-ylmethoxy)-7-(thiomorpholin-4-yl)-1,2,4-triazolo[4,3-b]pyridazine;
6-[2-(4-methylthiazol-5-yl)ethoxy]-3,7-diphenyl-1,2,4-triazolo[4,3-b]pyridazine;
(±)-7-(2-methylpyrrolidin-1-yl)-3-phenyl-6-(pyridin-2-ylmethoxy)-1,2,4-triazolo[4,3-b]pyridazine;
6-(1-methyl-1H-1,2,4-triazol-3-ylmethoxy)-3-phenyl-7-(pyridin-4-yl)-1,2,4-triazolo[4,3-b]pyridazine;
7-cyclopentyl-6-(1-methyl-1H-1,2,4-triazol-3-ylmethoxy)-3-phenyl-1,2,4-triazolo[4,3-b]pyridazine;
7-isopropyl-6-(1-methyl-1H-1,2,4-triazol-3-ylmethoxy)-3-phenyl-1,2,4-triazolo[4,3-b]pyridazine;
3-cyclopropyl-6-(1-methyl-1H-1,2,4-triazol-3-ylmethoxy)-7-phenyl-1,2,4-triazolo[4,3-b]pyridazine;
3-(2-fluorophenyl)-6-(2-methyl-2H-1,2,4-triazol-3-ylmethoxy)-7-phenyl-1,2,4-triazolo[4,3-b]pyridazine;
3-(2-fluorophenyl)-6-(1-methyl-1H-1,2,4-triazol-3-ylmethoxy)-7-phenyl-1,2,4-triazolo[4,3-b]pyridazine;
6-(1-methyl-1H-1,2,4-triazol-3-ylmethoxy)-7-phenyl-3-(thiophen-2-yl)-1,2,4-triazolo[4,3-b]pyridazine;
6-(1-methyl-1H-1,2,4-triazol-3-ylmethoxy)-7-phenyl-3-(pyridin-3-yl)-1,2,4-triazolo[4,3-b]pyridazine;
6-(2-methyl-2H-1,2,4-triazol-3-ylmethoxy)-7-phenyl-3-(thiophen-2-yl)-1,2,4-triazolo[4,3-b]pyridazine;
6-(2-methyl-2H-1,2,4-triazol-3-ylmethoxy)-7-phenyl-3-(pyridin-3-yl)-1,2,4-triazolo[4,3-b]pyridazine;
3-(furan-3-yl)-6-(1-methyl-1H-1,2,4-triazol-3-ylmethoxy)-7-phenyl-1,2,4-triazolo[4,3-b]pyridazine;
6-(1-methyl-1H-1,2,4-triazol-3-ylmethoxy)-7-phenyl-3-(thiophen-2-yl)-1,2,4-triazolo[4,3-b]pyridazine;
6-(5-methyl-1,2,4-oxadiazol-3-ylmethoxy)-3,7-diphenyl-1,2,4-triazolo[4,3-b]pyridazine;
7-phenyl-3-(thiophen-2-yl)-6-(2H-1,2,4-triazol-3-ylmethoxy)-1,2,4-triazolo[4,3-b]pyridazine;
3-(furan-2-yl)-6-(1-methyl-1H-1,2,4-triazol-3-ylmethoxy)-7-phenyl-1,2,4-triazolo[4,3-b]pyridazine;
6-(1-methyl-1H-1,2,4-triazol-3-ylmethoxy)-3-phenyl-7-(thiophen-3-yl)-1,2,4-triazolo[4,3-b]pyridazine;
6-(2-methyl-2H-1,2,4-triazol-3-ylmethoxy)-7-(thiophen-3-yl)-1,2,4-triazolo[4,3-b]pyridazine;
3-phenyl-7-(thiophen-3-yl)-6-(2H-1,2,4-triazol-3-ylmethoxy)-1,2,4-triazolo[4,3-b]pyridazine;
6-(2-methyl-2H-1,2,4-triazol-3-ylmethoxy)-3-phenyl-7-(thiophen-2-yl)-1,2,4-triazolo[4,3-b]pyridazine;
6-(1-methyl-1H-1,2,4-triazol-3-ylmethoxy)-3-phenyl-7-(thiophen-2-yl)-1,2,4-triazolo[4,3-b]pyridazine;
7-(furan-2-yl)-6-(2-methyl-2H-1,2,4-triazol-3-ylmethoxy)-3-phenyl-1,2,4-triazolo[4,3-b]pyridazine;
7-(furan-2-yl)-6-(1-methyl-1H-1,2,4-triazol-3-ylmethoxy)-3-phenyl-1,2,4-triazolo[4,3-b]pyridazine;
6-(3-methyl-1,2,4-oxadiazol-5-ylmethoxy)-3,7-diphenyl-1,2,4-triazolo[4,3-b]pyridazine;
3-(4-fluorophenyl)-6-(1-methyl-1H-1,2,4-triazol-3-ylmethoxy)-7-phenyl-1,2,4-triazolo[4,3-b]pyridazine;
3,7-diphenyl-6-(2H-1,2,3-triazol-4-ylmethoxy)-1,2,4-triazolo[4,3-b]pyridazine;
3,7-diphenyl-6-(pyrazin-2-ylmethoxy)-1,2,4-triazolo[4,3-b]pyridazine;
3-(4-methylphenyl)-6-(1-methyl-1H-1,2,4-triazol-3-ylmethoxy)-7-phenyl-1,2,4-triazolo[4,3-b]pyridazine;
6-(4-methylthiazol-2-ylmethoxy)-3,7-diphenyl-1,2,4-triazolo[4,3-b]pyridazine;
6-(5-methylthiazol-2-ylmethoxy)-3,7-diphenyl-1,2,4-triazolo[4,3-b]pyridazine;
3,7-diphenyl-6-(pyrimidin-4-ylmethoxy)-1,2,4-triazolo[4,3-b]pyridazine;
3,7-diphenyl-6-(pyridazin-3-ylmethoxy)-1,2,4-triazolo[4,3-b]pyridazine;
6-(1-methyl-1H-1,2,4-triazol-3-ylmethoxy)-7-(morpholin-4-yl)-3-(thiophen-2-yl)-1,2,4-triazolo[4,3-b]pyridazine;
3,7-diphenyl-6-(thiazol-4-ylmethoxy)-1,2,4-triazolo[4,3-b]pyridazine;
6-(5-methylisoxazol-3-ylmethoxy)-3,7-diphenyl-1,2,4-triazolo[4,3-b]pyridazine;
3-(3-fluorophenyl)-6-(1-methyl-1H-1,2,4-triazol-3-ylmethoxy)-7-(morpholin-4-yl)-1,2,4-triazolo[4,3-b]pyridazine;
3,7-diphenyl-6-(pyrimidin-2-ylmethoxy)-1,2,4-triazolo[4,3-b]pyridazine;
6-(2-methyl-2H-1,2,3-triazol-4-ylmethoxy)-3,7-diphenyl-1,2,4-triazolo[4,3-b]pyridazine;
7-(1-methylcyclobutyl)-6-(1-methyl-1H-1,2,4-triazol-3-ylmethoxy)-3-phenyl-1,2,4-triazolo[4,3-b]pyridazine;
7-isopropyl-6-(2-methyl-2H-1,2,4-triazol-3-ylmethoxy)-3-phenyl-1,2,4-triazolo[4,3-b]pyridazine;
7-tert-butyl-3-(2-fluorophenyl)-6-(1-methyl-1H-1,2,4-triazol-3-ylmethoxy)-1,2,4-triazolo[4,3-b]pyridazine;
7-cyclopentyl-3-(4-methoxyphenyl)-6-(2-methyl-2H-1,2,4-triazol-3-ylmethoxy)-1,2,4-triazolo[4,3-b]pyridazine;
7-(1-methylcyclopentyl)-6-(1-methyl-1H-1,2,4-triazol-3-ylmethoxy)-3-phenyl-1,2,4-triazolo[4,3-b]pyridazine;
7-(1-methylcyclopentyl)-6-(2-methyl-2H-1,2,4-triazol-3-ylmethoxy)-3-phenyl-1,2,4-triazolo[4,3-b]pyridazine;
7-cyclopentyl-3-(furan-2-yl)-6-(2-methyl-2H-1,2,4-triazol-3-ylmethoxy)-1,2,4-triazolo[4,3-b]pyridazine;
7-cyclopentyl-3-(furan-2-yl)-6-(1-methyl-1H-1,2,4-triazol-3-ylmethoxy-1,2,4-triazolo[4,3-b]pyridazine;
3-(3,7-diphenyl-1,2,4-triazolo[4,3-b]pyridazin-6-yloxymethyl)-1,2,4-triazol-1-ylacetonitrile;
7-(1-methylcyclopropyl)-6-(2-methyl-2H-1,2,4-triazol-3-ylmethoxy)-3-phenyl-1,2,4-triazolo[4,3-b]pyridazine;
7-(1-methylcyclopropyl)-6-(1-methyl-1H-1,2,4-triazol-3-ylmethoxy)-3-phenyl-1,2,4-triazolo[4,3-b]pyridazine;
3-(3-fluorophenyl)-6-(1-methyl-1H-1,2,4-triazol-3-ylmethoxy)-7-phenyl-1,2,4-triazolo[4,3-b]pyridazine;
7-(1-methylcyclopentyl)-6-(3-methylpyridin-2-ylmethoxy)-3-phenyl-1,2,4-triazolo[4,3-b]pyridazine;
6-(1-methyl-1H-1,2,3-triazol-4-ylmethoxy)-3,7-diphenyl-1,2,4-triazolo[4,3-b]pyridazine;
3-(5-methylthiophen-2-yl)-6-(1-methyl-1H-1,2,4-triazol-3-ylmethoxy)-7-phenyl-1,2,4-triazolo[4,3-b]pyridazine;
2-[3-(3,7-diphenyl-1,2,4-triazolo[4,3-b]pyridazin-6-yloxymethyl)-1,2,4-triazol-1-yl]-N,N-dimethylacetamide;
3,7-diphenyl-6-[1-pyridin-2-ylmethyl)-1H-1,2,4-triazol-3-ylmethoxy]-1,2,4-triazolo[4,3-b]pyridazine;
6-(1-benzyl-1H-1,2,4-triazol-3-ylmethoxy)-3,7-diphenyl-1,2,4-triazolo[4,3-b]pyridazine;
2-[5-(3,7-diphenyl-1,2,4-triazolo[4,3-b]pyridazin-6-yloxymethyl)-1,2,4-triazol-1-yl]acetamide;
N-[2-[3-(3,7-diphenyl-1,2,4-triazolo[4,3-b]pyzidazin-6-yloxymethyl)-1,2,4-triazol-1-yl]ethyl]-N,N-dimethylamine;
3,7-diphenyl-6-(pyrimidin-6-ylmethoxy)-1,2,4-triazolo[4,3-b]pyridazine;
6-[1-(2-(morpholin-4-yl)-ethyl)-1H-1,2,4-triazol-3-ylmethoxy]-3,7-diphenyl-1,2,4-triazolo[4,3-b]pyridazine;
6-(2-methyl-2H-1,2,4-triazol-3-ylmethoxy)-3-phenyl-7-(pyrrolidin-1-yl)-1,2,4-triazolo[4,3-b]pyridazine;
7-(5-chlorothiophen-2-yl)-6(2-methyl-2H-1,2,4-triazol-3-ylmethoxy)-3-phenyl-1,2,4-triazolo[4,3-b]pyridazine;
7-(5-chlorothiophen-2-yl)-6-(1-methyl-1H-1,2,4-triazol-3-ylmethoxy)-3-phenyl-1,2,4-triazolo[4,3-b]pyridazine;
6-(1H-benzimidazol-2-ylmethoxy)-3-(2,4-difluorophenyl)-7-(1-methylcyclopentyl)-1,2,4-triazolo[4,3-b]pyridazine;

3-(furan-3-yl)-6-(2-pyridyl)methyloxy-7,8,9,10-tetrahydro-1,2,4-triazolo[3,4-a]phthalazine;

7-cyclobutyl-3-phenyl-6-(prop-2-ynyloxy)-1,2,4-triazolo[4,3-b]pyridazine;

(7-cyclobutyl-3-phenyl-1,2,4-triazolo[4,3-b]pyridazin-6-yloxy)acetonitrile;

N-[4-(7-cyclobutyl-3-phenyl-1,2,4-triazolo[4,3-b]pyridazin-6-yloxy)but-2-ynyl]-N,N-dimethylamine;

2-[3-(3,7-diphenyl-1,2,4-triazolo[4,3-b]pyridazin-6-yloxymethyl)-1,2,4-triazol-1-yl]ethylamine;

3,7-diphenyl-6-[1-(2-(pyrrolidin-1-yl)ethyl)-1H-1,2,4-triazol-3-ylmethoxy]-1,2,4-triazolo[4,3-b]pyridazine;

6-[1-(1-methylpiperidin-4-yl)-1H-1,2,4-triazol-3-ylmethoxy]-3,7-diphenyl-1,2,4-triazolo[4,3-b]pyridazine;

3,7-diphenyl-6-[1-(2-(piperazin-1-yl)ethyl)-1H-1,2,4-triazol-3-ylmethoxy]-1,2,4-triazolo[4,3-b]pyridazine;

7-(1-methylcyclopentyl-6-(2-methyl-2H-1,2,4-triazol-3-ylmethoxy)-3-(2,4-difluorophenyl)-1,2,4-triazolo[4,3-b]pyridazine;

7-(cyclobut-1-enyl)-6-(2-methyl-2H-1,2,4-triazol-3-ylmethoxy)-3-phenyl-1,2,4-triazolo[4,3-b]pyridazine;

7-(furan-3-yl)-6-(1-methyl-1H-1,2,4-triazol-3-ylmethoxy)-3-phenyl-1,2,4-triazolo[4,3-b]pyridazine;

N,N-diethyl-N-[6-(1-methyl-1H-1,2,4-triazol-3-ylmethoxy)-3-phenyl-1,2,4-triazolo[4,3-b]pyridazin-7-yl]amine;

7-(1-methylcyclopentyl)-6-(1-methyl-1H-1,2,4-triazol-3-ylmethoxy)-3-(2,4-difluorophenyl)-1,2,4-triazolo[4,3-b]pyridazine;

7-(1,1-dimethylpropyl)-6-(1-methyl-1H-1,2,4-triazol-3-ylmethoxy)-3-phenyl-1,2,4-triazolo[4,3-b]pyridazine;

6-(2-methyl-2H-1,2,4-triazol-3-ylmethoxy)-3-(4-fluorophenyl)-7-(thiophen-3-yl)-1,2,4-triazolo[4,3-b]pyridazine;

6-(1-methyl-1H-1,2,4-triazol-3-ylmethoxy)-3-(4-fluorophenyl)-7-(thiophen-3-yl)-1,2,4-triazolo[4,3-b]pyridazine;

6-(2-methyl-2H-1,2,4-triazol-3-ylmethoxy)-3-(2-fluorophenyl-7-(thiophen-3-yl)-1,2,4-triazolo[4,3-b]pyridazine;

3-(2-fluorophenyl)-7-(1-methylcyclobutyl)-6-(2-methyl-2H-1,2,4-triazol-3-ylmethoxy)-1,2,4-triazolo[4,3-b]pyridazine;

3-(2-fluorophenyl)-7-(1-methylcyclobutyl)-6-(1-methyl-1H-1,2,4-triazol-3-ylmethoxy)-1,2,4-triazolo[4,3-b]pyridazine;

6-(1-methyl-1H-1,2,4-triazol-3-ylmethoxy)-3-(2-fluorophenyl)-7-(thiophen-3-yl)-1,2,4-triazolo[4,3-b]pyridazine;

8-methyl-7-(1-methylcyclobutyl)-6-(1-methyl-1H-1,2,4-triazol-3-ylmethoxy)-3-phenyl-1,2,4-triazolo[4,3-b]pyridazine;

8-methyl-7-(1-methylcyclobutyl)-6-(2-methyl-2H-1,2,4-triazol-3-ylmethoxy)-3-phenyl-1,2,4-triazolo[4,3-b]pyridazine;

6-(1-methyl-1H-1,2,4-triazol-3-ylmethoxy)-3-phenyl-7-(pyrrolidin-1-yl)-1,2,4-triazolo[4,3-b]pyridazine;

7-cyclobutyl-8-methyl-6-(2-methyl-2H-1,2,4-triazol-3-ylmethoxy)-3-phenyl-1,2,4-triazolo[4,3-b]pyridazine;

7-cyclobutyl-8-methyl-6-(1-methyl-1H-1,2,4-triazol-3-ylmethoxy)-3-phenyl-1,2,4-triazolo[4,3-b]pyridazine;

7-(1-methylcyclopentyl)-6-(2-methyl-2H-1,2,4-triazol-3-ylmethoxy)-3-(2-fluorophenyl)-1,2,4-triazolo[4,3-b]pyridazine;

7-(1-methylcyclopentyl)-6-(1-methyl-1H-1,2,4-triazol-3-ylmethoxy)-3-(2-fluorophenyl)-1,2,4-triazolo[4,3-b]pyridazine;

7-cyclobutyl-6-[4-(2,6-dimethylmorpholin-4-yl)but-2-ynyloxy]-3-phenyl-1,2,4-triazolo[4,3-b]pyridazine;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

In another aspect, the present invention provides a non-sedating anxiolytic compound which is a modulator of the benzodiazepine binding site of the human $GABA_A$ receptor, having a binding affinity ($K_i$) for the α3 subunit of the human $GABA_A$ receptor of 10 nM or less, which elicits at least a 40% potentiation of the GABA $EC_{20}$ response in stably transfected recombinant cell lines expressing the α3 subunit of the human $GABA_A$ receptor, and which elicits at most a 30% potentiation of the GABA $EC_{20}$ response in stably transfected cell lines expressing the α1 subunit of the human $GABA_A$ receptor.

In this aspect of the invention, the binding affinity ($K_i$) of compounds for the α3 subunit of the human $GABA_A$ receptor is conveniently as measured in the assay described hereinbelow. The α3 subunit binding affinity ($K_i$) of compounds fulfilling this aspect of the invention is 10 nM or less, preferably 2 nM or less, and more preferably 1 nM or less.

In this aspect of the invention, the potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds fulfilling this aspect of the invention will elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds fulfilling this aspect of the invention will elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The compounds fulfilling this aspect of the invention exhibit anxiolytic activity, as demonstrated by a positive response in the elevated plus maze and conditioned suppression of drinking tests (cf. Dawson et al., *Psychopharmacology*, 1995, 121, 109–117). Moreover, the compounds fulfilling this aspect of the invention are substantially non-sedating, as confirmed by an appropriate result obtained from the response sensitivity (chain-pulling) test (cf. Bayley et al., *J. Psychopharmacol.*, 1996, 10, 206–213).

The compounds fulfilling this aspect of the invention also exhibit anticonvulsant activity. This is demonstrated by their ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds fulfilling this aspect of the invention will be brain-penetrant; in other words, these compounds will be capable of crossing the so-called "blood-brain barrier" Preferably, the compounds fulfilling this aspect of the invention will be capable of exerting their beneficial therapeutic action following administration by the oral route.

A representative compound fulfilling this aspect of the invention is 7-cyclobutyl-6-(2-methyl-2H-1,2,4-triazol-3-ylmethoxy)-3-phenyl-1,2,4-triazolo[4,3-b]pyridazine.

In a further aspect, the present application provides a method of screening for non-sedating anxiolytic compounds, which comprises:

(1) contacting a panel of test compounds with (a) a stably transfected recombinant cell line expressing the α3 subunit of the human GABA$_A$ receptor; and (b) a stably transfected recombinant cell line expressing the α1 subunit of the human GABA$_A$ receptor;

(2) measuring the potentiation of the GABA EC$_{20}$ response elicited by each test compound in each of the stably transfected cell lines (a) and (b); and (3) selecting out those test compounds which elicit at least a 40% potentiation of the GABA EC$_{20}$ response in the cell line expressing the α3 subunit, and at most a 30% potentiation of the GABA EC$_{20}$ response in the cell line expressing the α1 subunit.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises reacting a compound of formula III with a compound of formula IV:

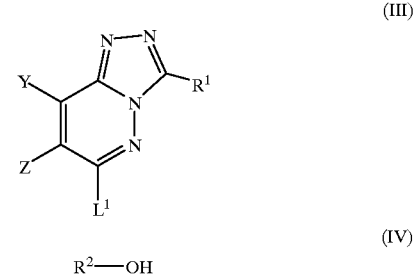

(III)

(IV)

R$^2$—OH wherein Y, Z, R$^1$ and R$^2$ are as defined above; and L$^1$ represents a suitable leaving group.

The leaving group L$^1$ is typically a halogen atom, especially chloro.

The reaction between compounds III and IV is conveniently effected by stirring the reactants in a suitable solvent, typically N,N-dimethylformamide, in the presence of a strong base such as sodium hydride or lithium bis (trimethylsilyl)amide.

The intermediates of formula III above may be prepared by reacting a compound of formula V with a substantially equimolar amount of a hydrazine derivative of formula VI:

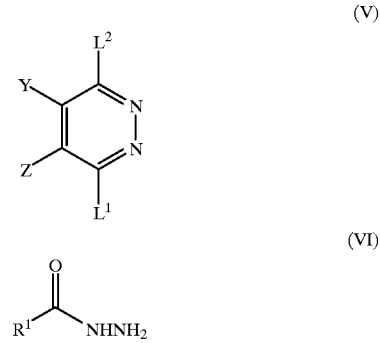

(V)

(VI)

wherein Y, Z, R$^1$ and L$^1$ are as defined above, and L$^2$ represents a suitable leaving group; followed, if necessary, by separation of the resulting mixture of isomers by conventional means.

The leaving group L$^2$ is typically a halogen atom, especially chloro. In the intermediates of formula V, the leaving groups L$^1$ and L$^2$ may be the same or different, but are suitably the same, preferably both chloro.

The reaction between compounds V and VI is conveniently effected by heating the reactants in the presence of a base such as triethylamine, typically at reflux in an inert solvent such as xylene or 1,4-dioxane.

Where Y and Z are different, the reaction between compounds V and VI will, as indicated above, usually give rise to a mixture of isomeric products depending upon whether the hydrazine derivative VI displaces the leaving group $L^1$ or $L^2$. Thus, in addition to the required product of formula III, the isomeric compound wherein the Y and Z moieties are reversed will usually be obtained to some extent. For this reason it will generally be necessary to separate the resulting mixture of isomers by conventional methods such as chromatography.

In another procedure, the compounds of formula I as defined above may be prepared by a process which comprises reacting a compound of formula VII with a compound of formula VIII:

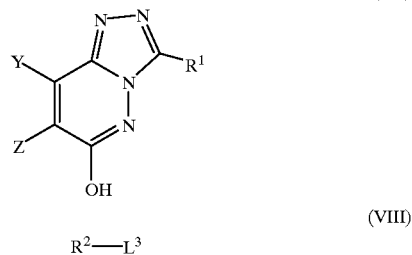

(VII)

(VIII)

$R^2$—$L^3$ wherein Y, Z, $R^1$ and $R^2$ are as defined above; and $L^3$ represents a suitable leaving group.

The leaving group $L^3$ is suitably a halogen atom, typically chloro or bromo.

The reaction between compounds VII and VIII is conveniently effected by stirring the reactants in a suitable solvent, typically N,N-dimethylformamide, in the presence of a strong base such as sodium hydride.

The intermediates of formula VII above may conveniently be prepared by reacting a compound of formula III as defined above with an alkali metal hydroxide, e.g. sodium hydroxide. The reaction is conveniently effected in an inert solvent such as aqueous 1,4-dioxane, ideally at the reflux temperature of the solvent.

In a further procedure, the compounds of formula I as defined above may be prepared by a process which comprises reacting a compound of formula Z—$CO_2$H with a compound of formula IX:

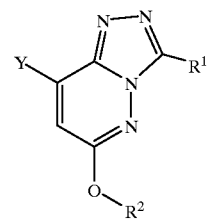

(IX)

wherein Y, Z, $R^1$ and $R^2$ are as defined above; in the presence of silver nitrate and ammonium persulphate.

The reaction is conveniently carried out under acidic conditions in a suitable solvent, for example using sulphuric acid in water or aqueous acetonitrile, typically at an elevated temperature.

The intermediates of formula IX correspond to the compounds of formula I as defined above wherein Z is hydrogen, and they may therefore be prepared by methods analogous to those described above for preparing the corresponding compounds of formula I.

In a still further procedure, the compounds of formula I as defined above may be prepared by a process which comprises reacting a compound of formula X with a compound of formula XI:

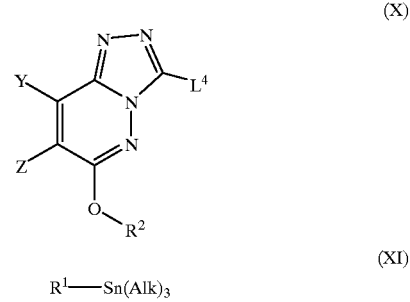

(X)

$R^1$—Sn(Alk)$_3$ (XI)

wherein Y, Z, $R^1$ and $R^2$ are as defined above, Alk represents a $C_{1-6}$ alkyl group, typically n-butyl, and $L^4$ represents a suitable leaving group; in the presence of a transition metal catalyst.

The leaving group $L^4$ is suitably a halogen atom, e.g. bromo.

A suitable transition metal catalyst of use in the reaction between compounds X and XI comprises dichlorobis(triphenylphosphine)palladium(II).

The reaction between compounds X and XI is conveniently effected in an inert solvent such as N,N-dimethylformamide, typically at an elevated temperature.

The intermediates of formula X may be prepared by reacting a compound of formula IV as defined above with a compound of formula XII:

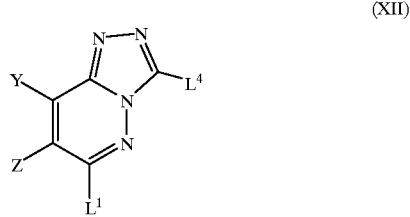

(XII)

wherein Y, Z, $L^1$ and $L^4$ are as defined above; under conditions analogous to those described above for the reaction between compounds III and IV.

Where they are not commercially available, the starting materials of formula IV, V, VI, VII, XI and XII may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula IJ or IK as defined above wherein $R^3$ is hydrogen can be subjected to catalytic hydrogenation under standard conditions to afford the corresponding compound of formula IG or IH respectively wherein $R^4$ is hydrogen. Moreover, a compound of formula IG or IH as defined above wherein $R^4$ is hydrogen may be converted into the corresponding compound wherein $R^4$ is $C_{1-6}$ alkyl by a conventional reductive alkylation procedure, for example by treatment with the appropriate aldehyde or ketone in the presence of a reducing agent such as sodium cyanoborohydride. Similarly, a compound of formula I initially obtained wherein $R^2$ is unsubstituted may be converted into a corresponding compound wherein $R^2$ is substituted, typically by standard alkylation procedures, for example by treatment with a haloalkyl derivative in the presence of sodium hydride and N,N-dimethylformamide, or with a hydroxyalkyl derivative in the presence of triphenylphosphine and diethyl azodicarboxylate. Furthermore, a compound of formula I initially obtained wherein $R^2$ represents cyano($C_{1-6}$)alkyl may be converted into the corresponding 3-substituted 1,2,4-triazol-5-yl($C_{1-6}$)alkyl analogue by treatment with the appropriate acyl hydrazine derivative in the presence of a base such as sodium methoxide. Similarly, a compound of formula I initially obtained wherein $R^2$ represents an optionally substituted propargyl moiety may be converted into the corresponding 1,2,3-triazolylmethyl analogue by treatment with azide anion. A compound of formula I initially obtained wherein the $R^2$ substituent is substituted by a halogen atom, e.g. chloro, may be converted into the corresponding compound wherein the $R^2$ substituent is substituted by a di($C_{1-6}$)alkylamino moiety by treatment with the appropriate di(Ci)alkylamine, typically with heating in a solvent such as 1,4-dioxane in a sealed tube.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (-)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 subunit stably expressed in Ltk⁻ cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]Ro 15-1788 from the α2 and/or α3 subunit of the human $GABA_A$ receptor of 100 nM or less.

EXAMPLE 1

3-Phenyl-6-(2-pyridyl)methyloxy-7,8,9,10-tetrahydro-(7,10-ethano)-1,2,4-triazolo[3,4-a]phthalazine a) 4,5-Diazatricyclo[6.2.2.2,7]dodec-2(7)-ene-3,6-dione Bicyclo[2.2.2]oct-2-ene-2,3-dicarboxylic acid anhydride (prepared as described in *J. Org. Chem.*, 1993, 6740–6744) (60.8 g, 0.342 mol) was dissolved in 50% aqueous acetic acid (1600 ml) with sodium acetate trihydrate (55.5 g, 1.2 mol eq) and hydrazine hydrate (19.82 ml, 1.2 mol eq). The reaction mixture was heated under reflux for 16 h then allowed to cool. The solid produced was collected by filtration and washed with water and diethyl ether before drying in a vacuum oven at 80° C. to give the required product (59.3 g, m.p.=214° C.). $^1$H NMR (250 MHz, DMSO) δ 1.16 (4H, d, J=7.1 Hz), 1.69 (4H, d, J=7.1 Hz), 3.18 (2H, s), 11.31 (2H, br, s, NH); MS (ES⁺) m/e 193 [MH]⁺.

b) 3,6-dichloro-4,5-diazatricyclo[6.2.2.2,7]dodeca-2(7),3,5-triene

The product from Example 1 Step a) (59.2 g) was dissolved in phosphorus oxychloride (300 ml) and heated under reflux for 14 h. The solvent was removed under vacuum and azeotroped 2× toluene. The residue was dissolved in dichloromethane (200 ml) and stirred rapidly and the solution was neutralised by the addition of solid and aqueous sodium hydrogen carbonate (cautiously). When effervescence had ceased, the organic layer was separated and the aqueous layer was extracted with dichloromethane (2×200 ml). The combined organic layers were dried (MgSO$_4$), filtered and evaporated to give to give the required product (59.5 g, m.p. >370° C.). $^1$H NMR (250 MHz, CDCl$_3$) δ 1.39 (4H, d, J=8.1 Hz), 1.92 (4H, d, J=8.1 Hz), 3.47 (2H, s); MS (ES$^+$) m/e 229 [MH]$^+$.

c) 6-Chloro-3-phenyl-7,8,9,10-tetrahydro-(7,10-ethano)-1,2,4-triazolo[3,4-a]phthalazine The product from Example 1 Step b) (2.5 g, 0.011 mol) was suspended in xylene (50 ml) with benzoylhydrazine (1.65 g, 1.1 mol eq) and triethylamine (1.68 ml, 1.1 mol eq) and the reaction mixture was heated under reflux for 6 days. The solvent was removed under high vacuum and the residue was purified by chromatography on silica gel using 0–50% ethyl acetate in dichloromethane as eluent followed by recrystallisation from ethyl acetate/hexane to give the required product (1.3 g, m.p.=186–188° C.). $^1$H NMR (250 MHz, CDCl$_3$) δ 1.43–1.59 (4H, m), 1.91–2.05 (4H, m), 3.57 (1H, s), 4.07 (1H, s), 7.58 (3H, m), 8.58 (2H, dd, J=7.8 and 1.5 Hz); MS (ES$^+$) m/e 311 [MH]$^+$. Anal. Found C, 65.56; H, 4.83; N, 17.74. C$_{17}$H$_{15}$ClN$_4$ requires C, 65.70; H. 4.87; N, 18.03%.

d) 3-Phenyl-6-(2-pyridyl)methyloxy-7,8,9,10-tetrahydro-(7,10-ethano)-1,2,4-triazolo[3,4-a]phthalazine To a solution of 2-pyridylcarbinol (0.263 ml, 0.0024 mol) in DMF (20 ml) was added sodium hydride (0.113 g of a 60% dispersion in oil, 1.75 mol eq) and the reaction mixture was stirred at room temperature for 15 minutes. After this time, the product from Example 1 Step c) (0.5 g, 0.0016 mol) was added and the reaction mixture was stirred at room temperature for 1 hour. Water was added until the solution became cloudy and after stirring for a further 15 minutes a solid was collected by filtration. This solid was recrystallized from ethyl acetate to give the required product (0.112 g, m.p.=196–198° C.). $^1$H NMR (360 MHz, CDCl$_3$) δ 1.45 (4H, m), 1.95 (4H, m), 3.58 (1H, s), 4.00 (1H, s), 7.26 (1H, m), 5.48 (2H, s), 7.44–7.53 (4H, m), 7.77 (1H, m), 8.40 (2H, dd, J=7.8 and 1.5 Hz), 8.68 (1H, m); MS (ES$^+$) m/e 384 [MH]$^+$. Anal. Found C, 71.76; H, 5.54; N, 18.03. C$_{24}$H$_{21}$N$_5$O requires C, 72.04; H, 5.52; N, 18.26%.

EXAMPLE 2

3,7-Diphenyl-6-(2-pyridyl)methyloxy-1,2,4-triazolo[4,3-b]pyridazine

This compound was prepared using the procedures described in Example 1 Steps a), b), c) and d) with phenylmaleic anhydride being used instead of bicyclo[2.2.2]oct-2-ene-2,3-dicarboxylic acid anhydride in Step a). The 7-phenyl isomer produced in Step c) was lower running on tlc than the 8-phenyl isomer and so separation of the regioisomers was effected at this stage by silica gel chromatography using 0–5% ethyl acetate in dichloromethane as eluent. Data for the title compound: m.p.=203° C. $^1$H NMR (360 MHz, CDCl$_3$) δ 5.65 (2H, s), 7.24 (1H, m), 7.34 (1H, d, J=7.8 Hz), 7.53 (6H, m), 7.69 (3H, m), 8.07 (1H, s), 8.41 (2H, d, J=6.6 Hz), 8.65 (1H, m); MS (ES$^+$) m/e 380 [MH]$^+$. Anal. Found C, 72.59; H, 4.47; N, 18.04. C$_{23}$H$_{17}$N$_5$O requires C, 72.81; H, 4.52; N, 18.46%.

EXAMPLE 3

3-Phenyl-6-(2-pyridyl)methyloxy-7,8,9,10-tetrahydro-1,2,4-triazolo[3,4-a]phthalazine This compound was prepared using the procedures described in Example 1 Steps a), b), c) and d) with tetrahydrophthalic anhydride being used instead of bicyclo[2.2.2]oct-2-ene-2,3-dicarboxylic acid anhydride in Step a). Data for the title compound: m.p.=194° C. $^1$H NMR (360 MHz, CDCl$_3$) δ 1.94 (4H, m), 2.74 (2H, m), 3.14 (2H, m), 5.56 (2H, s), 7.27 (1H, m), 7.47 (4H, m), 7.73 (1H, m), 8.36 (2H, d, J=6.6 Hz), 8.66 (1H, m); MS (ES$^+$) m/e 358 [MH]$^+$. Anal. Found C, 70.50; H, 5.25; N, 19.27. C$_{21}$H$_{19}$N$_5$O requires C, 70.57; H, 5.76; N, 19.59%.

EXAMPLE 4

7,8-Dimethyl-3-phenyl-6-(2-pyridyl)methyloxy-1,2,4-triazolo[4,3-b]pyridazine

This compound was prepared using the procedures described in Example 1 Steps c) and d) with 3,6-dichloro-4,5-dimethylpyridazine being used instead of 3,6-dichloro-4,5-diazatricyclo[6.2.2.2,7]dodeca-2(7),3,5-triene in step c). Data for the title compound: m.p.=185° C. $^1$H NMR (360 MHz, CDCl$_3$) δ 2.35 (3H, s), 2.69 (3H, s), 5.58 (2H, s), 7.27 (1H, m), 7.47 (4H, m), 7.75 (1H, ddd, J=7.8, 7.8 & 1.8 Hz), 8.37 (2H, d, J=7.6 Hz), 8.65 (1H, m); MS (ES$^+$) m/e 332 [MH]$^+$. Anal. Found C, 68.38; H, 4.82; N, 20.64. C$_{19}$H$_{17}$N$_5$O requires C, 68.87; H, 5.17; N, 21.13%.

EXAMPLE 5

7-Methyl-3-phenyl-6-(2-pyridyl)methyloxy-1,2,4-triazolo[4,3-b]pyridazine

This compound was prepared using the procedures described in Example 1 Steps c) and d) with 3,6-dichloro-4-methylpyridazine being used instead of 3,6-dichloro-4,5-diazatricyclo[6.2.2.2,7]dodeca-2(7),3,5-triene in Step c). The 7-methyl isomer produced in Step c) was lower running on tlc than the 8-methyl isomer and so separation of the regioisomers was effected at this stage by silica gel chromatography using 0–10% ethyl acetate in dichloromethane as eluent. Data for the title compound: m.p.=199° C. $^1$H NMR (360 MHz, CDCl$_3$) δ 2.42 (3H, s), 5.59 (2H, s), 7.28 (1H, m), 7.49 (4H, m), 7.76 (1H, ddd, J=7.8, 7.8 & 1.8 Hz), 7.83 (1H, s), 8.37 (2H, d, J=7.6 Hz), 8.65 (1H, m); MS (ES$^+$) m/e 318 [MH]$^+$. Anal. Found C, 68.09; H, 4.31; N, 22.01. C$_{18}$H$_{15}$N$_5$O requires C, 68.12; H, 4.76; N, 22.06%.

EXAMPLE 6

7-Ethyl-3-phenyl-6-(2-pyridyl)methyloxy-1,2,4-triazolo[4,3-b]pyridazine bis-hydrochloride This compound was prepared using the procedures described in Example 1 Steps a), b), c) and d) with ethyl maleic anhydride (*Synth. Commun.*, 1990, 2491) being used instead of bicyclo[2.2.2]oct-2-ene-2,3-dicarboxylic acid anhydride in Step a). The 7-ethyl isomer produced in Step c) was lower running on tlc than the 8-ethyl-isomer and so separation of the regioisomers was effected at this stage by silica gel chromatography using 0–10% ethyl acetate in dichloromethane as eluent. Data for the title compound: m.p.=193° C. $^1$H NMR (360 MHz, DMSO) δ 1.31 (3H, t, J=7.4Hz), 2.81 (2H, q, J=7.4Hz), 5.85 (2H, s), 7.58 (3H, m), 7.80 (1H, m), 7.99 (1H, d, J=7.9 Hz), 8.23 (3H, m), 8.34 (1H, m), 8.84 (1H, d, J=4.7 Hz); MS (ES$^+$) m/e 332 [MH]$^+$. Anal. Found C, 56.20; H, 4.53; N, 17.28. C$_{19}$H$_{17}$N$_5$O.2HCl requires C, 56.45; H, 4.74; N, 17.32%.

EXAMPLE 7

7,8-Benzo-3-phenyl-6-(2-pyridyl)methyloxy-7,8,9,10-tetrahydro-1,2,4-triazolo[3,4-a]phthalazine This compound was prepared using the procedures described in Example 1 Steps a), b), c) and d) with 3,4- dihydro-1,2-napthalenedicarboxylic anhydride being used instead of bicyclo[2.2.2]oct-2-ene-2,3-dicarboxylic acid anhydride in Step a). The 7,8-benzo isomer produced in Step c) was lower running on tlc than the 9,10-benzo isomer and so separation of the regioisomers was effected at this stage by silica gel chromatography using 0–30% ethyl acetate in dichloromethane as eluent. Data for the title compound: m.p.=240° C. $^1$H NMR (360 MHz, CDCl$_3$) δ 3.02 (2H, t, J=7.9 Hz), 3.38 (2H, t, J=7.9 Hz), 5.74 (2H, s), 7.31 (4H, m), 7.51 (4H, m), 7.74 (1H, m), 8.37 (3H, m), 8.71 (1H, m); MS (ES$^+$) m/e 406 [MH$^+$. Anal. Found C, 73.81; H, 4.48; N, 16.96. C$_{25}$H$_{19}$N$_5$O requires C, 74.06; H, 4.72; N, 17.27%.

EXAMPLE 8

8-Methyl-3,7-diphenyl-6-(2-pyridyl)methyloxy-1,2,4-triazolo[4,3-b]pyridazine

This compound was prepared using the procedures described in Example 1 Steps a), b), c) and d) with 3-methyl-4-phenyl maleic anhydride being used instead of bicyclo[2.2.2]oct-2-ene-2,3-dicarboxylic acid anhydride in Step a). The 7-phenyl-8-methyl isomer produced in Step c) was lower running on tlc than the 7-methyl-8-phenyl isomer and so separation of the regioisomers was effected at this stage by silica gel chromatography using 0–15% ethyl acetate in dichloromethane as eluent. Data for the title compound: m.p.=182° C. $^1$H NMR (360 MHz, DMSO) δ 2.45 (3H, s), 5.50(2H, s), 7.30 (2H, m), 7.54 (8H, m), 7.77 (1H, m), 8.25 (2H, d, J=7.8 Hz), 8.58 (1H, m); MS (ES$^+$) m/e 394 [MH]$^+$. Anal. Found C, 72.05; H, 4.94; N, 16.55. C$_{24}$H$_{19}$N$_5$O.0.5 EtOAc. requires C, 72.27; H, 5.09; N, 16.86%.

EXAMPLE 9

(±)-3-Phenyl-6-(2-pyridyl)methyloxy-7,8,9,10-tetrahydro-(7,10-methano)-1,2,4-triazolo[3,4-a]phthalazine This compound was prepared using the procedures described in Example 1 Steps a), b), c) and d) with 2-norbornene-2,3-dicarboxylic anhydride being used instead of bicyclo[2.2.2]oct-2-ene-2,3-dicarboxylic acid anhydride in Step a). Data for the title compound: m.p.=182° C. $^1$H NMR (360 MHz, CDCl$_3$) δ 1.31 (2H, m), 1.69 (1H, d, J=9.2 Hz), 1.95 (1H, d, J=9.2 Hz), 2.12 (2H, m), 3.76 (1H, s), 4.14 (1H, s), 5.59 (2H, s), 7.28 (1H, m), 7.48 (4H, m), 7.76 (1H, m), 8.36 (2H, d, J=7.8 Hz), 8.68 (1H, m); MS (ES$^+$) m/e 370 [MH]$^+$. Anal. Found C, 71.53; H, 5.18; N, 18.96. C$_{22}$H$_{19}$N$_5$O requires C, 72.08; H. 5.13; N, 18.89%.

EXAMPLES 10 and 11

3-Phenyl-5-(pyridin-2-ylmethoxy)-1,2,3a,4,7-pentaazacyclopenta-[α]naphthalene 0.25 Hydrate and 3-Phenyl-5-(pyridin-2-ylmethoxy)-1,2,3a,4,8-pentaazacyclopenta[α]naphthalene 0.5 Hydrate a) 5-Chloro-3-phenyl-1,2,3a,4,7-pentaazacyclopenta[α]naphthalene and 5-Chloro-3-phenyl-1,2,3a,4,8-pentaazacyclopenta[α]naphthalene This 1:1 mixture of chloroimidates was prepared using the procedures described in Example 1, Steps a), b) and c) with 3,4-pyridinedicarboxylic anhydride being used instead of bicyclo[2.2.2]oct-2-ene-2,3-dicarboxylic acid anhydride. Data for the mixture: $^1$H NMR (250 MHz, CDCl$_3$) δ 7.54–7.62 (3H, m), 8.04 (0.5H, dd, J=7.3, 1.5 Hz), 8.38–8.46 (2H, m), 8.71 (0.5H, dd, J=7.3, 1.5 Hz), 9.15(0.5H, d, J=8.0 Hz), 9.17 (0.5H, d, J=8.0 Hz), 9.60 (0.5H, s), 10.11 (0.5H, s); MS (ES$^+$) m/e 284 [MH]$^+$, 282 [MH]$^+$.

b) 3-Phenyl-5-(pyridin-2-ylmethoxy)-1,2,3a,4,7-pentaazacyclopenta[α]naphthalene 0.25 Hydrate and 3-Phenyl-5-(pyridin-2-ylmethoxy)-1,2,3a,4,8-pentaazacyclopenta[α]naphthalene 0.5 Hydrate Sodium hydride (76 mg of a 60% dispersion in oil, 1.9 mmol) was added to a solution of 2-pyridyl carbinol (180 ml, 1.9 mmol) in dry DMF (10 ml) at room temperature under nitrogen. After 45 minutes the mixture of chloroimidates from Step a) (380 mg, 1.35 mmol) was added. After a further 1 hour at room temperature the reaction mixture was diluted with water (200 ml) and extracted with dichloromethane (400 ml and 2×200 ml). The combined extracts were washed with brine (100 ml), dried (MgSO$_4$), filtered and evaporated. The residue was recrystallised from methanol to give the mixture of phthalazines (136 mg) as a 1:1 mixture—inseparable by conventional chromatography. The two isomers were separated by preparative HPLC using a Pirkle type 3,5-dinitrobenzoyl phenyl glycine column to give:

first eluting: 3-Phenyl-5-(pyridin-2-ylmethoxy)-1,2,3a,4,7-pentaazacyclopenta[α]naphthalene 0.25 Hydrate: m.p. >190° C.; $^1$H NMR (360 MHz, CDCl$_3$) δ 5.79 (2H, 8), 7.34–7.37 (1H, m), 7.52–7.58 (3H, m), 7.61 (1H, d, J=7.9 Hz), 7.83 (1H, t, J=7.7 Hz), 8.34 (2H, d, J=8.9 Hz), 8.47 (1H, d, J=7.8 Hz), 8.90 (1H, d, J=4.0 Hz), 9.11 (1H, d, J=5.3 Hz), 9.61 (1H, s); (Regiochemistry was established using nOe data). MS (ES$^+$) m/e 355 [MH]$^+$. Anal. Found C, 67.00; H, 3.87; N, 23.37. C$_{20}$H$_{14}$N$_6$O.0.25 H$_2$O requires C, 66.93; H, 4.07; N, 23.42%.

and second eluting: 3-Phenyl-5-(pyridin-2-ylmethoxy)-1,2,3a,4,8-pentaazacyclopenta[α]naphthalene 0.5 Hydrate: m.p. >170° C.; $^1$H NMR (360 MHz, CDCl$_3$) δ 5.75 (2H, s), 7.33–7.37 (1H, m), 7.50–7.60 (4H, m), 7.82 (1H, t, J=7.8 Hz), 8.07 (1H, d, J=5.3 Hz), 8.29–8.33 (2H, m), 8.68–8.70 (1H, m), 9.05 (1H, d, J=5.3 Hz), 10.03 (1H, s); (Regiochemistry was established using nOe data). MS (ES$^+$) m/e 355 [MH]$^+$. Anal. Found C, 66.25; H, 3.89; N, 22.73. C$_{20}$H$_{14}$N$_6$O.0.5 H$_2$O requires C, 66.11; H, 4.16; N, 23.13%.

EXAMPLE 12

(±)-8-Methyl-3-phenyl-6-(2-pyridyl)methyloxy-7,8,9,10-tetrahydro-1,2,4-triazolo[3,4-a]phthalazine a) Ethyl 4-methyl-2-(trifluoromethanesulfonyloxy)cyclohex-1-enecarboxylate To a solution of ethyl 4-methyl-2-cyclohexanone-1-carboxylate (50 g, 0.27 mol) in dichloromethane (500 ml) at −10° C. was added N,N-diisopropylethylamine (52 ml, 0.3 mol) followed by dropwise addition of trifluoromethanesulphonyl chloride (57 ml, 0.3 mol) keeping the temperature between −5 and −100° C. The reaction mixture was allowed to warm to room temperature and stirred for 3 hours. TLC showed 80% reaction, it was cooled to −5° C. and more N,N-diisopropylethylamine (14 ml, 0.1 mol) was added followed by trifluoromethanesulphonyl chloride (15.5 ml, 0.1 mol) and the reaction mixture was stirred for 15 hours at room temperature. The mixture was washed with cold water (2×200 ml), cold saturated sodium bicarbonate (2×200 ml) and brine (1×200 ml). The organic layer was dried (MgSO$_4$), filtered and evaporated to give the required product (85 g) as a colourless oil. $^1$H NMR (250 MHz, CDCl$_3$) δ 1.04 (3H, d, J=6.5 Hz), 1.43 (3H, m), 1.73–2.09 (4H, m), 2.39–2.63 (3H, m), 4.25 (2H, m).

b) 1-Ethyl-2-methyl 4-methylcyclohex-1-ene-1,2-dicarboxylate

To a solution of the product from Example 12 Step a (85 g, 0.27 mol) in DMF (500 ml) at −20° C. was added palladium(II) acetate (1.85 g, 0.0083 mol), bis(diphenylphosphino)ferrocene (9 g, 0.0162 mol), methanol (250 ml) and triethylamine (75.5 ml, 0.54 mol). Carbon monoxide gas was passed through the solution for 15 minutes and then the reaction was heated to 60° C. and kept under an atmosphere of carbon monoxide for 15 hours. The solution was left to cool and solvent was removed under high vacuum. The residue was dissolved in ethyl acetate, then washed with water (4×200 ml) and brine (1×200 ml). The organic layer was dried (MgSO$_4$), filtered and evaporated to give the crude product which was purified by chromatography on silica gel using 0–10% ethyl acetate in hexane to give the required product (27 g) as a pale yellow oil. $^1$H NMR (250 MHz, CDCl$_3$) δ 1.12 (3H, d, J=6.5 Hz), 1.33 (3H, m), 1.70–1.96 (4H, m), 2.35–2.61 (3H, m), 3.73 (3H, s) 4.25 (2H, m).

c) 4-Methylcyclohex-1-ene-1,2-dicarboxylic Acid

To a solution of the product from Example 12 Step b (33 g, 0.15 mol) in ethanol (200 ml) was added a solution of potassium hydroxide (32.7 g, 0.6 mol) in water (20 ml) and heated at reflux for 15 hours. The solution was left to cool, solvent was removed under high vacuum, water (200 ml) was added, then concentrated hydrochloric acid added until pH 2. The aqueous layer was extracted with dichloromethane (5×200 ml), the combined organic layers were washed with brine (1×200 ml), dried (MgSO$_4$), filtered and evaporated to give the required product as a pale yellow oil (16.7 g). $^1$H NMR (250 MHz, DMSO) δ 1.15 (3H, d, J=6.5 Hz), 1.21 (1H, m), 1.86 (3H, m), 2.37 (3H, m), 3.34 (2H, bs).

d) 4-Methyl-(3,4,5,6-tetrahydro)phthalic Anhydride

The product from Example 12 Step c (16.5 g, 0.89 mol) was refluxed in acetic anhydride (200 ml) for 15 hours. The acetic anhydride was removed under high vacuum, the residue was dissolved in toluene and then evaporated to give the required product as an oil (15.2 g). $^1$H NMR (250 MHz, DMSO) δ 1.03 (3H, d, J=6.5 Hz), 1.24 (1H, m), 1.96 (3H, m), 2.23 (3H, m).

e) 6-Methyl-5,6,7,8-tetrahydrophthalazine-1,4-dione

This compound was prepared using the procedures described in Example 1 Step a) using 4methyl-(3,4,5,6-tetrahydro)phthalic anhydride instead of bicyclo[2.2.2]oct-2-ene-2,3-dicarboxylic acid anhydride. Data for the title compound: $^1$H NMR (250 MHz, DMSO) 1.13 (3H, d, J=6.8 Hz), 1.19 (1H, m), 1.76 (3H, m), 2.29 (1H, m), 2.50 (2H, m), 11.2 (2H, bs); MS (ES$^+$) m/e 181 [MH]$^+$.

f) 1,4-Dichloro-6-methyl-5,6,7,8-tetrahydrophthalazine

This compound was prepared using the procedures described in Example 1 Step b) using 6-methyl-5,6,7,8tetrahydrophthalazine-1,4-dione instead of 4,5-diazatricyclo[6.2.2.2,7]dodec-2(7)-ene-3,6-dione. Data for the title compound: $^1$H NMR (250 MHz, CDCl$_3$) δ 1.29 (3H, d, J=7.0 Hz), 1.90 (4H, m), 2.54 (1H, m), 2.93 (3H, m), 3.18 (1H, m); MS (ES$^+$) m/e 217+219 [MH]$^+$.

g) (±)-6-Chloro-8-methyl-3-phenyl-7,8,9,10-tetrahydro-1,2,4-triazolo[3,4a]phthalazine and (±)-6-chloro-9-methyl-3-phenyl-7,8,9,10-tetrahydro-1,2,4-triazolo[3,4-a]phthalazine This compound was prepared using the procedures described in Example 1 Step c) using 1,4-dichloro-6-methyl-5,6,7,8-tetrahydrophthalazine instead of 3,6-dichloro-4,5-diazatricyclo[6.2.2.2,7-dodeca-2(7),3,5-triene. The reaction gave a mixture of the title compounds in an approximate ratio of 1:1. The compounds were not separated at this stage. Data for the mixture of title compounds: $^1$H NMR (250 MHz, CDCl$_3$) δ 1.12 (3H, m), 1.44 (1H, m), 2.21,(2H, m), 2.77 (3H, m), 3.40 (1H, m), 7.74 (3H, m), 8.43 (2H, m); MS (ES$^+$) m/e 299+301 [MH]$^+$.

h) (±)-8-Methyl-3-phenyl-6-(2-pyridyl)methyloxy-7,8,9,10-tetrahydro-1,2,4-triazolo[3,4-a]phthalazine This compound was prepared using the procedures described in Example 1 Step d) using the mixture from Example 12 Step g) instead of 3-phenyl-6-(2-pyridyl)methyloxy-7,8,9,10-tetrahydro-(7,10-ethano)-1,2,4-triazolo[3,4-a]phthalazine. The two products were separated using silica gel chromatography, 0–8% methanol in dichloromethane. The higher R$_f$ product was recrystallised from ethyl acetate/dichloromethane to give the title compound. $^1$H NMR (250 MHz, DMSO) δ 1.23 (3H, d, J=6.3 Hz), 2.05 (2H, m), 2.35 (1H, m), 3.00 (2H, m), 3.24 (1H, m), 5.71 (2H, s), 7.58 (5H, m), 8.08 (1H, m), 8.36 (2H, m), 8.80 (1H, m); m.p. 185–187° C.; MS (ES$^+$) m/e 372 [MH]$^+$.

The lower R$_f$ product was also isolated and shown to be (±)-9-methyl-3-phenyl-6-(2-pyridyl)methyloxy-7,8,9,10-tetrahydro-1,2,4-triazolo[3,4-a]phthalazine. Data for this compound is for the trifluoroacetate salt; $^1$H NMR (250 MHz, DMSO) δ 1.13 (3H, d, J=6.5 Hz), 1.24 (1H, m), 1.96 (2H, m), 2.80 (3H, m), 3.16 (1H, m), 5.60 (2H, s), 7.70 (5H, m), 8.08 (1H, d, J=7.8 Hz), 8.20 (2H, m), 8.65 (1H, m); m.p.152–154° C.; MS (ES$^+$) m/e 372 [MH]$^+$. The structure was proven by COSY and NOE experiments.

EXAMPLE 13

3-Phenyl-6-(2-pyridyl)methyloxy-(7,8-pentano)-1,2,4-triazolo[4,3-b]pyridazine

This compound was prepared using the procedures described in Example 1 Steps a), b), c) and d) with 1-cycloheptene-1,2-dicarboxylic anhydride (*Proc. Indian Acad. Sci., Sect. A,* 1978, 87A (10), 371) being used instead of bicyclo[2.2.2]oct-2-ene-2,3-dicarboxylic acid anhydride in Step a). Data for the title compound: m.p.=208° C. $^1$H NMR (360 MHz, CDCl$_3$) δ 1.71 (2H, m), 1.81 (2H, m), 1.99 (2H, m), 3.01 (2H, m), 3.38 (2H, m), 5.58 (2H, s), 7.28(1H, m), 7.48 (4H, m), 7.76 (1H, m), 8.37 (2H, d, J=7.8 Hz), 8.67 (1H, m); MS (ES$^+$) m/e 372 [MH]$^+$. Anal. Found C, 70.52; H, 5.25; N, 18.44. C$_{22}$H$_{21}$N$_5$O.0.1H$_2$O requires C, 70.80; H, 5.72; N, 18.76%.

8,8-Dimethyl-3-phenyl-6-(2-pyridyl)methyloxy-7,8,9,10-tetrahydro-1,2,4-triazolo[3,4-a]phthalazine a) Dimethyl 4,4-(dimethyl)cyclohexene-1,2-dicarboxylate This compound was prepared in 62% yield by a similar procedure to that described in Example 12, Step a), but using 2-carbomethoxy-4,4-dimethylcyclohexanone (Liu, H.-J.; Browne, E. N. C.; Chew, S. Y., *Can. J. Chem.,* 1988, 66, 2345–2347). $^1$H NMR (360 MHz, CDCl$_3$) δ 0.96 (6H, s), 1.42 (2H, t, J=6.4 Hz), 2.12 (2H, t, J=2.6 Hz), 2.38 (2H, m), 3.76 (3H, s), 3.76 (3H, s); MS (ES$^+$) m/e 249 [M+Na]$^+$, 227 [M+H]$^+$, 195 [M-OMe]$^+$.

b) 4,4-(Dimethyl)cyclohexene-1,2-dicarboxylic Acid

A mixture of the product from Example 14, Step a) (3.78 g, 16.7 mmol) and potassium hydroxide (3.50 g, 66.9 mmol) in ethanol (23 ml) and water (28 ml) was heated at 80° C. for 23 h. After cooling, the mixture was concentrated to about 15 ml, introduced onto a Dowex 50WX8-200 ion exchange column, and eluted with 0–20% MeOH/H$_2$O to give 2.73 g (82%) of the required product as a pale brown solid. $^1$H NMR (250 MHz, d$_6$-DMSO) δ 1.09 (9H, s), 1.61 (2H, t, J=6.2 Hz), 2.26 (2H, t, J=2.8 Hz), 2.48 (2H, m).

c) 4,4-(Dimethyl)cyclohexene-1,2-dicarboxylic Anhydride

This compound was prepared in 93% yield by a similar procedure to that described in Example 12, Step d), but using the product from Example 14, Step c). $^1$H NMR (250 MHz, $d_6$-DMSO) δ 0.96 (6H, s), 1.48 (2H, t, J=6.2 Hz), 2.13 (2H, t, J=2.8 Hz), 2.35 (2H, m).

d) 6,6-Dimethyl-5,6,7,8-tetrahydrophthalazine-1,4-dione

This compound was prepared in 92% yield by a similar procedure to that described in Example 1, Step a), but using the product from Example 14, Step c). $^1$H NMR (250 MHz, $d_6$-DMSO) δ 0.92 (6H, s), 1.43 (2H, t, J=6.4 Hz), 2.16 (2H, s), 2.38 (2H, t, J=6.4 Hz); MS (ES) m/e 195 [M+H]$^+$.

e) 1,4-Dichloro-5,6,7,8-tetrahydro-6,6-dimethylphthalazine

This compound was prepared in 99% yield by a similar procedure to that described in Example 1, Step b), but using the product from Example 14, Step d). $^1$H NMR (360 MHz, CDCl$_3$) 1.04 (6H, s), 1.65 (2H, t, J=6.6 Hz), 2.53 (2H, s), 2.78 (2H, t, J=6.6 and 1.3 Hz); MS (ES) m/e 235/233/231 [M+H]$^+$.

f) 6-Chloro-7,8,9,10-tetrahydro-8,8-dimethyl-3-phenyl-1,2,4-triazolo[3,4-a]phthalazine A mixture of the product from Example 14, Step e) (2.53 g, 10.9 mmol), triethylamine (1.83 ml, 13.1 mmol) and benzoic hydrazide (1.79 g, 13.1 mmol) in xylene (50 ml) was heated at reflux for 3 days with a Dean-Stark trap fitted. The solvent was removed in vacuo and dichloromethane (50 ml) was added to the residue. The mixture was stirred, filtered from a white solid, and the filtrate was evaporated in vacuo. The residue was purified by flash chromatography (silica gel, 10–20% EtOAc/CH$_2$Cl$_2$) to give 2.18 g (64%) of a partly separated mixture of the 9,9-dimethyl isomer and the required product. $^1$H NMR (250 MHz, CDCl$_3$) δ 1.10 (6H, s), 1.72 (2H, t, J=6.5 Hz), 2.56 (2H, m), 3.26 (2H, m), 7.51–7.60 (3H, m), 8.42–8.47 (2H, m); MS (ES) m/e 315/313 [M+H]$^+$.

g) 8,8-Dimethyl-3-phenyl-6-(2-pyridyl)methyloxy-7,8,9,10-tetrahydro-1,2,4-triazolo[3,4-a]phthalazine To a stirred mixture of sodium hydride (60% dispersion in oil, 40.4 mg, 1.01 mmol) in anhydrous DMF (5 ml), under nitrogen, was added 2-pyridylcarbinol (95 ml, 0.985 mmol) and the mixture was stirred at room temperature for 1 h. This was then added by cannula to a stirred mixture of the product from Example 14, Step f) (0.205 g, 0.655 mmol) in anhydrous DMF (5 ml) and the mixture was stirred for another 28 h, adding more sodium hydride (8.4 and 7.6 mg) after 18 and 25 h. The mixture was partitioned between EtOAc (50 ml) and water (50 ml) and the aqueous layer was extracted further with EtOAc (2×50 ml). The combined organic extracts were dried (Na$_2$SO$_4$) and evaporated in vacuo. The residue was purified by flash chromatography (silica gel, 2% MeOH/CH$_2$Cl$_2$ then alumina, 80% EtOAc/CH$_2$Cl$_2$) to give 71.4 mg (28%) of the required product; mp 133–136° C. (CH$_2$Cl$_2$—EtOAc-hexane); $^1$H NMR (360 MHz, $d_6$-DMSO) 1.10 (6H, s), 1.71 (2H, t, J=6.5 Hz), 2.53 (2H, m), 3.20 (2H, m), 5.59 (2H, s), 7.31 (1H, m), 7.47–7.54 (4H, m), 7.80 (1H, dd, J=7.8 and 1.7 Hz), 8.37 (2H, dd, J=8.0 and 1.3 Hz), 8.67 (1H, m); MS (ES) m/e 386 M+H]$^+$. Anal. found C, 71.41; H, 6.12; N, 17.99. C$_{23}$H$_{23}$N$_5$O requires C, 71.67; H, 6.01; N, 18.17%.

EXAMPLE 15

3-Phenyl-7-(piperidin-1-yl)-6-(pyridin-2-ylmethoxy)-1,2,4-triazolo[4,3-b]pyridazine, 0.45 Hydrate a) 4Bromo-1,2-dihydropyridazine-3,6-dione A mixture of bromomaleic anhydride (50 g, 283 mmol) and sodium acetate (76.5 g, 562 mmol) in 40% acetic acid/water (750 ml) was treated with hydrazine monohydrate (16.5 ml, 339 mmol) at room temperature under nitrogen. The brown solution was stirred and heated at 100° C. for 18 hours. Upon cooling the mixture was poured into water (1 l) and extracted with ethyl acetate (6×500 ml). The combined extracts were dried (MgSO$_4$), filtered and evaporated to afford the title compound (20 g, 37%) as an orange solid. $^1$H NMR (250 MHz, $d_6$-DMSO) δ 7.68 (1H, br s). MS (ES$^+$) m/e 193 [MH]$^+$, 191 [MH]$^+$. This material was used without further purification.

b) 4-Bromo-3,6-dichloropyridazine

A solution of 4-bromo-1,2-dihydropyridazine-3,6-dione (10 g, 52 mmol) in phosphorus oxychloride (100 ml) was stirred and heated at 100° C. under nitrogen for 16 hours. Upon cooling the excess phosphorus oxychloride was removed in vacuo. The residue was azeotroped with toluene (×2), then taken up in dichloromethane/water. The mixture was carefully basified with sodium hydrogen carbonate (solid). It was necessary to further dilute the mixture to get two clear layers. The two layers were separated and the aqueous was extracted with dichloromethane (×3). The combined extracts were dried (Na$_2$SO$_4$), filtered and evaporated. The residue was purified by chromatography on silica gel, eluting with dichloromethane to afford the title compound (5.0 g, 42%) as a colourless solid. $^1$H NMR (250 MHz, CDCl$_3$) δ 7.68 (1H, br s). MS (ES$^+$) m/e 230 [MH]$^+$, 228 [MH]$^+$.

c) 3,6-Dichloro-4-piperidin-1-yl)pyridazine

Piperidine (475 ml, 4.8 mmol) was added to a stirred solution/suspension of 4-bromo-3,6-dichloropyridazine (1.0 g, 4.4 mmol) and potassium carbonate (1.2 g, 8.7 mmol) in dry DMF (40 ml) at room temperature under nitrogen. The mixture was stirred at room temperature for 16 hours, then at 60° C. for 3 hours. The reaction was poured into water (250 ml). The aqueous was extracted with ethyl acetate (×3). The combined extracts were dried (MgSO$_4$), filtered and evaporated. The residue was purified by chromatography on silica gel, eluting with 0.5% methanol/dichloromethane to afford the title compound (1.0 g, 98%) as a colourless oil. $^1$H NMR (250 MHz, CDCl$_3$) δ 1.63–1.81 (6H, m), 3.24–3.29 (4H, m), 6.84 (1H, s). MS (ES$^+$) m/e 234 [MH]$^+$, 232 [MH]$^+$.

d) 6-Chloro-3-phenyl-7-(piperidin-1-yl)-1,2,4-triazolo[4,3-b]pyridazine

A mixture of 3,6-dichloro-4-(piperidin-1-yl)pyridazine (0.55 g, 2.4 mmol), benzoyl hydrazine (370 mg, 2.7 mmol), triethylamine (375 ml, 2.7 mmol) and p-toluenesulphonic acid monohydrate (510 mg, 2.7 mmol) in xylene (mixture of isomers, 10 ml) was stirred and heated at reflux under nitrogen for 24 hours. Upon cooling the xylene was removed in vacuo and the residue was partitioned between dichloromethane and water. The aqueous was further extracted with dichloromethane (×3). The combined extracts were dried (Na$_2$SO$_4$), filtered and evaporated. The residue was purified by chromatography on silica gel, eluting with 30% ethyl acetate/dichloromethane to afford the undesired regioisomer (less polar) (177 mg, 23%) and the title compound (383 mg, 50%) (more polar). Data for the title compound: $^1$H NMR (250 MHz, CDCl$_3$) δ 1.62–1.86 (6H, m), 3.09–3.13 (4H, m), 7.42 (1H, s), 7.50–7.60 (3H, m), 8.40–8.44 (2H, m).

e) 3-Phenyl-7-(piperidin-1-yl)-6-(pyridin-2-ylmethoxy)-1,2,4-triazolo[4,3-b]-pyridazine, 0.45 Hydrate Sodium hydride (60% dispersion in oil, 39 mg, 0.96 mmol) was added to a solution of 2-pyridyl carbinol (104 mg, 0.96 mmol) in dry DMF (10 ml) at room temperature under nitrogen. After 1 hour at room temperature a solution of 6-chloro-3-phenyl-7-(piperidin-1-yl)-1,2,4-triazolo[4,3-b]pyridazine (200 mg, 0.64 mmol) in dry DMF (10 ml) was added via syringe. The mixture was stirred at room temperature for 16 hours. The DMF was then removed in vacuo and the residue was partitioned between dichloromethane and water. The aqueous was further extracted with dichloromethane (2×100 ml). The combined extracts were dried ($Na_2SO_4$), filtered and evaporated. The residue (248 mg) was purified by crystallisation from ethyl acetate/hexane (×2) to afford the title compound (130 mg, 53%). $^1$H NMR (250 MHz, $CDCl_3$) δ 1.64–1.86 (6H, m), 3.20–3.26 (4H, m), 5.63 (2H, br s), 7.22–7.32 (2H, m), 7.42–7.56 (4H, m), 7.76 (1H, td, J=7.7, 1.6 Hz), 8.31–8.35 (2H, m), 8.66 (1H, br s). (Regiochemistry was established using nOe data). MS ($ES^+$) m/e 387 $[MH]^+$. Anal. Found C, 66.97; H, 5.85; N, 21.30. $C_{22}H_{22}N_6O.0.45\ H_2O$ requires C, 67.08; H, 5.63; N, 20.96%.

EXAMPLE 16

3-Phenyl-7-(pyridin-4-yl)-6-(pyridin-2-ylmethoxy)-1,2,4-triazolo[4,3-b]pyridazine, 0.5 Hydrate a) 3,6-Dichloro-4-(pyridin-4-yl)pyridazine A mixture of 4-bromo-1,2-dihydropyridazine-3,6-dione (see Example 15, Step a) (530 mg, 28 mmol) and 4-pyridyl boronic acid, di-lithium salt (500 mg, 3.7 mmol) and sodium carbonate (800 mg, 7.6 mmol) in 1,2-dimethoxyethane (20 ml) was deoxygenated by three evacuate/fill with nitrogen cycles. Tetrakis(triphenylphosphine)palladium(0) (350 mg, 0.3 mmol) was then added and the reaction mixture was deoxygenated again with another three evacuate/fill with nitrogen cycles. The mixture was then stirred and heated at reflux under nitrogen and protected from light for 16 hours. Upon cooling the volatiles were removed in vacuo. The residue was used without further purification.

The solid from above was taken up in phosphorus oxychloride (10 ml). The dark suspension was heated at reflux for 20 hours. Upon cooling the volatiles were removed in vacuo. The residue was azeotroped with toluene (×2), then partitioned between dichloromethane and water. The mixture was cautiously basified with solid sodium carbonate. The two layers were separated (a precipitate forms which may be removed by filtration through celite). The aqueous was further extracted with dichloromethane (×3). The combined extracts were dried ($MgSO_4$), filtered and evaporated. The residue was purified by chromatography on silica gel, eluting with 3% methanol/dichloromethane to afford the title compound (240 mg, 38% over the two steps) as a pale yellow solid. $^1$H NMR (250 MHz, $d_6$-DMSO) δ 7.77–7.79 (2H, m), 8.37 (1H, s), 8.90–8.93 (2H, m). MS ($ES^+$) m/e 226 $[MH]^+$, 228 $[MH]^+$.

b) 6-Chloro-3-phenyl-7-(pyridin-4-yl)-1,2,4-triazolo[4,3-b]pyridazine

A mixture of 3,6-dichloro-4-(pyridin-4-yl)pyridazine (390 mg, 1.7 mmol), benzoyl hydrazine (260 mg, 1.9 mmol), triethylamine (270 ml, 1.9 mmol) and p-toluenesulphonic acid (32 mg, 0.2 mmol) in xylene (mixture of isomers) (5 ml) was stirred and heated at reflux under nitrogen for 20 hours. The mixture was partitioned between dichloromethane and saturated aqueous potassium carbonate. The aqueous was further extracted with dichloromethane (×3). The combined extracts were dried (sodium sulphate), filtered and evaporated. The residue was purified by chromatography on silica gel eluting with 3% methanol/dichloromethane to afford the title compound (218 mg, 42%) as a pale yellow solid. $^1$H NMR (360 MHz, $d_6$-DMSO) δ 7.60–7.69 (5H, m), 8.36–8.38 (2H, m), 8.72 (1H, s), 8.78–8.80 (2H, m). MS ($ES^+$) m/e 308 $[MH]^+$, 310 $[MH]^+$.

c) 3-Phenyl-7-(pyridin-4-yl)-6-(pyridin-2-ylmethoxy)-1,2,4-triazolo[4,3-b]pyridazine, 0.5 Hydrate 2-Pyridylcarbinol (105 ml, 1.1 mmol) was added to a stirred suspension of sodium hydride (60% dispersion in oil, 40 mg, 1.0 mmol) in dry DMF (10 ml) at room temperature under nitrogen. After 1 hour a solution of the 6-chloro-3-phenyl-7-(pyridin-4-yl)-1,2,4-triazolo[4,3-b]pyridazine (200 mg, 0.65 mmol) in dry DMF (10+5 ml) was added. The solution was stirred at room temperature for 16 hours, then poured into water (100 ml). The aqueous was extracted with ethyl acetate (5×100 ml). The combined extracts were dried ($Na_2SO_4$), filtered and evaporated. The residue was triturated with ethyl acetate (20 ml) at room temperature. The remaining solid (170 mg) was recrystallised from hot ethyl acetate to afford the title compound (120 mg, 49%) as a colourless solid, m.p.=215° C. dec. $^1$H NMR (360 MHz, $d_6$-DMSO) δ 5.76 (2H, s), 7.47–7.50 (1H, m), 7.67–7.72 (4H, m), 7.97–8.02 (3H, m), 8.38–8.42 (2H, m), 8.72–8.78 (2H, m), 8.87–8.89 (2H, m). MS ($ES^+$) 381 $[MH]^+$. Anal. Found C, 68.21; H, 4.10; N, 21.34. $C_{22}H_{16}N_6O.0.5\ H_2O$ requires C, 67.86; H, 4.40; N, 21.58%.

EXAMPLES 17 and 18

3-Phenyl-5-(pyridin-2-ylmethoxy)-6,7,8,9-tetrahydro-1,2,3a,4,8-pentaazacyclopenta[α]naphthalene 0.35 Hydrate and 3-Phenyl-5-(pyridin-2-ylmethoxy)-6,7,8,9-tetrahydro-1,2,3a,4,7-pentaazacyclopenta[α]naphthalene 0.75 Hydrate a) 3-Phenyl-5-(pyridin-2-ylmethoxy)-6,7,8,9-tetrahydro-1,2,3a,4,8-pentaazacyclopenta[α]naphthalene and 3-Phenyl-5-(pyridin-2-ylmethoxy)-6,7,8,9-tetrahydro-1,2,3a,4,7-pentaazacyclopenta[α]naphthalene A mixture of 3-phenyl-5-(pyridin-2-ylmethoxy)-1,2,3a,4,7-pentaazacyclopenta[α]naphthalene and 3-phenyl-5-pyridin-2-ylmethoxy)-1,2,3a,4,8-pentaazacyclopenta[α]naphthalene (see Examples 10 and 11), 2N HCl (1.0 ml, 2 mmol) in methanol (140 ml) was hydrogenated over platinum oxide (140 mg) at 30 psi for 45 minutes at room temperature. The catalyst was removed by filtration through celite, washing with methanol. The filtrate was evaporated and the residue was purified by chromatography on silica gel eluting with dichloromethane/methanol/ammonia—80:8:1 to afford the title amines (465 mg, 65%) as a yellow solid. The mixture was inseparable by flash chromatography. The two isomers were separated using the protocol described in Steps b), c) and d) below.

b) 3-Phenyl-5-(pyridin-2-ylmethoxy)-6,9-dihydro-7H-1,2,3a,4,8-pentaazacyclopenta[α]naphthalene-8-carboxylic Acid tert-butyl Ester and 3-Phenyl-5-(pyridin-2-ylmethoxy)-8,9-dihydro-6H-1,2,3a,4,7-pentaazacyclopenta[α]naphthalene-7-carboxylic Acid tert-butyl Ester Di-tert-butyl dicarbonate (700 mg, 3.2 mmol) was added to a stirred solution of a mixture of 3-phenyl-5-pyridin-2-ylmethoxy)-6,7,8,9-tetrahydro-1,2,3a,4,8-pentaazacyclopenta[α]naphthalene and 3-phenyl-5-(pyridin-2-ylmethoxy)-6,7,8,9-tetrahydro-1,2,3a,4,7-pentaazacyclopenta[α]naphthalene (555 mg, 1.55 mmol) and triethylamine (550 ml, 3.9 mmol) and 4-dimethylaminopyridine (20 mg, 0.16 mmol) in dry. dichloromethane at 0° C. under nitrogen. The reaction was allowed to come to room temperature over 1 hour, then stirred at this temperature for 16 hours. The mixture was partitioned between dichloromethane and saturated aqueous sodium hydrogen carbonate. The aqueous was further extracted with dichloromethane (×2). The combined extracts were dried ($Na_2SO_4$), filtered and evaporated. The residue was purified by chromatography on silica gel, eluting with 5% methanol/dichloromethane to afford the title compounds as a mixture (610 mg, 86%) as a colourless solid.

The two components could be separated by medium pressure liquid chromatography on silica, eluting with ethyl acetate to give:

less polar: 3-Phenyl-5-(pyridin-2-ylmethoxy)-6,9-dihydro-7H-1,2,3a,4,8-pentaazacyclopenta[α]naphthalene-8-carboxylic acid tert-butyl ester (274 mg). A sample was recrystallised from ethyl acetate/hexane: m.p.=170–173° C. $^1$H NMR (250 MHz, $CDCl_3$) δ 1.52 (9H, s), 2.84–2.90 (2H, m), 3.81 (2H, t, J=5.8 Hz), 5.00 (2H, br s), 5.60 (2H, s), 7.32 (1H, dd, J=7.5, 4.9 Hz), 7.49–7.55 (4H, m), 7.79 (1H, td, J=7.7, 1.8 Hz), 8.34–8.38 (2H, m), 8.64–8.69 (1H, m). MS ($ES^+$) m/e 459 [$MH$]$^+$. Anal. Found C, 61.83; H, 5.60; N, 17.52. $C_{25}H_{26}N_6O_3$.1.4 $H_2O$ requires C, 62.07; H, 6.00; N, 17.37%.

more polar: 3-Phenyl-5-(pyridin-2-ylmethoxy)-8,9-dihydro-6H-1,2,3a,4,7-pentaazacyclopenta[α]naphthalene-7-carboxylic acid tert-butyl ester (227 mg). A sample was recrystallised from ethyl acetate/hexane: m.p.=166–168° C. $^1$H NMR (250 MHz, $CDCl_3$) δ 1.53 (9H, s), 3.20–3.26 (2H, m), 3.82 (2H, t, J=5.8 Hz), 4.62 (2H, br s), 5.61 (2H, s), 7.31 (1H, dd, J=7.0, 5.5 Hz), 7.48–7.56 (4H, m), 7.79 (1H, td, J=7.7, 1.7 Hz), 8.35–8.38 (2H, m), 8.64–8.68 (1H, m). MS ($ES^+$) m/e 459 [$MH$]$^+$. Anal Found C, 65.76; H, 5.81; N, 18.25. $C_{25}H_{26}N_6O_3$ requires C, 65.49; H, 5.71; N. 18.32%.

c) 3-Phenyl-5-(pyridin-2-ylmethoxy-6,7,8,9-tetrahydro-1,2,3a,4,8-pentaazacyclopenta[α]naphthalene 0.35 Hydrate Trifluoroacetic acid (3 ml) was added to a solution of 3-phenyl-5-(pyridin-2-ylmethoxy)-6,9-dihydro-7H-1,2,3a,4,8-pentaazacyclopenta[α]naphthalene-8-carboxylic acid tert-butyl ester (255 mg, 0.56 mmol) in dry dichloromethane (3 ml) at 0° C. under nitrogen. After 1 hour the volatiles were removed in vacuo and the residue was partitioned between dichloromethane and saturated aqueous potassium carbonate. The aqueous was further extracted with dichloromethane (×2). The combined extracts were dried ($Na_2SO_4$), filtered and evaporated. The residue was purified by chromatography on silica gel, eluting with dichloromethane/methanol/ammonia (60:8:1→50:8:1) to afford the title amine (176 mg, 88%) as a colourless solid, m.p.=175–178° C. $^1$H NMR (360 MHz, $d_6$-DMSO) δ 2.62–2.66 (2H, m), 3.08 (2H, t, J=5.7 Hz), 4.13 (2H, s), 5.56 (2H, s), 7.37 (1H, dd, J=6.9, 5.3 Hz), 7.50–7.59 (4H, m), 7.87 (1H, td, J=7.7, 1.7), 8.22–8.25 (2H, m), 8.62–8.64 (1H, m). MS ($ES^+$) m/e 359 [$MH$]$^+$. Anal. Found C, 66.14; H, 4.98; N, 22.71. $C_{20}H_{18}N_6O$.0.35 $H_2O$ requires C, 65.86; H, 5.17; N, 23.04%.

d) 3-Phenyl-5-(pyridin-2-ylmethoxy)-6,7,8,9-tetrahydro-1,2,3a,4,7-pentaazacyclopenta[α]naphthalene 0.75 Hydrate Trifluoroacetic acid (3 ml) was added to a solution of 3-phenyl-5-(pyridin-2-ylmethoxy)-8,9-dihydro-6H-1,2,3a,4,7-pentaazacyclopenta[α]-naphthalene-7-carboxylic acid tert-butyl ester (217 mg, 0.47 mmol) in dry dichloromethane (3 ml) at 0° C. under nitrogen. After 1 hour the volatiles were removed in vacuo and the residue was partitioned between dichloromethane and saturated aqueous potassium carbonate. The aqueous was further extracted with dichloromethane (×2). The combined extracts were dried ($Na_2SO_4$), filtered and evaporated. The residue was purified by chromatography on silica gel, eluting with dichloromethane/methanol/ammonia (60:8:1) to afford the title amine (162 mg, 96%) as a colourless solid, m.p.= 157–159° C. $^1$H NMR (360 MHz, $d_6$-DMSO) δ2.92–2.96 (2H, m), 3.07 (2H, t, J=5.8 Hz), 3.84 (2H, s), 5.56 (2H, s), 7.36 (1H, dd, J=6.7, 4.9 Hz), 7.52–7.60 (4H, m), 7.87 (1H, td, J=7.8, 1.7), 8.23 (2H, dd, J=6.3, 1.9 Hz), 8.62–8.64 (1H, m). MS ($ES^+$) m/e 359 [$MH$]$^+$. Anal. Found C, 64.93; H, 5.31; N, 22.30. $C_{20}H_{18}N_6O$.0.75 $H_2O$ requires C, 64.59; H, 5.29; N, 22.60%.

EXAMPLE 19

7-Methyl-3-phenyl-5-(pyridin-2-ylmethoxy)-6,7,8,9-tetrahydro-1,2,3a,4,7-pentaazacyclopenta[α]naphthalene Sodium cyanoborohydride (55 mg, 0.88 mmol) was added to a stirred solution of 3-phenyl-5-(pyridin-2-ylmethoxy)-6,7,8,9-tetrahydro-1,2,3a,4,7-pentaazacyclopenta[α]naphthalene (126 mg, 0.35 mmol) and acetic acid (100 ml, 1.75 mmol) in dry methanol (10 ml) at room temperature under nitrogen. The mixture was cooled to 0° C. and aqueous formaldehyde (35 ml, 0.48 mmol) was added. The reaction was stirred at 0° C. for 30 minutes, then at room temperature for 5 hours. The reaction was quenched with saturated aqueous potassium carbonate (5 ml). The volatiles were removed in vacuo, then the residue was partitioned between dichloromethane and water. The aqueous was further extracted with dichloromethane (×3). The combined extracts were dried ($Na_2SO_4$), filtered and evaporated. The residue was purified by chromatography on silica gel, eluting with dichloromethane/methanol/ammonia (95:5:0.5→92:7:1) to afford the title amine (130 mg, 100%) as a colourless solid. This material was recrystallised from ethyl acetate: m.p. 186–188° C. $^1$H NMR (360 MHz, $CDCl_3$) δ 2.57 (3H, s), 2.84 (2H, t, J=5.7 Hz), 3.27–3.31 (2H, m), 3.61 (2H, br s), 5.59 (2H, s), 7.28 (1H, dd, J=6.7, 4.9 Hz), 7.45–7.52 (4H, m), 7.75 (1H, td, J=7.8, 1.8 Hz), 8.35 (2H, dd, J=8.3, 1.8 Hz), 8.64–8.68 (1H, m). MS ($ES^+$) m/e 373 [$MH$]$^+$. Anal. Found C, 67.95; H, 5.57; N, 22.43. $C_{21}H_{20}N_6O$ requires C, 67.73; H, 5.41; N, 22.57%.

EXAMPLE 20

3-Phenyl-6-(pyridin-2-ylmethoxy)-7-(thiophen-2-yl)-1,2,4-triazolo[4,3-b]pyridazine 0.45 Hydrate This compound was prepared using the procedures described in Example 16 Steps a), b) and c) except 2-thiophene boronic acid was used instead of 4-pyridyl boronic acid, dilithium salt in Step a) and 1.1 equivalents of p-toluenesulphonic acid was used in Step b) instead of 0.1 equivalents.

Data for the title compound: $^1$H NMR (250 MHz, $CDCl_3$) δ 5.74 (2H, s), 7.18 (1H, dd, J=5.2, 3.8 Hz), 7.28–7.34 (1H, m), 7.50–7.58 (5H, m), 7.74–7.77 (2H, m), 8.28 (1H, s), 8.38–8.42 (2H, m), 8.68–8.72 (1H, m). MS ($ES^+$) m/e 386 [$MH$]$^+$. Anal Found C, 64.46; H, 4.16; N, 17.63. $C_{21}H_{15}N_5OS$. 0.45 $H_2O$. 0.05 ($C_4H_{10}O$) requires C, 64.10; H, 3.82; N, 17.35%.

EXAMPLE 21

3-Phenyl-6-(pyridin-2-ylmethoxy)-7-(thiophen-3-yl)-1,2,4-triazolo[4,3-b]pyridazine 0.2 Hydrate This compound was prepared using the procedures described in Example 16 Steps a), b) and c) except 3-thiophene boronic acid was used instead of 4-pyridyl boronic acid, dilithium salt in Step a) and 1.1 equivalents of p-toluenesulphonic acid was used in Step b) instead of 0.1 equivalents.

Data for the title compound: $^1$H NMR (250 MHz, CDCl$_3$) δ 5.70 (2H, s), 7.26–7.32 (1H, m), 7.44–7.58 (6H, m), 7.70–7.80 (1H, m), 7.96 (1H, br s), 8.20 (1H, s), 8.40–8.43 (2H, m), 8.58 (1H. br d, J=5.6 Hz). MS (ES$^+$) m/e 386 [MH]$^+$. Anal. Found C, 64.83; H, 4.11; N, 17.78. C$_{21}$H$_{15}$N$_5$OS.0.2 H$_2$O. 0.07 (C$_4$H$_{10}$O) requires C, 65.04; H, 3.69; N, 17.38%.

EXAMPLE 22

(±)-3-Phenyl-6-(2-pyridyl)methyloxy-7,8,9,10-tetrahydro-(7,10-ethano)-1,2,4-triazolo[3,4-a]phthalazine This compound was prepared using the procedures described in Example 1 Steps a), b), c) and d) with bicyclo[3.2.2]non-6-ene-6,7-dicarboxylic acid anhydride (*J. Chem. Soc.*, 2524, 1970) being used instead of bicyclo[2.2.2]oct-2-ene-2,3-dicarboxylic acid anhydride in Step a). Data for the title compound: m.p.=187° C. $^1$H NMR (360 MHz, CDCl$_3$) δ 1.42–2.19 (10H, m), 3.56 (1H, s), 3.98 (1H, s), 5.60 (2H, s), 7.28 (1H, m), 7.48 (4H, m), 7.74 (1H, m), 8.38 (2H, d, J=7.8 Hz), 8.66 (1H, m); MS (ES$^+$) m/e 398 [MH]$^+$. Anal. Found C, 72.93; H, 5.85; N, 17.64. C$_{24}$H$_{23}$N$_5$O requires C, 72.52; H, 5.83; N, 17.62%.

EXAMPLE 23

3-(4-Methyl)phenyl-6-(2-pyridyl)methyloxy-7,8,9,10-tetrahydro-(7,10-ethano)-1,2,4-triazolo[3,4-a]phthalazine This compound was prepared using the procedures described in Example 1 Steps a), b), c) and d) with 4-toluic hydrazide being used instead of benzoyl hydrazine in Step c). Data for the title compound: m.p.=167° C. $^1$H NMR (360 MHz, DMSO) δ 1.40 (4H, m), 1.90 (4H, m), 2.40 (3H, s), 3.48 (1H, s), 3.74 (1H, s), 5.57 (2H, s), 7.36 (3H, m), 7.57 (1H, d, J=7.8 Hz), 7.87 (1H, ddd, J=7.8, 7.8 & 1.7 Hz), 8.14 (2H, d, J=8.2 Hz), 8.68 (1H, m); MS (ES$^+$) m/e 398 [MH]$^+$. Anal. Found C, 72.37; H, 5.73; N, 17.62. C$_{24}$H$_{23}$N$_5$O requires C, 72.52; H. 5.83; N, 17.62%.

EXAMPLE 24

3-(3-Methoxy)phenyl-6-(2-pyridyl)methyloxy-7,8,9,10-tetrahydro-(7,10-ethano)-1,2,4-triazolo[3,4-a]phthalazine This compound was prepared using the procedures described in Example 1 Steps a), b), c) and d) with 3-methoxybenzhydrazide being used instead of benzoyl hydrazine in Step c). Data for the title compound: m.p.=185° C. $^1$H NMR (360 MHz, DMSO) δ 1.40 (4H, m), 1.91 (4H, m), 3.49 (1H, s), 3.76 (1H, s), 3.85 (3H, s), 5.59 (2H, s), 7.08 (1H, m), 7.37 (1H, m), 7.47 (1H, t, J=8.0 Hz), 7.59 (1H, d, J=7.9 Hz), 7.88 (2H, m), 7.96 (1H, m), 8.64 (1H, m); MS (ES$^+$) m/e 414 [MH]$^+$. Anal. Found C, 69.36; H, 5.65; N, 16.58. C$_{24}$H$_{23}$N$_5$O$_2$ requires C, 69.72; H, 5.61; N, 16.94%.

EXAMPLE 25

3-(2-Fluoro)phenyl-6-(2-pyridyl)methyloxy-7,8,9,10-tetrahydro-(7,10-ethano)-1,2,4-triazolo[3,4-a]phthalazine This compound was prepared using the procedures described in Example 1 Steps a), b), c) and d) with 2-fluorobenzhydrazide being used instead of benzoyl hydrazine in Step c). Data for the title compound: m.p.=159° C. $^1$H NMR (360 MHz, CDCl$_3$) δ 1.51 (4H, m), 1.92 (4H, m), 3.56 (1H, s), 3.98 (1H, s), 5.46 (2H, s), 7.26 (3H, m), 7.44 (1H, d, J=7.8 Hz), 7.54 (1H, m), 7.71 (1H, m), 7.80 (1H, m), 8.63 (1H, m); MS (ES$^+$) m/e 402 [MH]$^+$. Anal. Found C, 68.81; H, 4.81; N, 17.17. C$_{23}$H$_{20}$FN$_5$O requires C, 68.81; H, 5.02; N, 17.45%.

EXAMPLE 26

3-(3-Pyridyl)-6-(2-pyridyl)methyloxy-7,8,9,10-tetrahydro-(7,10-ethano)-1,2,4-triazolo[3,4-a]phthalazine This compound was prepared using the procedures described in Example 1 Steps a), b), c) and d) with nicotinic acid hydrazide being used instead of benzoyl hydrazine in Step c). Data for the title compound: m.p.=198° C. $^1$H NMR (360 MHz, CDCl$_3$) δ 1.49 (4H, m), 1.96 (4H, m), 3.59 (1H, s), 3.99 (1H, s), 5.61 (2H, s), 7.28 (1H, m), 7.49 (2H, m), 7.78 (1H, m), 8.72 (3H, m), 9.69 (1H, s); MS (ES$^+$) m/e 385 [MH]$^+$. Anal. Found C, 67.56; H, 5.66; N, 19.51. C$_{22}$H$_{20}$N$_6$O requires C, 67.27; H, 5.65; N, 19.61%.

EXAMPLE 27

3-Cyclopropyl-6-(2-pyridyl)methyloxy-7,8,9,10-tetrahydro-(7,10-ethano)-1,2,4-triazolo[3,4-a]phthalazine This compound was prepared using the procedures described in Example 1 Steps a), b), c) and d) with cyclopropanecarboxylic acid hydrazide being used instead of benzoyl hydrazine in Step c). Data for the title compound: m.p.=160° C. $^1$H NMR (360 MHz, CDCl$_3$) δ 1.09 (2H, m), 1.31 (2H, m), 1.44 (4H, m), 1.89 (4H, m), 2.38 (1H, m), 3.52 (1H, s), 3.90 (1H, s), 5.57 (2H, s), 7.28 (1H, m), 7.52 (1H, d, J=7.9 Hz), 7.76 (1H, m), 8.64 (1H, m); MS (ES$^+$) m/e 348 [MH]$^+$. Anal. Found C, 69.12; H, 5.85; N, 20.19. C$_{20}$H$_{21}$N$_5$O requires C, 69.14; H, 6.09; N, 20.16%.

EXAMPLE 28

6-((6-Methyl)-2-pyridyl)methyloxy-3-phenyl-7,8,9,10-tetrahydro-(7,10-ethano)-1,2,4-triazolo[3,4-a]phthalazine Hydrochloride This compound was prepared using the procedures described in Example 1 Steps a), b), c) and d) with 6-methyl-2-hydroxymethyl pyridine being used instead of 2-pyridylcarbinol in Step d). An additional step at the end of the synthesis was to dissolve the compound in a solution of hydrogen chloride in methanol before evaporation and recrystallisation. Data for the title compound: m.p.=255° C. $^1$H NMR (360 MHz, DMSO) δ 1.42 (4H, m), 1.91 (4H , m), 2.71 (3H, s), 3.51 (1H, s), 3.78 (1H, s), 5.80 (2H, s, 7.59 (4H, m), 7.80 (1H, d, J=7.8 Hz), 8.22 (1H, m), 8.30 (2H, d, J=7.9 Hz); MS (ES$^+$) m/e 398 [MH]$^+$. Anal. Found C, 61.67; H, 5.36; N, 14.74. C$_{24}$H$_{23}$N$_5$O.HCl requires C, 61.28; H, 5.36; N, 14.89%.

EXAMPLE 29

6-((3-Methyl)-2-pyridyl)methyloxy-3-phenyl-7,8,9,10-tetrahydro-(7,10-ethano)-1,2,4-triazolo[3,4a]phthalazine This compound was prepared using the procedures described in Example 1 Steps a), b), c) and d) with 3-methyl- 2-hydroxymethyl pyridine being used instead of 2-pyridylcarbinol in Step d); Data for the title compound. m.p.=245° C. $^1$H NMR (360 MHz, CDCl$_3$) δ 1.48 (4H, m), 1.88 (4H, m), 2.43 (3H, s), 3.47 (1H, s), 3.98 (1H, s), 5.63 (2H, s), 7.26 (1H, m), 7.49 (3H, m), 7.60 (1H, d, J=7.5 Hz), 8.43 (2H, d, J=7.8 Hz), 8.48 (1H, d, J=7.1Hz); MS (ES$^+$) m/e 398 [MH]$^+$. Anal. Found C, 72.09; H, 5.76; N, 17.79. C$_{24}$H$_{23}$N$_5$O.0.1H$_2$O requires C, 72.20; H, 6.86; N, 17.54%.

EXAMPLE 30

6-((4Methyl)-2-pyridyl)methyloxy-3-phenyl-7,8,9, 10-tetrahydro-(7,10-ethano)-1,2,4-triazolo[3,4-a] phthalazine This compound was prepared using the procedures described in Example 1 Steps a), b), c) and d) with 4-methyl-2-hydroxymethyl pyridine being used instead of 2-pyridylcarbinol in Step d). Data for the title compound: m.p.=190° C. $^1$H NMR (360 MHz, CDCl$_3$) δ 1.49 (4H, m), 1.93 (4H, m), 2.39 (3H, s), 3.58 (1H, s), 3.99 (1H, s), 6.59 (2H, s), 7.13 (1H, d, J=7.3 Hz), 7.35 (1H, s), 7.50 (3H, m), 8.41 (2H, d, J=7.8 Hz), 8.51 (1H, d, J=7.3 Hz); MS (ES$^+$) m/e 398 [MH]$^+$. Anal. Found C, 72.91; H, 5.78; N, 17.32. C$_{24}$H$_{23}$N$_5$O requires C, 72.52; H, 5.83; N, 17.62%.

EXAMPLE 31

6-((5-Methyl)-2-pyridyl)methyloxy-3-phenyl-7,8,9, 10-tetrahydro-(7,10-ethano)-1,2,4-triazolo[3,4-a] phthalazine This compound was prepared using the procedures described in Example 1 Steps a), b), c) and d) with 5-methyl-2-hydroxymethyl pyridine being used instead of 2-pyridylcarbinol in Step d). Data for the title compound: m.p.=205° C. $^1$H NMR (360 MHz, CDCl$_3$) δ 1.48 (4H, m), 1.92 (4H, m), 2.38 (3H, s), 3.56 (1H, s), 3.99 (1H, s), 5.58 (5H, s), 8.45 (3H, m); MS (ES$^+$) m/e 398 [MH]$^+$. Anal. Found C, 72.66; H, 5.72; N, 17.32. C$_{24}$H$_{23}$N$_5$O requires C, 72.52; H, 5.83; N, 17.62%.

EXAMPLE 32

3-Phenyl-6-(3-pyridyl)methyloxy-7,8,9,10-tetrahydro-(7,10-ethano)-1,2,4-triazolo[3,4-a] phthalazine This compound was prepared using the procedures described in Example 1 Steps a), b), c) and d) with 3-pyridylcarbinol being used instead of 2-pyridylcarbinol in Step d). Data for the title compound: m.p.=202° C. $^1$H NMR (360 MHz, DMSO) δ 1.39 (4H, m), 1.90 (4H, m), 3.40 (1H, s), 3.74 (1H, s), 5.68 (2H, s), 7.46 (1H, m), 7.56 (3H, m), 7.97 (1H, d, J=7.8 Hz), 8.36 (2H, d, J=7.9 Hz), 8.58 (1H, m), 8.77 (1H, m); MS (ES$^+$) m/e 384 [MH]$^+$. Anal. Found C, 72.70; H, 5.49; N, 18.19. C$_{24}$H$_{21}$N$_5$O requires C, 72.04; H, 5.52; N, 18.26%.

EXAMPLE 33

3-Phenyl-6-(4-pyridyl)methyloxy-7,8,9,10-tetrahydro-(7,10-ethano)-1,2,4-triazolo[3,4-a] phthalazine This compound was prepared using the procedures described in Example 1 Steps a), b), c) and d) with 4-pyridylcarbinol being used instead of 2-pyridylcarbinol in Step d). Data for the title compound: m.p.=205° C. $^1$H NMR (360 MHz, CDCl$_3$) δ 1.49 (4H, m), 1.95 (4H, m), 3.55 (1H, s), 3.99 (1H, s), 5.49 (2H, s), 7.41 (2H, d, J=6.0 Hz), 7.49 (3H, m), 8.32 (2H, d, J=7.8 Hz), 8.69 (2H, d, J=6.0 Hz); MS (ES$^+$) m/e 384 [MH]$^+$. Anal. Found C, 71.29; H, 5.16; N, 17.82. C$_{24}$H$_{21}$N$_5$O.0.1H$_2$O requires C, 71.70; H, 5.54; N, 18.18%.

EXAMPLE 34

3-Phenyl-6-(2-(1-methyl)imidazolyl)methyloxy-7,8, 9,10-tetrahydro-(7,10-ethano)-1,2,4-triazolo[3,4-a] phthalazine This compound was prepared using the procedures described in Example 1 Steps a), b), c) and d) with 1-methyl-2-hydroxymethylimidazole being used instead of 2-pyridylcarbinol in Step d). Data for the title compound: m.p.=274° C. $^1$H NMR (360 MHz, CD$_3$OD) δ 1.52 (4H, m), 2.03 (4H, m), 3.50 (1H, s), 3.82 (3H, s), 3.88 (1H, s), 5.64 (2H, s), 7.05 (1H, s), 7.23 (1H, s), 7.66 (3H, m), 8.41 (2H, d, J=7.8 Hz); MS (ES$^+$) m/e 387 [MH]$^+$. Anal. Found C, 68.20; H, 5.69; N, 21.77. C$_{22}$H$_{22}$N$_6$O requires C, 68.38; H, 5.74; N, 21.75%.

EXAMPLE 35

6-(3-Cyanophenyl)methyloxy-3-phenyl-7,8,9,10-tetrahydro-(7,10-ethano)-1,2,4-triazolo[3,4-a] phthalazine a) 6-Hydroxy-3-phenyl-7,8,9,10-tetrahydro-(7,10-ethano)-1,2,4-triazolo[3,4-a]phthalazine The product from Example 1 Step c) (3.0 g, 9.6 mmol) was dissolved in 10% aqueous 1,4-dioxan (100 ml) with sodium hydroxide solution (24 ml of 2 N, 5 molar equivs) and the reaction mixture was heated under reflux for 3 days. The organic solvent was removed by rotary evaporation and the residue was partitioned between water (250 ml) and diethyl ether (250 ml). The aqueous layer was separated and washed twice more with diethyl ether (100 ml), then treated with 5 N hydrochloric acid until a pH of 2 was attained. The solid which precipitated out of solution was collected by filtration to give the required product (2.7 g, m.p. ~300° C., dec.). $^1$H NMR (250 MHz, CDCl$_3$) δ 1.35 (4H, m), 2.00 (4H, m), 3.49 (1H, s), 3.84 (1H, s), 7.71 (3H, m), 8.54 (2H, d, J=7.8 Hz); MS (ES$^+$) m/e 293 [MH]$^+$. Anal. Found C, 69.33; H, 5.32; N, 19.17. C$_{17}$H$_{15}$N$_4$O requires C, 69.86; H, 5.19; N, 19.23%.

b) 6-(3-Cyanophenyl)methyloxy-3-phenyl-7,8,9,10-tetrahydro-(7,10-ethano)-1,2,4-triazolo[3,4-a]phthalazine The product from Example 35 Step a) (0.3 g, 1.02 mmol) was dissolved in dimethylformamide (40 ml) with 60% sodium hydride (0.049 g, 1.2 mol eq) and heated at 80° C. for 20 minutes. Then α-bromo-meta-toluonitrile (0.22 g, 1.1 mol eq) was added and heating continued for 14 h. Water was added until the solution became cloudy and the solid that was precipitated was collected by filtration then purified by chromatography on silica gel using 0–30% ethyl acetate in dichloromethane as eluent. The product was recrystallised from ethyl acetate/hexane to give the required compound (0.22 g). Data for the title compound: m.p.=216° C. $^1$H NMR (360 MHz, CDCl$_3$) δ 1.48 (4H, m), 1.93 (4H, m), 3.54 (1H, s), 3.98 (1H, s), 5.80 (2H, s), 7.42 (1H, d, J=3.2 Hz), 7.50 (3H, m), 7.86 (1H, d, J=3.2 Hz), 8.45 (2H, d, J=7.8 Hz); MS (ES$^+$) m/e 408 [MH]$^+$. Anal. Found C, 64.54; H, 4.98; N, 17.79. C$_{21}$H$_{19}$N$_5$OS requires C, 64.76; H, 4.92; N, 17.98%.

EXAMPLE 36

6-(1-(3,5-Dimethyl)pyrazolyl)methyloxy-3-phenyl-7,8,9,10-tetrahydro-(7,10-ethano)-1,2,4-triazolo[3,4-a]phthalazine This compound was prepared using the procedures described in Example 1 Steps a), b), c) and d) with 1-hydroxymethyl-3,5-dimethylpyrazole being used instead of 2-pyridylcarbinol in Step d). Data for the title compound: m.p.=210° C. $^1$H NMR (360 MHz, CDCl$_3$) δ 1.43 (4H, m), 1.89 (4H, m), 2.27 (3H, s), 2.32 (3H, s), 3.41 (1H, s), 3.96 (1H, s), 5.96 (1H, s), 6.27 (2H, s), 7.54 (3H, m), 8.51 (2H, d, J=7.8Hz); MS (ES$^+$) m/e 401 [MH]$^+$. Anal. Found C, 69.32; H, 6.07; N, 21.01. C$_{23}$H$_{24}$N$_6$O requires C, 68.98; H, 6.04; N, 20.99%.

EXAMPLE 37

6-(4-(2-Methyl)thiazolyl)methyloxy-3-phenyl-7,8,9, 10-tetrahydro-(7,10-ethano)-1,2,4-triazolo[3,4-a] phthalazine This compound was prepared using the procedure described in Example 35 Step b) with 4-chloromethyl-2-methylthiazole being used instead of α-bromo-meta-toluonitrile. Data for the title compound: m.p.=180° C. $^1$H NMR (360 MHz, CDCl$_3$) δ 1.47 (4H, m), 1.91 (4H, m), 2.76 (3H, s), 3.53 (1H, s), 4.00 (1H, s), 5.55 (2H, s), 7.26 (1H, s), 7.52 (3H, m), 8.48 (2H, d, J=7.8 Hz); MS (ES$^+$) m/e 404 [MH]$^+$. Anal. Found C, 65.82; H, 5.17; N, 17.25. C$_{24}$H$_{21}$N$_5$OS requires C, 65.49; H, 5.25; N, 17.36%.

EXAMPLE 38

3-Phenyl-6-(2-quinoxalinyl)methyloxy-7,8,9,10-tetrahydro-(7,10-ethano)-1,2,4-triazolo[3,4-a] phthalazine This compound was prepared using the procedure described in Example 35 Step b) with 2-chloromethylquinoxaline being used instead of α-bromo-meta-toluonitrile. Data for the title compound: m.p.=250° C. $^1$H NMR (360 MHz, DMSO) δ 1.43 (4H, m), 1.92 (4H, m), 3.54 (1H, s), 3.75 (1H, s), 5.88 (2H, s), 7.44 (3H, m), 7.89 (2H, m), 8.13 (4H, m), 9.18 (1H, s); MS (ES$^+$) m/e 435 [MH]$^+$. Anal. Found C, 71.15; H, 5.10; N, 18.66. C$_{26}$H$_{22}$N$_6$O.0.375 H$_2$O requires C, 70.77; H, 5.20; N, 19.05%.

EXAMPLE 39

3-Phenyl-6-(3-pyridazinyl)methyloxy-7,8,9,10-tetrahydro-(7,10-ethano)-1,2,4-triazolo[3,4-a] phthalazine This compound was prepared using the procedure described in Example 35 Step b) with 3-chloromethylpyridazine (prepared by the procedure of Jeronim et al., Chem. Ber., 1987, 120, 649–651) being used instead of α-bromo-meta-toluonitrile. 3-Chloromethylpyridazine is a particularly unstable reagent and appears to rapidly polymerise on heating, so the reaction was carried out immediately after formation of the alkylating agent. Data for the title compound: m.p=215° C. $^1$H NMR (360 MHz, CDCl$_3$) δ 1.49 (4H, m), 1.91 (4H, m), 3.54 (1H, s), 4.01 (1H, s), 5.85 (2H, s), 7.54 (4H, m), 7.71 (1H, dd, J=8.5 and 1.7 Hz), 8.36 (2H, d, J=7.8 Hz), 9.22 (1H, dd, J=4.9 and 1.7 Hz); MS (ES$^+$) m/e 385 [MH]$^+$. Anal. Found C, 68.60; H, 5.31; N, 21.65. C$_{22}$H$_{20}$N$_6$O requires C, 68.73; H, 5.24; N, 21.86%.

EXAMPLE 40

6-(1-Benzyl-2-imidazolyl)methyloxy-3-phenyl-7,8, 9,10-tetrahydro-(7,10-ethano)-1,2,4-triazolo[3,4-a] phthalazine This compound was prepared using the procedures described in Example 1 Steps a), b), c) and d) with 1-benzyl-2-(hydroxymethyl)imidazole (prepared according to the procedure of Birker, Godefroi, Helder and Reedijk, J. Am. Chem. Soc., 1982, 104, 7556) being used instead of 2-pyridylcarbinol in Step d). Data for the title compound: m.p.=205° C. $^1$H NMR (360 MHz, CDCl$_3$) δ 1.20 (2H, m), 1.43 (2H, m), 1.80 (4H, m), 3.11 (1H, t, J=2.8 Hz), 3.92 (1H, t, J=2.7 Hz), 5.24 (2H, s), 5.55 (2H, s), 7.03 (3H, m), 7.18 (1H, d, J=1.2 Hz), 7.28 (3H, m), 7.50 (3H, m), 8.43 (2H, m); MS (ES$^+$) m/e 463 [MH]$^+$. Anal. Found C, 71.49; H, 5.62; N, 17.82. C$_{28}$H$_{26}$N$_6$O.0.5H$_2$O requires C, 71.32; H, 5.77; N, 17.82%.

EXAMPLE 41

3-Phenyl-6-(isoquinolin-1-yl)methyloxy-7,8,9,10-tetrahydro-(7,10-ethano)-1,2,4-triazolo[3,4-a] phthalazine This compound was prepared using the procedure described in Example 35 Step b) with 1-chloromethylisoquinoline being used instead of α-bromo-meta-toluonitrile. Data for the title compound: m.p.=230° C. $^1$H NMR (360 MHz, CDCl$_3$) δ 1.45 (4H, m), 1.88 (4H, m), 3.45 (1H, s), 3.97 (1H, s), 6.09 (2H, s), 7.43 (3H, m), 7.71 (3H, m), 7.93 (1H, d, J=8.2 Hz), 8.24 (1H, d, J=8.4 Hz), 8.42 (2H, m), 8.58 (1H, d, J=6.2 Hz); MS (ES$^+$) m/e 434 [MH]$^+$. Anal. Found C, 75.04; H, 5.25; N, 16.40. C$_{27}$H$_{23}$N$_5$O requires C, 74.81; H, 5.35; N, 16.16%.

EXAMPLE 42

6-(1-Ethyl-2-imidazolyl)methyloxy-3-phenyl-7,8,9, 10-tetrahydro-(7,10-ethano)-1,2,4-triazolo[3,4-a] phthalazine This compound was prepared using the procedures described in Example 1 Steps a), b), c) and d) with 1-ethyl-2-(hydroxymethyl)imidazole (prepared according to the procedure of Tasaka, Teranishi, Matsushita, Tamura, Hayashi, Okanogi and Itoh, Chem. Pharm. Bull., 1994, 42, 85) being used instead of 2-pyridylcarbinol in Step d). Data for the title compound. m.p.=254° C. $^1$H NMR (500 MHz, DMSO) δ 1.34 (3H, t, J=7.2 Hz), 1.36 (4H, m), 1.87 (4H, m), 3.28 (1H, s), 3.74 (1H, s), 5.58 (2H, q, J=7.2 Hz), 5.55 (2H, s), 6.96 (1H, s), 7.33 (1H, s), 7.58 (3H, m), 8.50 (2H, m); MS (ES$^+$) m/e 401 [MH]$^+$. Anal. Found C, 68.98; H, 6.07; N, 20.74. C$_{23}$H$_{24}$N$_6$O requires C, 68.98; H, 6.04; N, 20.99%.

EXAMPLE 43

3-Phenyl-6-(1-pyrazolyl)methyloxy-7,8,9,10-tetrahydro-(7,10-ethano)-1,2,4-triazolo[3,4-a] phthalazine This compound was prepared using the procedures described in Example 1 Steps a), b), c) and d) with 1-(hydroxymethyl)pyrazole (prepared according to the procedure of Julia, Martinez-Martorell and Elguero, Heterocycles, 1986, 24, 2233) being used instead of 2-pyridylcarbinol in Step d). In the final step, it was necessary to add the product from Step c) at the same time as the sodium hydride, in order to yield the correct product. Data for the title compound: m.p.=196° C. $^1$H NMR (360 MHz, DMSO) δ 1.47 (4H, m), 1.99 (4H, m), 3.38 (1H, s), 3.87 (1H, s), 6.51 (1H, m), 6.62 (2H, s), 7.73 (4H, m), 8.18 (1H, m), 8.60 (2H, m); MS (ES$^+$) m/e 373 [MH]$^+$. Anal. Found C, 67.73; H, 5.42; N, 22.48. C$_{21}$H$_{20}$N$_6$O requires C, 67.73; H, 5.41; N, 22.57%.

EXAMPLE 44

3-Phenyl-6-(N-pyrrolidinylcarbonyl)methyloxy-7,8, 9,10-tetrahydro-(7,10-ethano)-1,2,4-triazolo[3,4-a] phthalazine a) N-Chloromethylcarbonylpyrrolidine To a solution of pyrrolidine (5 g, 0.07 mol) in dichloromethane (100 ml) at 0° C. was added triethylamine (11.8 ml, 0.084 mol) followed by dropwise addition of chloroacetyl chloride (6.2 ml 0.077 mol) in dichoromethane (20 ml), stirred for 2 hrs, left to warm to room temperature. The reaction was washed with water (2×100 ml), brine (1×100 ml), the organic layers were dried (MgSO$_4$), filtered and evaporated to give the required product (9.8 g) which was used without purification.

b) 3-Phenyl-6-(N-pyrrolidinylcarbonyl)methyloxy-7,8,9,10-tetrahydro-(7,10-ethano)-1,2,4-triazolo[3,4-a]phthalazine This compound was prepared using the procedure described in Example 35 Step b) with N-chloromethylcarbonylpyrrolidine being used instead of α-bromo-meta-toluonitrile. Data for the title compound: m.p.=219–221° C. $^1$H NMR (360 MHz, DMSO) δ 1.38 (4H, m), 1.77 (2H, m), 1.95 (6H, s), 3.30 (2H, m), 3.39 (1H, s), 3.44 (2H, m), 3.75 (1H, s), 5.11 (2H, s), 7.53 (3H, m), 8.29 (2H, m); MS (ES$^+$) m/e 404 [MH]$^+$. Anal. Found C, 68.12; H, 6.23; N, 17.03. $C_{23}H_{25}NrO_2$ requires C, 68.47; H, 6.24; N, 17.36%.

EXAMPLE 45

6-(4-(3-Methyl)pyridyl)methyloxy-3-phenyl-7,8,9,10-tetrahydro-(7,10-ethano)-1,2,4-triazolo[3,4a]phthalazine This compound was prepared using the procedures described in Example 1 Steps a), b), c) and d) with 4-hydroxymethyl-3-methylpyridine being used instead of 2-pyridylcarbinol in Step d). Data for the title compound: m.p.=226° C. $^1$H NMR (360 MHz, CDCl$_3$), 1.48 (4H, m), 1.93 (4H, m), 2.40 (3H, s), 3.54 (1H, s), 4.00 (1H, s), 5.49 (2H, s), 7.39 (1H, d, J=5.0 Hz), 7.45 (3H, m), 8.31 (2H, m), 8.47 (2H, d, J=7.8Hz); MS (ES$^+$) m/e 399 [MH]$^+$. Anal. Found C, 71.50; H, 6.11; N, 16.50. $C_{24}H_2N_5O$ requires C, 71.16; H, 6.00; N, 16.87%.

EXAMPLE 46

3-Phenyl-6-(2-quinolinyl)methyloxy-7,8,9,10-tetrahydro-(7,10-ethano)-1,2,4-triazolo[3,4-a]phthalazine This compound was prepared using the procedure described in Example 35 Step b) with 2-chloromethylquinoline being used instead of α-bromo-meta-toluonitrile. Data for the title compound: m.p.=203° C. $^1$H NMR (360 MHz, CDCl$_3$) δ 1.51 (4H, m), 1.95 (4H, m), 3.61 (1H, s), 4.00 (1H, s), 5.80 (2H, s), 7.44 (3H, m), 7.53 (2H, m), 7.82 (2H, m), 8.30 (4H, m); MS (ES$^+$) m/e 434 [MH]$^+$. Anal. Found C, 74.92; H, 5.38; N, 15.96. $C_{27}H_{23}N_5O$ requires C, 74.81; H, 5.35; N, 16.16%.

EXAMPLE 47

6-(2-Imidazolyl)methyloxy-3-phenyl-7,8,9,10-tetrahydro-(7,10-ethano)-1,2,4-triazolo[3,4-a]phthalazine Hydrochloride a) 2-(Hydroxymethyl)-1-[[2-(trimethylsilyl)ethoxy]methyl]imidazole To 1-[[2-(trimethylsilyl)ethoxy]methyl]-1H-imidazole-2-carboxaldehyde (prepared according to the procedure of Whitten, Matthews and McCarthy, *J. Org. Chem.*, 1986, 51, 1891) (7.45 g) in methanol (30 ml) was added sodium borohydride (0.42 g) at 0° C. with stirring. The solution was stirred at 0° C. for 40 min. Saturated sodium chloride solution (15 ml) was added, and the mixture stirred at room temperature for 15 min. The methanol was removed in vacuo, and the resultant aqueous solution was washed with ethyl acetate (3×50 ml). The organic layers were combined, dried (sodium sulfate) and concentrated in vacuo to yield an oil, which crystallised at 0° C. The solid was washed and recrystallised from hexane to yield 1-[[2-(trimethylsilyl)ethoxy]methyl]-2-(hydroxymethyl)imidazole as colourless crystals (1.99 g). $^1$H NMR (250 MHz, CDCl$_3$) δ 0.00 (9H, s), 0.93 (2H, t, J=8.2 Hz), 3.54 (2H, t, J=8.2 Hz), 4.73 (2H, s), 4.77 (2H, br s), 5.39 (2H, s), 6.94 (1H, d, J=1.4 Hz), 7.00 (1H, d, J=1.4 Hz); MS (ES$^+$) m/e 229 [MH]$^+$.

b) 6-(2-Imidazolyl)methyloxy-3-phenyl-7,8,9,10-tetrahydro-(7,10-ethano)-1,2,4-triazolo[3,4-a]phthalazine Hydrochloride This compound was prepared using the procedures described in Example 1 Steps a), b), c) and d) with 1-[[2-(trimethylsilyl)ethoxy]methyl]-2-(hydroxymethyl)imidazole being used instead of 2-pyridylcarbinol in Step d). An additional step was to take the product of Step d) and stir it at 50° C. in 5 N hydrochloric acid for 90 min before evaporation and recrystallisation from ethyl acetate/methanol. Data for the title compound: m.p.=219° C. (dec.). $^1$H NMR (360 MHz, DMSO) δ 1.42 (4H, m), 1.91 (4H, m), 3.51 (1H, s), 3.78 (1H, s), 5.84 (2H, s), 7.59 (3H, m), 7.76 (2H, s), 8.23 (2H, m); MS (ES) m/e 373 [MH]$^+$. Anal. Found C, 55.07; H, 5.11; N, 18.22. $C_{21}H_{20}N_6O \cdot 2HCl \cdot 0.7H_2O$ requires C, 55.08; H, 5.15; N, 18.35%.

EXAMPLE 48

3-Phenyl-6-(2-thiazolyl)methyloxy-7,8,9,10-tetrahydro-(7,10-ethano)-1,2,4-triazolo[3,4-a]phthalazine This compound was prepared using the procedures described in Example 1 Steps a), b), c) and d) with 2-hydroxymethylthiazole being used instead of 2-pyridylcarbinol in Step d). Data for the title compound: m.p.=183° C. $^1$H NMR (360 MHz, CDCl$_3$) δ 1.48 (4H, m), 1.92 (4H, m), 3.51 (1H, s), 3.99 (1H, s), 5.49 (2H, s), 7.52 (4H, m), 7.69 (2H, m), 7.81 (1H, m), 8.35 (2H, d, J=7.8 Hz); MS (ES$^+$) m/e 390 [MH]$^+$. Anal. Found C, 73.93; H, 5.17; N, 17.37. $C_{25}H_{21}N_5O$ requires C, 73.68; H, 5.19; N, 17.19%.

EXAMPLE 49

6-(2-(5-Methyl)thiazolyl)methyloxy-3-phenyl-7,8,9,10-tetrahydro-(7,10-ethano)-1,2,4-triazolo[3,4-a]phthalazine This compound was prepared using the procedures described in Example 1 Steps a), b), c) and d) with 2-hydroxymethyl-5-methylthiazole being used instead of 2-pyridylcarbinol in Step d). Data for the title compound: m.p.=228° C. $^1$H NMR (360 MHz, CDCl$_3$) δ 1.47 (4H, m), 1.93 (4H, m), 2.50 (3H, s), 3.53 (1H, s), 3.99 (1H, s), 5.74 (2H, s), 6.95 (1H, s), 7.51 (3H, m), 8.45 (2H, d, J=7.8 Hz); MS (ES$^+$) m/e 404 [MH]$^+$. Anal. Found C, 65.92; H. 5.30; N, 17.21. $C_{22}H_{21}N_9OS$ requires C, 65.49; H, 5.25; N, 17.36%.

EXAMPLE 50

6-(2-(4-Methyl)thiazolyl)methyloxy-3-phenyl-7,8,9,10-tetrahydro-(7,10-ethano)-1,2,4-triazolo[3,4-a]phthalazine This compound was prepared using the procedures described in Example 1 Steps a), b), c) and d) with 2-hydroxymethyl-4-methylthiazole being used instead of 2-pyridylcarbinol in Step d). Data for the title compound: m.p.=165° C. $^1$H NMR (360 MHz, CDCl$_3$) δ 1.47 (4H, m), 1.92 (4H, m), 2.49 (3H, s), 3.52 (1H, s), 3.98 (1H, s), 5.70 (2H, s), 7.49 (4H, m), 8.46 (2H, d, J=7.9 Hz); MS (ES$^+$) m/e 404 [MH]$^+$. Anal. Found C, 65.92; H, 5.33; N, 17.09. C$_{22}$H$_{21}$N$_5$OS requires C, 65.49; H, 5.25; N, 17.36%.

EXAMPLE 51

6-(2-(3,5-Dimethyl)pyridyl)methyloxy-3-phenyl-7,8, 9,10-tetrahydro-(7,10-ethano)-1,2,4-triazolo[3,4-a] phthalazine This compound was prepared using the procedures described in Example 1 Steps a), b), c) and d) with 2-hydroxymethyl-3,5-dimethylpyridine (prepared by the procedure of Boekelheide and Linn, *J. Am. Chem. Soc.*, 1954, 76, 1286) being used instead of 2-pyridylcarbinol in Step d). Data for the title compound: m.p.=199° C. $^1$H NMR (360 MHz, CDCl$_3$) δ 1.46 (4H, m), 1.86 (4H, m), 2.34 (3H, s), 2.38 (3H, s), 3.44 (1H, s), 3.96 (1H, s), 5.57 (2H, s), 7.39 (1H, s), 7.49 (3H, m), 8.31 (1H, s), 8.47 (2H, d, J=7.8 Hz); MS (ES$^+$) m/e 412 [MH]$^+$. Anal. Found C, 72.51; H, 6.12; N, 16.86. C$_{25}$H$_{25}$N$_5$O.0.1H$_2$O requires C, 72.65; H, 6.15; N, 16.94%.

EXAMPLE 52

3-Phenyl-6-(2-pyrazinyl)methyloxy-7,8,9,10-tetrahydro-(7,10-ethano)-1,2,4-triazolo[3,4-a] phthalazine This compound was prepared using the procedure described in Example 35 Step b) with 2-chloromethylpyrazine prepared by the procedure of Jeronim et al., *Chem. Ber.*, 1987, 120, 649–651) being used instead of α-bromo-meta-toluonitrile. Data for the title compound: m.p.=215° C. $^1$H NMR (360 MHz, CDCl$_3$) δ 1.50 (4H, m), 1.94 (4H, m), 3.57 (1H, s), 4.00 (1H, s), 5.65 (2H, s), 7.51 (3H, m), 8.38 (2H, d, J=7.8 Hz), 8.63 (2H, m), 8.84 (H, s): MS (ES$^+$) m/e 385 [MH]$^+$. Anal. Found C, 68.53; H, 5.24; N, 21.86. C$_{22}$H$_{20}$N$_6$O requires C, 68.73; H, 5.24; N, 21.86%.

EXAMPLE 58

6-(2-(4,6-Dimethyl)pyridyl)methyloxy-3-phenyl-7,8, 9,10-tetrahydro-(7,10-ethano)-1,2,4-triazolo[3,4-a] phthalazine This compound was prepared using the procedure described in Example 1 Steps a), b), c) and d) with 2-hydroxymethyl-4,6-dimethylpyridine (prepared in an analogous manner to the procedure of Boekelheide and Linn, *J. Am. Chem. Soc.*, 1954, 76, 1286) being used instead of 2-pyridylcarbinol in Step d). Data for the title compound: m.p.=200° C. $^1$H NMR (360 MHz, CDCl$_3$) δ 1.48 (4H, m), 1.93 (4H, m), 2.34 (3H, s), 2.59 (3H, s), 3.57 (1H, s), 3.98 (1H, s), 5.55 (2H, s), 6.98 (1H, s), 7.14 (1H, s), 7.51 (3H, m), 8.43 (2H, m); MS (ES$^+$) m/e 412 [MH]$^+$.

EXAMPLE 54

3-Phenyl-6-(4-thiazolyl)methyloxy-7,8,9,10-tetrahydro-(7,10-ethano)-1,2,4-triazolo[3,4-a] phthalazine This compound was prepared using the procedures described in Example 1 Steps a), b), c) and d) with 4-hydroxymethylthiazole (prepared in an analogous manner to the procedure of Boekelheide and Linn, *J. Am. Chem. Soc.*, 1954, 76, 1286) being used instead of 2-pyridylcarbinol in Step d). Data for the title compound: m.p.=219° C. $^1$H NMR (360 MHz, CDCl$_3$) δ 1.46 (4H, m), 1.89 (4H, m), 3.51 (1H, s), 3.97 (1H, s), 5.66 (2H, s), 7.52 (4H, m), 8.46 (2H, d, J=7.8 Hz), 8.88 (1H, s); MS (ES$^+$) m/e 390 [MH]$^+$. Anal. Found C, 64.71; H, 4.90; N, 17.88. C$_{21}$H$_{19}$N$_5$OS requires C, 64.76; H, 4.91; N, 17.98%.

EXAMPLE 55

6-(2-(5,6-Dimethyl)pyridyl)methyloxy-3-phenyl-7,8, 9,10-tetrahydro-(7,10-ethano)-1,2,4-triazolo[3,4-a] phthalazine This compound was prepared using the procedures described in Example 1 Steps a), b), c) and d) with 2-hydroxymethyl-5,6-dimethylpyridine (prepared as described in WO 93/21158) being used instead of 2-pyridylcarbinol in Step d). Data for the title compound: m.p.=250° C. $^1$H NMR (360 MHz, CD$_3$OD) δ 1.58 (4H, m), 2.10 (4H, m), 2.56 (3H, s), 2.84 (3H, s), 3.71 (1H, s), 3.83 (1H, s), 5.95 (2H, s), 7.75 (3H, m), 8.05 (1H, d, J=8.06 Hz), 8.39 (3H, m); MS (ES$^+$) m/e 412 [MH]$^+$. Anal. Found C, 62.62; H, 5.44; N, 14.39. C$_{25}$H$_{25}$N$_5$O.1.9HCl requires C, 62.46; H, 5.64; N, 14.53%.

EXAMPLE 56

6-(4-Methyl-2-imidazolyl)methyloxy-3-phenyl-7,8, 9,10-tetrahydro-(7,10-ethano)-1,2,4-triazolo[3,4-a] phthalazine Hydrochloride a) 2-(Hydroxymethyl)-4-methyl-1-[[2-(trimethylsilyl) ethoxy]methyl]imidazole and 2-(Hydroxymethyl)-5-methyl-1-[[2-(trimethylsilyl)ethoxy]methyl]imidazole This mixture of compounds was prepared in an analogous manner to 1-[[2-(trimethylsilyl)ethoxy]methyl]-2-(hydroxymethyl)imidazole (see Example 47, Step a). No attempt was made to separate the 4- and 5-methyl substituted isomers, as both compounds would yield the desired product upon removal of the silicon protecting group. Data for 1-[[2-(trimethylsilyl)ethoxy]methyl]-4(5)-methyl-2-(hydroxymethyl)imidazole: $^1$H NMR (250 MHz, CDCl$_3$) δ 0.00 (9H, s), 0.91 (2H, m), 2.18 and 2.25 (3H, 2×s), 3.53 (2H, m), 3.53 (2H, m), 4.66 and 4.68 (2H, 2×s), 5.30 and 5.33 (2H, 2×s), 6.65 and 6.69 (1H, 2×s); MS (S+) m/e 243 [H]$^+$.

b) 6-(4-Methyl-2-imidazolyl]methyloxy-3-phenyl-7,8,9, 10-tetrahydro-(7,10-ethano)-1,2,4-triazolo[3,4-a] phthalazine Hydrochloride This compound was prepared using the procedure described in Example 1 Steps a), b), c) and d) with the products from Example 56 a) being used instead of 2-pyridylcarbinol in Step d). An additional step was to take the product of Step d) and stir it at 50° C. in 5 N hydrochloric acid for 90 min before evaporation and recrystallisation from ethanol/ethyl acetate. Data for the title compound: m.p.=220° C. (dec.). $^1$H NMR (360 MHz, DMSO) δ 1.43 (4H, m), 1.91 (4H, m), 2.29 (3H, s), 3.50 (1H, s), 3.77 (1H, s), 5.80 (2H, s), 7.43 (1H, s), 7.59 (3H, m), 8.28 (2H, m); MS (ES$^+$) m/e 387 [MH]$^+$. Anal. Found C, 54.0; H, 6.0; N, 16.5. C$_{22}$H$_{22}$N$_6$O.2HCl. 1.8H$_2$O. 0.2C$_4$H$_8$O$_2$ requires C, 53.76; H, 5.78; N, 16.48%.

EXAMPLE 57

3-Phenyl-6-(4-pyrimidinyl)methyloxy-7,8,9,10-tetrahydro-(7,10-ethano)-1,2,4-triazolo[3,4-a] phthalazine This compound was prepared using the procedure described in Example 35 Step b) with 4-chloromethylpyrimidine (prepared by the procedure of Jeronim et al., *Chem. Ber.*, 1987, 120, 649–651) being used instead of α-bromo-meta-toluonitrile. Data for the title compound: m.p.=194° C. $^1$H NMR (360 MHz, CDCl$_3$) δ 1.51 (4H, m), 1.96 (4H, m), 3.59 (1H, s), 4.01 (1H, s), 5.58 (2H, s), 7.49 (4H, m), 8.33 (2H, d, J=7.8 Hz), 8.81 (1H, m), 9.26 (1H, s); MS (ES$^+$) m/e 385 [MH]$^+$. Anal. Found C, 68.64; H, 5.29; N, 21.58. C$_{22}$H$_{20}$N$_6$O requires C, 68.73; H, 5.24; N, 21.86%.

EXAMPLE 58

6-(4-(2-Ethyl)thiazolyl)methyloxy-3-phenyl-7,8,9, 10-tetrahydro-(7,10-ethano)-1,2,4-triazolo[3,4-a] phthalazine Hydrochloride This compound was prepared using the procedure described in Example 35 Step b) with 4-chloromethyl-2-ethylthiazole being used instead of α-bromo-meta-toluonitrile. Data for the title compound: m.p. 168° C. $^1$H NMR (360 MHz, CDCl$_3$) δ 1.46 (7H, m), 1.99 (4H, m), 3.13 (2H, t, J=7.6 Hz), 3.66 (1H, s), 4.53 (1H, s), 5.67 (2H, s), 7.42 (1H, s), 7.62 (3H, m), 8.45 (2H, m); MS (ES$^+$) m/e 418 [MH]$^+$. Anal. Found C, 59.66; H, 5.32; N, 14.90. C$_{23}$H$_{23}$N$_5$OS. HCl. 0.5H$_2$O requires C, 59.67; H, 5.44, 15.12%.

EXAMPLE 59

6-(6-Chloro-3-pyridazinyl)methyloxy-3-phenyl-7,8, 9,10-tetrahydro-(7,10-ethano)-1,2,4-triazolo[3,4-a] phthalazine This compound was prepared using the procedure described in Example 35 Step b) with 3-chloromethyl-6chloro-pyridazine (prepared by the procedure of Jeronim et al., *Chem. Ber.*, 1987, 120, 649–651) being used instead of α-bromo-meta-toluonitrile. Data for the title compound: m.p.=206° C. $^1$H NMR (360 MHz, CDCl$_3$) δ 1.51 (4H, m), 1.94 (4H, m), 3.51 (1H, s), 4.00 (1H, s), 5.81 (2H, s), 7.51 (4H, m), 7.67 (1H, d, J=8.8 Hz), 8.34 (2H, d, J=7.7 Hz); MS (ES$^+$) m/e 419 [MH]$^+$. Anal. Found C, 62.95; H, 4.43; N, 19.60. C$_{22}$H$_{19}$ClN$_6$O.0.1H$_2$O requires C, 62.81; H, 4.60; N, 19.98%.

EXAMPLE 60

6-(2-Imidazolyl)methyloxy-3-(4-methylphenyl)-7,8, 9,10-tetrahydro-(7,10-ethano)-1,2,4-triazolo[3,4-a] phthalazine Hydrochloride This compound was prepared using the procedure described in Example 1 Steps a), b), c) and d), with 4-toluic hydrazide being used instead of benzoyl hydrazine in Step c), and 1-[[2-(trimethylsilyl)ethoxy]methyl]-2-hydroxymethyl)imidazole (prepared as described in Example 47, Step a) being used instead of 2-pyridylcarbinol in Step d). An additional step was to take the product of Step d) and stir it at 50° C. in 5 N hydrochloric acid for 90 min before evaporation and recrystallisation from ethanol/ethyl acetate. Data for the title compound: m.p.=214° C. (dec.). $^1$H NMR (360 MHz, DMSO) δ 1.42 (4H, m), 1.91 (4H, m), 2.43 (3H, s), 3.51 (1H, s), 3.78 (1H, s), 5.86 (2H, s), 7.43 (2H, d, J=8.1 Hz), 7.76 (2H, s), 8.12 (2H, d, J=8.2 Hz) ; MS (ES$^+$) m/e 387 [MH]$^+$. Anal. Found C, 54.64; H, 5.72; N, 16.94. C$_{22}$H$_{22}$N$_6$O. 2HCl. 1.5 H$_2$O requires C, 54.33; H, 5.60; N, 17.28%.

EXAMPLE 61

6-(4-Hydroxymethylphenyl)methyloxy-3-phenyl-7, 8,9,10-tetrahydro-(7,10-ethano)-1,2,4-triazolo[3,4-a] phthalazine The title compound was prepared as part of a rapid analogue library using the following methodology. To 4-hydroxymethylbenzyl alcohol (200 mg) in a test tube with a ground glass joint sealed with a septum under nitrogen was added a solution of 6-chloro-3-phenyl-7,8,9,10-tetrahydro-(7,10-ethano)-1,2,4-triazolo[3,4-a]phthalazine (50 mg) in dimethylformamide (1.5 ml), followed by lithium bis (trimethylsilyl)amide as a 1 mol solution in hexanes (0.5 ml). The reaction was stirred at room temperature for 18 hrs. TLC showed complete reaction and so the mixture was poured into water (10 ml) and the precipitate formed was isolated by filtration and dried in a vacuum oven at 80° C. to yield the title compound (48 mg). It was characterized by mass spectrometry and HPLC; MS (ES) m/e 413 [MH]$^+$, HPLC >98% (run on an HP 1090, using a Hichrom S5ODS2, 23 cm column, flow rate of 1 ml/min and 50% acetonitrile/pH 3.5 phosphate buffer as the mobile phase).

EXAMPLE 62

6-(4-Hydroxybutyl)oxy-3-phenyl-7,8,9,10-tetrahydro-(7,10-ethano)-1,2,4-triazolo[3,4-a] phthalazine This compound was prepared using the procedure described in Example 61 with 1,4-dihydroxybutane being used instead of 4-hydroxymethylbenzyl alcohol. Data for the title compound: MS (ES$^+$) m/e 365 [MH]$^+$, HPLC >99% (run on an BP1090, using a Hichrom S5ODS2, 23 cm column, flow rate of 1 ml/min and 50% acetonitrile/pH 3.5 phosphate buffer as the mobile phase).

EXAMPLE 63

6-cis/trans-(4-Hydroxymethylcyclohexyl)methyloxy-3-phenyl-7,8,9,10-tetrahydro-(7,10-ethano)-1,2,4-triazolo[3,4-a]phthalazine This compound was prepared using the procedure described in Example 61 with cis/trans-1,4-dihydroxymethylcyclohexane being used instead of 4-hydroxymethylbenzyl alcohol. Data for the title compound: MS (ES$^+$) m/e 419 [MH]$^+$, HPLC 82% and 17% (run on an HP1090, using a Hichrom S5ODS2, 23 cm column, flow rate of 1 ml/min and 50% acetonitrile/pH 3.5 phosphate buffer as the mobile phase).

EXAMPLE 64

6-(3-Hydroxymethylphenyl)methyloxy-3-phenyl-7, 8,9,10-tetrahydro-(7,10-ethano)-1,2,4-triazolo[3,4-a] phthalazine This compound was prepared using the procedure described in Example 61 with 3-hydroxymethylbenzyl alcohol being used instead of 4-hydroxymethylbenzyl alcohol. Data for the title compound: MS (ES$^+$) m/e 413 [MH]$^+$, HPLC >99% (run on an HP1090, using a Hichrom S5ODS2, 23 cm column, flow rate of 1 ml/min and 50% acetonitrile/ pH 3.5 phosphate buffer as the mobile phase).

EXAMPLE 65

6-(1-Methyl-1,2,4-triazol-3-yl)methyloxy-3-phenyl-7,8,9,10-tetrahydro-(7,10-ethano)-1,2,4-triazolo[3, 4a]phthalazine This compound was prepared using the procedures described in Example 1 Steps a), b), c) and d) with (1-methyl-1H-1,2,4-triazol-3-yl)-methanol (prepared using the conditions described in EP-A-421210) being used instead of 2-pyridylcarbinol in Step d). Data for the title compound: m.p.=237° C. $^1$H NMR (360 MHz, CDCl$_3$) δ 1.47 (4H, m), 1.88 (4H, m), 3.51 (1H, s), 3.96 (4H, s), 5.54 (2H, s), 7.50 (3H, m), 8.07 (1H, s), 8.52 (2H, d, J=7.8 Hz); MS (ES$^+$) m/e 388 [MH]$^+$. Anal. Found C, 64.90; H, 5.38; N, 25.18. C$_{21}$H$_{21}$N$_7$O requires C, 65.10; H, 5.46; N, 23.51%.

EXAMPLE 66

6-(2-Methyl-1,2,4-triazol-3-yl)methyloxy-3-phenyl-7,8,9,10-tetrahydro-(7,10-ethano)-1,2,4-triazolo[3,4a]phthalazine This compound was prepared using the procedures described in Example 1 Steps a), b), c) and d) with (2-methyl-2H-1,2,4-triazol-3-yl)methanol (prepared using the conditions described in EP-A-421210) being used instead of 2-pyridylcarbinol in Step d). Data for the title compound: m.p.=270° C. $^1$H NMR (360 MHz, CDCl$_3$) δ 1.46 (4H, m), 1.93 (4H, m), 3.45 (1H, s), 3.96 (3H, s), 3.99 (1H, s), 6.62 (2H, s), 7.52 (3H, m), 7.94 (1H, s), 8.39 (2H, d, J=7.8 Hz); MS (ES$^+$) m/e 388 [MH]$^+$. Anal. Found C, 65.40; H, 5.47; N, 25.29. C$_{21}$H$_{21}$N$_7$O requires C, 65.10; H, 5.46; N, 23.51%.

EXAMPLE 67

3-Phenyl-6-(3-cyclopropylmethyloxy-2-pyridyl)methyloxy-7,8,9,10-tetrahydro-(7,10-ethano)-1,2,4-triazolo[3,4-a]phthalazine a) 3-Cyclopropylmethyloxy-2-hydroxymethyl Pyridine Potassium hydroxide (5.2 g, 0.093 mol) was ground to a powder under nitrogen, added to DMSO (30 ml) and stirred for 20 min under nitrogen at room temperature. The mixture was cooled to 0° C. and 3-hydroxy-2-hydroxymethyl pyridine hydrochloride (5.0 g, 0.031 mol) was added. The slurry was stirred at 0° C. for 1 h before the addition of cyclopropylmethyl bromide (3.01 ml, 4.2 g, 0.031 mol). The mixture was allowed to warm to room temperature and stirred under nitrogen overnight. Water (100 ml) was added, and the resultant solution was acidified to pH 1 with hydrochloric acid (5 N). The solution was washed with dichloromethane (3×100 ml), basified to pH 14 with sodium hydroxide solution (4 N), and washed again with dichloromethane (3×100 ml). The organic layers from the second extraction were combined, washed with water (1×100 ml) and saturated sodium chloride solution (1×100 ml), dried over magnesium sulfate and concentrated in vacuo to give 3-cyclopropylmethyloxy-2-hydroxymethyl pyridine as a dark brown solid (2.40 g). $^1$H NMR (250 MHz, CDCl$_3$) δ 0.35 (2H, m), 0.65 (2H, m), 1.26 (1H, m), 3.85 (2H, d, J=6.8 Hz), 4.33 (1H, br s), 4.77 (2H, s), 7.13 (2H, m), 8.13 (2H, m); MS (ES$^+$) m/e 180 [MH]$^+$.

b) 3-Phenyl-6-(3-cyclopropylmethyloxy-2-pyridyl)methyloxy-7,8,9,10-tetrahydro-(7,10-ethano)-1,2,4-triazolo[3,4-a]phthalazine This compound was prepared using the procedure described in Example 1 Steps a), b), c) and d) with 3-cyclopropylmethyloxy-2-hydroxymethyl pyridine being used instead of 2-pyridylcarbinol in Step d). Data for the title compound: m.p.=213° C. $^1$H NMR (360 MHz, CDCl$_3$) δ 0.28 (2H, m), 0.53 (2H, m), 1.17 (1H, m), 1.47 (4H, m), 1.88 (4H, m) 3.50 (1H, s), 3.88 (2H, d, J=6.7 Hz), 3.96 (1H, s), 5.67 (2H, s), 7.26 (2H, m), 7.47 (3H, m), 8.22 (1H, m), 8.46 (2H, d, J=6.6 Hz); MS (ES$^+$) m/e 454 [MH]$^+$. Anal. Found C, 71.43; H, 5.98; N, 15.39. C$_{27}$H$_{27}$N$_5$O$_2$ requires C, 71.50; H, 6.00; N, 15.44%.

EXAMPLE 68

3-Phenyl-6-(3-ethoxy-2-pyridyl)methyloxy-7,8,9,10-tetrahydro-(7,10-ethano)-1,2,4-triazolo[3,4-a]phthalazine a) 3-Ethoxy-2-hydroxymethyl Pyridine This compound was prepared using the procedure described in Example 67 Step a), with iodoethane being used instead of cyclopropylmethyl bromide. $^1$H NMR (250 MHz, CDCl$_3$) δ 1.44 (3H, t, J=7.0 Hz), 4.06 (2H, q, J=7.0 Hz), 4.75 (2H, s), 7.16 (2H, m), 8.14 (1H, m); MS (ES$^+$) m/e 154 [MH]$^+$.

b) 3-Phenyl-6-(3-ethoxy-2-pyridyl)methyloxy-7,8,9,10-tetrahydro-(7,10-ethano)-1,2,4-triazolo[3,4-a]phthalazine This compound was prepared using the procedure described in Example 1 Steps a), b), c) and d) with 3-ethoxy-2-hydroxymethyl pyridine being used instead of 2-pyridylcarbinol in step d). Data for the title compound: m.p.=230 ° C. $^1$H NMR (360 MHz, CDCl$_3$) δ 1.38 (3H, t, J=7 Hz), 1.44 (4H, m), 1.88 (4H, m), 3.50 (1H, t, J=2.6 Hz), 3.96 (1H, t, J=2.6 Hz), 4.10 (2H, q, J=6.9 Hz), 5.64 (2H, s), 7.26 (2H, m), 7.49 (3H, m), 8.23 (1H, m), 8.45 (2H, m); MS (ES$^+$) m/e 428 [MH]$^+$. Anal. Found C, 70.50; H, 5.93; N, 16.41. C$_{25}$H$_{25}$N$_5$O$_2$ requires C, 70.24; H, 5.89; N, 16.38%.

EXAMPLE 69

6-(6-Methylpyridin-2-yl)methyloxy-3-phenyl-1,2,4-triazolo[3,4-a]phthalazine a) 2-Acetoxymethyl-6-methylpyridine Acetic anhydride (23 ml) was heated to 110° C. and 2,6-lutidine-N-oxide (20 g) was added dropwise over 1 hour. The solution was heated at 110° C. for five hours. After cooling, the crude mixture was distilled to yield 2-acetoxymethyl-6-methylpyridine (18.4 g, b.p. 110–120° C. @ 15 mmHg).

b) 2-Hydroxymethyl-6-methylpyridine

2-Acetoxymethyl-6-methylpyridine (5 g) was added to saturated hydrochloric acid in methanol (250 ml, prepared by adding 25 ml of acetyl chloride to 225 ml of methanol). The reaction mixture was stirred at room temperature for 18 hours. The solvent was removed under vacuum and the residue was dissolved in dichloromethane (100 ml) and washed with 2N sodium hydroxide solution (3×50 ml). The combined organic layers were washed with brine (1×200 ml), then dried (MgSO$_4$), filtered and evaporated to give the required product as an oil (2.6 g). $^1$H NMR (250 MHz, CDCl$_3$) δ 2.54 (3H, s), 3.80 (1H, bs), 4.72 (2H, s), 7.04 (2H, d, J=7.7Hz), 7.57 (1H, t, J=7.7Hz).

c) 1-Chloro-4-hydrazinophthalazine Hydrochloride

To a stirred solution of hydrazine hydrate (40 ml) in ethanol (120 ml) at 80° C. was added 1,4-dichlorophthalazine (20 g). This reaction mixture was stirred at 80° C. for 0.5 hours, then left to cool and the product was collected by filtration and dried under vacuum to give 1-chloro-4-hydrazinophthalazine hydrochloride (14.6 g). $^1$H NMR (250 MHz, DMSO) δ 4.64 (2H, vbs), 7.2 (1H, vbs), 7.92 (4H, bm).

d) 6-Chloro-3-phenyl-1,2,4-triazolo[3,4-a]phthalazine

To a solution of 1-chloro-4-hydrazinophthalazine hydrochloride (10 g) in dioxan (220 ml) was added triethylamine (7.24 ml) and benzoyl chloride (6.04 ml). This mixture was heated at reflux for 8 hours under nitrogen. After cooling the reaction mixture was concentrated under vacuum and the solid obtained was collected by filtration, washed with water and diethyl ether and dried under vacuum, to yield the title compound (12.0 g). $^1$H NMR (250 MHz, DMSO) δ 7.60 (3H, m), 8.00 (1H, t, J=8.4Hz), 8.19 (1H, t, J=8.4Hz), 8.31 (3H, m), 8.61 (1H, d, J=6.3Hz).

e) 6-(6-Methylpyridin-2-yl)methyloxy-3-phenyl-1,2,4-triazolo[3,4-a]phthalazine

To a solution of 2-hydroxymethyl-6-methylpyridine (Example 67 part b, 0.5 g), in anhydrous dimethylformamide (20 ml) under nitrogen was added sodium hydride (107 mg of 60% in oil) and the reaction mixture was stirred at room temperature for 0.5 hours. To this mixture was added 6-chloro-3-phenyl-1,2,4-triazolo[3,4-a]phthalazine (Example 67 part d, 330 mg) and the solution was heated to 80° C. for 0.25 hours. After cooling the solvent was removed under vacuum, and the residue was dissolved in dichloromethane (30 ml) and washed with water and brine. After drying (MgSO$_4$), the solution was filtered and evaporated to give the required product which was recrystallised from a mixture of ethyl acetate and hexane to give the title compound (210 mg, m.p. 186–187° C.). $^1$H NMR (360 MHz, DMSO) δ 2.52 (3H, s), 5.65 (2H, s), 7.25 (1H, d, J=7.7Hz), 7.49 (1H, d, J=7.7Hz), 7.58 (3H, m), 7.76 (1H, t, J=7.7Hz), 7.94 (1H, t, J=7.6Hz), 8.08 (1H, t, J=7.7Hz), 8.30 (3H, m), 8.58 (1H, d, J=7.6Hz); MS (ES$^+$) m/e 368 [MH]$^+$. Anal. Found C, 71.32; H, 4.44; N. 18.53. $C_{22}H_{17}N_5O \cdot H_2O$ requires C, 71.22; H, 4.73; N, 18.88%.

EXAMPLE 70

6-(1-Methyl-1H-1,2,4-triazol-3-ylmethoxy)-3,7-diphenyl-1,2,4-triazolo[4,3-b]pyridazine This compound was prepared in 82% yield using a similar procedure to that described in Example 2, Step d, but using (1-methyl-1H-1,2,4-triazol-3-yl)methanol (prepared as described in Example 65) instead of 2-pyridylcarbinol. In this case the reaction mixture was partitioned between water and ethyl acetate with saturated aqueous NaCl added to aid in the separation of the layers. The aqueous layer was further extracted with ethyl acetate, and the combined organic extracts were dried (Na$_2$SO$_4$) and evaporated in vacuo. The residue was purified by flash chromatography (silica gel, 2% MeOH/CH$_2$Cl$_2$), and recrystallised from EtOAc—CH$_2$Cl$_2$. Data for the title compound: mp 229–233° C.; $^1$H NMR (360 MHz, CDCl$_3$) δ 3.92 (3H, s), 5.61 (2H, s), 7.45–7.59 (6H, m), 7.68 (2H, dd, J=7.9, J'=1.6 Hz), 8.03 (1H, s), 8.05 (1H, s), 8.55 (2H, m); MS (ES$^+$) m/e 384 [MH]$^+$. Anal. Found C, 66.05; H, 4.34; N, 25.68. $C_{21}H_{17}N_7O$ requires C, 65.79; H, 4.47; N, 25.57%.

EXAMPLE 71

6-(2-Methyl-2H-1,2,4-triazol-3-ylmethoxy-3,7-diphenyl-1,2,4-triazolo[4,3-b]pyridazine This compound was prepared in 40% yield using a similar procedure to that described in Example 2, Step d, but using (2-methyl-2H-1,2,4-triazol-3-yl)methanol (prepared as described in Example 66) instead of 2-pyridylcarbinol. Data for the title compound: mp 198–202° C.; $^1$H NMR (360 MHz, CDCl$_3$) δ 3.74 (3H, s), 5.67 (2H, s), 7.47–7.61 (8H, m), 7.90 (1H, s), 8.08 (1H, s), 8.42 (2H, m); MS (ES$^+$) m/e 384 [MH]$^+$. Anal. Found C, 63.70; H, 4.45; N, 24.59. $C_{21}H_{17}N_7O \cdot 0.7H_2O$ requires C, 63.69; H, 4.68; N, 24.75%.

EXAMPLE 72

3,7-Diphenyl-6-(2H-1,2,4-triazol-3-ylmethoxy)-1,2,4-triazolo[4,3-b]pyridazine a) [2-(2-(Trimethylsilanyl)ethoxymethyl)-2H-1,2,4-triazol-3-yl]methanol 1-(2-(Trimethylsilanyl)ethoxymethyl)-1H-1,2,4-triazole (6.57 g) (prepared as described by Fugina et al., *Heterocycles*, 1992, 303–314) was dissolved in THF (110 ml) and cooled to −70° C. whereupon butyllithium (23.12 ml of a 1.6 M solution in hexane) was added dropwise over 15 minutes keeping the temperature at −70° C. After 1 hour DMF (2.4 ml, 1 mol eq) was added and the reaction mixture was allowed to warm to 0° C. over 30 minutes. Saturated ammonium chloride solution (300 ml) was added and the mixture was extracted with ethyl acetate (2×300 ml). The organic layer was dried (Na$_2$SO$_4$), filtered and concentrated in vacuo to give a clear oil (6.5 g). This oil was dissolved in methanol (120 ml) and sodium borohydride (1.08 ml, 1 mol eq) was added in portions over 20 minutes. After 1 h the solvent was removed under vacuum and the residue was partitioned between water (50 ml) and dichloromethane (2×100 ml). The combined organic layers were washed with brine (1×30 ml) and dried (Na$_2$SO$_4$), filtered and concentrated in vacuo to give a clear oil which was purified by chromatography on silica gel using 0–4% methanol in dichloromethane as eluent to give the required compound (5 g) as a clear oil. $^1$H NMR (250 MHz, CDCl$_3$) δ 0.00 (9H, s), 0.93 (2H, t, J=8.2 Hz), 3.63 (2H, t, J=8.2 Hz), 4.87 (2H, s), 4.11 (1H, br s), 5.28 (2H, s), 7.85 (1H, s).

b) 3,7-Diphenyl-6-[2-(2-(trimethylsilanyl)ethoxymethyl)-2H-1,2,4-triazol-3-ylmethoxy]-1,2,4-triazolo[4,3-b]pyridazine This compound was prepared using the procedures described in Example 2 a), b), c) and d) with the product from Example 72 a) being used instead of 2-pyridylcarbinol. $^1$H NMR (250 MHz, CDCl$_3$) δ 0.00 (9H, s), 0.83 (2H, t, J=8.2 Hz), 3.55 (2H, t, J=8.2 Hz), 5.46 (2H, s), 5.78 (2H, s), 7.55–7.68 (8H, m), 8.00 (1H, s), 8.15 (1H, s), 8.45 (2H, d, J=7.8 Hz).

c) 3.7-Di-phenyl-6-(2H-1,2,4-triazol-3-ylmethoxy)-1,2,4-triazolo[4,3-b]pyridazine The product from Example 72 Step b) (0.68 g) was suspended in ethanol (10 ml) with 2 N hydrochloric acid (21 ml) and heated at 65° C. for 5.5 h. Saturated sodium carbonate solution was added dropwise until a solid precipitated and this was collected by filtration and washed several times with water in the sinter funnel. The solid was recrystallised from methanol to give the required product (0.245 g, m p.=248° C.). $^1$H NMR (360 MHz, d$_6$-DMSO) δ 5.61 (2H, s), 7.48–7.63 (6H, m), 7.44–7.77 (2H, m), 8.40 (4H, m), 14.13 (1H, br s); MS (ES$^+$) m/e 370 [MH]$^+$. Anal. Found C, 65.02; H, 4.04; N, 26.35. $C_{20}H_{15}N_7O$ requires C, 65.03; H, 4.09; N, 26.54%.

EXAMPLE 73

6-(2-Methyl-2H-tetrazol-5-ylmethoxy)-3,7-diphenyl-1,2,4-triazolo[4,3-b]-pyridazine a) 3,7-Diphenyl-1,2,4-triazolo[4,3-b]pyridazin-6-one To a solution of 6-chloro-3,7-diphenyl-1,2,4-triazolo[4,3-b]pyridazine (from Example 2, Step c) (1.02 g, 3.34 mmol) in 1,4-dioxane (60 ml) and water (12 ml) was added 4 M aqueous NaOH (4.17 ml, 16.7 mmol), and the solution was heated at reflux for 7.5 h whilst stirring magnetically. The mixture was then concentrated in vacuo and the aqueous residue was partitioned between water (200 ml) and diethyl ether (100 ml). The aqueous layer was then acidified with 5 M aqueous HCl until the pH was ca. 3. The resulting precipitated solid was collected by filtration, washed with water, then hexane, and dried at 60° C. under vacuum to give 0.8885 g (92%) of the title compound as a white solid. $^1$H NMR (360 MHz, d$_6$-DMSO) δ 7.47–7.63 (6H, m), 7.71 (2H, dd, J=8.0, J=1.8 Hz), 8.31 (1H, s), 8.46 (2H, m), 12.80 (1H, br s); MS (ES$^+$) m/e 289 [MH]$^+$.

b) 6-(2-Methyl-2H-tetrazol-5-ylmethoxy)-3,7-diphenyl-1,2,4-triazolo[4,3-b]pyridazine To the product from Example 73, Step a (0.15 g, 0.52 mmol) in anhydrous DMF (5 ml) was added sodium hydride (60% dispersion in oil, 31.2 mg, 0.780 mmol) and the mixture was stirred under nitrogen at room temperature for 45 min then at 80° C. for another 20 min. After allowing to cool, a solution of 5-chloromethyl-2-methyl-2H-tetrazole (Moderhack, D., *Chem. Ber.*, 1975, 108, 887–896) (0.103 g, 0.780 mmol) in anhydrous DMF (4 ml) was added and the mixture was stirred at room temperature under nitrogen for 1.5 h, then at 80° C. for 17 h. The mixture was then partitioned between water (30 ml) and ethyl acetate (40 ml). The aqueous layer was further extracted with ethyl acetate (9×40 ml) and the combined organic extracts were dried (MgSO$_4$), and evaporated in vacuo. The residue was recrystallised from EtOAc—CH$_2$Cl$_2$—MeOH to afford 0.1002 g (50%) of the title compound as a white solid: mp 228–233° C.; $^1$H NMR (360 MHz, CDCl$_3$) δ 4.36 (3H, s), 5.79 (2H, s), 7.47–7.60 (8H, m), 8.07 (1H, s), 8.48 (2H, m); MS (ES$^+$) m/e 385 [MH]$^+$. Anal. Found C, 62.01; H, 4.13; N, 28.92. C$_{20}$H$_{16}$N$_8$O. 0.17H$_2$O requires C, 62.00; H, 4.25; N, 28.92%.

EXAMPLE 74

3,7-Diphenyl-6-(2-propyl-2H-1,2,4-triazol-3-ylmethoxy)-1,2,4-triazolo[4,3-b]pyridazine a) 3- and 5-(tert-Butyldimethylsilanyloxymethyl)-1-propyl-1H-1,2,4-triazole To a stirred mixture of sodium hydride (60% dispersion in oil, 1.5 g, 37.5 mmol) and 1-iodopropane (4.4 ml, 45 mmol) in anhydrous DMF (100 ml), cooled under nitrogen to 0° C., was added dropwise over 10 min a solution of 3-(tert-butyldimethylsilanyloxymethyl)-1H-1,2,4-triazole (prepared as described in EP-A-421210) (8.0 g, 37.5 mmol) in anhydrous DMF (25 ml). The mixture was stirred under nitrogen at 0° C. for 25 min, more sodium hydride (60% dispersion in oil, 0.45 g, 11.3 mmol) was added, and the mixture was stirred for another 30 min. Water (300 ml) was then added and the mixture was extracted with ethyl acetate (3×100 ml). The combined organic extracts were washed with brine (100 ml), dried (Na$_2$SO$_4$) and evaporated in vacuo. The residue was purified by flash chromatography (silica gel, 40–50% EtOAc/hexane; and alumina, 15% EtOAc/hexane) to yield 4.10 g (43%) of 5-(tert-butyldimethylsilanyloxymethyl)-1-propyl-1H-1,2,4-triazole and 2.97 g (31%) of 3-(tert-butyldimethylsilanyloxymethyl)-1-propyl-1H-1,2,4-triazole as colourless oils.

3-(tert-Butyldimethylsilanyloxymethyl)-1-propyl-1H-1,2,4-triazole $^1$H NMR (250 MHz, CDCl$_3$) δ 0.12 (6H, 8), 0.92 (9H, s), 0.93 (3H, t, J=7.3 Hz), 1.91 (2H, sextet, J=7.3 Hz), 4.09 (2H, t, J=7.1Hz), 4.77 (2H, s), 8.03 (1H, s).

5-(tert-Butyldimethylsilanyloxymethyl)-1-propyl-1H-1,2,4-triazole $^1$H NMR (250 MHz, CDCl$_3$) δ 0.10 (6H, s), 0.90 (9H, s), 0.95 (3H, t, J=7.4 Hz), 1.92 (2H, sextet, J=7.4 Hz), 4.19 (2H, m), 4.84 (2H, s), 7.81 (1H, s).

b) (2-Propyl-2H-1,2,4-triazol-3-yl)methanol

To a solution of 5-(tert-butyldimethylsilanyloxymethyl)-1-propyl-1H-1,2,4-triazole (from Step a) (4.10 g, 16.1 mmol) in ethanol (18 ml) and methanol (36 ml) was added 4 M aqueous NaOH (6 ml, 24 mmol) and the mixture was stirred at room temperature for 19 h, then at 45° C. for another 5 h. The solvents were removed in vacuo and the residue was purified by flash chromatography (silica gel, EtOAc, then 10% MeOH/CH$_2$Cl$_2$) to leave 1.976 g (87%) of the title compound as a pale yellow oil: $^1$H NMR (250 MHz, CDCl$_3$) δ 0.95 (3H, t, J=7.4 Hz), 1.91 (2H, sextet, J=7.4 Hz), 4.16 (2H, t, J=7.3 Hz), 4.76 (2H, s), 7.81 (1H, s).

c) 3,7-Diphenyl-6-(2-propyl-2H-1,2,4-triazol-3-ylmethoxy)-1,2,4-triazolo[4,3-b]pyridazine This compound was prepared in 44% yield using a similar procedure to that described in Example 2, Step d, but using (2-propyl-2H-1,2,4-triazol-3-yl)methanol (from Step b) instead of 2-pyridylcarbinol. Data for the title compound: mp 211–213° C.; $^1$H NMR (250 MHz, CDCl$_3$) δ 0.68 (3H, t, J=7.4 Hz), 1.65 (2H, sextet, J=7.4 Hz), 3.96 (2H, t, J=7.4 Hz), 5.66 (2H, s), 7.45–7.63 (8H, m), 7.93 (1H, s), 8.09 (1H, s), 8.46 (2H, m); MS (ES$^+$) m/e 412 [MH]$^+$. Anal. Found C, 66.75; H, 4.82; N, 23.60. C$_{23}$H$_{21}$N$_7$O requires C, 67.14; H, 5.14; N, 23.83%.

EXAMPLE 75

3,7-Diphenyl-6-(1-propyl-1H-1,2,4-triazol-3-ylmethoxy)-1,2,4-triazolo[4,3-b]pyridazine a) (1-Propyl-1H-1,2,4-triazol-3-yl)methanol To a solution of 3-(tert-butyldimethylsilanyloxymethyl)-1-propyl-1H-1,2,4-triazole (from Example 74, Step a) (2.97 g, 11.6 mmol) in ethanol (13 ml) and methanol (26 ml) was added 4 M aqueous NaOH (4.3 ml, 17.4 mmol) and the mixture was stirred at 45° C. for 2 days. The solvents were removed in vacuo and the residue was purified by flash chromatography (silica gel, EtOAc, then 10% MeOH/CH$_2$Cl$_2$) to leave 1.509 g (92%) of the title compound as a white solid: $^1$H NMR (250 MHz, CDCl$_3$) δ 0.94 (3H, t, J=7.4 Hz), 1.92 (2H, sextet, J=7.4 Hz), 4.10 (2H, t, J=7.1 Hz), 4.76 (2H, s), 8.01 (1H, s).

b) 3,7-Diphenyl-6-(1-propyl-1H-1,2,4-triazol-3-ylmethoxy)-1,2,4-triazolo[4,3-b]pyridazine This compound was prepared in 70% yield using a similar procedure to that described in Example 2, Step d, but using (1-propyl-1H-1,2,4-triazol-3-yl)methanol (from Step a) instead of 2-pyridylcarbinol. Data for the title compound: mp 212–214° C.; $^1$H NMR (360 MHz, CDCl$_3$) δ 0.90 (3H, t, J=7.4 Hz), 1.90 (2H, sextet, J=7.3 Hz), 4.10 (2H, t, J=7.0 Hz), 5.62 (2H, s), 7.45–7.58 (6H, m), 7.68 (2H, m), 8.03 (1H, s), 8.06 (1H, s), 8.56 (2H, m); MS (ES$^+$) m/e 412 [MH]$^+$. Anal. Found C, 67.51; H, 5.01; N, 23.86. C$_{23}$H$_{21}$N$_7$O requires C, 67.14; H, 5.14; N, 23.83%.

EXAMPLE 76

6-(1-Methyl-1H-imidazol-4-ylmethoxy)-3,7-diphenyl-1,2,4-triazolo[4,3-b]pyridazine a) 4- and 6-(tert-Butyldimethylsilanyloxymethyl)-1-methyl-1H-imidazole To a solution of 5-(tert-butyldimethylsilanyloxymethyl)-1H-imidazole (Amino, Y.; Eto, H.; Eguchi, C., *Chem. Pharm. Bull.*, 1989, 37, 1481–1487) (3.158 g, 14.9 mmol) in anhydrous THF (25 ml), cooled to −78° C. under nitrogen, was added a 1.6 M solution of butyllithium in hexanes (10.2 ml, 16.4 mmol). The mixture was stirred under nitrogen at −78° C. for 30 min, then iodomethane (0.97 ml, 15.6 mmol) was added. The mixture was allowed to warm to room temperature and stirred for 5 h. Water (150 ml) was then added and the mixture was extracted with diethyl ether (150 ml). The organic extract was washed with brine, dried (MgSO$_4$) and evaporated in vacuo. The residue was purified by flash chromatography (alumina, 40% EtOAc/hexane) to yield 0.4732 g (14%) of 4-(tert-butyldimethylsilanyloxymethyl)-1-methyl-1H-imidazole and 1.463 g (43%) of 5-(tert-butyldimethylsilanyloxymethyl)-1-methyl-1H-imidazole.

4-(tert-Butyldimethylsilanyloxymethyl)-1-methyl-1H-imidazole $^1$H NMR (250 MHz, CDCl$_3$) δ 0.11 (6H, s), 0.93 (9H, s), 3.65 (3H, s), 4.68 (2H, s), 6.80 (1H, s), 7.35(1H, s).

5-(tert-Butyldimethylsilanyloxymethyl)-1-methyl-1H-imidazole $^1$H NMR (250 MHz, CDCl$_3$) δ 0.05 (6H, s), 0.88 (9H, s), 3.67 (3H, m), 4.65 (2H, s), 6.90 (1H, s), 7.41 (1H, s).

b) (1-Methyl-1H-imidazol-4-yl)methanol

To a solution of 4-(tert-butyldimethylsilanyloxymethyl)-1-methyl-1H-imidazole (from Step a) (0.4732 g, 2.09 mmol) in ethanol (2.4 ml) and methanol (4.7 ml) was added 4 M aqueous NaOH (0.778 ml, 3.14 mmol) and the mixture was stirred at 45° C. for 2 days. The mixture was then evaporated in vacuo and the residue was purified by flash chromatography (silica gel, CH$_2$Cl$_2$—MeOH—NH$_3$ (aq); 80:20:2) to leave 0.224 g (96%) of the title compound: $^1$H NMR (250 MHz, CDCl$_3$) δ 3.66 (3H, s), 4.58 (2H, s), 6.84 (1H, s), 7.39 (1H, s).

c) 6-(1-Methyl-1H-imidazol-4-ylmethoxy)-3,7-diphenyl-1,2,4-triazolo[4,3-b]pyridazine This compound was prepared in 44% yield using a similar procedure to that described in Example 2, Step d, but using (1-methyl-1H-imidazol-4-yl)methanol (from Step b) instead of 2-pyridylcarbinol. Data for the title compound: mp 199–202° C.; $^1$H NMR (360 MHz, CDCl$_3$) δ 3.63 (3H, s), 5.50 (2H, s), 6.88 (1H, s), 7.41–7.64 (9H, m), 8.02 (1H, s), 8.56 (2H, m); MS (ES$^+$) m/e 383 [MH]$^+$. Anal. Found C, 69.02; H, 4.42; N, 21.55. C$_{22}$H$_{18}$N$_6$O. 0.025H$_2$O requires C, 69.01; H, 4.75; N, 21.95%.

EXAMPLE 77

6-(3-Methyl-3H-imidazol-4-ylmethoxy)-3,7-diphenyl-1,2,4-triazolo[4,3-b]pyridazine a) (3-Methyl-3H-imidazol-4-yl)methanol To a solution of 5-(tert-butyldimethylsilanyloxymethyl)-1-methyl-1H-imidazole (from Example 76, Step a) (0.100 g, 0.442 mmol) in ethanol (0.5 ml) and methanol (1 ml) was added 4 M aqueous NaOH (0.165 ml, 0.66 mmol) and the mixture was stirred at room temperature for 2 h, then at 50° C. for 16 h. The mixture was then evaporated in vacuo and the residue was purified by flash chromatography (silica gel, CH$_2$Cl$_2$—MeOH—NH$_3$(aq); 80:20:2) to leave 31.3 mg (63%) of the title compound: $^1$H NMR (250 MHz, CDCl$_3$) δ 3.71 (3H, s), 4.62 (2H, s), 6.87 (1H, s), 7.38 (1H, s).

b) 6-(3-Methyl-3H-imidazol-4-ylmethoxy)-3,7-diphenyl-1,2,4-triazolo[4,3-b]pyridazine This compound was prepared in 30% yield using a similar procedure to that described in Example 2, Step d, but using (3-methyl-3H-imidazol-4-yl)methanol (from Step a) instead of 2-pyridylcarbinol. Data for the title compound: mp 195–196° C.; $^1$H NMR (250 MHz, CDCl$_3$) δ 3.53 (3H, s), 5.52 (2H, s), 7.20 (1H, s), 7.44–7.65 (9H, m), 8.04 (1H, s), 8.49 (2H, m); MS (ES$^+$) m/e 383 [MH]$^+$. Anal. Found C, 68.31; H, 4.38; N, 21.55. C$_{22}$H$_{18}$N$_6$O.0.12H$_2$O requires C, 68.70; H, 4.78; N, 21.85%.

EXAMPLE 78

6-(4-Methyl-4H-1,2,4-triazol-3-ylmethoxy)-3,7-diphenyl-1,2,4-triazolo[4,3-b]pyridazine This compound was prepared in 46% yield using a similar procedure to that described in Example 2, Step d, but using (4-methyl-4H-1,2,4-triazol-3-yl)methanol (WO 95/34542) instead of 2-pyridylcarbinol. Data for the title compound: mp 230–235° C.; $^1$H NMR (360 MHz, CDCl$_3$) δ 3.50 (3H, s), 5.74 (2H, s), 7.45–7.62 (8H, m), 8.07 (1H, s), 8.12 (1H, s), 8.49 (2H, m); MS (ES$^+$) m/e 384 [MH]$^+$. Anal. Found C, 65.48; H, 4.34; N, 25.31. C$_{21}$H$_{17}$N$_7$O requires C, 65.79; H. 4.47; N, 25.57%.

EXAMPLE 79

6-(5-Methyl-2H-1,2,4-triazol-3-ylmethoxy)-3,7-diphenyl-1,2,4-triazolo[4,3-b]pyridazine a) (3.7-Diphenyl-1,2,4-triazolo[4.3-b]pyridazin-6-yloxy)acetonitrile To a stirred solution of 3,7-diphenyl-1,2,4-triazolo[4,3-b]pyridazin-6-one (from Example 73, Step a) (0.4021 g, 1.39 mmol) in anhydrous DMF (20 ml) under nitrogen was added sodium hydride (60% dispersion in oil, 84.0 mg, 2.10 mmol) and the mixture was stirred at room temperature for 30 min,. then at 80° C. for 20 min. After allowing to cool, bromoacetonitrile (0.146 ml, 2.10 mmol) was added dropwise and the mixture was stirred at room temperature for 14 h. The mixture was then partitioned between ethyl acetate (100 ml) and water (100 ml), adding saturated aqueous NaCl to aid in the separation of the layers. The aqueous layer was extracted further with ethyl acetate (2×100 ml) and the combined organic extracts were dried (Na$_2$SO$_4$), and evaporated in vacua. The residue was purified by flash chromatography (silica gel 2% MeOH/CH$_2$Cl$_2$) to afford 0.4566 g (100%) of the title compound as a buff solid: $^1$H NMR (360 MHz, CDCl$_3$) δ5.11 (2 H, s), 7.52–7.63 (8 H, m), 8.12 (1 H, s), 8.45 (2 H, m); MS (ES$^+$) m/e 328 [MH]$^+$.

b) 6-(5-Methyl-2 H-1,2,4-triazol-3-ylmethoxy)-3,7-diphenyl-1,2,4-triazolo[4,3-b]pyridazine To an ice-cooled solution of the product from Step a (0.280 g, 0.855 mmol) in anhydrous methanol (35 ml) under nitrogen was added sodium methoxide (2.6 mg, 0.048 mmol), and the mixture was stirred at room temperature under nitrogen for 19 h, then at 50° C. for 3 days, adding anhydrous dichloromethane (3 ml) to dissolve solids. After allowing to cool, the mixture was neutralised by adding acetic acid (2.5 ml, 0.044 mmol). Acetic hydrazide (63 mg, 0.850 mmol) was then added and the mixture was stirred at room temperature for 20 h, then at 50° C. for 23 h. After allowing to cool, the resulting brown solid was collected by filtration, and washed with dichloromethane to leave 230 mg of the intermediate acylimidrazone. This was then heated at 145° C. under high vacuum for 2 days, and the residue was purified by preparative TLC (silica gel 5% MeOH/CH$_2$Cl$_2$) and recrystallised to leave 61 mg (19%) of the title compound as a white solid: mp 233–235° C.; $^1$H NMR (360 MHz, CDCl$_3$) δ2.50 (3 H, s), 5.61 (2 H), 7.41–7.52 (6 H, m), 7.58–7.59 (2 H, m), 7.96 (1 H, s), 8.44 (2 H, m); MS (ES$^+$) m/e 384 [MH]$^+$.

EXAMPLE 80

6-(3-Methyl-3 H-1,2,3-trizol-4-ylmethoxy)-3,7-diphenyl-1,2,4-triazolo[4,3-b]pyridazine a) 3-Methyl-3 H-1,2,3-triazole-4-carboxaldehyde To a stirred solution of 1-methyl-1 H-1,2,3-triazole (0.500 g, 6.02 mmol) in anhydrous THF (20 ml), cooled to −70° C.

under nitrogen, was added dropwise a 1.6 M solution of butyl lithium in hexanes (4.23 ml, 6.77 mmol). The mixture was stirred at this temperature for 1 h, then anhydrous DMF (0.465 ml, 6.02 mmol) was added, and the mixture was allowed to warm to 0° C. over 30 min. Saturated aqueous NH$_4$Cl (25 ml) was then added and the mixture was extracted with ethyl acetate. The organic layer was dried (Na$_2$SO$_4$) and evaporated in vacuo. The residue was purified by flash chromatography (silica gel, 40% EtOAc/hexane) to give 0.128 g (19%) of the title compound as a yellow oil: $^1$H NMR (360 MHz, d$_6$-DMSO) δ4.27 (3 H, s), 8.45 (1 H, s), 10.01 (1 H, s); MS (ES$^+$) m/e 144[M+MeOH+H]$^+$, 111[M]$^+$.

b) (3-Methyl-3 H-1,2,3-triazol-4-yl)-methanol

To a stirred solution of the product from Step a (0.128 g, 1.15 mmol) in anhydrous methanol (1.1 ml), cooled to 0° C. under nitrogen, was added sodium borohydride (14.8 mg, 0.390 mmol) and the mixture was stirred at this temperature for 1 h. Saturated aqueous NaCl (5 ml) was then added and the mixture was stirred for 10 min. The aqueous layer was extracted with ethyl acetate, and the combined organic extracts were dried (Na$_2$SO$_4$). and evaporated in vacuo. The residue was purified by flash chromatography (silica gel, 5% MeOH/CH$_2$Cl$_2$) to afford 86.3 mg (66%) of the title compound: $^1$H NMR (250 MHz, CDCl$_3$) δ4.10 (3 H, s), 4.77 (2 H, s), 7.53 (1 H, s).

c) 6-(3-Methyl-3 H-1,2,3-triazol-4-ylmethoxy)-3,7-diphenyl-1,2,4-triazolo[4,3-b]pyridazine This compound was prepared in 29% yield using a similar procedure to that described in Example 2, Step d, but using (3-methyl-3 H-1,2,3-triazol-4-yl)methanol (fom Step b) instead of 2-pyridylcarbinol. Data for the title compound: mp 190–193° C.; $^1$H NMR (360 MHz, CDCl$_3$) δ3.94 (3 H, s), 5.60 (2 H, s), 7.49 (5 H, s), 7.54–7.63 (3 H, m), 7.75 (1 H, s), 8.08 (1 H, s), 8.41 (2 H, dd, J=8.3, 1.6 Hz); MS (ES$^+$) m/e 384 [MH]$^+$. Anal. Found C, 62.88; H, 4.63; N, 24.10. C$_{21}$H$_{17}$N$_7$O.H$_2$O requires C, 62.83; H, 4.77; N, 24.42%.

EXAMPLE 81

3-(4-Methoxyphenyl)-6-(1-methyl-1 H-1,2,4-triazol-3-ylmethoxy)-7-phenyl-1,2,4-triazolo[4,3-b] pyridazine This compound was prepared using the procedures described in Example 2 a), b), c), d) with 4-methoxybenzyl hydrazide being used instead of benzoyl hydrazine in Step c) and (1-methyl-1 H-1,2,4-triazol-3-yl)methanol being used instead of 2-pyridylcarbinol in Step d).
Data for the title compound: m.p.=205–206° C. $^1$H NMR (360 MHz, d$_6$-DMSO) δ3.87 (6 H, s), 5.54 (2 H, s), 7.16–7.18 (2 H, d, J=7.2 Hz), 7.49 (3 H, m), 7.74 (2 H, m), 8.36 (1 H, s), 8.41–8.43 (2 H, d. J=7.2 Hz), 8.49 (1 H. s); MS (ES$^+$) m/e 414 [MH$^+$].

EXAMPLE 82

6-(3-Methylpyridin- 2-ylmethoxy)-3-phenyl-7-(piperidin-1-yl)-1,2,4-triazolo[4,3-b]pyridazine The compound was prepared using the procedures described in Example 15 Steps a), b), c), d) and e) with 3-methyl-2-pyridinemethanol being used instead of 2-pyridylcarbinol. Data for the title compound: mp=160° C. $^1$H NMR (250 MHz, CDCl$_3$) δ1.52–1.81 (6 H, m), 2.45 (1 H, s), 3.08–3.28 (4 H, m), 5.63 (1 H, s), 7.20–7.30 (1 H, m), 7.38–7.52 (4 H, m), 7.60 (1 H, d, J=7.6 Hz), 8.25–8.36 (2 H, m); MS (ES$^+$) m/e 401 [MH]$^+$. Anal. Found C, 69.01; H, 6.00; N, 21.00. C$_{23}$H$_{24}$N$_6$O requires C, 68.98; H, 6.04; N, 20.99%.

EXAMPLE 83

7-(Morpholin-4-yl)-3-phenyl-6-(pyridin-2-ylmethoxy)- 1,2,4-triazolo[4,3-b]pyridazine This compound was prepared using the procedures described in Example 15 Steps a), b), c), d) and e) with morpholine used instead of piperidine in Step c). Data for the title compound: mp=214° C. $^1$H NMR (360 MHz, CDCl$_3$) δ3.30–3.38 (4 H, m), 3.88–3.94(4 H, m), 5.64 (2 H, s), 7.30 (2 H, t, J=5.76 Hz), 7.45–7.58 (3 H, m), 7.78 (1 H, dt, J=7.8, 1.7 Hz), 8.26–8.35 (2 H, m), 8.67 (1 H, d, J=7.2 Hz); MS (ES$^+$) m/e 389 [MH]$^+$. Anal. Found C, 64.37, H, 5.22; N, 21.62. C$_{21}$H$_{20}$N$_6$O$_2$.0.15 H$_2$O requires C, 64.49; H, 5.22; N, 21.49%.

EXAMPLE 84

3-Phenyl-7-(pyridin-3-yl)-6-(pyridin-2-ylmethoxy)-1,2,4-triazolo[4,3-b]pyridazine This compound was prepared using the procedures described in Example 16 Steps a), b) and c) using 3-pyridyl boronic acid, instead of 4-pyridyl boronic acid in Step a). Data for the title compound. mp=206° C. $^1$H NMR (360 MHz, CDCl$_3$) δ5.66 (2 H, s), 7.28 (1 H, t, J=6.5 Hz), 7.35 (1 H, d, J=7.8 Hz), 7.40–7.62 (4 H, m), 7.72 (1 H, td, 7.7, 1.7 Hz), 8.04 (1 H, dt, J=7.7, 1.7 Hz), 8.11 (1 H, s), 8.43 (2 H, dd, J=9.6, 1.3 Hz), 8.64 (1 H, d, J=6.5 Hz), 8.74 (1 H, d, J=6.5 Hz), 8.95 (1 H, s); MS (ES$^+$) m/e 381 [MH]$^+$. Anal. Found C, 69.33; H, 4.27; N, 21.57. C$_{22}$H$_{16}$N$_6$O. 0.15(C$_2$H$_5$)$_2$O requires C, 69.33; H, 4.51; N, 21.47%.

EXAMPLE 85

8-Methyl-6-(2-methyl-2 H-1,2,4-triazol-3-ylmethoxy)-3,7-diphenyl-1,2,4-triazolo[4,3-b] pyridazine This compound was prepared using the procedures described in Example 8 Steps a), b), c) and d) with (2-methyl-2 H-1,2,4-triazol-3-yl)methanol (prepared using the conditions described in (EP-A-421210) being used instead of 2-pyridyl carbinol in Step d). Data for the title compound: mp=195° C. $^1$H NMR (360 Mz, CDCl$_3$) δ2.57 (3 H, s), 3.56 (3 H, s), 5.57 (2 H, s), 7.28.(2 H, dd, J=7.7, 2.2 Hz), 7.47–7.60 (6 H, m), 7.84 (1 H, s), 8.44 (2 H, dd, J=6.8, 2.0 Hz), 7.47–7.60 (6 H, m), 7.84 (1 H, s), 8.44 (2 H, dd, J=6.8, 2.0 Hz); MS (ES$^+$) m/e 398 [MH]$^+$. Anal. Found C, 66.52; H, 4.87; N, 23.74. C$_{22}$H$_{19}$N$_7$O requires C, 66.49; H, 4.82; N, 24.67%.

EXAMPLE 86

6-(1-Methyl-1 H-1,2,4-triazol-3-ylmethoxy)-7-(morpholin-4-yl)-3-phenyl-1,2,4-triazolo [4,3-b] pyridazine This compound was prepared using the procedures described in Example 15 Steps a), b), c), d) and e) with morpholine used instead of piperidine in Step c) and with (1-methyl-1 H-1,2,4-triazol-3-yl)methanol (prepared using the conditions in EP-A421210) being used instead of 2-pyridyl carbinol in Step e). Data for the title compound: mp=205–206° C. $^1$H NMR (360 MHz, CDCl$_3$) δ3.28 (4 H, t, J=5.5 Hz), 3.88 (4 H, t, J=4.7 Hz), 3.94 (3 H, s), 5.59 (2 H, s), 7.21 (1 H, s), 7.45–7.55 (3 H, m), 8.05 (1 H, s), 8.46 (2 H, dd, J=2.0, 6.9 Hz); MS (ES$^+$) m/e 393 [MH]$^+$. Anal. Found C, 58.55; H, 4.95; N, 28.42. C$_{19}$H$_{20}$N$_8$O$_2$ requires C, 58.15; H, 5.14; N, 28.55%.

EXAMPLE 87

6-(2-Methyl-2 H-1,2,4-triazol-3-ylmethoxy)-7-(morpholin-4-yl)-3-phenyl-1,2,4-triazolo[4,3-b]pyridazine This compound was prepared using the procedures described in Example 86 Steps a), b), c), d) and e) with (2-methyl-2 H-1,2,4-triazol-3-yl)-methanol (prepared using the conditions described in EP-A-421210) being used instead of (1-methyl-1 H-1,2,4-triazol-3-yl)methanol in Step e). Data for the title compound: mp=210–211° C. $^1$H NMR (360 MHz, CDCl$_3$) δ3.21 (4 H, t, J=4.7 Hz), 3.84.(4 H, t, J=4.7 Hz), 3.97 (3 H, s), 5.63 (2 H, s), 7.24 (1 H, s), 7.47–7.56 (3 H, m), 7.93 (1 H, s), 8.27 (2 H, dd, J=1.7, 8.3 Hz); MS (ES$^+$) m/e 393 [MH]$^+$. Anal Found C, 58.34; H, 4.88; N, 28.33. $C_{19}H_{20}N_8O_2$ requires C, 58.15; H, 5.14; N, 28.55%.

EXAMPLE 88

7-Cyclohexyl-6-(2-methyl-2 H-1,2,4-triazol-3-ylmethoxy)-3-phenyl-1,2,4-triazolo[4,3-b]pyridazine a) 6-Chloro-3-phenyl-1,2,4-triazolo[4,3-b]pyridazine 3,6-Dichloropyridazine (20 g, 134 mmol) was suspended in xylene (200 ml) with benzoylhydrazine (20.1 g, 1.1 mol eq) and triethylamine hydrochloride (20.3 g, 1.1 mol eq) and the reaction mixture was heated under reflux for 2 hours. The solvent was removed under high vacuum and the residue was purified by chromatography on silica gel using 1% methanol in dichloromethane as eluent to give the required product (17.1 g mp=199° C.). $^1$H NMR (250 MHz, CDCl$_3$) δ7.16 (1 H, d, J=9.7 Hz), 7.53–7.61 (3 H, m), 8.16 (1 H, d, J=9.7 Hz), 8.44–8.50 (2 H, m); MS (ES$^+$) m/e 231 [MH]$^+$.

b) 6-(2-Methyl-2 H-1,2,4-triazol-3-ylmethoxy)-3-phenyl-1,2,4-triazolo[4,3-b]pyridazine To a solution of (2-methyl-2 H-1,2,4-triazol-3-yl)methanol (0.9 g, 8.0 mmol) (prepared using the conditions described in EP-A-421210) in DMF (30 ml) was added sodium hydride (0.32 g of a 60% dispersion in oil, 1.6 mol eq.) and the reaction mixture was stirred at room temperature for 30 minutes. After this time the product from Example 88 Step a) (1.15 g, 5.0 mmol) was added as a solution in DMF (20 ml) and the reaction mixture was stirred at room temperature for 2 hours. The reaction mixture was diluted with water (200 ml) and the aqueous extracted with dichloromethane (4×150 ml). The combined extracts were dried (Na$_2$SO$_4$), filtered and evaporated. The residue was purified by chromatography on silica gel using 4% MeOH in dichloromethane as eluent to give the required product, (1.5 g, mp=254° C.). $^1$H NMR (360 MHz, CDCl$_3$) δ3.98 (3 H, s), 5.61 (2 H, s), 6.90 (1 H, d, J=9.8 Hz), 7.51–7.60 (3 H, m), 7.94(1 H, s), 8.12 (1 H, d, J=9.8 Hz), 8.39 (2 H, dd, J=9.6, 1.5 Hz); MS (ES$^+$) m/e 308 [MH]$^+$.

c) 7-Cyclohexyl-6-(2-methyl-2 H-1,2,4-triazol-3-ylmethoxy)-3-phenyl-1,2,4-triazolo[4,3-b]pyridazine To the product from Example 88 Step c) (0.91 g, 3.0 mmol) was added water (12 ml) and sulphuric acid (0.24 mL 1.5 mol eq, sp.gr.=1.84). The mixture was heated to 70° C. and cyclohexane carboxylic acid (0.85 g, 2.3 mol eq) and silver nitrate (0.05 g, 0.1 mol eq) added. The reaction mixture was degassed with nitrogen and a solution of ammonium persulphate (1.0 g, 1.5 mol eq) in water (5 ml) added via syringe over 5 minutes. After an additional hour of heating at 70° C., the reaction was poured onto ice, basified to pH 8–9 with aqueous ammonium hydroxide and extracted into dichloromethane (2×100 ml). The combined organic extracts were dried (Na$_2$SO$_4$), filtered and evaporated to give the required product (0.21 g, m.p.=192° C.). $^1$H NMR (250 MHz, CDCl$_3$) δ1.22–1.54 (6 H, m), 1.72–2.04 (4 H, m), 2.79 (1 H, m), 3.98 (3 H, s), 5.64 (2 H, s), 7.48–7.60 (3 H, m), 7.88 (1 H, d, J=0.9 Hz), 7.95 (1 H, s), 8.34–8.38 (2 H, m); MS (ES$^+$) m/e 398 [MH]$^+$. Anal. Found C, 65.01; H, 5.82; N, 25.10%. $C_{21}H_{23}N_7O$ requires C, 64.78; H, 5.95; N, 25.18%.

EXAMPLE 89

7-Cyclohexyl-6-(1-methyl-1 H-1,2,4-triazol-3-ylmethoxy)-3-phenyl-1,2,4-triazolo[4,3-b]pyridazine This compound was prepared using the procedures described in Example 88 Steps a), b) and c) with (1-methyl-1 H-1,2,4-triazol-3-yl)methanol (prepared using the conditions described in EP-A-421210) used instead of (2-methyl-2 H-1,2,4-triazol-3-yl)methanol in Step b). Data for the title compound: $^1$H NMR (360 MHz, CDCl$_3$) δ1.20–1.52 (5 H, m), 1.72–1.92 (3 H, m), 1.20–2.03 (2 H, m), 2.83–2.93 (1 H, m), 3.94 (3 H, s), 5.57 (2 H, s), 7.48–7.56 (3 H, m), 7.83 (1 H, s), 8.06 (1 H, s), 8.48–8.54 (2 H, m); MS (ES$^+$) m/e 398 [MH]$^+$. Anal. Found C, 64.40; H, 5.95; N, 23.89%. $C_{21}H_{23}N_7O$ 0.15 $C_6H_{14}$ 0.1 $H_2O$ requires C, 64.79; H, 6.33; N, 24.15%.

EXAMPLE 90

7-Cyclopentyl-6-(2-methyl-2 H-1,2,4-triazol-3-ylmethoxy)-3-phenyl-1,2,4-triazolo[4,3-b]pyridazine This compound was prepared using the procedures described in Example 88 Steps a), b) and c) with cyclopentane carboxylic acid used instead of cyclohexane carboxyhic acid in Step c). Data for the title compound: $^1$H NMR (360 MHz, CDCl$_3$) δ1.56–1.88 (6 H, m), 2.04–2.16 (2 H, m), 3.15–3.25 (1 H, m), 3.97 (3 H, s), 5.63 (2 H, s), 7.51–7.57 (3 H, m), 7.91 (1 H, d, J=0.8 Hz), 7.95 (1 H, s), 8.37 (2 H, dd, J=6.6, 1.3 Hz); MS (ES$^+$) m/e 376 [MH]$^+$. Anal. Found C, 63.65; H, 5.51; N, 25.26%. $C_{20}H_{21}N_7O$. 0.2 $C_2H_6O$ requires C, 63.70; H, 5.82; N, 25.49%.

EXAMPLE 91

8-Methyl-6-(1-methyl-1 H-1,2,4-triazol-3-ylmethoxy)-3,7-diphenyl-1,2,4-triazolo[4,3-b]pyridazine This compound was prepared using the procedures described in Example 8 Steps a), b), c) and d) with (1-methyl-1 H-1,2,4-triazol-3-yl)methanol (prepared using the conditions described in EP-A-421210) used in Step d) instead of 2-pyridylcarbinol. Data for the title compound: $^1$H NMR (360 MHz, CDCl$_3$) δ2.56 (3 H, s), 3.87 (3 H, s), 5.49 (2 H, s), 7.36–7.57 (8 H, m), 7.97 (1 H, s), 8.50–8.56 (2 H, m); MS (ES$^+$s) m/e 398 [MH]$^+$. Anal. Found C, 66.45; H, 4.36; N, 23.95. $C_{22}H_{19}N_7O$ requires C, 66.49; H, 4.82; N, 24.67%.

EXAMPLE 92

7-Cyclobutyl-6-(1-methyl-1 H-1,2,4-triazol-3-ylmethoxy)-3-phenyl-1,2,4-triazolo[4,3-b]pyridazine This compound was prepared using the procedures described in Example 88 Steps a), b) and c) using (1-methyl-1 H-1,2,4-triazol-3-yl)methanol (prepared using the conditions described in EP-A-421210) instead of (2-methyl-2 H-1,2,4-triazol-3-yl)methanol in Step b) and using cyclobutane carboxylic acid instead of cyclohexane

63 carboxylic acid in Step c). Data for title compound: $^1$H NMR (360 MHz, CDCl$_3$) δ1.88–2.05 (2 H, m), 2.06–2.39 (2 H, m), 2.40–2.50 (2 H, m), 3.67–3.71 (1 H, m), 3.95 (3 H, s), 5.53 (2 H, s), 7.49–7.85 (3 H, m), 8.06 (1 H, s), 8.49 (1 H, s), 8.51 (2 H, d, J=1.3 Hz); MS (ES$^+$) m/e 362 [MH]$^+$. Anal. Found C, 62.98; H, 5.07; N, 26.90. C$_{19}$H$_{19}$N$_7$O requires C, 63.14; H, 5.30; N, 27.13%.

EXAMPLE 93

7-tert-Butyl-6-(2-methyl-2 H-1,2,4-triazol-3-ylmethoxy)-3-phenyl-1,2,4-triazolo[4.3-b]pyridazine This compound was prepared using the procedures described in Example 88 Steps a), b) and c) using trimethylacetic acid instead of cyclohexane carboxylic acid in Step c). Data for the title compound: $^1$H NMR (360 MHz, CDCl$_3$) δ1.41 (9 H, s), 3.97 (3 H, s), 5.65 (2 H, s), 7.50–7.57 (3 H, m), 7.96 (1 H, s), 8.01 (1 H, s), 8.36–8.38 (2 H, m); MS (ES$^+$) m/e 364 [MH]$^+$. Anal. Found C, 62.38; H, 5.83; N, 26.45. C$_{19}$H$_{21}$N$_7$O 0.15 H$_2$O requires C, 62.33; H, 5.86; N, 26.78%.

EXAMPLE 94

7-Cyclobutyl-6-(2-methyl-2 H-1,2,4-triazol-3-ylmethoxy)-3-phenyl-1,2,4-triazolo[4,3-b]pyridazine This compound was prepared using the procedures described in Example 88 Steps a), b) and c) using cyclobutane carboxylic acid instead of cyclohexane carboxylic acid in Step c). Data for the title compound: mp=228° C. $^1$H NMR (360 MHz, CDCl$_3$) δ1.86–1.98 (1 H, m), 2.00–2.22 (3 H, m), 2.26–2.45 (2 H, m), 3.54–3.68 (1 H, m), 3.97 (3 H, s), 5.59 (2 H, s), 7.47–7.60 (3 H, m), 7.86 (1 H, d, J=1.6 Hz), 7.94 (1 I, s), 8.35–8.42 (2 H, m); MS (ES$^+$) m/e 397 [MH]$^+$. Anal. Found C, 63.38; H, 5.22; N, 27.19. C$_{19}$H$_{19}$N$_7$O requires C, 63.14; H, 5.30; N, 27.13%.

EXAMPLE 95

7-Ethyl-6-(2-methyl-2 H-1,2,4-triazol-3-ylmethoxy)-3-phenyl-1,2,4-triazolo[4,3-b]-pyridazine This compound was prepared using the procedures described in Example 88 Steps a), b) and c) using propionic acid instead of cyclohexane carboxylic acid in Step c). Data for the title compound: $^1$H NMR (360 MHz, CDCl$_3$) δ1.31 (3 H, t, J=7.4 Hz), 2.71 (2 H, q, J=7.4 Hz), 3.99 (3 H, s), 5.63 (2 H, s), 7.47–7.60 (3 H, m), 7.87 (1 H, s), 7.94 (1 H, s), 8.34–8.42 (2 H, m); MS (ES$^+$) m/e 336 [MH]$^+$. Anal. Found C, 60.85; H, 5.39; N, 28.22. C$_{17}$H$_{17}$N$_7$O 0.1 H$_2$O requires C, 60.50; H. 4.98; N, 27.77%.

EXAMPLE 96

7-tert-Butyl-6-(1-methyl-1 H-1,2,4-triazol[4,3-b]pyridazine

This compound was prepared using the procedures described in Example 88 Steps a), b) and c) using (1-methyl-1 H-1,2,4-triazol-3-yl)methanol (prepared using the conditions described in EP-A-421210) instead of (2-methyl-2 H-1,2,4-triazol-3-yl)methanol in Step b), and using trimethylacetic acid instead of cyclohexane carboxylic acid in Step c). Data for the title compound: $^1$H NMR (360 MHz, CDCl$_3$) δ1.45 (9 H, s), 3.95 (3H, s), 5.59 (2 H, s), 7.43–7.60 (3 H, m), 7.95 (1 H, s), 8.06 (1 H, s), 8.49–8.55 (2 H, m); MS (ES$^+$) m/e 364 [MH]$^+$. Anal. Found C, 62.03; H, 5.58; N, 25.67. C$_{19}$H$_{21}$N$_7$O 0.12 C$_6$H$_{14}$ 0.33 H$_2$O requires C, 62.36; H. 6.19; N, 25.84%.

64

EXAMPLE 97

7-Ethyl-6-(1-methyl-1 H-1,2,4-triazol-3-ylmethoxy)-3-phenyl-1,2,4-triazolo[4,3-b]pyridazine This compound was prepared using the procedures described in Example 88 Steps a), b) and c) using (1-methyl-1 H-1,2,4-triazol-3-yl)methanol (prepared using the conditions described in EP-A-421210) instead of (2-methyl-2 H-1,2,4-triazol-3-yl)methanol in Step b) and using propionic acid instead of cyclohexane carboxylic acid in Step c). Data for the title compound: $^1$H NMR (360 MHz, CDCl$_3$) δ1.31 (3 H, t, J=7.4 Hz), 2.68–2.84 (2 H, q, J=7.4 Hz), 3.94 (3 H, s), 5.56 (2 H, s), 7.43–7.64 (3 H, m), 7.82 (1 H, s), 8.06 (1 H, s), 8.46–8.60 (2 H, m); MS (ES$^+$) m/e 336 [MH]$^+$. Anal. Found C, 60.91; H, 4.73; N, 29.07. C$_{17}$H$_{17}$N$_7$O requires C, 60.88; H, 5.11; N, 29.24%.

EXAMPLE 98

7-Methyl-6-(2-methyl-2 H- 1,2,4-triazol-3-ylmethoxy)-3-phenyl-1,2,4-triazolo[4,3-b]pyridazine This compound was prepared using the procedures described in Example 5 Steps c) and d) using (2-methyl-2 H-1,2,4-triazol-3-yl)methanol (prepared using the conditions described in EP-A-421210) instead of 2-pyridyl carbinol in Step d). Data for title compound: $^1$H NMR (360 MHz, CDCl$_3$) δ2.34 (3 H, d, J=1.2 Hz), 3.99 (3 H, s), 5.62 (2 H, s), 7.47–7.60 (3 H, m), 7.85 (1 H, d, J=1.3 Hz), 7.94 (1 H, a), 8.34–8.41 (2 H, m); MS (ES$^+$) m/e 322 [MH]$^+$. Anal. Found C, 60.26; H, 4.45; N, 30.18. C$_{16}$H$_{15}$N$_7$O 0.05 C$_6$H$_{14}$ requires C, 60.12; H, 4.86; N, 30.11%.

EXAMPLE 99

7-(1-Methylcyclobutyl)-6-(2-methyl-2 H-1,2,4-triazol-3-ylmethoxy)-3-phenyl-1,2,4-triazolo[4,3-b]pyridazine This compound was prepared using the procedures described in Example 88 Steps a), b) and c) using 1-methylcyclobutane carboxylic acid (*Journal of Organometallic Chemistry,* 1988,352, 263–272) instead of cyclohexane carboxylic acid in Step c). Data for the title compound: $^1$H NMR (360 MHz, CDCl$_3$) δ1.51 (3 H, s), 1.80–1.92 (1 H, m), 2.02–2.26 (3 H, m), 2.34–2.45 (2 H, m), 3.95 (3 H, 8), 5.60 (2 H, s), 7.47–7.60 (3 H, m), 7.47 (1 H, s), 7.94 (1 H, s), 8.38 (2 H, dd, J=6.6, 1.7 Hz); MS (ES$^+$) m/e 376 [MH]$^+$. Anal. Found C, 63.82; H, 5.53; N, 25.82. C$_{20}$H$_{21}$N$_7$O requires C, 63.98; H, 5.64; N, 26.12%.

EXAMPLE 100

7-Methyl-6-(1-methyl-1 H-1,2,4-triazol-3-ylmethoxy)-3-phenyl-1,2,4-triazolo[4,3-b]pyridazine This compound was prepared using the procedures described in Example 5, Steps c) and d) using (1-methyl-1H-1,2,4-triazol-3-yl)methanol (prepared using the conditions described in EP-A421210) instead of hydroxymethyl pyridine in Step d). Data for the title compound: $^1$H NMR (360 MHz, CDCl$_3$) δ2.37 (3 H, s), 3.95,(3 H, s), 5.55 (2 H, s), 7.4514 7.59 (3 H, m), 7.83 (1 H, d, J=1.2 Hz), 8.07 (1 H, s), 8.43–8.54 (2 H, m); MS (ES$^+$) m/e 322 [MH]$^+$.Anal. Found C, 59.51; H, 4.45; N, 29.88. C$_{16}$H$_{15}$N$_7$O requires C, 59.80; H, 4.71; N, 30.51%.

EXAMPLE 101

7-Cyclobutyl-3-phenyl-6-(2 H-1,2,4-triazol-3-ylmethoxy)-1,2,4-triazolo[4,3-b]pyridazine This compound was prepared in a way to that described in Example 102 Steps a), b) and c) using cyclobutane carboxylic acid instead of cyclopentane carboxylic acid in Step a), using benzoic hydrazide instead of 2-thiophene carboxylic acid hydrazide in Step b) and using 3-hydroxymethyl-2-[2-(trimethylsilanyl)ethoxy]methyl-2 H-1,2,4-triazole (prepared in Example 72 Step a) instead of 2-hydroxymethylpyridine in Step c). This was followed by the procedure described in Example 72 Step c) to give the title compound. Data for the title compound: $^1$H NMR (360 MHz, $d_6$-DMSO) δ1.74–1.90 (1 H, m), 1.90–2.29 (5 H, m), 3.50–3.71 (1 H, m), 5.54 (2 H, s), 7.48–7.69 (3 H, m), 8.14 (1 H, d, J=1.0 Hz), 8.30–8.49 (2 H, m), 8.52 (1 H, br s); MS (ES$^+$) m/e 348 [MH$^+$. Anal. Found C, 61.93; H, 4.65; N, 27.58. $C_{18}H_{17}N_7O_3$ 0.17 $H_2O$ requires C, 61.69; H, 4.99; N, 27.98%.

EXAMPLE 102

7-Cyclopentyl-6-(pyridin-2-ylmethoxy)-3-(thiophen-2-yl)-1,2,4-triazolo[4,3-b]pyridazine a) 3,6-Dichloro-4-cyclopentylpyridazine 3,6-Dichloropyridazine (10 g) was suspe n ded in water (200 ml), conc. $H_2SO_4$ (19.7 g) and cyclopentane carboxylic acid (32.7 g) was added and the reaction degassed under $N_2$ at 70° C. Silver nitrate (2.28 g) was added followed by dropwise a ddition of ammonium persulfate (45.9 g) in water (120 ml). After ail additional one hour heating at 70° C., the reaction was poured onto ice, basfied to pH 8–9 with aqueous ammonium hydroxide and extracted into ethyl acetate (3×500 ml), dried (MgSO$_4$) and evaporated to dryness. Purified with hexane-ethyl acetate mixtures to obtain pure product (13.4 g). $^1$H NMR (360 MHz, CDCl$_3$) δ1.57 (2 H, m), 1.82 (4 H, m), 2.20 (1 H, m), 3.30 (1 H, m), 7.38 (1 H, s); MS (ES$^+$) m/e 217 [MH]$^+$.

b) 6-Chloro-7-cyclopentyl-3-(thiophen-2-yl)1,2,4-triazolof[4,3-b]pyridazine 3,6-Dichloro-4-cyclopentylpyridazine (1.6 g) was heated with 2-thiophene carboxylic acid hydrazide (1.16 g) and triethylamine hydrochloride (1.16 g) in xylene (10 ml) at 140° C. for 18 hours. The cooled reaction was partioned between ethyl acetate and sodium carbonate solution, the organic phase separated, dried (MgSO$_4$), evaporated to dryness and purified on silica gel eluting with hexane-ethyl acetate mixtures to give both 7- and 8-cyclopentyl isomers. $^1$H NMR (360 MHz, CDCl$_3$) δ1.89 (6 H, m), 2.30 (2 H, m), 6.93 (1 H, s), 7.23 (1 H, dd, J=5.2, 3.9 Hz), 7.54 (1 H, dd, J=4.9, 0.9 Hz), 8.25 (1 H, dd, J=3.8, 1.0 Hz); MS (ES$^+$) m/e 305 [MH]$^+$ (less polar isomer). $^1$H NMR (360 MHz, CDCl$_3$) δ1.70 (6 H, m), 2.23 (2 H, m), 3.36 (1 H, m), 7.24 (1 H, m), 7.55 (1 H, dd, J=7.0, 1.6 Hz), 7.99 (1 H, s), 8.24 (1 H, dd, J=5.3, 1.6 Hz); MS (ES$^+$) m/e 305 [MH]$^+$ (more polar isomer).

c) 7-Cyclopentyl-6-(pyridin-2-ylmethoxy)-3-(thiophen-2-yl)-1,2,4-triazolo[4,3-b]pyridazine b 2-Hydroxymethylpyridine (56 mg) was dissolved in dimethylformamide (2 ml) under $N_2$. Sodium hydride (60% w/w in oil, 21 mg) was added followed after 5–10 minutes by 6-chloro-7-cyclopentyl-3-(thiophen-2-yl)-1,2,4-triazolo[4,3-b]pyridazine (100 mg). Reaction was stirred at room temperature for 18 hours, partitioned between ethyl acetate and water, organic phase separated dried (MgSO$_4$) and evaporated to dryness. Recrystallized in ethyl acetate in ether or methanol to give pure product. $^1$H NMR (250 MHz, CDCl$_3$) δ1.73 (6 H, m), 2.16 (2 H, m) 3.38 (1 H, m), 5.68 (2 H, s), 7.21 (1 H, m), 7.28 (1 H, m), 7.51 (2 H, m), 7.77 (1 H, m), 7.88 (1 H, d, J=1.1 Hz), 8.15 (1 H, m), 8.65 (1 H, m); MS (ES$^+$) m/e 377 [MH]$^+$.

EXAMPLE 103

7-Cyclopentyl-3-(2,4-difluorophenyl)-6-(1-methyl-1 H-1,2,4-triazol-3-ylmethoxy)-1,2,4-tiazolo[4,3-b]pyridazine Prepared in an analogous procedure as outlined in Example 102b using 2,4-difluorobenzoic acid hydrazide and Example 102c using (1-methyl-1 H-1,2,4-triazol-3-yl)methanol to give the title compound. $^1$H NMR (360 MHz, CDCl$_3$) δ1.75 (6 H, m), 2.14 (2 H, m) 3.24 (1 H, m), 3.93 (3 H, s), 5.42 (2 H, s), 7.14 (2 H, m), 7.86 (1 H, s), 7.90 (1 H, m), 8.04 (1 H, s); MS (ES$^+$) m/e 412 [MH]$^+$.

EXAMPLE 104

7-Cyclopentyl6-(1-methyl-1 H-1,2,4-triazol-3-ylmethoxy)-3-(thiophen-2-yl)-1,2,4-triazolo[4,3-b]pyridazine Prepared in an analogous procedure as outlined in Example 102b using 2-thiophene carboxylic acid hydrazide and Example 102c using (1-methyl-1 H-1,2,4-triazol-3-yl)methanol to give the title compound. $^1$H NMR (250 MHz, CDCl$_3$) δ1.32 (6 H, m), 2.14 (2 H, m), 3.28 (1 H, m), 3.95 (3 H, s), 5.61 (2 H, s), 7.24 (1 H, m), 7.50 (1 H, dd, J=1.2, 5.1 Hz), 7.84 (1 H, d, J=1.1 Hz), 8.07 (1 H, s), 8.25 (1 H, dd, J=3.7, 1.1 Hz); MS (ES$^+$) m/e 382 [MH]$^+$.

EXAMPLE 105

7-Cyclopentyl-6-(2-methyl-2 H-1,2,4-triazol-3-ylmethoxy)-3-(thiophen-2-yl)-1,2,4-triazolo[4,3-b]pyridazine Prepared in an analogous procedure as outlined in Example 102b using 2-thiophene carboxyhic acid hydrazide and Example 102c using (2-methyl-2 H-1,2,4-triazol-3-yl)methanol to give the title compound. $^1$H NMR (250 MHz, CDCl$_3$) δ1.73 (6 H, m), 2.08 (2 H m), 3.18 (1 H, m), 4.03 (3 H, s), 5.69 (2 H, s), 7.24 (1 H, m), 7.52 (1 H, dd, J=5.0, 1.2 Hz), 7.88 (1 H, d, J=1.1 Hz), 8.01 (1 H, a), 8.18 (1 H, dd, J=3.7, 1.1 Hz); MS (ES$^+$) m/e 382 [MH]$^+$.

EXAMPLE 106

7-Cyclopentyl-6-(2-methyl-2 H-1,2,4-triazol-3-ylmethoxy)-3-(pyridin-4-yl)-1,2,4-triazolo[4,3-b]pyridazine Prepared in an analogous procedure as outlined in Example 102b using isonicotinic hydrazide and Example 102c using (2-methyl-2 H-1,2,4-triazol-3-yl)methanol to give the title compound. $^1$H NMR (250 MHz, CDCl$_3$) δ1.75 (6 H, m), 2.12 (2 H, m), 3.22 (1 H, m), 4.02 (3 H, s), 5.68 (2 H, s), 7.96 (1 H, m), 8.43 (2 H, d, J=6.2 Hz), 8.83 (2 H, d, J=6.0 Hz); MS (ES$^+$) m/e 377 [MH]$^+$.

EXAMPLE 107

7-Cyclopentyl-3-(2-fluorophenyl)-6-(1-methyl-1 H-1,2,4-triazol-3-ylmethoxy)-1,2,4-triazolo[4,3-b]pyridazine Prepared in an analogous procedure as outlined in Example 102b using o-fluorobenzyl hydrazide and Example 102c using (1-methyl-1 H-1,2,4-triazol-3-yl)methanol to give the title compound. $^1$H NMR (250 MHz, CDCl$_3$) δ1.69 (6 H, m), 2.12 (2 H, m), 3.23 (1 H, m), 3.93 (3 H, s), 5.41 (2 H, s), 7.29 (2 H m), 7.51 (1 H, m), 7.85 (1 H, d, J=0.7 Hz), 7.97 (1 H, m), 8.04 (1 H, s); MS (ES$^+$) m/e 394 [MH]$^+$.

EXAMPLE 108

7-Cyclopentyl-3-(2-fluorophenyl)-6-(2-methyl-2 H-1,2,4-triazol-3-ylmethoxy)-1,2,4-triazolo[4,3-b]pyridazine Prepared in an analogous procedure as outlined in Example 102b using o-fluorobenzyl hydrazide and Example 102c using (2-methyl-2 H-1,2,4-triazol-3-yl)methanol to give the title compound. $^1$H NMR (250 MHz, CDCl$_3$) δ1.72 (6 H, m), 2.08 (2 H, m), 3.19 (1 H, m), 3.84 (3 H, s), 5.49 (2 H, s), 7.32 (2 H, m), 7.58 (1 H, m), 7.87 (2 H, m), 7.90 (1 H, m); MS (ES$^+$) m/e 394

EXAMPLE 109

7-Cyclopentyl-3-(2-fluoronphenyl)-6-(pyridin-2-ylmethoxy)-1,2,4-triazolo[4,3-b]pyridazine Prepared in an analogous procedure as outlined in Example 102b using o-fluorobenzyl hydrazide and Example 102c using 2-hydroxymethyl pyridine to give the title compound. $^1$H NMR (250 MHz, CDCl$_3$) δ1.74 (6 H, m), 2.16 (2 H, m), 3.32 (1 H, m), 5.48 (2 H, s), 7.25 (3 H, m), 7.42 (1 H, m), 7.51 (1 H, m), 7.51 (1 H, m), 7.71 (1 H, d, J=1.1 Hz), 7.88 (1 H, d, J=0.7 Hz), 8.60 (1 H, m); MS (ES$^+$) m/e 390 [MH]$^+$.

EXAMPLE 110

7-Cyclopentyl-3-(2,4-difluorophenyl)-6-(2-methyl-2 H-1,2,4-triazol-3-ylmethoxy)-1,2,4-triazolo[4,3-b]pyridazine Prepared in an analogous procedure as outlined in Example 102b using 2,4-difluorobenzoic acid hydrazide and Example 102c using (2-methyl-2 H-1,2,4-triazol-3-yl)methanol to give the title compound. $^1$H NMR (250 MHz, CDCl$_3$) δ1.73 (6 H, m), 2.09 (2 H, m), 3.18 (1 H, m), 3.85 (3 H, s), 5.49 (2 H, s), 7.07 (2 H, m), 7.90 (3 H, m); MS (ES$^+$) m/e 412 [MH]$^+$.

EXAMPLE 111

7-Cyclopentyl-3-phenyl-6-(pyridin-2-ylmethoxy)-1,2,4-triazolo[4,3-b]pyridazine

Prepared in an analogous procedure as outlined in Example 102b using benzoic hydrazide and Example 102c using 2-hydroxymethyl pyridine to give the title compound. $^1$H NMR (250 MHz, CDCl$_3$) δ1.76 (6 H, m), 2.18 (2 H, m), 3.34 (1 H, m), 5.62 (2 H, s), 7.30 (1 H, m), 7.50 (4 H, m), 7.77 (1 H, m), 7.88 (1 H, d, J=0.7 Hz), 8.36 (2 H, m), 8.65 (1 H, m); MS (ES$^+$) m/e 372 [MH]$^+$.

EXAMPLE 112

7-Cyclopentyl-8-methyl-6-(2-methyl-2 H-1,2,4-triazol-3-ylmethoxy)-3-phenyl-1,2,4-triazolo[4,3-b]pyridazine Prepared in an analogous procedure as outlined in Example 102a using 3,6-dichloro-4-methylpyridazine, Example 102b using benzoic hydrazide and Example 102c using (2-methyl-2 H-1,2,4-triazol-3-yl)methanol to give the title compound. $^1$H NMR (250 MHz, CDCl$_3$) δ1.63 (4 H, m), 1.83 (4 H, m), 2.74 (3 H, s), 3.46 (1 H, m), 3.94 (3 H, s), 5.57 (2 H, s), 7.51 (3 H, m), 7.95 (1 H, s), 8.36 (2 H, m); MS (ES$^+$) m/e 390 [MH]$^+$.

EXAMPLE 113

7- Cyclopentyl-3-phenyl-6-(2 H-1,2,4-triazol-3-ylmethoxy)-1,2,4-triazolo[4.3-b]pyridazine This compound was prepared using the procedures described in Example 102 Steps a), b) and c) using benzoic hydrazide instead of 2-thiophene carboxylic acid hydrazide in Step b) and using 3-hydroxymethyl-2-[2-(trimethylsilanyl)ethoxy]methyl-2 H-1,2,4-triazole (prepared in Example 72 Step a) instead of 2-hydroxymethylpyridine in Step c). This was followed by the procedure decribed in Example 72 Step c) to give the title compound. Data for the title compound: $^1$H NMR (250 MHz, CDCl$_3$) δ1.74 (6 H, m), 2.11 (2 H, m), 3.12 (1 H, br s), 3.22 (1 H, m), 5.58 (2 H, m), 7.50 (3 H, m), 7.85 (1 H, d, J=0.7 Hz), 8.27 (1 H, m), 8.37 (2 H, m); MS (ES$^+$) m/e 362 [MH]$^+$.

EXAMPLE 114

3-(4-Methylphenyl)-7-phenyl-6-(pyridin-2-ylmethoxy)-1,2,4-triazolo[4,3-b]pyridazine This compound was prepared using the procedures described in Example 2 Steps a), b), c) and d) except that in Step c) p-toluic hydrazide was used instead of benzoylhydrazide. Data for the title compound: $^1$H NMR (250 MHz, CDCl$_3$) δ2.45 (3 H, s), 5.68 (2 H, s), 7.29–7.39 (1 H, m), 7.51–7.55 (3 H, m), 7.66–7.77 (3 H, m), 8.07 (1 H, s), 8.18–8.31 (2 H, m), 8.64 (1 H, br d, J=5.6 Hz). MS (ES$^+$) m/e 394 [MH]$^+$.

EXAMPLE 115

3-(4-Methylphenyl)-6-(3-methylpyridin-2-ylmethoxy)-7-phenyl-1,2,4-triazolo[4,3-b]pyridazine This compound was prepared using the procedures described in Example 2 Steps a), b), c) and d) except that in Step c) p-toluic hydrazide was used instead of benzoylhydrazide; and in Step d) 3-methyl-2-pyridinemethanol was used instead of 2-pyridylcarbinol. Data for the title compound: $^1$H NMR (250 MHz, CDCl$_3$) δ2.31 (3 H, s), 2.45 (3 H, s), 5.68 (2 H, s), 7.24 (1 H, dd, J=7.7, 4.9 Hz), 7.32–7.46 (5 H, m), 7.54–7.64 (3 H, m), 8.03 (1 H, s), 8.30 (2 H, d, J=8.3 Hz), 8.46 (1 H, br d, J=5.5 Hz). MS (ES$^+$) m/e 408 [MH]$^+$.

EXAMPLE 116

6-(1-Ethyl-1 H-imidazol-2-ylmethoxy)-3-(4-methylphenyl)-7-phenyl-1,2,4-triazolo[4.3-b]pyridazine This compound was prepared using the procedures described in Example 2 Steps a), b), c) and d) except that in Step c) p-toluic hydrazide was used instead of benzoylhydrazide; and in Step d) 1-ethyl-2-(hydroxymethyl)imidazole was used instead of 2-pyridylcarbinol. Data for the title compound: $^1$H NMR (250 MHz, CDCl$_3$) δ1.14 (3 H, t, J=7.3 Hz), 2.46 (3 H, s), 3.88 (2 H, q, J=7.3 Hz), 5.62 (2 H, s), 6.98 (1 H, d, J=1.3 Hz), 7.10 (1 H, d, J=1.2 Hz), 7.34–7.54 (7 H, m), 8.02 (1 H, s), 8.40 (2 H, d, J=8.3 Hz). MS (ES$^+$) m/e 411 [MH]$^+$.

EXAMPLE 117

3-Phenyl-6-(pyridin-2-ylmethoxy)-7-(thiomorpholin-4-yl)-1,2,4-triazolo[4,3-b]pyrdazine This compound was prepared using the procedures described in Example 15 Steps a), b), c), d) and e) except that thiomorpholine was used instead of piperidine in Step c). Data for the title compound: $^1$H NMR (360 MHz, CDCl$_3$) δ2.81–2.84 (4 H, m), 3.56–3.58 (4 H, m), 5.62 (2 H, s), 7.29–7.32 (2 H, m), 7.49–7.53 (4 H, m), 7.79 (1 H, td, J=7.7, 1.7 Hz), 8.31 (2 H, dd, J=8.3, 2.4 Hz), 8.64–8.66 (2 H, m).

MS (ES$^+$) m/e 405 [MH]$^+$. Anal. Found C, 62.30; H, 4.90; N, 20.60. $C_{21}H_{20}N_6OS$ requires C, 62.36; H, 4.98; N, 20.78%.

EXAMPLE 118

6-[2-(4-Methylthiazol-5yl)ethoxy]-3,7-diphenyl-1,2,4-triazolo[4,3-b]pyridazine

This compound was prepared using the procedure described in Example 61 except that 5-(2-hydroxyethyl)-4-methylthiazole was used instead of 4-hydroxymethylbenzyl alcohol. Data for the title compound: MS (ES$^+$) m/e 414 [MH]$^+$. HPLC 90% (run on a HP1090 using Hichrom S5ODS2, 23 cm column, flow rate of 1 ml/min and 70% acetonitrile/pH 3.5 phosphate buffer as the mobile phase).

EXAMPLE 119

(±)-7-(2-Methylpyrrolidin-1-yl)-3-phenyl-6-(pyridin-2-ylmethoxy)-1,2,4-triazolo[4,3-b]pyridazine This compound was prepared using the procedures described in Example 15 Steps a), b), c), d) and e) except that 2-methylpyrrolidine (racemic) was used instead of piperidine in Step c). Data for the title compound: 1H NMR (360 MHz, CDCl$_3$) δ1.17 (3 H, d, J=6.1 Hz), 1.64–1.69 (1 H, m), 1.87–2.24 (3 H, m), 3.42–3.48 (1 H, m), 3.67–3.74 (1 H, m), 4.23–4.28 (1 H, m), 5.60 (2 H, s), 6.81 (1 H, s), 7.29 (1 H, dd, J=7.5, 4.8 Hz), 7.42–7.49 (4 H, m), 7.74 (1 H, td, J=7.7, 1.8 Hz), 8.27–8.30 (2 H, m), 8.66 (1 H, br d, J=5.5 Hz). MS (ES$^+$) m/e 387 [MH]$^+$. Anal. Found C, 68.24; H, 5.76; N, 21.67. $C_{22}H_{22}N_6O$ requires C, 68.38; H, 5.74; N, 21.74%.

EXAMPLE 120

6-(1-Methyl-1 H-1,2,4-triazol-3-ylmethoxy)-3-phenyl-7-(pyridin-4yl)-1,2,4-triazolo[4,3-b]pyridazine This compound was prepared using the procedures described in Example 16 Steps a), b), c), d) and e) except that (1-methyl-1 H-1,2,4-triazol-3-yl)methanol (EP-A-421210) was used instead of 2-pyridyl carbinol in Step c). Data for the title compound: $^1$H NMR (360 MHz, d$_6$-DMSO) δ3.87 (3 H, s), 5.56 (2 H, s), 7.55–7.65 (3 H, m), 7.75–7.77 (2 H, m), 8.46–8.50 (3 H, m), 8.61 (1 H, s), 8.71 (2 H, br d, J=7 Hz). MS (ES$^+$) m/e 385 [MH]$^+$. Anal. Found C, 61.66; H, 4.09; N, 28.14. $C_{20}H_{26}N_8O$. 0.05 ($C_4H_8O_2$). 0.3 ($H_2O$) requires C, 61.55; H, 4.35; N, 28.43%.

EXAMPLE 121

7-Cyclopentyl-6-(1-methyl-1 H-1,2,4-triazol-3-ylmethoxy)-3-phenyl-1,2,4-triazolo[4,3-b]pyridazine This compound was prepared as described in Example 88 Steps a), b) and c), except that (1-methyl-1 H-1,2,4-triazol-3-yl)methanol (EP-A-421210) was used instead of (2-methyl-2 H-1,2,4-triazol-3-yl)methanol in Step b) and cyclopentane carboxylic acid was used instead of cyclohexane carboxylic acid in Step c). Data for the title compound: $^1$H NMR (360 MHz, CDCl$_3$) δ1.62–1.86 (6 H, m), 2.10–2.18 (2 H, m), 3.22–3.32 (1 H, m), 3.95 (3 H, s), 5.57 (2 H, s), 7.46–7.57 (3 H, m), 7.88 (1 H, s), 8.02 (1 H, s), 8.50 (2 H, br d, J=8 Hz). MS (ES$^+$) m/e 376 [MH]$^+$. Anal. Found C, 63.73; H, 5.56; N, 25.16. $C_{20}H_{21}N_7O$. 0.1 ($C_4H_{10}O$). 0.1 ($H_2O$) requires C, 63.70; H, 5.82; N, 25.59%.

EXAMPLE 122

7-Isopropyl-6-(1-methyl-1 H-1,2,4-triazol-3-ylmethoxy)-3-phenyl-1,2,4-triazolo[4,3-b]pyridazine This compound was prepared as described in Example 88 Steps a), b) and c), except that (1-methyl-1 H-1,2,4-triazol-3-yl)methanol (EP-A-421210) was used instead of (2-methyl-2 H-1,2,4-triazol-3-yl)methanol in Step b) and 2-methylpropionic acid was used instead of cyclohexane carboxylic acid in Step c). Data for the title compound: $^1$H NMR (360 MHz, CDCl$_3$) δ1.31 (6 H, d, J=6.9 Hz), 3.25 (1 H, hept, J=6.7 Hz), 3.94 (3 H, s), 5.57 (2 H, s), 7.46–7.56 (3 H, m), 7.86 (1 H, s), 8.06 (1 H, s), 8.50 (2 H, br d, J=8 Hz). MS (ES$^+$) m/e 350 [MH]$^+$. Anal. Found C, 61.86; H, 5.43; N, 27.71. $C_{18}H_{19}N_7O$ requires C, 61.88; H, 5.48; N, 28.06%.

EXAMPLE 123

3-Cyclopropyl-6-(1-methyl-1 H-1,2,4-triazol-3-ylmethoxy)-7-phenyl-1,2,4-triazolo[4,3-b]pyridazine This compound was prepared using procedures described in Example 2 a), b), c), d) with cyclopropyl hydrazide being used instead of benzoyl hydrazine in Step c) and (1-methyl-1 H-1,2,4-triazol-3-yl)methanol being used instead of 2-pyridylcarbinol in Step d). $^1$H NMR (360 MHz, CDCl$_3$) δ1.14–1.18 (2 H, m), 1.36–1.40 (2 H, m), 2.42–2.46 (1 H, m), 3.92 (3 H, s), 5.55 (2 H, s), 7.41–7.45 (3 H, m), 7.61–7.64 (2 H, m), 7.89 (1 H, s), 8.03 (1 H, s); MS (ES$^+$) m/e 348 [MH$^+$]. Anal. Found C, 60.79; H, 4.79; N, 27.33. $C_{18}H_{17}N_7O$+0.5% $H_2O$ requires C, 60.66; H, 5.09; N, 25.71%.

EXAMPLE 124

3-(2-Fluorophenyl)-6-(2-methyl-2 H-1,2,4-triazol-3-ylmethoxy)-7-phenyl-1,2,4-triazolo[4,3-b]pyridazine This compound was prepared using procedures described in Example 2 a), b), c), d) with 2-fluorobenzyl hydrazide being used instead of benzoyl hydrazine in Step c) and (2-methyl-2 H-1,2,4-triazol-3-yl)methanol being used instead of 2-pyridylcarbinol in Step d). $^1$H NMR (360 MHz, CDCl$_3$) δ3.89 (3 H, s), 5.47 (2 H, s), 7.32 (6 H, m), 7.65–7.68 (2 H, m), 7.96 (3 H, m); MS (ES$^+$) m/e 402 [MH$^+$]. Anal. Found C, 61.85; H, 3.35; N, 23.77. $C_{21}H_{16}N_7OF$+1% Na requires C, 61.78; H, 3.95; N, 24.01%.

EXAMPLE 125

3-(2-Fluorophenyl)-6-(1-methyl-1 H-1,2,4-triazol-3-ylmethoxy)-7-phenyl-1,2,4-triazolo[4,3-b]pyridazine This compound was prepared using procedures described in Example 2 a), b), c), d) with 2-fluorobenzyl hydrazide being used instead of benzoyl hydrazine in Step c) and (1-methyl-1 H-1,2,4-triazol-3-yl)methanol being used instead of 2-pyridylcarbinol in Step d). $^1$H NMR (360 MHz, CDCl$_3$) δ3.66 (3 H, s), 5.53 (2 H, s), 7.27 (8 H, m), 7.85–7.88 (2 H, m), 8.06 (1 H, s); MS (ES$^+$) m/e 402 [MH$^+$]. Anal. Found C, 62.49; H, 3.73; N, 23.81. $C_{21}H_{16}N_7OF$+ 0.5% Na requires C, 62.48; H, 3.96; N, 24.29%.

EXAMPLE 126

6-(1-Methyl 1 H-1,2,4-triazol-3-ylmethoxy)-7-phenyl-3-(thiophen-2-yl)-1,2,4-triazolo[4,3-b]pyridazine This compound was prepared using the procedures described in Example 2 a), b), c) and d) with 2-thiophene carboxylic hydrazide being used instead of benzoyl hydrazine in Step c) and (1-methyl-1 H-1,2,4-triazol-3-yl)methanol (prepared as described in EP-A-421210) being used instead of 2-pyridylcarbinol in Step d). $^1$H NMR (360

MHz, CDCl$_3$) δ3.91 (3 H, a), 5.66 (2 H, s), 7.25 (1 H, m), 7.43–7.69 (6 H, m), 8.03 (2 H, m), 8.31 (1 H, m); MS (ES$^+$) m/e 390 [MH]$^+$. Anal. Found C, 59.01; H, 3.64; N, 25.10. C$_{19}$H$_{15}$N$_7$OS requires C, 58.60; H, 3.88; N, 25.17%.

EXAMPLE 127

6-(1-Methyl-1 H-1,2,4-triazol-3-ylmethoxy)-7-phenyl-3-(pyridin-3-yl)-1,2,4-triazolo[4,3-b]pyridazine This compound was prepared using procedures described in Example 2 a), b), c), d) with 2-pyridyl hydrazide being used instead of benzoyl hydrazine in Step c) and (1-methyl-1 H-1,2,4-triazol-3-yl)methanol being used instead of 2-pyridylcarbinol in Step d). $^1$H NMR (360MHz, d$_6$-DMSO) δ3.86 (3 H, s), 5.55 (2 H, s), 7.49–7.51 (3 H, m), 7.64 (1 H, m), 7.73 (2 H, m), 8.44–8.48 (2 H, d, J=14.4 Hz), 8.66 (1 H, m), 8.82–8.84 (1 H, d, J=7.2 Hz), 9.56 (1 H, s); MS (ES$^+$) m/e 385 [MH$^+$]. Anal. Found C, 62.03; H, 3.97; N, 28.54. C$_{20}$H$_{16}$N$_8$O+0.2% H$_2$O requires C, 61.91; H, 4.26; N, 28.88%.

EXAMPLE 128

6-(2-Methyl-2 H-1,2,4-triazol-3-ylmethoxy)-7-phenyl-3-(thiophen-2-yl)-1,2,4-triazolo[4,3-b]pyridazine This compound was prepared using the procedures described in Example 2 a), b), c) and d) with 2-thiophene carboxylic hydrazide being used instead of benzoyl hydrazine in Step c) and (2-methyl-2 H-1,2,4-triazol-3-yl) methanol (prepared as described in EP-A-421210) being used instead of 2-pyridylcarbinol in Step d). $^1$H NMR (360 MHz, CDCl$_3$) δ3.79 (3 H, s), 5.74 (2 H, s), 7.26 (1 H, m), 7.47–7.57 (6 H, m), 7.90 (1 H, s), 8.05 (1 H, s),8.24 (1 H, m); MS (ES$^+$) m/e 390 [MH]$^+$.Anal. Found C, 58.20; H, 4.09; N, 25.02. C$_{19}$H$_{15}$N$_7$OS requires C, 58.60; H, 3.88; N, 25.17%.

EXAMPLE 129

6-(2-Methyl-2 H-1,2,4-triazol-3-ylmethoxy)-7-phenyl-3-(pyridin-3-yl)-1,2,4-triazolo[4,3-b]pyridazine This compound was prepared using the procedures described in Example 2 a), b), c) and d) with 3-pyridyl carboxylic hydrazide being used instead of benzoyl hydrazine in Step c) and (2-methyl-2 H-1,2,4-triazol-3-yl) methanol (prepared as described in EP-A-421210) being used instead of 2-pyridylcarbinol in Step d). $^1$H NMR (360 MHz, CDCl$_3$) δ3.79 (3 H, s), 5.69 (2 H, s), 7.47–7.57 (6 H, m), 7.90 (1 H, s), 8.10 (1 H, s), 8.77 (2 H, m), 9.76 (1 H, s); MS (ES$^+$) m/e 385 [MH]$^+$. Anal. Found C, 62.48; H, 4.02; N, 25.56. C$_{20}$H$_{16}$N$_8$O requires C, 62.49; H1 4.20; N, 29.15%.

EXAMPLE 130

3-(Furan-3-yl)-6-(1-methyl-1 H-1,2,4-triazol-3-ylmethoxy)-7-phenyl-1,2,4-triazolo[4,3-b]pyridazine This compound was prepared using procedures described in Example 2 a), b), c), d) with 2-furan hydrazide being used instead of benzoyl hydrazine in Step c) and (1-methyl-1 H-1,2,4-triazol-3-yl)methanol being used instead of 2-pyridyl carbinol in Step d). $^1$H NMR (360 MHz, d$_6$-DMSO) δ3.85 (3 H, s), 5.57 (2 H, s), 6.84 (1 H, m), 7.47 (3 H, m), 7.68 (3 H, m), 8.01 (1 H, s), 8.39 (1 H, s), 8.47 (1 H, s). MS (ES$^+$) m/e 374 [MH$^+$]. Anal. Found C, 60.46; H, 4.12; N, 24.14. C$_{19}$H$_{15}$N$_7$O$_2$+0.1% H$_2$O, 0.1% Na requires C, 60.46; H, 4.06; N, 25.97%.

EXAMPLE 131

6-(1-Methyl-1 H-1,2,4-triazol-3-ylmethoxy)-7-phenyl-3-(thiophen-2-yl)-1,2,4-triazolo[4,3-b]pyridazine This compound was prepared using procedures described in Example 2 a), b), c), d) with 2-thiophene hydrazide being used instead of benzoyl hydrazine in Step c) and (1-methyl-1 H-1,2,4-triazol-3-yl)methanol being used instead of 2-pyridylcarbinol in Step d). $^1$H NMR (360 MHz, d$_6$-DMSO) δ3.86 (3 H, s), 5.60 (2 H, s), 7.34 (4 H, m), 7.74–7.76 (2 H, d, J=7.2 Hz), 7.84–7.86 (1 H, d, J=7.2 Hz), 8.29 (1 H, m), 8.39 (1 H, s), 8.48 (1 H, s). MS (ES$^+$) m/e 390 [MH$^+$]. Anal. Found C, 58.33; H. 3.50; N, 24.63. C$_{19}$H$_{15}$N$_7$OS+0.1% H$_2$O requires C, 58.33; H, 3.92; N, 25.06%.

EXAMPLE 132

6-(5-Methyl-1,2,4-oxadiazol-3-ylmethoxy)-3,7-diphenyl-1,2,4-triazolo[4,3-b]pyridazine This compound was prepared using the procedures described in Example 2 a), b), c) and d) with 3-hydroxymethyl-5-methyl-1,2,4-oxadiazole (*J. Med. Chem.*, 1991, 34, 1086–94) being used instead of 2-pyridylcarbinol in Step d). $^1$H NMR (360 MHz, CDCl$_3$) δ2.62 (3 H, s), 5.70 (2 H, s), 7.50–7.80 (7 H, m), 8.45 (2 H, m), 8.48 (1 H, s); MS (ES$^+$) m/e 385 [MH$^+$]. Anal. Found C, 65.24; H, 3.94; N, 21.21. C$_{21}$H$_{16}$N$_6$O$_2$0.25 H$_2$O requires C, 64.85; H, 4.28; N. 21.61%.

EXAMPLE 133

7-Phenyl-3-(thiophen-2-yl)-6-(2 H-1,2,4-triazol-3-ylmethoxy)-1,2,4-triazolo[4,3-b]pyridazine This compound was prepared using the procedures described in Examples 2 a), b), c), d) and 72,c) with 2-thiophene carboxylc hydrazide being used instead of benzoyl hydrazine in Step 2c) and the product of 72a) being used instead of 2-pyridylcarbinol in Step 2d). $^1$H NMR (360 MHz, CDCl$_3$) δ5.14 (2 H, s), 6.72 (1 H, m), 6.91 (3 H, m), 7.05–7.26 (3 H, m), 7.55 (1 H, s), 7.76 (2 H, m), 13.41 (1 H, br s); MS (ES$^+$) m/e 376 [MH]$^+$. Anal. Found C, 57.19; H, 2.98; N, 25.61. C$_{18}$H$_{13}$N$_7$OS requires C, 57.58; H, 3.49; N, 26.12%.

EXAMPLE 134

3-(Furan-2-yl)-6-(1-methyl-1 H-1,2,4-triazol-3-ylmethoxy)-7-phenyl-1,2,4-triazolo[4,3-b]pyridazine This compound was prepared using the procedures described in Example 2 a), b), c) and d) with 2-furyl carboxylc hydrazide being used instead of benzoyl hydrazine in Step c) and (1-methyl-1 H-1,2,4-triazol-3-yl) methanol (prepared as described in EP-A-421210) being used instead of 2-pyridylcarbinol in Step d). $^1$H NMR (360 MHz, CDCl$_3$) δ3.91 (3 H, s), 5.63 (2 H, s), 6.66 (1 H, m), 7.26–7.69 (7 H, m), 8.02 (2 H, m); MS (ES$^+$) m/e 374 [MH]$^+$. Anal. Found C, 60.77; H, 3.93; N, 25.82. C$_{19}$H$_{15}$N$_7$O$_2$ requires C, 61.12; H, 4.05; N, 26.26%.

EXAMPLE 135

6-(1-Methyl-1 H-1,2,4-triazol-3-ylmethoxy)-3-phenyl-7-(thiophen-3-yl)-1,2,4-triazolo4,3-b]pyridazine This compound was prepared using the procedures described in Example 16 Steps a), b) and c) except 3-thiophene boronic acid was used instead of 4-pyridyl boronic acid, di-lithium salt in Step a), 1.1 equivalents of triethylamine hydrochloride was used in Step b) instead of 1.1 equivalents of p-toluenesulphonic acid and triethylamine, and (1-methyl-1 H-1,2,4-triazol-3-yl) methanol (Example 65) was used in Step c) instead of 2-pyridylcarbinol. Data for the title compound: m.p. 233–235° C. (MeOH). $^1$H NMR (360 MHz, DMSO) δ3.89 (3 H, s), 5.61 (2 H, s), 7.56–7.65 (3 H, m), 7.71 (1 H, dd, J=5, 2 Hz), 7.80 (1 H, d, J=5 Hz), 8.29 (1 H, d, J=2 Hz), 8.47 (2 H, d, J=7 Hz), 8.50 (1 H, s), 8.65 (1 H, s). MS (ES$^+$) 390 [MH]$^+$. Anal. Found C, 57.92; H, 3.81; N, 24.79. $C_{19}H_{15}N_7OS$. 0.25 $H_2O$ requires C, 57.93; H, 3.97; N, 24.89%.

EXAMPLE 136

6-(2-Methyl-2 H-1,2,4-triazol-3-ylmethoxy)-7-(thiophen-3-yl)-1,2,4-triazolo[4,3-b]pyridazine This compound was prepared using the procedures described in Example 16 Steps a), b) and c) except 3-thiophene boronic acid was used instead of 4-pyridyl boronic acid, di-lithium salt in Step a), 1.1 equivalents of triethylamine hydrochloride was used in Step b) instead of 1.1 equivalents of p-toluenesulphonic acid and triethylamine, and (2-methyl-2 H-1,2,4-triazol-3-yl) methanol (Example 66) was used in Step c) instead of 2-pyridylcarbinol. Data for the title compound. m.p. 220–222° C. MeOH). $^1$H NMR (360 MHz, DMSO) δ3.91 (3 H s), 5.79 (2 H, s), 7.58–7.65 (3 H, m), 7.71–7.74 (2 H, m), 8.00 (1 H, s), 8.20 (1 H, br s), 8.39 (2 H, d, J=7 Hz), 8.68 (1 H, s). MS (ES$^+$) 390 [MH]$^+$. Anal. Found C, 58.46; H, 3.86. $C_{19}H_{15}N_7OS$ requires C, 58.60; H, 3.88%.

EXAMPLE 137

3-Phenyl-7-(thiophen-3-yl)-6-(2 H-1,2,4-triazol-3-ylmethoxy)-1,2,4-triazolo[4,3-b]pyridazine This compound was prepared using the procedures described in Example 16 Steps a) and b) and Example 72 Steps b) and c) except 3- thiophene boronic acid was used instead of 4-pyridyl boronic acid, di-lithium salt in Example 16 Step a) and 1.1 equivalents of triethylamine hydrochloride was used in Example 16 Step b) instead of. 1.1 equivalents of p-toluenesulphonic acid and triethylamine. Data for the title compound: m.p. 264–266° C. (MeOH). $^1$H NMR (500 MHz, DMSO, 330 K) δ5.68 (2 H, s), 7.54–7.62 (3 H, m), 7.66 (1 H, dd J=5, 2 Hz), 7.77 (1 H, d, J=5 Hz), 8.26 (1 H, d, J=2 Hz), 8.41 (2 H, d, J=7 Hz), 8.50 (1 H, br s), 8.58 (1 H, s). MS (ES$^+$) 376 [MH]$^+$. Anal. Found C, 56.23; H, 3.28. $C_{18}H_{13}N_7OS$. 0.14 $CH_2Cl_2$ requires C, 56.26; H, 3.46%.

EXAMPLE 138

6-(2-Methyl-2 H-1,2,4-triazol-3-ylmethoxy)-3-phenyl-7-(thioi)hen-2-yl)-1,2,4-triazolo[4,3-b]pyridazine This compound was prepared using the procedures described in Example 16 Steps a), b) and c) except 2-thiophene boronic acid was used instead of 4-pyridyl boronic acid, di-lithium salt in Step a), 1.1 equivalents of triethylamine hydrochloride was used in Step b) instead of 1.1 equivalents of p-toluenesulphonic acid and triethylamine, and (2-methyl-2 H-1,2,4-triazol-3-yl) methanol (Example 66) was used in Step c) instead of 2-pyridylcarbinol. Data for the title compound: m.p. 250–254° C. (DMF-$H_2O$). $^1$H NMR (360 MHz, d$_6$,-DMSO) δ3.96 (3 H, s), 5.82 (2 H, s), 7.24 (1 H, dd, J=5 and 4 Hz), 7.52–7.65 (3 H, m), 7.80 (1 H, d, J=5 Hz), 8.00 (1 H, d, J=4 Hz), 8.02 (1 H, s), 8.42 (2 H, d, J=7 Hz), 8.80 (1 H, s). MS (ES$^+$) 390 [MH]$^+$. Anal. Found C, 58.56; H, 3.93; N, 25.35. $C_{19}H_{15}N_7OS$ requires C, 58.60; H, 3.88; N, 25.18%.

EXAMPLE 139

6-(1-Methyl-1 H-1,2,4-triazol-3-ylmethoxy)-3-phenyl-7-(thiophen-2-yl)-1,2,4-triazolo[4.3-b] pyridazine This compound was prepared using the procedures described in Example 16 Steps a), b) and c) except 2-thiophene boronic acid was used instead of 4-pyridyl boronic acid, di-lithium salt in Step a), 1.1 equivalents of triethylamine hydrochloride was used in Step b) instead of 1.1 equivalents ofp-toluenesulphonic acid and triethylamine, and (1-methyl-1 H-1,2,4-triazol-3-yl)methanol Example 65) was used in Step c) instead of 2-pyridylcarbinol. Data for the title compound: m.p. 237–239° C. (DMF-$H_2O$). $^1$H NMR (360 MHz, CDCl$_3$) δ3.96 (3 H, s), 5.69 (2 H, s), 7.14 (1 H, dd, J=6, 5 Hz), 7.47 (1 H, d, J=6 Hz), 7.50–7.60 (3 H, m), 7.81 (1 H, d, J=5 Hz), 8.08 (1 H, s), 8.27 (1 H, s), 8.56 (2 H, d, J =7 Hz). MS (ES$^+$) 390 [MH]$^+$. Anal. Found C, 57.11; H, 3.96; N, 24.70. $C_{19}H_{15}N_7OS$. 0.5 $H_2O$ requires C, 57.27; H. 4.05; N. 24.61%.

EXAMPLE 140

7-(Furan-2-yl)-6-(2-methyl 2 H-1,2,4-triazol-3-ylmethoxy)-3-phenyl-1,2,4-triazolo[4,3-b]pyridazine a) 3.6-Dichloro-4-(furan-2-yl)-pyridazine A mixture of 4-bromo-1,2-dihydropyridazine-3,6-dione (see Example 15 part a) (3.5 g, 18.3 mmol), 2-tributylstannylfuran (6.3 ml 20 mmol) and dichloropalladium bis(triphenylphosphine) (1.42 g, 11 mol %) in dry THF (60 ml) was degassed and purged with nitrogen, then stirred at 70° C. for 1 hour. Upon cooling, the mixture was concentrated. The residues were triturated and washed with hexane, then diethyl ether, to give the crude coupled product as a beige powder (5.23 g) which was used without purification.

The above solid was mixed with phosphorus oxychloride (80 ml) and refluxed for 4 hours. Excess phosphorus oxychloride was removed by evaporation and azeotroping with toluene. The residue was diluted with ice (100 ml) and dichloromethane (200 ml) and neutralised with saturated aqueous sodium hydrogen carbonate (200 ml). The mixture was filtered and the two phases were separated. The organic layer was dried ($Na_2SO_4$), filtered and concentrated; Filtration on a short silica column, eluting with ethyl acetate, gave the title compound as brown erystals (1.67 g, 44% over the two steps). $^1$H NMR (250 MHz, CDCl$_3$) δ6.67 (1 H, dd, J=4, 2 Hz), 7.63 (1 H, d, J=4 Hz), 7.71 (1 H, d, J=2 Hz), 7.92 (1 H, s). MS (ES$^+$) 215 and 217 [MH]$^+$.

b) 7-(Furan-2-yl)-6-(2-methyl-2 H-1,2,4-triazol-3-ylmethoxy)-3-phenyl-1,2,4-triazolo[4,3-b]pyridazine This compound was prepared from 3,6-dichloro-4-(furan-2-yl)-pyridazine using the procedures described in Example 16 Steps b) and c) except 1.1 equivalents of triethylamine hydrochloride was used in Step b) instead of 1.1 equivalents of p-toluenesulphonic acid and triethylamine, and (2-methyl-2 H-1,2,4-triazol-3-yl)methanol (Example 66) was used in Step c) instead of 2-pyridylcarbinol.

Data for the title compound: m.p. 263–265° C. (DMF). $^1$H NMR (360 MHz, d$_6$-DMSO) δ3.95 (3 H, s), 5.84 (2 H, s), 6.74 (1 H, dd, J=4, 2 Hz), 7.21 (1 H, d, J=4 Hz), 7.55–7.65(3 H, m), 8.00 (1 H, d; J=2 Hz), 8.03 (1 H, s), 8.41 (2 H, d, J=7 Hz), 8.47 (1 H, s). MS (ES$^+$) 374 [MH]$^+$. Anal. Found C, 60.93; H, 4.00; N, 26.09. $C_{19}H_{15}N_7O_2$ requires C, 61.12; H, 4.05; N, 26.26%.

EXAMPLE 141

7-(Furan-2-yl)-6-(1-methyl-1 H-1,2,4-triazol-3-ylmethoxy)-3-phenyl-1,2,4-triazolo[4,3-b]pyridazine This compound was prepared from 3,6-dichloro-4-(furan-2-yl)-pyridazine (Example 140 part a) using the procedures described in Example 16 Steps b) and c) except 1.1 equivalents of triethylamine hydrochloride was used in Step b) instead of 1.1 equivalents of p-toluenesulphonic acid and triethylamine, and (1-methyl-1 H-1,2,4-triazol-3yl) methanol (Example 65) was used in Step c) instead of 2-pyridylcarbinol. Data for the title compound: m.p. 257–259° C. (DMF). $^1$H NMR (360 MHz, d$_6$-DMSO) 3.91 (3 H s), 5.63 (2 H, s), 6.74 (1 H, dd, J=4 and 2 Hz), 7.33 (1 H, d, J=4 Hz), 7.54–7.65 (3 H, m), 7.99 (1 H, d, J=2 Hz), 8.44 (1 H, s), 8.46 (2 H, d, J=7 Hz), 8.57 (1 H, s). MS (ES$^+$) 374 [MH]$^+$. Anal. Found C, 60.68; H 4.11; N, 25.82. $C_{19}H_{15}N_7O_2$. 0.15 H$_2$O requires C, 60.68; H, 4.10; N, 26.07%.

EXAMPLE 142

6-(3-Methyl-1,2,4-oxadiazol-5-ylmethoxy)-3,7-diphenyl-1,2,4-triazolo[4,3-b]pyridazine a) 5-Chloromethyl-3-methyl-1,2,4-oxadiazole To a solution of acetamide oxime (1 g, 0.0135 mol) in dichloromethane (30 ml) was added triethylamine (2.06 ml, 0.015 mol) and cooled to 0° C. Chloroacetyl chloride (1.18 ml, 0.015 mol) was added dropwise over 5 minutes. The reaction was stirred at 0° C. for 10 minutes, then at room temperature for 1 hour. The reaction was diluted with -dichloromethane (40 ml) and washed with water (2×30 ml), brine (1×30 ml). The organic layer was dried (MgSO$_4$), filtered and evaporated to yield the crude product.

b) 6-(3-Methyl-1,2,4-oxadiazol-5-ylmethoxy)-3,7-diphenyl-1,2,4-triazolo[4,3-b]pyridazine This compound was prepared using the procedures described in Example 35 a) and b) using the product from Example 2 c) and the crude product from this Example part a). $^1$H NMR (360 MHz, CDCl$_3$) δ2.35 (3 H, s), 5.85 (2 H, s), 7.51–7.80 (7 H, m), 8.24 (2 H, m) 8.48 (1 H, s); MS (ES$^+$) m/e 385 [MH$^+$]. Anal. Found C, 65.19; H, 3.99; N, 21.07. $C_{21}H_{16}N_6O_2$. 0.05 CH$_2$Cl$_2$. 0.1 EtOAc requires C, 64.82; H, 4.29; N, 21.15%.

EXAMPLE 143

3-(4-Fluorophenyl)-6-(1-methyl-1 H-1,2,4-triazol-3-ylmethoxy)-7-phenyl-1,2,4-triazolo[4,3-b]-pyridazine This compound was prepared using procedures described in Example 2 a), b), c), d) with 4fluorobenzyl hydrazide being used instead of benzoyl hydrazine in Step c) and (1-methyl-1 H-1,2,4-triazol-3-yl)methanol being used instead of 2-pyridylcarbinol in Step d). m.p.=233–235° C. $^1$H NMR (360 MHz, d$_6$-DMSO) δ3.85 (3 H, s), 5.52 (2 H, s), 7.42 (5 H, m), 7.73 (2 H, m), 8.40 (1 H, s), 8.49 (3 H, m); MS (ES$^+$) m/e 402 [MH$^+$].

EXAMPLE 144

3,7-Diphenyl-6-(2 H-1,2,3-triazol-4-ylmethoxy)-1,2,4-triazolo[4,3-b]pyridazine a) 5-Formyl-1-[2-(trimethylsilanyl)ethoxy]methyl-1 H-1,2,3-triazole To a stirred solution of 1-[2-(trimethylsilanyl)ethoxy] methyl-1 H-1,2,3-triazole (Holzer, W.; Ruso, K, *J. Heterocycl. Chem.*, 1992, 29, 1203–7) (2.0344 g, 10.2 mmol) in anhydrous THF (30 ml), cooled to <–75° C. under nitrogen, was added dropwise, over 11 min, a 1.6 M solution of butyllithium in hexanes (6.70 ml, 10.7 mmol). The mixture was stirred at this temperature for 30 min, then allowed to warm to –20° C. over 13 min. The mixture was then recooled to <–75° C., and anhydrous DMF (0.87 ml, 11.3 mmol) was added dropwise over 8 min. The mixture was stirred at <–75° C. for 1.75 h, then at 0° C. for 75 min. Saturated aqueous NH$_4$Cl (50 ml) was then added and the mixture was extracted with diethyl ether (75 ml) then ethyl acetate (2×75 ml). The organic extracts were dried (Na$_2$SO$_4$) and evaporated int vacuo. The residue was purified by flash chromatography (silica gel, 40% EtOAc/hexane) to give 1.7256 g (74%) of the title compound as a colourless oil: $^1$H NMR (360 MHz, CDCl$_3$) δ–0.03 (9 H, s), 0.91 (2 H, m), 3.63 (2 H, m), 6.01 (2 , s), 8.28 (1 H, s), 10.08 (1 H, s); MS (ES$^+$) m/e 170 [M—SiMe$_2$+H]$^+$.

b) 5-Hydroxymethyl-1-[2-(trimethylsilanyl)ethoxy] methyl-1 H-1,2,3-triazole

To a stirred solution of the product fiom Step a (1.7204 g, 7.57 mmol) in anhydrous methanol (8 ml), cooled to 0° C. under nitrogen, was added sodium borohydride (0.2875 g, 7.60 mmol) and the mixture was stirred at this temperature for 20 min, then allowed to warm to room temperature over 30 min. The reaction was quenched by adding water, and the mixture was partitioned between saturated aqueous NaCl (40 ml) and dichloromethane (30 ml). The aqueous layer was further extracted with dichloromethane (3×30 ml), and the combined organic extracts were dried (Na$_2$SO$_4$) and evaporated in vacuo. The residue was purified by flash chromatography (silica gel, 3% MeOH/CH$_2$Cl$_2$) to afford 1.4642 g (84%) of the title compound: $^1$H NMR (360 MHz, CDCl$_3$) δ–0.02 (9 H, s), 0.90 (2 H, m), 3.59 (2 H, m), 4.82 (2 H, s), 5.78 (2 H, s), 7.67 (1 H, s); MS (ES$^+$) m/e 230 [M+H]$^+$, 119.

c) 3,7-Diphenyl-6-[1-[2-(trimethylsilanyl)ethoxy]methyl-1 H-1,2,3-triazol-5-yl]methoxy-1,2,4-triazolo[4,3-b]pyridazine This compound was prepared in 84% yield using a similar procedure to that described in Example 2, Step d, but using 5-hydroxymethyl-1-[2-(trimethylsilanyl)ethoxy]methyl-1 H-1,2,3-triazole (from Step b) instead of 2-pyridylcarbinol. Data for the title compound: $^1$H NMR (360 MHz, CDCl$_3$) δ–0.07 (9 H, s), 0.80 (2 H, m), 3.49 (2 H, m), 5.62 (2 H, s), 5.67 (2 H, s), 7.47–7.62 (8 H, m), 7.77 (1 H, s), 8.39 (1 H, s), 8.40 (2 H, dd); MS (ES$^+$) m/e 500 [MH]$^+$.

d) 3,7-Diphenyl-6-(2 H-1,2,3-triazol-4-ylmethoxy)-1,2,4-triazolo[4,3-b]pyridazine A mixture of the product from Step c (0.7025 g, 1.41 mmol) in ethanol (12 ml) and 2 M aqueous HCl (25 ml) was stirred at 60° C. for 5.5 h. The mixture was then neutralised by adding dropwise saturated aqueous Na$_2$CO$_3$. The resulting precipitate was collected by filtration, washed with water, then hexane, and dried under vacuum at 60° C. This was purified by recrystallisation (MeOH—CH$_2$Cl$_2$), then flash chromatography (silica gel, 3–5% MeOH/CH$_2$Cl$_2$) to afford 0.2044 g (39%) of the title compound as a white solid: mp 208–220° C.; $^1$H NMR (360 MHz, d$_6$-DMSO) δ5.66 (2 H, s), 7.48–7.49 (3 H, m), 7.58–7.72 (5 H, m), 7.94 (1 H, br s), 8.40 (1 H, s), 8.47 (2 H, d, J=7.2 Hz), 15.10 (1 H, br s); MS (ES$^+$) m/e 370 [MH]$^+$; Anal. Found C, 65.07; H, 4.05; N, 26.01. $C_{20}H_{15}N_7O$.0.1 H$_2$O requires C, 64.72; H, 4.13; N, 26.41%.

EXAMPLE 145

3,7-Diphenyl-6-(pyrazin-2-ylmethoxy)- 1,2,4-triazolo[4,3-b]pyridazine a) 2-Hydroxymethylpyrazine To methyl 2-pyrazinecarboxylate (1.80 g) in THF (60 ml) was added diisobutylaluminium hydride (1 M solution in THF; 39 ml) at −78° C. with stirring. The solution was allowed to warm to room temperature, and stirred for 24 h. The reaction was quenched with solid tartaric acid, then aqueous sodium potassium tartrate, and stirred for 30 min at room temperature. Saturated aqueous sodium hydrogen carbonate was added until the pH of the solution was >7. The solution was washed with ethyl acetate (3×200 ml), and the organic layers combined, washed with saturated sodium chloride solution (1×200 ml), dried (magnesium sulfate) and concentrated in vacuo. The residue was purified by flash chromatography (silica gel, eluent =5% methanol in dichloromethane) to yield 2-hydroxymethylpyrazine as a dark brown oil (0.16 g). $^1$H NMR (250 MHz, CDCs) δ3.42 (1 H, br s), 4.85 (2 H, s), 8.55 (2 H, m), 8.68 (1 H, s); MS (ES$^+$) m/e 111 [MH$^+$].

b) 3,7-Diphenyl-6-(pyrazin-2-ylmethoxy)-1,2,4-triazolo[4,3-b]pyridazine

This compound was prepared using the procedures described in Example 2 a), b), c) and d) with 2-hydroxymethylpyrazine being used instead of 2-pyridylcarbinol in Step d). $^1$H NMR (360 MHz, CDCl$_3$) δ5.69 (2 H, s), 7.54 (5 H, m), 7.65 (2 H, m), 8.09 (1 H, s), 8.39 (2 H, d, J=6.6 Hz), 8.56 (1 H, s), 8.60 (1 H, s), 8.67 (1 H, s); MS (ES$^+$) m/e 381 [MH$^+$].

EXAMPLE 146

3-(4-Methylphenyl)-6-(1-methyl-1 H-1,2,4-triazol-3-ylmethoxy)-7-phenyl-1,2,4-triazolo[4,3-b]pyridazine This compound was prepared using procedures described in Example 2 a), b), c), d) with 4-methylbenzoyl hydrazine being used instead of benzoyl hydrazine in Step c) and (1-methyl-1 H-1,2,4-triazol-3-yl)methanol being used instead of 2-pyridylcarbinol in Step d). m.p.=218.6–219.7° C. $^1$H NMR (360 MHz, DMSO) δ2.51 (3 H, s), 3.87 (3 H, s), 5.54 (2 H, s), 7.44 (5 H, m), 7.76 (2 H, s), 8.38 (4 H, m); MS (ES$^+$) m/e 398 [MH$^+$].

EXAMPLE 147

6-(4-Methylthiazol-2-ylmethoxy)-3,7-diphenyl-1,2.4-triazolo[4,3-b]pyridazine

This compound was prepared using the procedures described in Example 2 a), b), c) and d) with 2-hydroxymethyl-4-methylthiazole being used instead of 2-pyridylcarbinol in Step d). Data for the title compound: m.p.=177° C. $^1$H NMR (360 MHz, CDCl$_3$) δ2.47 (3 H, s), 5.79 (2 H1, s), 6.90 (1 H, s), 7.50–7.67 (8 H, m), 8.08 (1 H, s), 8.50 (2 H, d, J=7.9 Hz); MS (ES$^+$) m/e 400 [MH]$^+$. Anal. Found C, 66.25; H, 3.90; N, 17.47. C$_{22}$H$_{17}$N$_5$OS requires C, 66.14; H, 4.29; N, 17.53%.

EXAMPLE 148

6-(5-Methylthiazol-2-ylmethoxy)-3,7-diphenyl-1,2,4-triazolo[4,3-b]pyridazine

This compound was prepared using the procedures described in Example 2 a), b), c) and d) with 2-hydroxymethyl-5-methylthiazole being used instead of 2-pyridylcarbinol in Step d). Data for the title compound: m.p.=182° C. $^1$H NMR (360 MHz, CDCl$_3$) δ2.46 (3 H, s), 5.75 (2 H, s), 7.45–7.65 (9 H, m), 8.07 (1 H, s), 8.49 (2 H, d, J=7.9 Hz); MS (ES$^+$) m/e 400 [MH]$^+$. Anal. Found C, 66.17; H, 4.02; N, 17.67. C$_{22}$H$_{17}$N$_5$OS requires C, 66.14; H, 4.29; N, 17.53%.

EXAMPLE 149

3,7-Diphenyl-6-(pyrimidin-4-ylmethoxy)-1,2,4-triazolo[4,3-b]pyridazine

This compound was prepared using the procedures described in Example 79 a) and b), with 4-chloromethylpyrimidine (prepared by the procedure of Jeronim et al., Chem. Ber., 1987, 120, 649–651) being used instead of bromoacetonitrile in Step b). Data for the title compound: $^1$H NMR (360 MHz, CDCl$_3$) δ5.61 (2 H, s), 7.33 (1 H, d, J=5.1 Hz), 7.55 (6 H, m), 7.67 (2 H, m), 8.10 (1 H, s), 8.38 (2 H, m), 8.74 (1 H, d, J=5.1 Hz); MS (ES$^+$) m/e 381 [MH$^+$]. Anal. Found C, 70.01; H, 3.96; N, 21.97. C$_{22}$H$_{16}$N$_6$O requires C, 69.46; H, 4.24; N, 22.09%.

EXAMPLE 150

3,7-Diphenyl-6-(pyridazin-3-ylmethoxy)-1,2,4-triazolo[4,3-b]pyridazine

This compound was prepared using the procedures described in Example 79 a) and b), with 3-chloromethylpyridazine (prepared by the procedure of Jeronim et al., Chem. Ber., 1987, 120, 649–651) being used instead of bromoacetonitrile in Step b). $^1$H NMR (360 MHz, CDCl$_3$) δ5.89 (2 H, s), 7.53 (6 H, m), 7.64 (2 H, m), 8.09 (1 H s), 8.40 (2 H, m), 9.18 (1 H, m); MS (ES$^+$) m/e 381 [MH$^+$].

EXAMPLE 151

6-(1-Methyl-1 H-1,2,4-triazol-3-ylmethoxy)-7-(morpholin-4-yl)-3-(thiophen-2-yl)-1,2,4-triazolo[4,3-b]pyridazine a) 4-(3,6-Dichloropyridazin-4-yl)morpholine This was prepared using the procedure described in Example 15 part c) except that morpholine was used instead of piperidine. Data for the title compound: $^1$H NMR (250 MHz, CDCl$_3$) δ3.30–3.34 (4 H, m), 3.87–3.95 (4 H, m), 6.89 (1 H, s); MS (ES$^+$) m/e 234, 236, 238 [MH$^+$].

b) 6-Chloro-5-(morpholin-4-yl)pyridazin-3-ylhydrazine

A mixture of 4-(3,6-dichloropyridazin-4-yl)morpholine (5 g, 21.3 mmol) and hydrazine hydrate (7.0 ml, 141 mmol) in 1,4-dioxan (100 ml) was stirred and heated at reflux for 20 hours. Upon cooling the 1,4-dioxan was removed in vacuo. The residue was then partitioned between dichloromethane and saturated aqueous sodium hydrogen carbonate. The aqueous layer was further extracted with dichloromethane (x2). The combined organic extracts were dried (Na$_2$SO$_4$), filtered and evaporated. The residue was purified by chromatography on silica gel, eluting with dichloromethane/methanol/aqueous ammonia (91:8:1) to give 6-chloro-5-(morpholin-4-yl)-pyridazine-3-ylhydrazine (3.6 g, 74%): $^1$H NMR (250 MHz, d$_6$-DMSO) δ3.37–3.17 (4 H, m), 3.72–3.77 (4 H, m), 4.31 (2 H, br s), 6.58 (1 H, s), 7.97 (1 H, br s); MS (ES$^+$) m/e 230, 232 [MH$^+$].

c) 6-Chloro-7-(morpholin-4-yl)-2 H-1,2,4-triazolo[4,3-b]pyridazin-3-one

Triphosgene (750 mg, 2.5 mmol) was added to a stirred solution of 6-chloro-5-(morpholin-4-yl)pyridazin-3-ylhydrazine (1.42 g, 6.2 mmol) in 1,2-dichloroethane (60 ml) at room temperature under nitrogen. The mixture was then stirred and heated at reflux for 22 hours. Upon cooling the precipitate was collected by filtration. The solid was washed with diethyl ether anid then dried in vacuo to give 6-chloro-7-(morpholin-4-yl)-2 H-1,2,4-triazolo[4,3-b]pyridazin-3-one (1.1 g, 67%) which was used without further purification. Data for the title compound: $^1$H NMR (250

MHz, $d_6$-DMSO) δ3.02–3.05 (4 H, m), 3.72–3.76 (4 H, m), 7.19 (1 H, s), 12.57 (1 H, br s); MS (ES$^+$) m/e 256, 258 [MH$^+$].

d) 3-Bromo-6-(1-methyl-1 H-1,2,4-triazol-3-ylmethoxy)-7-(morpholin-4-yl)-1,2,4-triazolo[4,3-b]pyridazine A mixture of 6-chloro-7-(morpholin-4-yl)-2 H-1,2,4-triazolo[4,3-b]pyridazin-3-one (1.1 g, 4.3 mmol) and phosphoryl bromide (25 g) was stirred and heated at 80° C. for 24 hours. Upon cooling the mixture was treated with ice. The aqueous was then basified with aqueous ammonia. The aqueous was then extracted with dichloromethane (x3). The combined extracts were dried (Na$_2$SO$_4$), filtered and evaporated. The residue was purified by chromatography on silica gel, eluting with 5% methanol/dichloromethane to give 3-bromo-6-chloro-7-(morpholin-4-yl)-1,2,4-triazolo[4,3-b]pyridazine (600 mg). $^1$H NMR and mass spectrum revealed the product to be a mixture of the desired compound and the 6-bromo compound. This mixture was used without further purification. Sodium hydride (60% dispersion in oil, 80 mg, 2.0 mmol) was added in one portion to a stirred solution of the product from above (600 mg) and (1-methyl-1 H-1,2,4-triazol-3-yl)methanol (240 mg, 2.1 mmol, prepared as described in Example 65) in dry DMF at 0° C. under nitrogen. The ice bath was removed and the mixture was stirred at room temperature for 2 hours. The reaction was quenched with water and then partitioned between ethyl acetate and water. The aqueous layer was further extracted with dichloromethane (x3). The combined organic extracts were dried (Na$_2$SO$_4$), filtered and evaporated. The residue was purified by chromatography on silica gel, eluting with 5 to 8% methanol/dichloromethane to give the title compound (358 mg, 48% for 2 steps). $^1$H NMR (360 MHz, $d_6$-DMSO) δ3.20–3.22 (4 H, m), 3.69–3.71 (4 H, m), 3.68 (3 H, s), 5.47 (2 H, s), 7.41 (1 H, s), 8.49 (1 Hi s); MS (ES$^+$) m/e 395, 397 [MH$^+$].

e) 6-(1-Methyl-1 H-1,2,4-triazol-3-ylmethoxy)-7-(morpholin-4-yl)-3-(thiophen-2-yl)-1,2,4-triazolo[4,3-b]-pyridazine A mixture of 3-bromo-6-(1-methyl-1 H-1,2,4-triazol-3-ylmethoxy)-7-(morpholin-4-yl)-1,2,4-triazolo[4,3-b] pyridazine (100 mg, 0.25 mmol) and 2-(tributylstannyl) thiophene (240 mL 0.75 mmol) in dry DMF (3 ml) was deoxygenated by bubbling through nitrogen gas for 15 minutes. Dichlorobis(triphenylphosphine)palladium (II) (20 mg) was then added. The whole apparatus was further deoxygenated by three 'evacuate/fill N$_2$' cycles. The mixture was then stirred and heated at 100° C. for 16 hours under nitrogen. The reaction mixture was partitioned between dichloromethane and water. The aqueous layer was further extracted with dichloromethane (x2). The combined extracts were dried (Na$_2$SO$_4$), filtered and evaporated. Residual DMF was removed under high vacuum. The residue was purified by chromatography on silica gel, eluting with 5% methanol/dichloromethane to give the title compound (60 mg, 60%). Data for the title compound: $^1$H NMR (360 MHz, CDCl$_3$) δ3.26–3.29 (4 H, m), 3.85–3.89 (4 H, m), 3.94 (3 H,-s), 5.64 (2 H, s), 7.19–7.23 (2 H, m), 7.47–7.59 (1 H, m), 8.05 (1 H, s), 8.18–8.20 (1 H, m); MS (ES$^+$) m/e 399 [MH$^+$]. Anal. Found C, 50.84; H, 4.39; N, 27.35. $C_{17}H_{18}N_8O_2S$. 0.3(H$_2$O) requires C, 50.56; H, 4.64; N, 27.75%.

EXAMPLE 152

3.7-Diphenyl-6-(thiazol-4-ylmethoxy)-1,2,4-triazolo[4,3-b]pyridazine

This compound was prepared using the procedures described in Example 2 a), b), c) and d) with 4-hydroxymethylthiazole being used instead of 2-pyridylcarbinol in Step d). Data for the title compound: m.p.=236° C. $^1$H NMR (360 MHz, CDCl$_3$) δ5.73 (2 H, s), 7.29 (1 H, s), 7.49–7.66 (8 H, m), 8.06 (1 H, s), 8.49 (2 H, d, J=7.9 Hz), 8.85 (1 H, s); MS (ES$^+$) m/e 386 [MH$^+$]. Anal. Found C, 65.11; H, 3.72; N, 17.97. $C_{21}H_{15}N_5OS$ requires C, 65.44; H, 3.92; N, 18.17%.

EXAMPLE 153

6-(5-Methylisoxazol-3-ylmethoxy)-3,7-diphenyl-1,2,4-triazolo[4,3-b]pyridazine

This compound was prepared using the procedures described in Example 2 a), b), c) and d) with 5-methylisoxazol-3-ylmethanol being used instead of 2-pyridylcarbinol in Step d). Data for the title compound: m.p.=180° C. $^1$H NMR (360 MHz, CDCl$_3$) δ2.42 (3 H, s), 5.57 (2 H, s), 6.00 (1 H, s), 7.49–7.61 (8 H, m), 8.06 (1 H, s), 8.47 (2 H, d, J=7.9 Hz); MS (ES$^+$) m/e 384 [MH$^+$]. Anal. Found C, 68.45; H, 4.09; N, 17.79. $C_{22}H_{17}N_5OS$.0.1 H$_2$O requires C, 68.92; H, 4.47; N, 18.27%.

EXAMPLE 154

3-(3-Fluorophenyl)-6-(1-methyl-1 H-1,2,4-triazol-3-ylmethoxy)-7-(morpbolin-4-yl)-1,2,4-triazolo-3-ylmethoxy)-7-(morpholin-4-yl)-1,2,4-triazolo[4,3-b]pyridazine A mixture of 3-bromo-6-(1-methyl-1 H-1,2,4-triazol-3-ylmethoxy)-7-(morpholin-4-yl)-1,2,4-triazolo[4,3-b] pyridazine (100 mg, 0.25 mmol, from Example 151 part d), 3-fluorobenzene boronic acid (50 mg, 0.35 mmol) and anhydrous sodium carbonate (70 mg, 0.66 mmol) in 1,2-dimethoxyethane/water (2:1, 5 ml) was deoxygenated by bubbling through nitrogen gas for 15 minutes. Tetrakis (triphenylphosphine)palladium (0) (30 mg) was then added. The whole apparatus was further deoxygenated by three 'evacuate/fill N$_2$' cycles. The mixture was then stirred and heated at 110° C. for 16 hours under nitrogen. Upon cooling the reaction mixture was partitioned between dichloromethane and water. The aqueous layer was further extracted with dichloromethane (x2). The combined extracts were dried (Na$_2$SO$_4$), filtered and evaporated. The residue was purified by chromatography on silica gel eluting with 5% methanol/dichloromethane to give the title compound (65 mg, 63%). Data for the title compound: $^1$H NMR (360 MHz, CDCl$_3$) δ3.27–3.29 (4 H, m), 3.87–3.90 (4 H, m), 3.94 (3 H, s), 5.60 (2 H, s), 7.14–7.19 (1 H, m), 7.20 (1 H, s), 7.46–7.52 (1 H, m), 8.05 (1 H, s), 8.21–8.28 (1 H, m); MS (ES$^+$) m/e 411 [MH$^+$]. Anal. Found C, 53.16; H, 4.85; N, 25.59. $C_{19}H_{19}N_8O_2F$. 1.2(H$_2$O) requires C, 52.82; H, 4.99; N, 25.94%.

EXAMPLE 155

3,7-Diphenyl-6-(pyrimidin-2-ylmethoxy)-1,2,4-triazolo[4,3-b]pyridazine a) Dimethyl 2-(pyrimidin-2-yl)malonate To dimethyl malonate (41.6 g) in 1,4-dioxane (900 ml) was added sodium hydride (60% dispersion in mineral oil; 18.9 g) portionwise. To the resultant gel was added 2-bromopyrimidine (50.0 g) in 1,4-dioxane (200 ml) dropwise. The mixture was stirred at room temperature for 1 h, then at reflux overnight. To the cooled solution was added water (400 ml), and 5 N hydrochloric acid until the pH was ~1. The solution was washed with ethyl acetate (2×400 ml), the organic layers combined, washed with saturated sodium hydrogen carbonate solution (1×400 ml) and saturated sodium chloride solution (1×400 ml), dried (magnesium sulfate) and concentrated in vacuo. The residue was purified by flash chromatography (silica gel, eluent =0 to 20% ethyl acetate in dichloromethane) to yield dimethyl 2-(pyrimidin-2-yl)malonate as a yellow/orange oil (24.1 g). $^1$H NMR (250 MHz, CDCl$_3$) δ3.83 (6 H, s), 5.16 (1 H, s)7.28 (1 H, t, J=5.0 Hz), 8.87 (2 H, d, J=5.0 Hz); MS (ES$^+$) m/e 211 [MH$^+$].

b) 2-Methylpyrimidine

Dimethyl 2-(pyrimidin-2-yl)malonate (14.0 g), sodium chloride (17.1 g) and water (5.24 ml) were heated together in DMSO (50 ml) at 160° C. overnight. The solution was allowed to cool, and the inorganic material filtered off. The filtrate was distilled at atmospheric pressure, and the fraction boiling between 95 and 112° C. was collected. The distillate was redistilled at atmospheric pressure, with the fraction boiling between 97 and 99° C. being collected—this was a mixture of 2-methylpyrimidine and dimethylsulfide, present in a 2:1 ratio respectively (1.41 g). This material was used in the next step without further purification. $^1$H NMR (250 MHz, CDCl$_3$) δ2.70 (3 H, s), 7.13 (1 H, t, J=4.9 Hz), 8.66 (2 H, d, J=4.9 Hz); MS (ES$^+$) m/e 95 [MH$^+$].

c) 2-Chloromethylpyrimidine

Trichloroisocyanuric acid (0.62 g) was added portionwise to the product from Example 155 Step b) (0.60 g) in refluxing chloroform (30 ml), and the slurry was stirred at reflux for 3 h. A further quantity of trichloroisocyanuric acid (0.62 g) was added, and the mixture stirred as before for 6 h. The slurry was allowed to cool to room temperature, filtered to remove insoluble material and the filtrate washed with 1 M sodium hydroxide solution (1×25 ml) and saturated sodium chloride solution (1×25 ml). The filtrate was dried (magnesium sulfate) and concentrated in vacuo to give 2-chloromethylpyrimidine as a pale orange/brown oil (0.11 g). Data for the title compound: $^1$H NMR (250 MHz, CDCl$_3$) δ4.77 (2 H, s), 7.27(1 H, t, J=4.9 Hz), 8.79 (2 H, d, J=4.9 Hz); MS (ES$^+$) m/e 129 [MH$^+$].

d) 3,7-Diphenyl-6-(pyrimidin-2-ylmethoxy)-1,2,4-triazolo[4,3-b]-pyridazine

This compound was prepared using the procedures described in Example 79 a) and b), with 2-chloromethylpyrimidine being used instead of bromoacetonitrile in Step b). Data for the title compound: $^1$H NMR (360 MHz, CDCl$_3$) δ5.74 (2 H, s), 7.23 (1 H, t, J=4.9 Hz), 7.48 (6 H, m), 7.81 (2 H, m), 8.06 (1 H, s), 8.22 (2 H, m), 8.76 (2 H, d, J=4.9 Hz); MS (ES$^+$) m/e 381 [MHP$^+$]. Anal. Found C, 69.45; H, 3.81; N, 22.11. C$_{22}$H$_{16}$N$_6$O requires C, 69.46; H, 4.24; N, 22.09%.

EXAMPLE 156

6-(2-Methyl-2 H-1,2,3-triazol-4-ylmethoxy)-3,7-diphenyl-1,2,4-triazolol[4,3-b]pyridazine To a stirred mixture of sodium hydride (60% dispersion in oil, 22.6 mg, 0.565 mmol) and iodomethane (29.6 ml, 0.475 mmol) in anhydrous DMF (2 ml), cooled under nitrogen to −5° C., was added dropwise, over 10 min, a solution of 3,7-diphenyl-6-(2 H-1,2,3-triazol-4-ylmethoxy)-1,2,4-triazolo[4,3-b]pyridazine (from Example 144, Step d) (0.1675 g, 0.453 mmol) in anhydrous DMF (7 ml). The mixture was then allowed to warm to room temperature over 2.5 h, then partitioned between water (40 ml) and ethyl acetate (40 ml). The aqueous layer was extracted further with ethyl acetate (4×30 ml), adding saturated aqueous NaCl to facilitate separation of the layers. The combined organic extracts were dried (Na$_2$SO$_4$) and evaporated in vacuo. The residue was purified by flash chromatography (silica get 50–100% EtOAc/CH$_2$Cl$_2$) to give 69.8 mg (40%) of the title compound as a white solid together with 75.8 mg (44%) of a mixture of the 2-methyl-2 H-1,2,3-triazol-4-yl analogue and the 1-methyl-1 H-1,2,3-triazol-5-yl analogue in a 63:37 ratio. Data for the title compound: mp 203–205° C. (CH$_2$Cl$_2$—EtOAc); $^1$H NMR (360 MHz, CDCl$_3$) δ4.19 (3 H, s), 5.61 (2 H, s), 7.47–7.61 (9 H, m), 8.05 (1 H, s), 8.40 (1 H, s), 8.52 (2 H, m); MS (ES$^+$) m/e 384 [MH]$^+$; Anal. Found C, 65.27; H, 4.17; N, 25.14. C$_{21}$H$_{17}$N$_7$. 0.1 H$_2$O requires C, 65.48; H, 4.50; N, 25.45%.

EXAMPLE 157

7-(1-Methylcyclobutyl)-6-(1-methyl-1 H-1,2,4-triazol-3-ylmethoxy)-3-phenyl-1,2,4-triazolo[4,3-b]pyridazine This compound was prepared using the procedures described in Example 88 Steps a), b) and c) using (1-methyl-1 H-1,2,4-triazol-3-yl)methanol (prepared using the conditions described in EP-A-421210) instead of (2-methyl-2 H-1,2,4-triazol-3-yl)methanol in Step b) and using 1-methylcyclobutane carboxylic acid (*Journal of Organometallic Chemistry*, 1988, 352, 263–272) instead of cyclohexane carboxylic acid in Step c). Data for the title compound: $^1$H NMR (360 MHz, CDCl$_3$) δ1.56 (3 H, s), 1.80–1.91 (1 H, m), 2.08–2.24 (3 H, m), 2.38–2.52 (2 H, m), 3.93 (3 H, s), 5.54 (2 H, s), 7.46–7.60 (3 H, m), 7.69 (1 H, s), 8.04 (1 H, s), 8.48–8.55 (2 H, m); MS (ES$^+$) m/e 376 [MH]$^+$. Anal. Found C, 64.01; H, 5.51; N, 26.00. C$_{20}$H$_{21}$N$_7$O requires C, 63.98; H, 5.64; N, 26.12%.

EXAMPLE 158

7-Isopropyl-6-(2-methyl-2 H-1,2,4-triazol-3-ylmethoxy)-3-phenyl-1,2,4-triazolo[4,3-b]pyridazine This compound was prepared using the procedures described in Example 88 Steps a), b) and c) using 2-methylpropionic acid instead of cyclohexane carboxylic acid in Step c). Data for the title compound: $^1$H NMR (360 MHz, CDCl$_3$) δ1.32 (6 H, d, J=6.8 Hz), 3.10–3.25 (1 H, m), 3.98 (3 H, s), 5.63 (2 H, s), 7.47–7.61 (3 H, m), 7.91 (1 H, d, J=0.7 Hz), 7.94 (1 H, s), 8.32–8.43 (2 H, m); MS (ES$^+$) m/e 350 [MH]$^+$. Anal. Found C, 62.20; H, 5.28, N, 27.78. C$_{18}$H$_{19}$N$_7$O requires C, 61.88; H. 5.48; N, 28.06%.

EXAMPLE 159

7-tert-Butyl-3-(2-fluorophenyl)-6-(1-methyl-1 H-1,2,4-triazol-3-ylmethoxy)-1,2,4-triazolo[4,3-b]pyridazine This compound was prepared using the procedures described in Example 102 Steps a), b) and c) using trimethylacetic acid instead of cyclopentane carboxylic acid in Step a), using 2-fluorobenzoic hydrazide instead of 2-thiophene carboxylic acid hydrazide in Step b) and using (1-methyl-1 H-1,2,4-triazol-3-yl)methanol (prepared using the conditions described in EP-A-421210) instead of 2-hydroxymethylpyridine in Step c). Data for the title compound: $^1$H NMR (360 MHz, CDCl$_3$) δ1.43 (9 H, s), 3.93 (3 H, s), 5.44 (2 H, s), 7.23–7.37 (2 H, m), 7.48–7.58 (1 H, m), 7.94 (1 H, s), 7.95–8.00 (1 H, m), 8.04 (1 H, s); MS (ES$^+$) m/e 382 [MH]$^+$. Anal. Found C, 60.20; H, 4.98; N, 25.53. C$_{19}$H$_{20}$N$_7$OF requires C, 59.83; H, 5.29; N, 25.71%.

EXAMPLE 160

7-Cyclopentyl-3-(4-methoxyphenyl)-6-(2-methyl-2 H-1,2,4-triazol-3-ylmethoxvy)-1,2,4-triazolo[4,3-b]pyridazine Prepared in an analogous procedure as outlined in Example 102b using 4-methoxybenzoic acid hydrazide and Example 102c using (2-methyl-2 H-1,2,4-triazol-3-yl)methanol to give the title compound. $^1$H NMR (250 MHz, CDCl$_3$) δ1.30 (3 H, s), 1.75 (4 H, m), 1.88 (4 H, m), 3.96 (3 H, s), 5.62 (2 H, s), 7.53 (3 H, m), 7.96 (2 H, s), 8.38 (2 H, m); MS (ES$^+$) m/e 390 [MH]$^+$.

EXAMPLE 161

7-(1-Methylcyclopentyl)-6-(1-methyl-1 H-1,2,4-triazol-3-ylmethoxy)-3-phenyl-1,2,4-triazolo[4,3-b]pyridazine Prepared in an analogous procedure as outlined in Example 102a using 1-methylcydopentanoic acid, Example 102b using benzoic acid hydrazide and Example 102c using (1-methyl-1 -1,2,4-triazol-3-yl)methanol to give the title compound. $^1$H NMR (250 MHz, CDCl$_3$) δ1.73 (6 H, m), 2.08 (2 H, m) 3.18 (1 H, m), 3.90 (3 H, s), 3.99 (3 H, s), 5.62 (2 H, s), 7.06 (3 H, m), 7.88 (1 H, d, J=1.1 Hz), 7.95 (1 H, s), 8.36 (2 H, m); MS (ES$^+$) m/e 406 [MH]$^+$.

EXAMPLE 162

7-(1-Methylcyclopentyl) -6-(2-methyl-2 H-1,2,4-triazol-3-ylmethoxy)-3-phenyl-1,2,4-triazolo[4.3-b]pyridazine Prepared in an analogous procedure as outlined in Example 102a using 1-methylcyclopentanoic acid, Example 102b using benzoic acid hydrazide and Example 102c using (2-methyl-2 H-1,2,4-triazol-3-yl)methanol to give the title compound. $^1$H NMR (250 MHz, CDCl$_3$) δ1.35 (3 H, s), 1.64 (4 H, m), 1.72 (4 H, m), 3.94 (3 H, s), 5.57 (2 H, s), 7.52 (3 H, m), 7.91 (1 H, s), 8.06 (1 H, s), 8.49 (2 H, m); MS (ES$^+$) m/e 390 [MH]$^+$.

EXAMPLE 163

7-Cyclopentyl-3-(furan-2-yl)-6-(2-methyl-2 H-1,2,4-triazol-3-ylmethoxy)-1,2,4-triazolo[4,3-b]pyridazine Prepared in an analogous procedure as outlined in Example 102b using 2-furoic acid hydrazide and Example 102c using (2-methyl-2 H-1,2,4-triazol-3-yl)methanol to give the title compound. $^1$H NMR (250 MHz, CDCl$_3$) δ1.72 (6 H, m), 2.08 (2 H, m), 3.19 (1 H, m), 4.04 (3 H, s), 5.67 (2 H, s), 6.64 (1 H, m), 7.42 (1 H, d, J=3.5 Hz), 7.68 (1 H, d, J=1.6 Hz), 7.86 (1 H, d, J=1 Hz), 7.95 (1 H, s); MS (ES$^+$) m/e 365 [MH]$^+$.

EXAMPLE 164

7-Cyclopentyl-3-(furan-2-yl)-6-(1-methyl-1 H-1,2,4-triazol-3-ylmethoxy)-1,2,4-triazol[4,3-b]pyridazine Prepared in an analogous procedure as outlined in Example 102b using furoic acid hydrazide and Example 102c using (1-methyl-1 H-1,2,4-triazol-3-yl)methanol to give the title compound. $^1$H NMR (250 MHz, CDCl$_3$) δ1.74 (6 H, m), 2.13 (2 H, m), 3.26 (1 H, m), 3.95 (3 H, s), 5.59 (2 H, s), 6.64 (1 H, m), 7.55 (1 H, d, J=3.5 Hz), 7.66 (1 H, d, J=1.4 Hz), 7.83 (1 H, d, J=1.1 Hz), 8.06 (1 H, s); MS (ES$^+$) m/e 365 [MH]$^+$.

EXAMPLE 165

3-(3,7-Diphenyl-1,2,4-triazolo[4,3-b]pyridazin-6-yloxymethyl)-1,2,4-triazol-1-ylacetonitrile The product from Example 72 Step c) (0.10 g) was suspended in DMF (5 ml). Sodium hydride (15 mg of a 60% dispersion in mineral oil) was added, and the mixture strrred at room temperature for 15 min. Chloroacetonitrile (41 µl) was added, and the mixture stirred as before for 2 days. Water (25 ml) was added, and the resultant precipitate filtered off and purified by flash chromatography (silica gel, 0 to 3% methanol in dichloromethane). The product was recrystallised from ethyl acetate/ethanol to yield colourless crystals (17 mg). $^1$H NMR (360 MHz, d$_6$-DMSO) δ5.60 (2 H, s), 5.61 (2 H, s), 7.58 (6 H, m), 7.76 (2 H, m), 8.41 (1 H, s), 8.44 (2 H, m), 8.68 (1 H, s); MS (ES$^+$) m/e 409 [MH$^+$]. Anal. Found C, 64.62; H, 3.74; N, 26.82. C$_{22}$H$_{16}$N$_8$O. 0.1 C$_4$H$_8$O$_2$ requires C, 64.62; H, 4.06; N, 26.87%.

EXAMPLE 166

7-(1-Methylcyclopropyl)-6-(2-methyl-2 H-1,2,4-triazol-3-ylmethoxy)-3-phenyl-1,2,4-triazolo[4,3-b]pyridazine Prepared in an analogous procedure as outlined in Example 102a using 1-methylcydopropanoic acid, Example 102b using benzoic acid hydrazide and Example 102c using (2-methyl-2 H-1,2,4-triazol-3-yl)methanol to give the title compound. $^1$H NMR (360 MHz, CDCl$_3$) δ0.79–0.88 (4 H, m), 1.37 (3 H, s), 4.02 (3 H, s), 5.67 (2 H, s), 7.51–7.58 (3 H, m), 7.94 (2 H, d, J=4.8 Hz), 8.38 (2 H, d, J=6.6 Hz); MS (ES$^+$) m/e 362 [MH$^+$].

EXAMPLE 167

7-(1-Methylcyclopropyl)-6-(1-methyl-1 H-1,2,4-triazol-3-ylmethoxy)-3-phenyl-1,2,4-triazolo[4,3-b]pridazine Prepared in an analogous procedure as outlined in Example 102a using 1-methylcyclopropanoic acid, Example 102b using benzoic acid hydrazide and Example 102c using (1-methyl-1 H-1,2,4-triazol-3-yl)methanol to give the title compound. $^1$H NMR (360 MHz, CDCl$_3$) δ0.78–0.90 (4 H, m), 1.42 (3 H, s), 3.94 (3 H, s), 5.60 (2 H, s), 7.46–7.58 (3 H, m), 7.87 (1 H, s), 8.05 (1 H, s), 8.49 (2 H, d, J=6.6 Hz); MS (ES$^+$) m/e 362 [MH$^+$].

EXAMPLE 168

3-(3-Fluorophenyl)-6-(1-methyl-1 H-1,2,4-triazol-3-ylmethoxy)-7-phenyl-1,2,4-triazolo[4,3-b]pyridazine This compound was prepared using procedures described in Example 2 a), b), c), d) with 3-fluorobenzyl hydrazide being used instead of benzoyl hydrazine in Step c) and (1-methyl-1 H-1,2,4-triazol-3-yl)methanol being used instead of 2-pyridylcarbinol in Step d). Data for the title compound: m.p.=250–251° C. $^1$H NMR (360 MHz, d$_6$-DMSO) δ3.55 (3 H, s), 5.25 (2 H, s), 7.36 (3 H, m), 7.42 (3 H, m), 7.95 (1 H, d, J=7.2 Hz), 7.98 (1 H, d, J=7.2 Hz), 8.12 (1 H, s), 8.17 (1 H, s); (ES$^+$) m/e 402 [MH$^+$]. Anal. Found C, 61.66; H, 3.87; N, 23.29. C$_{21}$H$_{16}$N$_7$OF+0.5% H$_2$O+0.1% EtOAc requires C, 61.64; H, 4.16; N, 23.51%.

EXAMPLE 169

7-(1-Methylcyclopentyl)-6-(3-methylpyridin-2-ylmethoxv)-3-phenyl-1,2,4-triazolo[4,3-b]pyridazine 2-Hydroxymethyl-3-methylpyridine (43 mg) was dissolved in dimethylformamide (2 ml) under N$_2$. Sodium hydride (60% w/w in oil, 14 mg) was added followed after 5–10 minutes by 6-chloro-7-(1-methylcyclopentyl)-3-phenyl-1,2,4-triazolo[4,3-b]pyridazine (100 mg). Reaction was stirred at room temperature for 18 hours, partitioned between ethyl acetate and water, organic phase separated, dried (MgSO$_4$) and evaporated to dryness. Recrystled from ethyl acetate to give pure product. $^1$H NMR (360 MHz, CDCl$_3$) δ1.30 (3 H, s), 1.77 (6 H, m), 1.93 (2 H, m), 2.44 (3 H, s), 5.62 (2 H, s), 7.25 (1 H, m), 7.50 (3 H, m), 7.58 (1 H, d, J=7.8 Hz), 7.92 (1 H, s), 8.42 (2 H, d, J=6.4 Hz), 8.50 (1 H, m), ms (ES$^+$) m/e 400 [MH]$^+$.

EXAMPLE 170

6-(1-Methyl-1 H-1,2,3-triazol-4-ylmethoxy)-3,7-diphenyl-1,2,4-triazolo[4,3-b]pyridazine The mixture of the title compound and the 2-methyl-2 H-1,2,3-triazol-4-yl analogue (from Example 156) was separated by preparative HPLC using a KR100-SC18 (250× 4.6 mm) column, eluting with 35% MeCN/0.1% aqueous TFA at 1 ml/min. The fractions containing the slower eluting isomer were combined and evaporated in vacuo. The residue was partitioned between saturated aqueous NaHCO$_3$ (30 ml) and dichloromethane (15 ml). The aqueous layer was further extracted with dichloromethane (2×15 ml), and the combined organic extracts were dried (Na$_2$SO$_4$) and evaporated in vacua. The residue was recrystallised from CH$_2$Cl$_2$—EtOAc-hexane to give the title compound as a white solid with a purity of >95% by HPLC; $^1$H NMR (360 MHz, CDCl$_3$) δ4.05 (3 H, s), 5.67 (2 H, s), 7.46–7.62 (9 H, m), 8.04 (1 H, s), 8.51 (2 H, m); MS (ES$^+$) m/e 384

EXAMPLE 171

3-(5-Methylthiophen-2-yl)-6-(1-methyl-1 H-1,2,4-triazol-3-ylmethoxy)-7-phenyl-1,2,4-triazolo[4,3-b]pyridazine This compound was prepared using the procedures described in Example 2 a), b), c), d) with 5-methylthiophene hydrazide being used instead of benzoyl hydrazine in Step c) and (1-methyl-1 H-1,2,4-triazol-3-yl)methanol being used instead of 2-pyridylcarbinol in Step d). m.p.=209–210° C. $^1$H NMR (360 MHz, d$_6$-DMSO) δ2.37 (3 H, s), 3.66 (3 H, s), 5.37 (2 H, s), 6.83–6.84 (1 H, d, J=3.6 Hz), 7.28 (3 H, m), 7.52 (2 H, m), 7.88–7.89 (1 H, d, J=3.6 Hz), 8.17 (1 H s), 8.28 (1 H, s); MS (ES$^+$) m/e 404 [MH$^+$].

EXAMPLE 172

2-[3-(3,7-Diphenyl-1,2,4-triazolo[4,3-b]pyridazi-6-yloxymethyl)-1,2,4-triazol-1-yl]-N,N-dimethylacetamide This compound was prepared using the procedure described in Example-165, with 2-chloro-N,N-dimethylacetamide being used instead of chloroacetonitrile. $^1$H NMR (360 MHz, CDCl$_3$) δ2.99 (3 H, s), 3.07 (3 H, s), 4.99 (2 H, s), 5.62 (2 H, s), 7.50 (6 H, m), 8.04 (1 H, s), 8.24 (1 H, s), 8.54 (2 H, m); MS (ES$^+$) m/e 455 [MH$^+$]. Anal. Found C, 62.83; H, 4.46; N, 24.31. C$_{24}$H$_{22}$N$_8$O$_2$. 0.25 H$_2$O requires C, 62.80; H, 4.94; N, 24.41%.

EXAMPLE 173

3,7-Diphenyl-6-[1-(pvridin-2-ylmethyl)-1H-1,2,4-triazol-3-ylmethoxy]-1,2,4-triazolo[4,3-b]pyridazine This compound was prepared using the procedure described in Example 165, with 2-picolyl chloride being used instead of chloroacetonitrile. $^1$H NMR (360 MHz, CDCl$_3$) δ5.42 (2 H, s), 5.63 (2 H, s), 7.08 (1 H, d, J=7.8 Hz), 7.21 (1 H, m), 7.51 (7 H, m), 7.68 (2 H, m), 8.03 (1 H, s), 8.24 (1 H, s), 8.51 (3 H, m); MS (ES$^+$) m/e 461 [MH$^+$]. Anal. Found C, 67.23; H, 4.22; N, 23.75. C$_{26}$H$_{20}$N$_8$O. 0.1 C$_4$H$_8$O$_2$ requires C, 67.57; H, 4.47; N, 23.88%.

EXAMPLE 174

6-(1-Benzyl-1 H-1,2,4-triazol-3-ylmethoxy)-3,7-diphenyl-1,2,4-triazolo[4,3-b]pyridazine This compound was prepared using the procedure described in Example 165, with benzyl bromide being used instead of chloroacetonitrile. $^1$H NMR (360 MHz, CDCl$_3$) δ5.30 (2 H, s), 5.62 (2 H, s), 7.22 (2 H, m), 7.33 (3 H, m), 7.50 (6 H, m), 7.68 (2 H, m), 8.03 (1 H, s), 8.04 (1 H, s), 8.53 (2 H, m); MS (ES$^+$) m/e 460 [MH$^+$]. Anal. Found C, 70.40; H, 4.20; N, 21.40. C$_{27}$H$_{21}$N$_7$O requires C, 70.57; H, 4.61; N, 21.34%.

EXAMPLE 175

2-[5-(3,7-Diphenyl-1,2,4-triazolo[4,3-b]pyridazin-6-yloxymethyl)-1,2,4-triazol-1-yl]acetamide This compound was prepared using the procedure described in Example 165, with iodoacetamide being used instead of chloroacetonitrile. $^1$H NMR (400 MHz, CDCl$_3$+d$_6$-DMSO) δ4.82 (2 H, s), 5.74 (2 H, s), 6.55 (1 H, br s), 7.18 (1 H, br s), 7.54 (8 H, m), 7.90 (1 H, s), 8.06 (1 H, s), 8.39 (2 H, m); MS (ES$^+$) m/e 427 [MH$^+$].

EXAMPLE 176

N-[2-[3-(3,7-Diphenyl-1,2,4-triazolo[4,3-b] pyridazine-6-yloxmethyl)-1,2,4-triazol-1-yl]ethyl]-N,N-dimethylamine The product from Example 72 Step c) (0.10 g) was suspended in THF (5 ml). Triphenylphosphine (71 mg), N,N-dimethylethanolamine (30 μl) and diethylazodicarboxylate (43 μl) were added, and the mixture was stirred at room temperature for 24 h. More triphenylphosphine (71 mg) and diethylazodicarboxylate (43 μl) were added, and the mixture was stirred as before for 24 h. Water (50 ml) was added, and the resultant solution was acidified (pH ~1) with 5 N hydrochloric acid. The solution was washed with dichloromethane (3×25 ml), basified with 4 N sodium hydroxide (pH ~14), and extracted again with dichloromethane (3×25 ml). The organic layers from the second extraction were combined, dried (magnesium sulfate) and concentrated in vacuo. The residue was purified by flash chromatography (silica gel 0 to 9% methanol in dichloromethane) and recrystallised from ethyl acetate/hexane to yield colourless crystals (33 mg). $^1$H NMR (360 MHz, CDCl$_3$) δ2.22 (6 H, s), 2.70 (2 H, t, J=6.2 Hz), 4.21 (2 H, t, J=6.2 Hz), 5.61 (2 H, s), 7.52 (6 H, m), 8.04 (1 H, s), 8.16 (1 H, s), 8.55 (2 H, m); MS (ES$^+$) m/e 441 [MH$^+$]. Anal. Found C, 64.97; H, 5.22; N, 25.06. C$_{24}$H$_{24}$N$_8$O requires C, 65.44; H, 5.49; N, 25.44%.

EXAMPLE 177

3.7-Diphenyl-6-(pyrimidin-5-ylmethoxy)-1,2,4-triazolo[4,3-b]pyridazine a) 5-Bromomethylpyrimidine 5-Methylpyrimidine (3.0 g), N-bromosuccinimide (7.1 g) and benzoyl peroxide (63 mg) were heated together at reflux in carbon tetrachloride (480 ml) under irradiation from a 60 W light bulb for 2 h. The slurry was allowed to cool to room temperature, and filtered. The filtrate was washed with 10% sodium bicarbonate solution (2×250 ml), dried (magnesium sulfate) and concentrated in vacuo to yield an orange solid—this was a mixture of 5-bromomethylpyrimidine and 5-dibromomethylpyrimidine, present in a 3:2 ratio respectively (4.2 g). This material was used in the next step without further purification. $^1$H NMR (250 MHz, d$_6$-DMSO) δ4.98 (2 H, s), 9.30 (2 H, s), 9.43 (1 H, s); MS (ES$^+$) m/e 172, 174 (1:1 ratio) [MH$^+$].

b) 3,7-Diphenyl-6-(pyrimidin-5-ylmethoxy)-1,2,4-triazolo[4,3-b]pyridazine

This compound was prepared using the procedures described in Example 79 a) and b), with 5-bromomethylpyrimidine being used instead of bromoacetonitrile in Step b). $^1$H NMR (360 MHz, CDCl$_3$) δ5.56 (2 H, s), 7.56 (8 H, m), 8.07 (1 H, s), 8.38 (2 H, m), 8.82 (2 H, s), 9.22 (1 H, s); MS (ES$^+$) m/e 381 [MH$^+$].

EXAMPLE 178

6-[1-(2-(Morpholin-4-yl)-ethyl)-1 H-1,2,4-triazol-3-ylmethoxy]-3,7-diphenyl-1,2,4-triazolo[4,3-b]pyridazine This compound was prepared using the procedure described in Example 176, with 4-(2-hydroxyethyl) morpholine being used instead of N,N-dimethylethanoamine. $^1$H NMR (400 MHz, CDCl$_3$) δ2.41 (4 H, t, J=4.6 Hz), 2.75 (2 H, t, J=6.2 Hz), 3.63 (4 H, t, J=4.6 Hz), 4.23 (2 H, t, J=6.2 Hz), 5.61 (2 H, s), 7.51 (6 H, m), 7.69 (2 H, m), 8.05 (1 H, s), 8.17 (1 H, s), 8.55 (2 H, m); MS (ESS$^+$) m/e 483 [MH$^+$].

EXAMPLE 179

6-(2-Methyl-2 H-1,2,4-triazol-3-ylmethoxy)-3-phenyl-7-(pyrrolidin-1-yl)-1,2,4-triazolo[4,3-b]pyridazine a) 6-Chloro-3-phenyl-7-(pyrrolidin-1-yl)-1,2,4-triazolo[4,3-b]pyridazine This compound was prepared using the procedures described in Example 15 Steps a, b, c, d with pyrrolidine being used in Step c.

b) 6-(2-Methyl-2 H-1,2,4-triazol-3-ylmethoxy)-3-phenyl-7-(pyrrolidin-1-vl)-1,2,4-triazolo[4,3-b]pyridazine To a solution of 6-chloro-3-phenyl-7-(pyrrolidin-1-yl)-1,2,4-triazolo[4,3-b]pyridazine (100 mg, 0.33 mmol) and 3-hydroxymethyl-2-methyl-1,2,4-triazole in dry DMF (5 ml) was added sodium hydride (60% dispersion in oil, 20 mg, 0.36 mmol). The mixture was stirred at room temperature for 2 hours. The reaction mixture was diluted with water (50 ml) and extracted with dichloromethane (3×25 ml). The combined extracts were washed with brine, dried over magnesium sulphate, filtered and evaporated. The solid was triturated with methanol, and collected by filtration to afford the title pyridazine (68 mg, 55%). $^1$H NMR (360 MHz, CDCl$_3$) δ1.93–1.97 (4 H, m), 3.41–3.45 (4 H, m), 4.00 (3 H, s), 5.58 (2 H, s), 6.66 (1 H, s), 7.43–7.53 (3 H, m), 7.94 (1 H, s), 8.28 (2 H, d, J=8.3 Hz). MS (ES$^+$) 377 [MH$^+$].

EXAMPLE 180

7-(5-Chlorothiophen-2-yl)-6-(2-methyl-2 H-1,2,4-triazol-3-ylmethoxy)-3-phenyl-1,2,4-triazolo[4,3-b]pyridazine This compound was prepared using the procedures described in Example 16 Steps a), b) and c) except 5-chloro-2-thiophene boronic acid was used instead of 4-pyridyl boronic acid, di-lithium salt in Step a), 1.1 equivalents of triethylamine hydrochloride was used in Step b) instead of 1.1 equivalents of p-toluenesulphonic acid and triethylamine, and 3-hydroxymethyl-2-methyl-1,2,4-triazole (Example 65) was used in Step c) instead of 2-pyridylcarbinol. Data for the title compound: m.p. 244–247° C. (EtOAc). $^1$H NMR (360 MHz, d$_6$-DMSO) δ3.95 (3 H, s), 5.82 (2 , s), 7.30 (1 H, d, J=4 Hz), 7.55–7.65 (3 H, m), 7.93 (1 H, d, J=4 Hz), 8.03 (1 H, s), 8.41 (2 H, d, J=7 Hz), 8.88 (1 H, s). MS (ES$^+$) 424 [MH]$^+$. Anal. Found C, 53.01; H, 3.37. C$_{19}$H$_{14}$N$_7$ClOS. 0.35H$_2$O requires C, 53.05; H, 3.44%.

EXAMPLE 181

7-(5-Chlorothiophen-2-yl-6-(1-methyl-1 H-1,2,4-triazol-3-ylmethoxy)-3-phenyl-1,2,4-triazolo[4,3-b]pyridazine This compound was prepared using the procedures described in Example 16 Steps a), b) and c) except 5-chloro-2-thiophene boronic acid was used instead of 4-pyridyl boronic acid, di-lithium salt in Step a), 1.1 equivalents of triethylamine hydrochloride was used in Step b) instead of 1.1 equivalents of p-toluenesulphonic acid and triethylamine, and 3-hydroxymethyl-1-methyl-1,2,4-triazole (Example 65) was used in Step c) instead of 2-pyridylcarbinol. Data for the title compound: m.p. 248–250° C. (EtOAc). $^1$H NMR (360 MHz, d$_6$-DMSO) δ3.89 (3 H, s), 5.64 (2 H, s), 7.29 (1 H, d, J=4 Hz), 7.56–7.62 (3 H, m), 7.93 (1 H, d, J=4 Hz), 8.45 (2 H, d, J=7 Hz), 8.54 (1 H, s), 8.83 (1 H, s). MS (ES$^+$) 424 [MH]$^+$. Anal. Found C, 53.56; H, 3.36. C$_{19}$H$_{14}$N$_7$ClOS. 0.1H$_2$O requires C, 53.61; H, 3.36%.

EXAMPLE 182

6-(1 H-Benzmidazol-2-ylmethoxy)-3-(2,4-difluorophenyl)-7-(1-methylcyclopentyl)-1,2,4-triazolo[4,3-b]pyridazine 2-(Hydroxymethyl)benzimidazole (39 mg) was dissolved in dimethylformamide (2 ml) under N$_2$. Sodium hydride (60% w/w in oil, 11 mg) was added followed after 5–10 minutes by 6-chloro-7-(1-methyl-cyclopentyl)-3-phenyl-1,2,4-triazolo[3,4-b]pyridazine (80 mg). Reaction was stirred at room temperature for 18 hours, partitioned between ethyl acetate and water, organic phase separated, dried (MgSO4) and evaporated to dryness. Chromatography on silica eluting with ethyl acetate gave pure product. $^1$H NMR (500 MHz, CDCl$_3$) 1.33 (3 H, s), 1.67 (4 H, m), 1.80 (2 H, m), 1.93 (2 H, m), 5.69 (2 H, s), 7.04 (1 H, m), 7.13 (1 H, m), 7.31 (2 H, m), 7.40 (1 H, m), 7.79 (1 H, m), 7.88 (1 H, m), 7.96 (1 H, s); ms (ES$^+$) m/e 461 [MH]$^+$.

EXAMPLE 183

3-(Furan-3-yl)-6-(2-pyridyl)methyloxy-7,8,9,10-tetrahydro-1,2,4-triazolo[3,4-a]phthalazine a) 2,3,5,6,7,8-Hexahydrophthalazine-1.4-dione 3,4,5,6-Tetrahydrophthalic anhydride (25 g, 0.164 mol) was dissolved in 40% aqueous acetic acid (500 ml) with sodium acetate trihydrate (26.8 g, 0.197 mol) and hydrazine hydrate (9.58 ml, 0.197 mol). The reaction mixture was heated under reflux overnight and then allowed to cool. The resulting solid was collected by filtration, washed with water and diethyl ether and dried in vacio to give the title-product (23 g, 84%), $^1$H NMR (250 MHz, d$_6$-DMSO) δ1.64 (4 H, br s, 2 of CH$_2$), 2.34 (4 H, br s, 2 of CH$_2$), 11.30 (2 H, br s, 2 of NH); MS (ES$^+$) m/e 167 [MH]$^+$.

b) 1,4-Dichloro-5,6,7,8-tetrahydrophthalazine

The preceding dione (23 g, 0.14 mol) was dissolved in phosphorus oxychloride (200 ml) and heated at reflux overnight. The solvent was evaporated in vacuo and azeotroped with toluene. The residue was dissolved in dichloromethane (200 ml), stirred rapidly and saturated sodium bicarbonate solution (200 ml) added slowly. Solid sodium bicarbonate was added cautiously until effervescence ceased and the mixture then partitioned between dichloromethane and water. The organic layer was separated, dried (MgSO$_4$) and evaporated in vacuo. The residue was triturated with diethyl ether and dried in vacuo to give the title-product (25.8 g, 92%), $^1$H NMR (250 MHz, CDCl$_3$) δ1.84–1.90 (4 H, m, 2 of CH$_2$), 2.72–2.78 (4 H, m, 2 of CH$_2$).

c) 1-Chloro-4-hydrazino-5,6,7,8-tetrahydrophthalazine

A mixture of the preceding product (18.3 g, 0.090 mol) and hydrazine monohydrate (13.6 ml, 0.28 mol) in ethanol (280 ml) was heated at reflux overnight. The mixture was cooled to room temperature and the resulting precipitate filtered off. The filtrate was evaporated in vacuo to give the title-product (14.86 g, 83%), $^1$H NMR (250 MHz, CDCl$_3$/d$_6$-DMSO) δ1.79–1.92 (4 H, m, 2 of CH$_2$), 2.59–2.65 (2 H, m, CH$_2$), 2.73–2.78 (2 H, m, CH$_2$).

d) 6-Chloro-3-(furan-3-yl)-7,8,9,10-tetrahydro-1,2,4-triazolo[3,4-a]phthalazine 1,1'-Carbonyldiimidazole-(0.98 g, 6.1 mmol) was added to a stirred mixture of 3-furoic acid (0.68 g, 6.1 mmol) in THF (30 ml). The mixture was stirred for 0.75 h before adding the preceding hydrazine (1.0 g, 5.1 mmol). After 4 h at room temperature, the solvent was evaporated in vacuo, water added and the mixture stirred for 0.5 h. The resultant solid was collected by filtration, washed with water and hexane and dried in vacuo to give the ketohydrazine. A mixture of the ketohydrazine (0.80 g) and triethylamine hydrochloride (0.10 g, 0.73 mmol) in xylene (10 ml) was heated at reflux overnight. The solution was cooled to room temperature and the solvent removed in vacuo. The residue was chromatographed on silica gel, eluting with 5% methanol/dichloromethane, to give the title-phthalazine (0.21 g), $^1$H NMR (250 MHz, CDCl$_3$) δ1.90–2.02 (4 H, m, 2 of CH$_2$), 2.74–2.80 (2 H, m, CH$_2$), 3.16–3.24 (2 H, m, CH$_2$), 7.28 (1 H, m, Ar—H), 7.58 (1 H, t, J=1.7 Hz, Ar—H), 8.53 (1 H, m, Ar—H).

e) 3-(Furan-3-yl)-6-(2-pyridyl)methyloxy-7,8,9,10-tetrahydro-1,2,4-triazolo[3,4-a]phthalazine Sodium hydride (55 mg of a 60% dispersion in oil, 1.4 mmol) was added to a solution of 2-pyridylcarbinol (160 mg, 1.46 mmol) in DMF (10 ml) and the mixture was stirred at room temperature for 0.5 h. After this time, the preceding product (100 mg, 0.365 mmol) was added and the reaction mixture stirred at room temperature for 3 h before being poured into water. The mixture was extracted with ethyl acetate (x3) and the combined extracts washed with water (x1) and brine (x1), dried (Na$_2$SO$_4$) and evaporated in vacuo. The resultant solid was washed with ethyl acetate to give the title-compound, $^1$H NMR (250 MHz, CDCl$_3$) δ1.92–2.02 (4 H, m, 2 of CH$_2$), 2.72–2.78 (2 H, m, CH$_2$), 3.12–3.16 (2 H, m, CH$_2$), 5.60 (2 H, s, CH$_2$), 7.24 (1 H, m, Ar—H), 7.31 (1 H, m, Ar—H), 7.51–7.57 (2 H, m, Ar—H), 7.79 (1 H, m, Ar—H), 8.44 (1 H, m, Ar—H), 8.64 (1 H, m, Ar—H); MS (ES$^+$) m/e 348 [MH]$^+$; Anal. Found C, 62.84; H, 4.98; N, 18.99. C$_{19}$H$_{17}$N$_5$O$_2$. 0.9H$_2$O requires C, 62.77; H. 5.21; N, 19.26%.

EXAMPLE 184

7-Cyclobutyl-3-phenyl-6-(prop-2-ynyloxy)-1,2,4-triazolo[4,3-b]pyridazine

To a stirred solution of propargyl alcohol (47 mg, 0.84 mmol) in DMF (2 ml) was added 60% sodium hydride suspension in oil (31 mg, 0.77 mmol). Left to stir for 5 minutes prior to the addition of 6-chloro-7-cyclobutyl-3-phenyl-1,2,4-triazolo[4,3-b]pyridazine (200 mg, 0.70 mmol). Left to stir for 90 minutes. Quenched (120), extracted (ethyl acetate), washed (H$_2$O, brine), dried (MgSO$_4$) and evaporated in vacuo. The residue was purified via silica gel chromatography using 50/50 ethyl acetate/hexane to elute. The title compound was obtained as a white solid. $^1$H NMR (250 MHz, CDCl$_3$) δ2.19–2.26 (1 H, m), 2.37–2.55 (3 H, m), 2.69–2.80 (2 H, m), 2.90 (1 H, m), 3.97 (1 H, m), 5.35 (2 H, d, J=2.4 Hz), 7.77–7.89 (3 H, m), 8.13 (1 H, s), 8.80 (1 H, s), 8.86 (1 H, s). Mass spec. ES$^+$(M+1)=305.

EXAMPLE 185

(7-Cyclobutyl-3-phenyl-1,2,4-triazolo[4,3-b]pyridazin-6-yloxy)acetonitrile a) 7-Cyclobutyl-3-phenyl-1,2,4-triazolo[4,3-b]pyridazin-6-one 6-Chloro-7-cyclobutyl-3-phenyl-1,2,4-triazolo[4,3-b]pyridazine (2.0 g, 7.0 mmol), 2 N NaOH (50 ml) and 1,4-dioxane (10 ml) were heated at reflux for 16 hours. Cooled and water (150 ml) added. Precipitate filtered, suspended in H$_2$O, acidified (2 N HCl), filtered and dried to give a white solid. $^1$H NMR (250 MHz, CDCl$_3$) δ1.89–2.02 (1 H, m), 2.08–2.25 (3 H, m), 2.36–2.48 (1 H, m), 3.56–3.70 (1 H, m), 7.48–7.60 (3 H, m), 7.88 (1 H, s), 8.38 (1 H, m). Mass spec ES$^+$ (M+1)=267.

b) (7-Cyclobutyl-3-phenyl-1,2,4-triazolo[4,3-b]pyridazin-6-yloxy)-acetonitrile

The foregoing product (300 mg, 1.13 mmol), bromoacetonitrile (200 mg, 1.69 mmol) and 60% sodium hydride suspension in oil (54 mg, 1.35 mmol) were stirred together in DMF for 90 minutes. Quenched (H$_2$O), extracted (ethyl acetate), washed (H$_2$O, brine), dried (MgSO$_4$) and evaporated in vacuo. Purified via silica gel chromatography using 50/50 ethyl acetate/hexane to elute. The title compound was obtained as a white solid. $^1$H NMR (250 MHz, CDCl$_3$) δ1.95 (1 H, m), 2.15–2.19 (3 H, m), 2.41–2.47 (2 H, m), 3.61–3.65 (1 H, m), 5.09 (2 H, s), 7.49–7.59 (3 H, m), 7.89 (1 H, s), 8.39 (2 H, m). Mass spec ES$^+$ (M+1)=306.

EXAMPLE 186

N-[4-(7-Cyclobutyl-3-phenyl-1,2,4-triazolo[4,3-b]pyridazin-6-yloxy)but-2-vnyl]-N,N-dimethylamine a) 6-(4-Chlorobut-2-vnyloxy)-7-cyclobutyl-3-phenyl-1,2,4-triazolo[4,3-b]pyridazine Potassium carbonate (311 mg, 2.2 mmol) and 1,4 dichloro-2-butyne (275 mg, 2.2 mol) in DMF (3 ml) were heated to 50° C. prior to the dropwise addition of the product from Example 185, Step a (200 mg, 0.75 mmol) in DMF (2 ml). The reaction mixture was left to stir for 2 hours. Cooled and partitioned (ethyl acetate/water). The organic layer was washed (H$_2$O, brine), dried MgSO$_4$) and evaporated in vacuo. Purified via silica gel chromatography using 50/50 ethyl acetate/hexane to elute. $^1$H NMR (250 MHz, CDCl$_3$) δ1.93 (1 H, m), 2.11–2.16 (3 H, m), 2.42 (2 H, m), 4.2 (2 H, m), 5.10 (2 H, m), 7.50–7.59 (3 H, m), 7.84 (1 H, s), 8.47 (2 H, m).

b) N-[4-(7-Cyclobutyl-3-phenyl-1,2,4-triazolo[4,3-b]pyridazin-6-yloxy)-but-2-ynyl]-N,N-dimethylamine The foregoing product (40 mg, 0.114 mmol) and dimethylamine (1 ml) in 1,4-dioxane (4 ml) were heated in a sealed tube at 50° C. for 60 minutes. Evaporated in vacuo. Purified via silica gel chromatography using 50/50 ethyl acetate/hexane to elute. The title compound was obtained as a white solid. $^1$H NMR (360 MHz, CDCl$_3$) δ1.93 (1 H, m), 2.14 (3 H, m), 2.25 (6 H, s), 2.43 (2 H, m), 3.30 (2 H, s), 3.66 (1 H, m), 5.09 (2 H, s), 7.48–7.55 (3 H, m), 7.82 (1 H, s), 8.49 (2 H, m).

EXAMPLE 187

2-[3-(3,7-Diphenyl-1,2,4-triazolo[4,3-b]pyridazin-6-yloxymethyl)-1,2,4-triazol-1-yl]ethylamine This compound was prepared using the procedure described in Example 176, with ethanolamine being used instead of N,N-dimethylethanolamine. $^1$H NMR (500 MHz, CDCl$_3$+DMSO) δ3.12 (2 H, t, J=5.7 Hz), 4.23 (2 H, t, J=5.8 Hz), 5.62 (2 H, s), 7.54 (6 H, m), 7.72 (2 H, d, J=7.9 Hz), 8.07 (1 H, s), 8.29 (s, 1 H), 8.53 (2 H, d, J=7.4 Hz); MS (ES$^+$) m/e 413 [MH$^+$].

EXAMPLE 188

3,7-Diphenyl-6-[1-(2-(pyrrolidin-1-yl)ethyl)-1 H-1,2,4-triazol-3-ylmethoxy]-1,2,4-triazolo[4,3-b]pyridazine This compound was prepared using the procedure described in Example 176, with 1-(2-hydroxyethyl) pyrrolidine being used instead of N,N-dimethylethanolamine. $^1$H NMR (400 MHz, CDCl$_3$) δ1.73 (6 H, m), 2,47 (4 H, s), 2.91 (2 H, t, J=6.4 Hz), 4.27 (2 H, t, J=6.4 Hz), 5.62 (2 H, s), 7.50 (6 H, m), 7.69 (2 H, m), 8.04 (1 H, s), 8.17 (1 H, s), 8.55 (2 H, m); MS (ES$^+$) m/e 467 [MH$^+$].

EXAMPLE 189

6-[1-(1-Methylpiperidin-4-yl)-1 H-1,2,4-triazol-3-ylmethoxy]-3,7-diphenyl-1,2,4-triazolo[4,3-b]pyridazine This compound was prepared using the procedure described in Example 176, with 4-hydroxy-1-methylpiperidine being used instead of N,N-dimethylethanolamine. $^1$H NMR (400 MHz, CDCl$_3$) δ2.07 (6 H, m), 2.33 (3 H, s), 2.96 (2 H1, m), 4.13 (1 H, m), 5.61 (2 H, s), 7.50 (6 H, m), 7.70 (2 H, m), 8.04 (1 H, s), 8.09 (1 H, s), 8.53 (2 H, m); MS (ES$^+$) m/e 467 [MH$^+$].

EXAMPLE 190

3,7-Diphenyl-6-[1-(2-(piperazin-1-yl)ethyl)-1 H-1,2, 4-triazol-3-ylmethoxy]-1,2,4-triazolo[4,3-b]pyridazine This compound was prepared using the procedure described in Example 176, with 1-(2-hydroxyethyl) piperazine being used instead of N,N-dimethylethanolamine. $^1$H NMR (400 MHz, CDCl$_3$) δ2.52 (4 H, s), 2.77 (2 H, t, J=6.0 Hz), 2.92 (4 H, s), 4.22 (2 H, t, J=5.9 Hz), 5.61 (2 H, s), 7.52 (6 H, m), 7.69 (2 H, m), 8.05 (1 H, s), 8.15 (1 H, s), 8.54 (2 H, m); MS (ES$^+$) m/e 482 [MH$^+$].

EXAMPLE 191

7-(1-Methylcyclopentyl)-6-(2-methyl-2 H-1,2,4-triazol-3-ylmethoxy)-3-(2,4-difluorophenyl)-1,2,4-triazolo[4,3-b]pyridazine Prepared in an analogous procedure as outlined in Example 102a using 1-methylcyclopentanoic acid, Example 102b using 2,4-difluorobenzoic acid hydrazide and Example 102c using 3-hydroxymethyl-2-methyl-2 H-1,2,4-triazole to give the title compound. $^1$H NMR (250 MHz, CDCl$_3$) δ1.30 (3 H, s), 1.68–1.94 (8 H, m), 3.88 (3 H, s), 5.50 (2 H, s), 6.99–7.14 (2 H, m), 7.82–7.95 (3 H, m), ms (ES$^+$) m/e 426 [MH]$^+$.

EXAMPLE 192

7-(Cyclobut-1-enyl)-6-(2-methyl-2 H-1,2,4-triazol-3-ylmethoxy)-3-phenyl-1,2,4-triazolo[4,3-b] pyridazine Prepared in an analogous procedure to that outlined in Example 102 using 1-fluorocyclobutanecarboxylic acid (E. D. Bergmann and S. Szinai, *J. Chem. Soc.,* 1956, 1521) instead of cyclopentanecarboxylic acid in Step (a), benzoic acid hydrazide instead of 2-thiophene carboxylic acid hydrazide in Step (b), and (2-methyl-2 H-1,2,4-triazol-3-yl) methanol instead of 2-hydroxymethylpyridine in Step (c) to give the title compound in 48% yield. $^1$H NMR (360 MHz, CDCl$_3$) δ2.63 (2 H, br s), 2.89–2.87 (2 H, m), 3.97 (3 H, s), 5.66 (2 H, s), 6.54 (1 H, s), 7.58–7.51 (3 H, s), 7.78 (1 H, s), 7.95 (1 H, s), 8.40–8.38 (2 H, m). MS (ES$^+$) m/e 360 [MH]$^+$.

EXAMPLE 193

7-(Furan-3-yl)-6-(1-methyl-1 H-1,2,4-triazol-3-ylmethoxy)-3-phenyl-1,2,4-triazolo[4,3-b]pyridazine This compound was prepared using procedures described in Example 139 with 3-furan boronic acid (*J. Heterocycl. Chem.,* 1975, 12, 195–196) being used instead of 2-thiophene boronic acid, m.p. 241° C. $^1$H NMR (360 MHz, CDCl$_3$) δ3.90 (3 H, s), 5.62 (2 H, s), 7.37 (1 H, d, J=1.8 Hz), 7.53–7.64 (3 H, m), 7.85 (1 H, t, J=1.8 Hz), 8.46 (3 H, m), 8.48 (1 H, s), 8.67 (1 H, s); MS (ES$^+$) m/e 374 [MH$^+$]. Anal. Found C, 60.96; H, 4.06; N, 25.94. C$_{19}$H$_{15}$N$_7$O$_2$ requires C, 61.12; H, 4.05; N, 26.26%.

EXAMPLE 194

N,N-Diethyl-N-[6-(1-methyl-1 H-1,2,4-triazol-3-ylmethoxy)-3-phenyl-1,2,4-triazolo[4,3-b]pyridazin-7-yl]amine a) N-(6-Chloro-3-phenyl-1,2,4-triazolo[4,3-b]pyridazin-7-yl)-N,N-diethylamine This compound was prepared using the procedures described in Example 15, Steps a, b, c and d with diethylmine being used in Step c.

b) N,N-Diethyl-N-[6-(1-methyl-1 H-1,2,4-triazol-3-ylmethoxy)-3-phenyl-1,2,4-triazolo[4,3-b]pyridazin-7-yl]amine To a solution of N-(6-chloro-3-phenyl-1,2,4-triazolo[4,3-b]pyridazin-7-yl)-N,N-diethylamine (180 mg, 0.33 mmol) and (1-methyl-1 H-1,2,4-triazol-3-yl)methanol (68 mg) in dry DMF (5 ml) was added sodium hydride (60% dispersion in oil, 34 mg, 0.36 mmol). The mixture was stirred at room temperature for 3 hours. The reaction mixture was diluted with water (50 ml) and extracted with dichloromethane (3×25 ml). The combined extracts were washed with brine, dried over magnesium sulphate, filtered and evaporated. The solid was recrystallised from ethyl acetate, and collected by filtration to afford the title pyridazine (81 mg, 36%). $^1$H NMR (500 MHz, DMSO-d$_6$) δ1.08 (6 H, t, J=8.5 Hz), 3.31 (4 H, q, J=8.5 Hz), 3.87 (3 H, s), 5.50 (2 H, s), 7.22 (1 H, s), 7.47–7.59 (3 H, m), 8.37 (2 H, d, J=8.5 Hz), 8.51 (1 H, s). MS (ES$^+$) 379 [MH]$^+$.

EXAMPLE 195

7-(1-Methylcyclopentyl)-6-(1-methyl-1 H-1,2,4-triazol-3-ylmethoxy)-3-(2,4-difluorophenyl)-1,2,4-triazolo[4,3-b]pyridazine Prepared in an analogous procedure as outlined in Example 102a using 1-methylcyclopentanoic acid, Example 102b using 2,4-difluorobenzoic acid hydrazide and Example 102c using 3-hydroxymethyl-1-methyl-1 H-1,2,4-triazole to give the title compound. $^1$H NMR (250 MHz, CDCl$_3$) δ1.33 (3 H, s), 1.58–2.00 (8 H, m), 3.93 (3 H, s), 5.43 (2 H, s), 6.96–7.14 (2 H, m), 7.92–8.05 (3 H, m), ms (ES$^+$) m/e 426 [MH]$^+$.

EXAMPLE 196

7-(1,1-Dimethylpropyl)-6-(1-methyl-1 H-1,2,4-triazol-3-ylmethoxy)-3-phenyl-1,2,4-triazolo[4,3-b]pyridazine The compound was prepared using the procedures described in Example 89, Steps a), b) and c) with 2,2-dimethylbutyric acid being used instead of cyclohexanecarboxylic acid in Step c). Data for the title compound: $^1$H NMR (360 MHz, CDCl$_3$) δ0.70(3 H, t, J=7.5 Hz), 1.41 (6 H, s), 1.89 (2 H, q, J=7.5 Hz), 3.94 (3 H, s), 5.58 (2 H, s), 7.46–7.56 (3 H, m), 7.90 (1 H, s), 8.06 (1 H, s), 8.51 (2 H, d, J=8.0 Hz); MS (ES$^+$) m/e 378 [MH]$^+$. Anal. Found C, 63.48; H, 6.19; N, 25.55. C$_{20}$H$_{23}$N$_7$O$_1$ requires C, 63.34; H, 6.17; N, 25.85%.

EXAMPLE 197

6-(2-Methyl-2 H-1,2,4-triazol-3-ylmethoxy)-3-(4-fluorophenyl)-7-(thiophen-3-yl)-1,2,4-triazolo[4,3-b]pyridazine This compound was prepared using the procedures described in Example 16, Steps a), b) and c) except that 3-thiophene boronic acid was used instead of 4-pyridyl boronic acid, di-lithium salt in Step a), 1.1 equivalents of 4-fluorobenzhydrazide and triethylamine hydrochloride were used in Step b) instead of 1.1 equivalents of benzhydrazide, p-toluenesulphonic acid and triethylamine, and (2-methyl-2 H-1,2,4-triazol-3-yl)methanol (Example 66) was used in Step c) instead of 2-pyridylcarbinol. Data for the title compound: m.p. 268–269° C. (MeOH). $^1$H NMR (360 MHz, DMSO) δ3.92 (3 H, s), 5.79 (2 H, s), 7.46 (2 H, t, J=9 Hz), 7.70–7.74 (2 H, m), 8.01 (1 H, s), 8.19–8.21 (1 H, m), 8.45–8.49 (2 H, m), 8.68 (1 H, s). MS (ES$^+$) 408 [MH]$^+$. Anal. Found C, 55.90; H, 3.44; N, 24.02. C$_{19}$H$_{14}$N$_7$FOS requires C, 56.01; H, 3.46; N, 24.07%.

EXAMPLE 198

6-(1-Methyl-1 H- 1,2,4-triazol-3-ylmethoxy)-3-(4-fluorophenyl)-7-(thiophen-3-yl)-1,2,4-triazolo[4,3-b]-pyridazine This compound was prepared using the procedures described in Example 16, Steps a), b) and c) except that 3-thiophene boronic acid was used instead of 4-pyridyl boronic acid, di-lithium salt in Step a), 1.1 equivalents of 4-fluorobenzhydrazide and triethylamine hydrochloride were used in Step b) instead of 1.1 equivalents of benzhydrazide, p-toluenesulphonic acid and triethylmine, and (1-methyl-1 H-1,2,4-triazol-3-yl)methanol (Example 65) was used in Step c) instead of 2-pyridylcarbinol. Data for the title compound: m.p. 254–255° C. (MeOH). $^1$H NMR (360 MHz, DMSO) δ3.89 (3 H, s), 5.61 (2 H, s), 7.46 (2 H, t, J=9 Hz), 7.71 (1 H, dd, J=5, 3 Hz), 7.80 (1 H, dd, J=5, 1 Hz), 8.28–8.29 (1 H, m), 8.51–8.56 (3 H, m), 8.67 (1 H, s). MS (ES$^+$) 408 [MH]$^+$. Anal. Found C, 55.88; H, 3.40; N, 23.98. C$_{19}$H$_{14}$N$_7$FOS requires C, 56.01; H, 3.46; N, 24.07%.

EXAMPLE 199

6-(2-Methyl-2 H-1,2,4-triazol-3-ylmethoxy)-3-(2-fluorophenyl)-7-(thiophen-3-yl)-1,2,4-triazolo[4,3-b] pyridazine. 0.6(Hydrate)

This compound was prepared using the procedures described in Example 16, Steps a), b) and c) except that 3-thiophene boronic acid was used instead of 4-pyridyl boronic acid, di-lithium salt in Step a), 1.1 equivalents of 2-fluorobenzhydrazide and triethylamine hydrochloride were used in Step b) instead of 1.1 equivalents of benzhydrazide, p-toluenesulphonic acid and triethylamine, and (2-methyl-2 H-1,2,4-triazol-3-yl)methanol (Example 66) was used in Step c) instead of 2-pyridylcarbinol. Data for the title compound: m.p. 175–176° C. (MeOH). $^1$H NMR (360 MHz, DMSO) δ3.81 (3 H, s), 5.66 (2 H, s), 7.48–7.59 (2 H, m), 7.70–7.80 (3 H, m), 7.96–8.02 (2 H, m), 8.24 (1 H, dd, J=4, 3 Hz), 8.75 (1 H, s). MS (ES$^+$) 408 [MH]$^+$. Anal. Found C, 54.58; H, 3.94. C$_{19}$H$_{14}$N$_7$FOS. 0.6 H$_2$O requires C, 54.66; H, 3.66%.

EXAMPLE 200

3-(2-Fluorophenyl)-7-(1-methylcyclobutyl)-6-(2-methyl-2 H-1,2,4-triazol-3-ylmethoxy)-1,2,4-triazolo[4,3-b]pyridazine The compound was prepared using the procedures described in Example 102, Steps a), b) and c) with 1-methylcyclobutane carboxylic acid (U.S. Pat. No. 4,220,795) being used instead of cyclopentane carboxylic acid in Step a), and 2-fluorobenzhydrazide being used instead of 2-thiophene carboxylic acid hydrazide in Step b), and (2-methyl-2 H-1,2,4triazol-3-yl)methanol (prepared using the conditions described in EP-A-421210) being used instead of 2-hydroxymethylpyridine in Step c). Data for the title compound: $^1$H NMR (360 MHz, CDCl$_3$) δ1.51 (3 H, s), 1.80–1.90 (1 H, m), 2.04–2.24 (3 H, m), 2.35–2.46 (2 H, m), 3.82 (3 H, s), 5.47 (2 H, s), 7.27 (1 H, br t, J=7.5 Hz), 7.34 (1 H, br t, J=7.5 Hz). 7.53–7.60 (1 H, m), 7.73 (1 H, s), 7.85 (1 H, br t, J=7.5 Hz), 7.88 (1 H, s); MS (ES$^+$) m/e 394 [MH]$^+$. Anal. Found C, 61.16; H, 5.14; N, 24.90. C$_{20}$H$_{20}$N$_7$OF requires C, 61.06; H, 5.12; N, 24.92%.

EXAMPLE 201

3-(2-Fluorophenyl)-7-(1-methylcyclobutyl)-6-(1-methyl-1 H- 1,2,4-triazol-3-ylmethoxy)-1,2,4-triazolo[4,3-b]pyridazine The compound was prepared using the procedures described in Example 102, Steps a), b) and c) with 1-methylcyclobutane carboxylic acid (U.S. Pat. No. 4,220,795) being used instead of cyclopentane carboxylic acid in Step a), and 2-fluorobenzhydrazide being used instead of 2-thiophene carboxylic acid hydrazide in Step b), and (1-methyl-1 H-1,2,4-triazol-3-yl)methanol (prepared using the conditions described in EP-A-421210) being used instead of 2-hydroxymethylpyridine in Step c). Data for the title compound: $^1$H NMR (360 MHz, CDCl$_3$) δ1.54 (3 H, s), 1.78–1.88 (1 H, m), 2.04–2.22 (3 H, m), 2.37–2.45 (2 H, m), 3.92 (3 H, s), 5.40 (2 H, s), 7.23–7.34 (2 H, m), 7.49–7.55

(1 H, m), 7.69 (1 H, s), 7.95 (1 H, br t, J=7 Hz), 8.02 (1 H, s); MS (ES⁺) m/e 394 [MH]⁺. Anal. Found C, 61.10; H, 4.96; N, 24.79. $C_{20}H_{20}N_7OF$ requires C, 61.06; H, 5.12; N, 24.92%.

EXAMPLE 202

6-(1-Methyl-1 H--1,2,4-triazol-3-ylmethoxy)-3-(2-fluorophenyl)-7-(thiophen-3-yl)-1,2,4-triazolo[4,3-b]pyridazine This compound was prepared using the procedures described in Example 16, Steps a), b) and c) except that 3-thiophene boronic acid was used instead of 4-pyridyl boronic acid, di-lithium salt in Step a), 1.1 equivalents of 2-fluorobenzhydrazide and triethylamine hydrochloride were used in Step b) instead of 1.1 equivalents of benzhydrazide, p-toluenesulphonic acid and triethylamine, and (1-methyl-1 H-1,2,4-triazol-3-yl)methanol (Example 65) was used in Step c) instead of 2-pyridylcarbinol. Data for the title compound: m.p. 216–218° C. (MeOH). ¹H NMR (360 MHz, DMSO) δ3.93 (3 H, s), 5.50 (2 H, s), 7.48–7.59 (2 H, m), 7.69–7.78 (2 H, m), 7.85 (1 H, dd, J=7, 2 Hz), 8.08–8.14 (1 H, m), 8.34 (1 H, dd, J=4, 2 Hz), 8.58 (1 H, s), 8.77 (1 H, s). MS (ES⁺) 408 [MH]⁺. Anal. Found C, 55.82; H, 3.57; N. 24.30. $C_{19}H_{14}N_7FOS$ requires C, 56.01; H, 3.46; N, 24.07%.

EXAMPLE 203

8-Methyl-7-(1-methylcyclobutyl)-6-(1-methyl-1 H-1,2,4-triazol-3-ylmethoxy)-3-phenyl-1,2,4-triazolo[4,3-b]pyridazine The compound was prepared using the procedures described in Example 102, Steps a), b) and c) with 1-methylcyclobutane carboxylic acid (U.S. Pat. No. 4,220,795) and 3,6-dichloro-4-methylpyridazine being used instead of cyclopentane carboxylic acid and 3,6-dichloropyridazine respectively in Step a), and benzoic acid hydrazide being used instead of 2-thiophene carboxylic acid hydrazide in Step b), and (1-methyl-1 H-1,2,4-triazol-3-yl)methanol (prepared using the conditions described in EP-A-421210) being used instead of 2-hydroxymethylpyridine in Step c). Data for the title compound: ¹H NMR (360 MHz, CDCl₃) δ1.57 (3 H, s), 1.74–1.84 (1 H, m), 2.02–2.14 (1 H, m), 2.20–2.26 (2 H, m), 2.50–2.58 (2 H, m), 2.62 (3 H, s), 3.93 (3 H, s), 5.48 (2 H, s), 7.44–7.54 (3 H, m), 8.04 (1 H, s), 8.49 (2 H, d, J=8 Hz); MS (ES⁺) m/e 390 [MH]⁺. Anal. Found C, 64.74; H, 5.92; N, 24.88. $C_{21}H_{23}N_7O$ requires C, 64.76; H, 5.95; N, 25.18%.

EXAMPLE 204

8-Methyl-7-(1-methylcyclobutyl)-6-(2-methyl-2 H-1,2,4-triazol-3-ylmethoxy)-3-phenyl-1,2,4-triazolo[4,3-b]pyridazine The compound was prepared using the procedures described in Example 102, Steps a), b) and c) with 1-methylcyclobutane carboxylic acid (U.S. Pat. No. 4,220,795) and 3,6-dichloro-4-methylpyridazine being used instead of cyclopentane carboxylic acid and 3,6-dichloropyridazine respectively in Step a), and benzoic acid hydrazide being used instead of 2-thiophene carboxylic acid hydrazide in Step b), and (2-methyl-2 H-1,2,4-triazol-3-yl)methanol (prepared using the conditions described in EP-A-421210) being used instead of 2-hydroxymethylpyridine in Step c). Data for the title compound: ¹H NMR (360 MHz, CDCl₃) δ1.54 (3 H, s), 1.76–1.84 (1 H, m), 2.04–2.16 (3 H, m), 2.46–2.53 (2 H, m), 2.64 (3 H, s), 3.94 (3 H, s), 5.53 (2 H, s), 7.46–7.56 (3 H, m), 7.93 (1 H, s), 8.34 (2 H, d, J=8 Hz); MS (ES⁺) m/e 390 [MH]⁺. Anal. Found C, 64.83; H, 5.82; N, 25.04. $C_{21}H_{23}N_7O$ requires C, 64.76; H, 5.95; N, 25.18%.

EXAMPLE 205

6-(1-Methyl-1 H-1,2,4-triazol-3-ylmethoxy)-3-phenyl-7-(pyrrolidin-1-yl)-1,2,4-triazolo[4,3-b]pyridazine ¹H NMR (250 MHz, CDCl₃) δ1.95–2.00 (4 H, m), 3.53–3.58 (4 H, m), 3.95 (3 H, s), 5.55 (2 H, s), 6.69 (1 H, s), 7.41–7.55 (3 H, m), 8.07 (1 H, s), 8.43–8.45 (2 H, m), ms (ES⁺) (M+1)=377.

EXAMPLE 206

7-Cyclobutyl-8-methyl-6-(2-methyl-2 H-1,2,4-triazol-3-ylmethoxy)-3-phenyl-1,2,4-triazolo[4,3-b]pyridazine Prepared in an analogous procedure as outlined in Example 102a using 1-methylcyclobutane carboxylic acid, Example 102b using benzoic acid hydrazide and Example 102c using 3-hydroxymethyl-2-methyl-2 H-1,2,4-triazole to give the title compound. ¹H NMR (360 MHz, CDCl₃) δ2.06–2.09 (2 H, m), 2.26 (3 H, s), 2.42–2.50 (2 H, m), 3.04–3.17 (2 H, m), 3.97 (3 H, s), 4.06 (1 H, t, J=10 Hz), 5.57 (2 H, s), 7.48–7.56 (3 H, m), 7.92 (1 H, s), 8.36 (2 H, d, J=7.7 Hz), ms (ES⁺) m/e 376 [MH]⁺.

EXAMPLE 207

7-Cyclobutyl-8-methyl-6-(1-methyl-1 H-1,2,4-triazol-3-ylmethoxy)-3-phenyl-1,2,4-triazolo[4,3-b]pyridazine Prepared in an analogous procedure as outlined in Example 102a using 1-methylcyclobutane carboxylic acid, Example 102b using benzoic acid hydrazide and Example 102c using 3-hydroxymethyl-1-methyl-1 H-1,2,4-triazole to give the title compound. ¹H NMR (360 MHz, CDCl₃) δ2.06–2.18 (2 H, m), 2.24 (3 H, s), 2.40–2.50 (2 H, m), 3.02–3.16 (2 H, m), 3.84 (3 H, s), 3.88–4.10 (1 H, m), 5.50 (2 H, s), 7.42–7.56 (3 H, m), 8.04 (1 H, s), 8.48–8.52 (2 H, m), ms (ES⁺) m/e 376 [MH]⁺.

EXAMPLE 208

7-(1-Methylcyclopentyl)-6-(2-methyl-2 H- 1,2,4-triazol-3-ylmethoxy)-3-(2-fluorophenyl)-1,2,4-triazolo[4,3-b]pyridazine Prepared in an analogous procedure as outlined in Example 102a using 1-methylcyclopentanoic acid, Example 102b using 2-fluorobenzoic acid hydrazide and Example 102c using 3-hydroxymethyl-2-methyl-2 H-1,2,4-triazole to give the title compound. ¹H NMR (360 MHz, CDCl₃) δ1.31 (3 H, s), 1.72–1.90 (8 H, m), 3.82 (3 H, s), 5.50 (2 H, s), 7.25–7.37 (2 H, m), 7.53–7.59 (1 H, rn), 7.83–7.87 (1 H, m), 7.90 (1 H, s), 7.94 (1 H, m), ms (ES⁺) m/e 409 [MH]⁺.

EXAMPLE 209

7-(1-Methycyclopentyl)-6-(1-methyl-1 H-1,2,4-triazol-3-ylmethoxy)-3-(2-fluorophenyl)-1,2,4-triazolo[4,3-b]pyridazine Prepared in an analogous procedure as outlined in Example 102a using 1-methylcyclopentanoic acid, Example 102b using 2-fluorobenzoic acid hydrazide and Example 102c using 3-hydroxymethyl-1-methyl-1 H-1,2,4-triazole to give the title compound. $^1$H NMR (360 MHz, CDCl$_3$) δ1.33 (3 H, s), 1.70–1.93 (8 H, m), 3.92 (3 H, s), 5.43 (2 H, s), 7.23–7.34 (2 H, m), 7.49–7.55 (1 H, m), 7.90 (1 H, s), 7.94–7.98 (1 H, m), 8.04 (1 H, m), ms (ES$^+$) m/e 409 [MH]$^+$.

EXAMPLE 210

7-Cyclobutyl-6-[4-(2,6-dimethylmorpholin-4-yl)but-2-ynyloxy]-3-phenyl-1,2,4-triazolo[4,3-b]pyridazine $^1$H NMR (250 MHz, CDCl$_3$) δ1.11 (3 H, s), 1.13 (3 H, s), 1.21 (1 H, m), 1.92 (3 H, m), 2.13–2.20 (3 H, m), 2.39–2.45 (2 H, m), 2.68 (2 H, m), 3.33 (2 H, m), 3.59–3.69 (3 H, m), 5.09 (2 H, m), 7.46–7.58 (3 H, m), 7.82 (1 H, d, J=1.6 Hz), 8.50 (2 H, m), ms (ES$^+$) (M+1)=432.

What is claimed is:

1. A compound of formula I, or a pharmaceutically acceptable salt thereof:

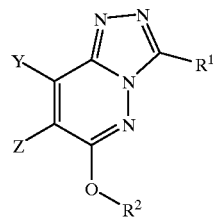

(I)

wherein

Y represents hydrogen or $C_{1-6}$ alkyl;

Z represents $C_{1-6}$alkyl, $C_{3-7}$cycloalkyl, $C_{4-7}$cycloalkenyl, phenyl, naphthyl, azetidinyl, pyrrolidinyl, piperidinyl, piperazinyl, morpholinyl, thiomorphoinyl, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indoly, pyrazolyl, indazolyl, oxazolyl, isoxazoly, thiazolyl, isothiazolyl, imidazolyl, benzimidazolyl, oxadiazolyl, thiadiazolyl, triazolyl, tetrazolyl, or di($C_{1-6}$) alkylamino, any of which groups may be optionally substituted with one or two substituents chosen from $C_{1-6}$alkyl, benzyl, phenylethyl, phenylpropyl, naphthylmethyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$cycloalkyl($C_{1-6}$) alkoxy, $C_{3-7}$cycloalkoxy, amino($C_{1-6}$)alkyl, di($C_{1-6}$) alkylamino($C_{1-6}$)alkyl, di($C_{1-6}$)alkylaminocarbonyl ($C_{1-6}$)alkyl, N-($C_{1-6}$)alkylpiperidinyl, pyrrolidinyl ($C_{1-6}$)alkyl, piperazinyl($C_{1-6}$)alkyl, morpholinyl (($C_{1-6}$)alkyl, di($C_{1-6}$) alkylmorpholinyl($C_{1-6}$)alkyl or imidazolyl($C_{1-6}$)alkyl;

R$^1$ represents $C_3$cycloalkyl, phenyl, furyl, thienyl or pyridinyl, any of which groups may be optionally substituted with one or two substituents chosen from $C_{1-6}$alkyl, benzyl, phenylethyl, phenylpropyl, naphtylmethyl, pyridyl($C_{1-6}$)alkyl, halogen, halo($C_{1-6}$) alkyl, cyano, cyano($C_{1-6}$)alkyl, hydroxy, hydroxymethyl, $C_{1-6}$alkoxy, $C_{3-7}$cycloalkyl($C_{1-6}$) alkoxy, $C_{3-7}$cycloalkoxy, amino($C_{1-6}$)alkyl, di($C_{1-6}$) alkylamino($C_{1-6}$)alkyl, di($C_{1-6}$)alkylaminocarbonyl ($C_{1-6}$)alkyl, N-($C_{1-6}$)alkylpiperidinyl, pyrrolidinyl ($C_{1-6}$)alkyl, piperazinyl($C_{1-6}$)alkyl, morpholinyl (($C_{1-6}$)alkyl, di($C_{1-6}$)alkylmorpholinyl($C_{1-6}$)alkyl or imidazolyl($C_{1-6}$)alkyl; and R$^2$ represents cyano($C_{1-6}$)alkyl group, hydroxy($C_{1-6}$) alkyl group, $C_{3-7}$cycloalkyl($C_{1-6}$)alkyl group, propargyl group, azetidinyl carbonyl($C_{1-6}$)alkyl group, pyrrolidinyl carbonyl($C_{1-6}$)alkyl group, piperidinyl carbonyl($C_{1-6}$)alkyl group, piperazinyl carbonyl($_{1-6}$) alkyl group, morpholinyl carbonyl($C_{1-6}$)alkyl group, thiomorpholinyl carbonyl($C_{1-6}$) alkyl group, benzyl group, phenylethyl group, phenylpropyl group, naphthylmethyl group, pyridinyl ($C_{1-6}$)alkyl group, quinolinyl ($C_{1-6}$)alkyl group, isoquinolinyl ($C_{1-6}$) group, pyridazinyl ($C_{1-6}$)alkyl group, pyrimidinyl ($C_{1-6}$)alkyl group, pyrazinyl ($C_{1-6}$)alkyl group, quinoxalinyl ($C_{1-6}$)alkyl group, furyl ($C_{1-6}$)alkyl group, benzofuryl ($C_{1-6}$)alkyl group, dibenzofuryl ($C_{1-6}$)alkyl group, thienyl ($C_{1-6}$)alkyl group, benzthienyl ($C_{1-6}$) alkyl group, pyrrolyl ($C_{1-6}$)alkyl group, indolyl ($C_{1-6}$) alkyl group, pyrazolyl ($c_{1-6}$)alkyl group, indazolyl ($C_{1-6}$)alkyl group, oxazolyl ($C_{1-6}$)alkyl group, isoxazolyl ($C_{1-6}$)alkyl group, thiazolyl ($C_{1-6}$)alkyl group, isothiazolyl ($C_{1-6}$)alkyl group, imidazolyl ($C_{1-6}$)alkyl group, benzimidazolyl ($C_{1-6}$)alkyl group, oxadiazolyl ($C_{1-6}$)alkyl group, thiadiacolyl ($C_{1-6}$)alkyl group, triazolyl ($C_{1-6}$)alkyl group, or tetrazolyl ($C_{1-6}$)alkyl group, any of which groups may be optionally substituted with one or two substituents chosen from $C_{1-6}$alkyl, benzyl, phenylethyl, phenylpropyl, naphthylmethyl, pyridyl ($C_{1-6}$)alkyl, halogen, halo($C_{1-6}$)alkyl, cyano, cyano ($C_{1-6}$)alkyl, hydroxy, hydroxymethyl, $C_{1-6}$alkoxy, $C_{3-7}$cycloalkyl($C_{1-6}$)alkoxy, $C_{3-7}$cycloalkoxy, amino ($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$) alkylpiperidinyl, pyrrolidinyl($C_{1-6}$)alkyl, piperazinyl ($C_{1-6}$)alkyl, morpholinyl(($C_{1-6}$)alkyl, di($C_{1-6}$) alklmorpholinyl($C_{1-6}$)alkyl or imidazolyl($C_{1-6}$)alkyl.

2. A compound as claimed in claim 1 represented by formula IIB, and pharmaceutically acceptable salts thereof:

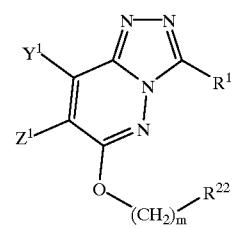

(IIB)

wherein

Y$^1$represents hydrogen or methyl;

Z$^1$ represents $C_{1-6}$alkyl, $C_{3-7}$cycloalkyl, $C_{4-7}$cycloalkenyl, phenyl, naphthyl, azetidinyl, pyrrolidinyl, piperidinyl, piperazinyl, morpholinyl, thiomorpholinyl, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, or di($C_{1-6}$)alkylamino, any of which groups may be optionally substituted with one or two substituents chosen from $C_{1-6}$alkyl, benzyl, phenylethyl, phenylpropyl, naphthylmethyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$cycloalkyl ($C_{1-6}$)alkoxy, $C_{3-7}$cycloalkoxy, amino($C_{1-6}$)alkyl, di($C_{1-6}$)alkylamino($C_{1-6}$)alkyl, di($C_{1-6}$)

alkylaminocarbonyl($C_{1-6}$)alkyl, N-($C_{1-6}$) alkylpiperidinyl, pyrrolidinyl($C_{1-6}$)alkyl, piperazinyl ($C_{1-6}$)alkyl, morpholinyl(($C_{1-6}$)alkyl, di($C_{1-6}$) alkylmorpholinyl($C_{1-6}$)alkyl or imidazolyl($C_{1-6}$)alkyl;

$R^1$ is as defined in claim 1;

m is 1 pr 2; and $R^{22}$ represents phenyl, naphthyl, pyridinyl, quinolinyl, isoquionlinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, any of which groups may be optionally substituted with one or two substituents chosen from $C_{1-6}$alkyl, benzyl, phenylethyl, phenylpropyl, naphthylmenthyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$cycloalkyl ($C_{1-6}$)alkoxy, $C_{3-7}$cycloalkoxy, amino($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$) alkylpiperidinyl, pyrrolidinyl($C_{1-6}$)alkyl, piperazinyl ($C_{1-6}$)alkyl, morpholinyl(($C_{1-6}$)alkyl, di($c_{1-6}$) alkylmorpholinyl($C_{1-6}$)alkyl or imidazolyl($C_{1-6}$)alkyl.

3. A compound as claimed in claim 2 represented by formula IIC, and pharmaceutically acceptable salts thereof:

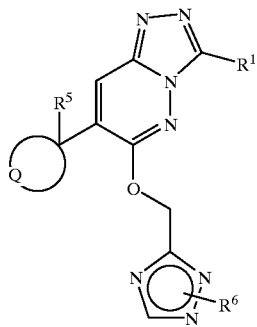

(IIC)

wherein $R^1$ is as defined in claim 1;

Q represents the residue of a cyclopropyl, cyclobutyl, cyclopentyl or cyclohexyl ring;

$R^5$ represents hydrogen or methyl; and $R^6$ represents hydrogen or methyl.

4. The compound of claim 1 selected from:
3,7-diphenyl-6-(2-pyridyl)methyloxy-1,2,4-triazolo[4,3-b]pyridazine;
7,8-dimethyl-3-phenyl-6-(2-pyridyl)methyloxy-1,2,4-triazolo[4,3-b]pyridazine;
7-methyl-3-phenyl-6-(2-pyridyl)methyloxy-1,2,4-triazolo[4,3-b]pyridazine;
7-ethyl-3-phenyl-6-(2-pyridyl) methyloxy-1,2,4-triazolo[4,3-b]pyridazine;
8-methyl-3,7-diphenyl-6-(2-pyridyl)methyloxy-1,2,4-triazolo[4,3-b]pyridazine;
3-phenyl-6-(2-pyridyl)methyloxy-(7,8-pentano)-1,2,4-triazolo[4,3-b]pyridazine;
3-phenyl-7-(piperidin-1-yl)-6-(pyridin-2-ylmethoxy)-1,2,4-triazolo[4,3-b]pyridazine;
3-phenyl-7-(pyridin-4-yl)-6-(pyridin-2-ylmethoxy)-1,2,4-triazolo[4,3-b]pyridazine;
3-phenyl-6-(pyridin-2-ylmethoxy)-7-(thiophen-2-yl)-1,2,4-triazolo[4,3-b]pyridazine;
3-phenyl-6-(pyridin-2-ylmethoxy)-7-(thiophen-3-yl)-1,2,4-triazolo[4,3-b]pyridazine;
and pharmaceutically acceptable salts thereof.

5. The compound of claim 1 selected from:
6-(6-methylpyridin-2-yl)methyloxy-3-phenyl-1,2,4-triazolophthalazine;
and pharmaceutically acceptable salts thereof.

6. The compound of claim 1 selected from:
6-(1-methyl-1 H-1,2,4-triazol-3-ylmethoxy)-3,7-diphenyl-1,2,4-triazolo[4,3-b]pyridazine;
6-(2-methyl-2 H-1,2,4-triazol-3-ylmethoxy)-1,2,4-triazolo[4,3-b]pyridazine;
3,7-diphenyl-6-(2 H-1,2,4-triazol-3ylmethoxy)-1,2,4-triazolo[4,3-b]pyridazine;
6-(2-methyl-2 H-tetrazol-5-ylmethoxy)-3,7-diphenyl-1,2,4-triazolo[4,3-b]-pyridazine;
3,7-diphenyl-6-(2-propyl-2 H-1,2,4-triazol-3-ylmethoxy)-1,2,4-triazolo[4,3-b]pyridazine;
3,7-diphenyl-6-(1-propyl-1 H-1,2,4-triazol-3-ylmethoxy)-1,2,4-triazolo[4,3-b]pyridazine;
6-(1-methyl-1 H-imidazol-4-ylmethoxy)-3,7-diphenyl-1,2,4-triazolo[4,3-b]pyridazine;
6-(3-methyl-3 H-imidazol-4-ylmethoxy)-3,7-diphenyl-1,2,4-triazolo[4,3-b]pyridazine;
6-(4-methyl-4 H-1,2,4-triazol-3-ylmethoxy)-3,7-diphenyl-1,2,4-triazolo[4,3-b]pyridazine;
6-(5-methyl-2 H-1,2,4-triazol-3-ylmethoxy)-3,7-dephenyl-1,2,4-triazolo[4,3-b]pyridazine;
6-(3-methyl-3 H-1,2,3-triazol-4-ylmethoxy)-3,7-diphenyl-1,2,4-triazolo[4,3-b]pyridazine;
3-(4-methoxyphenyl)-6-(1-methyl-1 H-1,2,4-triazol-3-ylmethoxy)7-phenyl-1,2,4-triazolo[4,3-b]pyridazine;
6-(3-methylpyridin-2-ylmethoxy)-3-phenyl-7-(piperidin-1-yl)-1,2,4-triazolo[4,3-b]pyridazine;
7-(morpholin-4-yl)-3-phenyl-6-(pyridin-2-ylmethoxy)-1,2,4-triazolo[4,3-b]pyridazine;
3-phenyl-7-(pyridin-3-yl)-6-(pyridin-2-ylmethoxy)-1,2,4-triazolo[4,3-b]pyridazine;
8-methyl-6-2-methyl-2 H-1,2,4-triazol-3-ylmethoxy)-7-(morpholin-4yl)-3-phenyl-1,2,4-triazolo[4,3-b]pyridazine;
6-(1-methyl-1 H-1,2,4-triazol-3-ylmethoxy)-7-(morpholin-4yl)-3-phenyl-1,2,4-triazolo[4,3-b]pyridazine;
6-(2-methyl-2 H-1,2,4-triazol-3-ylmethoxy)-7-(morpholin-4yl)-3-phenyl-1,2,4-triazolo[4,3-b]pyridazine;
7-cyclohexyl-6-(2-methyl-2 H-1,2,4-triazol-3-ylmethoxy)-3-phenyl-1,2,4-triazolo[4,3-b]pyridazine;
7-cyclohexyl-6-(1-methyl-1 H-1,2,4-triazol-3-ylmethoxy)-3-phenyl-1,2,3-triazolo[4,3-b]pyridazine;
7-cyclopentyl-6-(2-methyl-2 H-1,2,4-triazol-3-ylmethoxy)-3phenyl-1,2,4-triazolo[4,3-b]pyridazine;
8-methyl-6-(1-methyl-1 H-1,2,4-triazol-3-ylmethoxy)-3,7-diphenyl-1,2,4-triazolo[4,3-b]pyridazine;
7-cyclobutyl-6-(1-methyl-1 H-1,2,4-triazol-3-ylmethoxy)-3-phenyl-1,2,4-triazolo[4,3-b]pyridazine;
7-tert-butyl-6-(2-methyl-2 H-1,2,4-triazol-3-ylmethoxy)-3-phenyl-1,2,4-triazolo[4,3-b]pyridazine;
7-cyclobutyl-6-(2-methyl-2 H-1,2,4-triazol-3-ylmethoxy)-3-phenyl-1,2,4-triazolo[4,3-b]pyridazine;
7-ethyl-6-(2-methyl-2 H-1,2,4-triazol-3-ylmethoxy)-3-phenyl-1,2,4-triazolo[4,3-b]pyridazine;
7-tert-butyl-6-(1-methyl-1 H-1,2,4-triazol-3-ylmethoxy)-3-phenyl-1,2,4-triazolo[4,3-b]pyridazine;
7-ethyl-6-(1-methyl-1 H-1,2,4-triazol-3-ylmethoxy)-3-phenyl-1,2,4-triazolo[4,3-b]pyridazine;
7-methyl-6(2-methyl-2 H-1,2,4-triazol-3-ylmethoxy)-3-phenyl-1,2,4-triazolo[4,3-b]pyridazine;
7-(1-methylcyclobutyl)-6-(2-methyl-2 H-1,2,4-triazol-3-ylmethoxy)-3-phenyl-1,2,4-triazolo[4,3-b]pyridazine;

7-methyl-6-(1-methyl-1 H-1,2,4-triazol-3-ylmethoxy)-3-phenyl-1,2,4-triazolo[4,3-b]pyridazine;
7-cyclobutyl-3-phenyl-6-(2 H, 1,2,4-triazol-3-ylmethoxy)-1,2,4-triazolo[4,3-b]pyridazine;
7-cyclopentyl-6-(pyridin-2-ylmethoxy)-3-(thiophen-2-yl)-1,2,4-triazolo[4,3-b]pyridazine;
7-cyclopentyl-3-(2,4-difluorophenyl)-6-(1-methyl-1 H-1,2,4-triazol-3-ylmethoxy)-1,2,4-triazolo[4,3b]pyridazine;
7-cyclopentyl-6-(1-methyl-1 H-1,2,4-triazol-3-ylmethoxy)-3-ylmethoxy)-3-(thiophen-2-yl)-1,2,4-triazolo[4,3-b]pyridazine;
7-cyclopentyl-6-(2-methyl-2 H-1,2,4-triazol-3ylmethoxy)-3-(thiophen-2yl)-1,2,4-triazolo[4,3-b]pyridazine;
7-cyclopentyl-6-(2-methyl-2 H-1,2,4-triazol-3-ylmethoxy)-3-(pyridin-4-yl)-1,2,4-triazolo[4,3-b]pyridazine;
7-cyclopentyl-3-(2-fluorophenyl)-6-(1-methyl-1 H-1,2,4-triazol-3-ylmethoxy)-1,2,4-triazolo[4,3-b]pyridazine;
7-cyclopentyl-3-(2-fluorophenyl)-6-(2-methyl-2 H-1,2,4-triazol-3-ylmethoxy)-1,2,4-triazolo[4,3-b]pyridazine;
7-cyclopentyl-3-(2-fluorophenyl)-6-(pyridin-2-ylmethoxy)-1,2,4-triazolo[4,3-b]pyridazine;
7-cyclopentyl-3(2,4-difluorophenyl)-6-(2-methyl-2 H-1,2,4-triazol-3-ylmethoxy)-1,2,4-triazolo[4,3-b]pyridazine;
7-cyclopentyl-3-phenyl-6-(pyridin-2-ylmethoxy)-1,2,4-triazolo[4,3-b]pyridazine;
7-cyclopentyl-8-methyl-6-(2-methyl-2 H-1,2,4-triazol-3-ylmethoxy)-3-phenyl-1,2,4-triazolo[4,3-b]pyridazine;
7-cyclopentyl-3-phenyl-6-(2 H-1,2,4-triazol-3ylmethoxy)-1,2,4-triazolo[4,3-b]pyridazine;
3-(4-methylphenyl)-7-phenyl-6-(pyridin-2ylmethoxy)-1,2,4-triazolo[4,3-b]pyridazine;
3-(4-methylphenyl)-6-(3-methylpyridin-2-ylmethoxy)-7-phenyl-1,2,4-triazolo[4,3b]pyridazine;
6-(1-ethyl-1 H-imidazol-2-ylmethoxy)-3-(4-methylphenyl)-7-phenyl-1,2,4-triazolo[4,3-b]pyridazine;
3-phenyl-6-(pyridin-2-ylmethoxy)-7-(thiomorpholin-4yl)-1,2,4-triazolo[4,3-b]pyridazine;
6-[2-(4-methylthiazol-5-yl)ethoxy]-3,7-diphenyl-1,2,4-triazolo[4,3-b]pyridaine;
(±)-7-(2-methylpyrrolidin-1-yl)-3-phenyl-6-(pyridin-2-ylmethoxy)-1,2,4-triazolo[4,3b]pyridazine;
6-(1-methyl-1 H-1,2,4-triazol-3-ylmethoxy)-3-phenyl-7-(pyridin-4-yl)-1,2,4-triazolo[4,3-b]pyridazine;
7-cyclopentyl-6-(1-methyl-1 H-1,2,4-triazol-3-ylmethoxy)-3-phenyl-1,2,4-triazolo[4,3-b]pyridazine;
7-isopropyl-6-(1-methyl-1 H-1,2,4-triazol-3ylmethoxy)-3-phenyl-1,2,4-triazolo[4,3-b]pyridazine;
3-cyclopropyl-6-(1-methyl-1 H, 1,2,4-triazol-3-ylmethoxy)-7-phenyl-1,2,4-triazolo[4,3-b]pyridazine;
3-(2-fluorophenyl)-6-(2-methyl-2 H-1,2,4-triazol-3-ylmethoxy)-7-phenyl-1,2,4-triazolo[4,3-b]pyridazine;
3-(2-fluorophenyl)-6-(1-methyl-1 H-1,2,4-triazol-3-ylmethoxy)-7-phenyl-1,2,4-triazolo[4,3-b]pyridazine;
6-(1-methyl-1 H-1,2,4-triazol-3-ylmethoxy)-7-phenyl-3-(thiophen-2yl)-1,2,4-triazolo[4,3-b]pyridazine;
6-(1-methyl-1 H-1,2,4-triazol-3-ylmethoxy)-7-phenyl-3-(pyridin-3-yl)-1,2,4-triazolo[4,3b]pyridazine;
6-(2-methyl-2 H-1,2,4-triazol-3-ylmethoxy)-7-phenyl-3-(thiophen-2yl)-1,2,4-triazolo[4,3-b]pyridazine;
6-(2-methyl-2 H-1,2,4-triazol-3-ylmethoxy)-7-phenyl-3-(pyridin-3-yl)-1,2,4-triazolo[4,3-b]pyridazine;
3-(furan-3-yl)-6-(1-methyl-1 H-1,2,4-triazol-3-ylmethoxy)-7-phenyl-1,2,4-triazolo[4,3-b]pyridazine;
6-(1-methyl-1 H-1,2,4-triazol-3-ylmethoxy)-7-phenyl-3-(thiophen-2yl)-1,2,4-triazolo[4,3-b]pyridazine;
6-(5-methyl-1,2,4-oxadiazol-3-ylmethoxy)-3,7-diphenyl-1,2,4-triazolo[4,3-b]pyridazine;
7-phenyl-3(thiophen-2yl)-6-(2 H-1,2,4-triazol-3-ylmethoxy)-1,2,4-triazolo[4,3-b]pyridazine;
3-(furan-2yl)-6(1-methyl-1 H-1,2,4-triazol-3-ylmethoxy)-7-phenyl-1,2,4-triazolo[4,3-b]pyridazine;
6-(1-methyl-1 H-1,2,4-triazol-3-ylmethoxy)-3-phenyl-7-(thiophen-3yl)-1,2,4-triazolo[4,3-b]pyridazine;
6(2-methyl-2 H-1,2,4-triazol-3-ylmethoxy)-7-(thiophen-3yl)-1,2,4-triazolo[4,3b]pyridazine;
3-phenyl-7-(thiophen-3-yl)-6-(2 H-1,2,4-triazol-3-ylmethoxy)-1,2,4-triazolo[4,3-b]pyridazine;
6-(2-methyl-2 H-1,2,4-triazol-3-ylmethoxy)-3-phenyl-7-(thiophen-2-yl)-1,2,4-triazolo[4,3-b]pyridazine;
6-(1-methyl-1 H-1,2,4-triazol-3-ylmethoxy)-3-phenyl-7-(thiophen-2-yl)-1,2,4-triazolo[4,3-b]pyridazine;
7-(furan-2-yl)-6-(2-methyl-2 H-1,2,4-triazol-3-ylmethoxy)-3-phenyl-1,2,4-triazolo[4,3-b]pyridazine;
7-(furan-2-yl)-6-(1-methyl-1 H-1,2,4-triazol-3-ylmethoxy)-3-phenyl-1,2,4-triazolo[4,3-b]pyridazine;
6-(3-methyl-1,2,4-oxadiazol-5-ylmethoxy)-3,7-diphenyl-1,2,4-triazolo[4,3-b]pyridazine;
3-(4-fluorophenyl)-6-(1-methyl-1 H-1,2,4-triazol-3-ylmethoxy)-7-phenyl-1,2,4-triazolo[4,3-b]pyridazine;
3,7-diphenyl-6(2 H-1,2,3-triazol-4-ylmethoxyl)-1,2,4-triazolo[4,3-b]pyridazine;
3,7-diphenyl-6-(pyrazin-2-ylmethoxy)-1,2,4-triazolo[4,3-b]pyridazine;
3-(4-methylphenyl)-6-(1-methyl-1 H-1,2,4-triazol-3-ylmethoxy)-7-phenyl-1,2,4-triazolo[4,3-b]pyridazine;
6-(4-methylthiazol-2ylmethoxy)-3,7-diphenyl-1,2,4-triazolo[4,3-b]pyridazine;
6-(5-ethylthiazol-2-ylmethoxy)-3,7-diphenyl-1,2,4-triazolo[4,3-b]pyridazine;
3,7-diphenyl-6-(pyrimidin-4-ylmethoxy)-1,2,4-triazolo[4,3-b]pyridazine;
3,7-diphenyl-6-(pyridazin-3-ylmethoxy)-1,2,4-triazolo[4,3-b]pyridazine;
6-(1-methyl-1 H-1,2,4-triazol-3-ylmethoxy)-7-(morpholin-4-yl)-3-(thiophen-2-yl)-1,2,4-triazolo[4,3-b]pyridazine;
3,7-diphenyl-6-(thiazol-4-ylmethoxy)-1,2,4-triazolo[4,3-b]pyridazine;
6-(5-methylisoxazol-3-ylmethoxy)-3,7-diphenyl-1,2,4-triazolo[4,3-b]pyridazine;
3-(3-fluorophenyl)-6-(1-methyl-1 H-1,2,4-triazol-3-ylmethoxyl)-7-(morpholin-4yl)-1,2,4-triazolo[4,3-b]pyridazine;
3,7-diphenyl-6-(pyrimidin-2-ylmethoxy)-1,2,4-triazolo[4,3-b]pyridazine;
6-(2-methyl-2 H-1,2,3-triazol-4-ylmethoxy)-3,7-diphenyl-1,2,4-triazolo[4,3-b]pyridazine;
7-(1-methylcyclobutyl)-6(1-methyl-1 H-1,2,4-triazol-3-ylmethoxy)-3-phenyl-1,2,4-triazolo[4,3-b]pyridazine;
7-isopropyl-6-(2-methyl-2 H-1,2,4-triazol-3-ylmethoxy)-3-phenyl-1,2,4-triazolo[4,3-b]pyridazine;
7-tert-butyl-3-(2-fluorophenyl)-6-(1-methyl-1 H-1,2,4-triazol-3ylmethoxy)-1,2,4-triazolo[4,3-b]pyridazine;
7-cyclopentyl-3-(4-methoxyphenyl)-6-(2-methyl-2 H-1,2,4-triazol-3-ylmethoxy)-1,2,4-triazolo[4,3-b]pyridazine;
7-(1-methylcyclopentyl)-6-(1-methyl-1 H-1,2,4-triazol-3-ylmethoxy)-3-phenyl-1,2,4-triazolo[4,3-b]pyridazine;
7-(1-methylcyclopentyl)-6-(2-methyl-2 H-1,2,4-triazol-3-ylmethoxy)-3-phenyl-1,2,4-triazolo[4,3-b]pyridazine;
7-cyclopentyl-3-(furan-2-yl)-6-(2-methyl-2 H-1,2,4-triazol-3-ylmethoxy)-1,2,4-triazolo[4,3-b]pyridazine;
7-cyclopentyl-3-(furan-2-yl)-6-(1-methyl-1 H-1,2,4-triazol-3-ylmethoxy)-1,2,4-triazolo[4,3-b]pyridazine;
3-(3,7-diphenyl-1,2,4-triazolo[4,3-b]pyridazin-6-yloxymethyl)-1,2,4-triazol-1-ylacetonitrile;

7-(1-methylcyclopropyl)-6-(2-methyl-2 H-1,2,4-triazol-3-ylmethoxy)-3-phenyl-1,2,4-triazolo[4,3-b]pyridazine;
7-(1-methylcyclopropyl)-6-(1-methyl-1 H-1,2,4-triazol-3-ylmethoxy)-3-phenyl-1,2,4-triazolo[4,3-b]pyridazine;
3-(3-fluorophenyl)-6-(1-methyl-1 H-1,2,4-triazol-3-ylmethoxy)-7-phenyl-1,2,4-triazolo[4,3-b]pyridazine;
7-(1methylcyclopentyl)-6-(3-methylpyridin-2-ylmethoxy)-3-phenyl-1,2,4-triazolo[4,3-b]pyridazine;
6-(1-methyl-1 H-1,2,3-triazol-4-ylmethoxy)-3,7-diphenyl-1,2,4-triazolo[4,3-b]pyridazine;
3-(5-methylthiophen-2yl)-6-(1-methyl-1 H-1,2,4-triazol-3-ylmethoxy)-7-phenyl-1,2,4-triazolo[4,3-b]pyridazine;
2-[3-(3,7-diphenyl-1,2,4-triazolo[4,3-b]pyridazin-6-yloxymethyl)-1,2,4-triazol-1-yl]-N,N-dimethylacetamide;
3,7-diphenyl-6-[1-pyridin-2-ylmethyl)-1 H-1,2,4-triazol-3-ylmethoxy]-1,2,4-triazolo[4,3-b]pyridazine;
6-(1-benzyl-1 H-1,2,4-triazol-3-ylmethoxyl)-3,7-diphenyl-1,2,4-triazolo[4,3-b]pyridazine;
2-[5-(3,7-diphenyl-1,2,4-triazolo[4,3-b]pyridazin-6-yloxymethyl)-1,2,4-triazol-1-yl]acetamide;
N-[2-[3-(3,7-diphenyl-1,2,4-triazolo[4,3-b]pyridazin-6-yloxymethyl)-1,2,4-triazol-1-yl]ethyl]-N,N-dimethylamine;
3,7-diphenyl-6-(pyrimidin-5-ylmethoxy)-1,2,4-triazolo[4,3-b]pyridazine;
6-[1-(2-(morpholin-4-yl)-ethyl)-1 H-1,2,4-triazol-3-ylmethoxyl]-3,7-diphenyl-1,2,4-triazolo[4,3-b]pyridazine;
6-(2-methyl-2 H-1,2,4-triazol-3-ylmethoxy)-3-phenyl-7-(pyrrolidin-1-yl)-1,2,4-triazolo[4,3-b]pyridazine;
7-(5-chlorothiophen-2yl)-6-(2-methyl-2 H-1,2,4-triazol-3ylmethoxy)-3-phenyl-1,2,4-triazolo[4,3-b]pyridazine;
7-(5-chlorothiophen-2-yl)-6(1-methyl-1 H-1,2,4-triazol-3-ylmethoxy)-3-phenyl-1,2,4-triazolo[4,3-b]pyridazine;
6-(1 H-benzimidazol-2ylmethoxy)-3-(2,4-difluorophenyl)-7-(1-methylcyclopentyl)-1,2,4-triazolo[4,3b]pyridazine;
7-cyclobutyl-3-phenyl-6-(prop-2-ynyloxy)-1,2,4-triazolo[4,3-b]pyridazine;
(7-cyclobutyl-3-phenyl-1,2,4-triazolo[4,3-b]pyridazin-6-yloxy)acetonitrile;
N-[4-(7-cyclobutyl-3-phenyl-1,2,4-triazolo[4,3-b]pyridazin-6yloxy)but-2-ynyl]-N,N-dimethylamine;
and pharmaceutically acceptable salts thereof.

7. The compound of claim 1 selected from:
2-[3-(3,7-diphenyl-1,2,4-triazolo[4,3-b]pyridazin-6-yloxymethyl)-1,2,4-triazol-1-yl]ethylamine;
3,7-diphenyl-6-[1-(2-(pyrrolidin-1-yl)ethyl)-1 H-1,2,4-triazol-3-ylmethoxy]-1,2,4-triazolo[4,3-b]pyridazine;
6-[1-(1-methylpiperidin-4-yl)-1 H-1,2,4-triazol-3-ylmethoxy]-3,7-diphenyl-1,2,4-triazolo[4,3-b]pyridazine;
3,7-diphenyl-6-[1-(2-(piperazin-1-yl)ethyl)-1 H-1,2,4-triazol-3-ylmethoxy]-1,2,4-triazolo[4,3-b]pyridazine;
7-(1-methylcyclopentyl)-6-(2-methyl-2 H- 1,2,4-triazol-3-ylmethoxy)-3-(2,4-difluorophenyl)-1,2,4-triazolo[4,3-b]pyridazine;
7-(cyclobut-1-enyl)-6-(2-methyl-2 H-1,2,4-triazol-3-ylmethoxy)-3-phenyl-1,2,4-triazolo[4,3-b]pyridazine;
7-(furan-3-yl)-6-(1-methyl-1 H-1,2,4-triazol-3-ylmethoxy)-3-phenyl-1,2,4-triazolo[4,3-b]pyridazine;
N,N-diethyl-N-[6-(1-methyl-1 H-1,2,4-triazol-3-ylmethoxy)-3-phenyl-1,2,4-triazolo[4,3-b]pyridazin-7-yl]amine;
7-(1-methylcyclopentyl)-6-(1-methyl-1 H-1,2,4-triazol-3-ylmethoxy)-3-(2,4-difluorophenyl)-1,2,4-triazolo[4,3-b]pyridazine;
7-(1,1-dimethylpropyl)-6-(1-methyl-1 H- 1,2,4-triazol-3-ylmethoxy)-3-phenyl-1,2,4-triazolo[4,3-b]pyridazine;
6-(2-methyl-2 H-1,2,4-triazol-3-ylmethoxy)-3-(4-fluorophenyl)-7-(thiophen-3-yl)-1,2,4-triazolo[4,3-b]pyridazine;
6-(1-methyl-1 H-1,2,4-triazol-3-ylmethoxy)-3-(4-fluorophenyl)-7-(thiophen-3-yl)-1,2,4-triazolo[4,3-b]pyridazine;
6-(2-methyl-2 H-1,2,4-triazol-3-ylmethoxy)-3-(2-fluorophenyl)-7-(thiophen-3-yl)-1,2,4-triazolo[4,3-b]pyridazine;
3-(2-fluorophenyl)-7-(1-methylcyclobutyl)-6-(2-methyl-2 H-1,2,4-triazol-3-ylmethoxy)-1,2,4-triazolo[4,3-b]pyridazine;
3-(2-fluorophenyl)-7-(1-methylcyclobutyl)-6-(1-methyl-1 H- 1,2,4-triazol-3-ylmethoxy)-1,2,4-triazolo[4,3-b]pyridazine;
6-(1-methyl-1 H- 1,2,4-triazol-3-ylmethoxy)-3-(2-fluorophenyl)-7-(thiophen-3-yl)- 1,2,4-triazolo[4,3-b]pyridazine;
8-methyl-7-(1-methylcyclobutyl)-6-(1-methyl-1 H-1,2,4-triazol-3-ylmethoxy)-3-phenyl-1,2,4-triazolo[4,3-b]pyridazine;
8-methyl-7-(1-methylcyclobutyl)-6-(2-methyl-2 H-1,2,4-triazol-3-ylmethoxy)-3-phenyl-1,2,4-triazolo[4,3-b]pyridazine;
6-(1-methyl-1 H- 1,2,4-triazol-3-ylmethoxy)-3-phenyl-7-(pyrrolidin- 1-yl)-1,2,4-triazolo[4,3-b]pyridazine;
7-cyclobutyl-8-methyl-6-(2-methyl-2 H-1,2,4-triazol-3-ylmethoxy)-3-phenyl-1,2,4-triazolo[4,3-b]pyridazine;
7-cyclobutyl-8-methyl-6-(1-methyl-1 H-1,2,4-triazol-3-ylmethoxy)-3-phenyl-1,2,4-triazolo[4,3-b]pyridazine;
7-(1-methylcyclopentyl)-6-(2-methyl-2 H-1,2,4-triazol-3-ylmethoxy)-3-(2-fluorophenyl)-1,2,4-triazolo[4,3-b]pyridazine;
7-(1-methylcyclopentyl)-6(1-methyl-1 H-1,2,4triazol-3-ylmethoxy)-3-(2-fluorophenyl)-1,2,4-triazolo[4,3-b]pyridazine;
7-cyclobutyl-6-[4-(2,6-dimethylmorpholin-4-yl)but-2-ynyloxy]-3-phenyl-1,2,4-triazolo[4,3-b]pyridazine;
and pharmaceutically acceptable salts thereof.

8. The compound of claim 6 selected from: 7-cyclobutyl-6-(2-methyl-2 H-1,2,4-triazol-3-ylmethoxy)-3-phenyl-1,2,4-triazolo[4,3-b]pyridazine.

9. A pharmaceutical composition comprising a compound of formula I as defined in claim 1 or a pharmaceutically acceptable salt thereof thereof in association with a pharmaceutically acceptable carrier.

10. A method for the treatment of anxiety which comprises administering to a patient in need of such treatment an effective amount of a compound of formula I as defined in claim 1 or a pharmaceutically acceptable salt thereof.

11. A method for the treatment of convulsions which comprises administering to a patient in need of such treatment an effective amount of a compound of formula I as defined in claim 1 or a pharmaceutically acceptable salt thereof.

12. A pharmaceutical composition comprising the compound of claim 8 in association with a pharmaceutically acceptable carrier.

13. A method for the treatment of anxiety in a patient in need thereof, comprising administering to the patient a therapeutically effective amount of the compound of claim 8.

14. A method for the treatment of convulsions in a patient in need thereof, comprising administering to the patient a therapeutically effective amount of the compound of claim 8.

15. A process for the preparation of a compound as claimed in claim 1, which comprises:
(A) reacting a compound of formula III with a compound of formula IV:

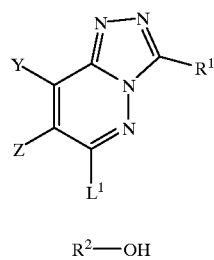

(III)

(IV)

R²—OH wherein Y, Z, R¹ and R² are as defined in claim 1, and L¹ represents a suitable leaving group; or (B) reacting a compound of formula VII with a compound of formula VIII:

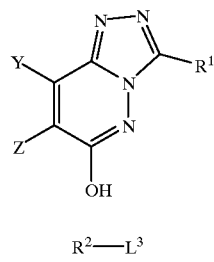

(VII)

(VIII)

R²—L³ wherein Y, Z, R¹ and R² are as defined in claim 1, and L³ represents a suitable leaving group; or (C) reacting a compound of formula Z—CO₂H with a compound of formula IX:

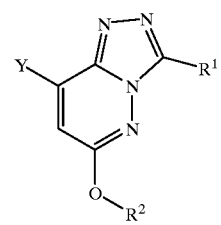

(IX)

wherein Y, Z, R¹ and R² are as defined in claim 1; in the presence of silver nitrate and ammonium persulphate; or (D) reacting a compound of formula X with a compound of formula XI:

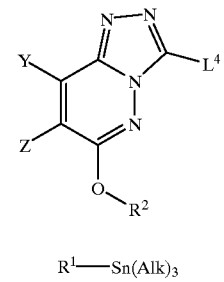

(X)

(XI)

R¹—Sn(Alk)₃ wherein Y, Z, R¹ and R² are as defined in claim 1, Alk represents a $C_{1-6}$ alkyl group, and L⁴ represents a suitable leaving group; in the presence of a transition metal catalyst.

* * * * *